(12) United States Patent
Weintraub et al.

(10) Patent No.: US 8,173,682 B2
(45) Date of Patent: May 8, 2012

(54) SUBSTITUTED PYRIDONES AS INHIBITORS OF POLY(ADP-RIBOSE) POLYMERASE (PARP)

(75) Inventors: Philip M. Weintraub, Warren, NJ (US); Paul R. Eastwood, Barcelona (ES); Shujaath Mehdi, Manville, NJ (US); David W. Stefany, Hillsborough, NJ (US); Kwon Yon Musick, Bridgewater, NJ (US); Neil Moorcroft, Bloomsbury, NJ (US); Sungtaek Lim, Flemington, NJ (US); John Z. Jiang, Hillsborough, NJ (US); Hartmut Rutten, Idstein (DE); Stefan Peukert, Frankfurt (DE); Uwe Schwahn, Sulzbach (DE)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 1494 days.

(21) Appl. No.: 11/535,127

(22) Filed: Sep. 26, 2006

(65) Prior Publication Data
US 2007/0032489 A1 Feb. 8, 2007

Related U.S. Application Data

(63) Continuation of application No. PCT/US2005/010517, filed on Mar. 29, 2005.

(60) Provisional application No. 60/557,459, filed on Mar. 30, 2004.

(51) Int. Cl.
*A61K 31/4436* (2006.01)
*C07D 401/14* (2006.01)

(52) U.S. Cl. .................. 514/343; 546/278.4; 546/278.7

(58) Field of Classification Search ............... 546/278.4, 546/278.7; 514/343
See application file for complete search history.

(56) References Cited

U.S. PATENT DOCUMENTS

| | | | |
|---|---|---|---|
| 3,878,215 A | 4/1975 | Houlihan et al. | |
| 3,989,704 A | 11/1976 | Houlihan et al. | |
| 4,431,651 A | 2/1984 | Lesher et al. | |
| 4,699,914 A | 10/1987 | Hilboll et al. | |

FOREIGN PATENT DOCUMENTS

| | | |
|---|---|---|
| EP | 0109628 | 5/1984 |
| EP | 0 326 389 A2 | 8/1989 |
| EP | 0 585 913 A2 | 3/1994 |
| EP | 1 148 056 A1 | 10/2001 |
| EP | 1 477 175 A1 | 11/2004 |
| JP | 1-242570 A | 9/1989 |
| JP | 3-112967 A | 5/1991 |
| JP | 7-10844 A | 1/1995 |
| JP | 2004-43458 A | 2/2004 |
| WO | 00/44726 A1 | 3/2000 |
| WO | 03/070707 A1 | 8/2003 |

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, pp. 1-2, 183-226.*
Singh, B., et. al. A Novel and Facile Two Step Synthesis of 5-Aryl-2(1H)-Pyridones, Synthesis (1985, pp. 305-306, vol. 3).
Cosi, C., et. al., New Inhibitors of poly (ADP-ribose) polymerase and their potential therapeutic targets, Expert Opin. Thor. Patents (2002, pp. 1047-1071, vol. 12, No. 7).
Southan, G. J., et. al., Poly(ADP-Ribose) Polymerase Inhibitors, Current Medicinal Chemistry (2003, pp. 321-340, vol. 10).
Kuzuya, M., et. al., Reactions of 1-Unsubstituted Tautomeric 2-Pyridones with Benzyne, Chem. Pharm. Bull (1985, pp. 2313-2322, vol. 33, No. 6).
Kuzuya, M., et. al., The Structure-Reactivity-Chemoselectivity Relationship on the Reactions of 1-Unsubstituted Tautomeric 2-Pyridones with Benzyne, The Chemical Society of Japan (1985, pp. 1149-1155, vol. 58).
Marsili, I.A., Conversion of indones to quinoline and isoquinoline derivatives, Annali di Chimica (Rome, Italy), 1962, vol. 52, pp. 3-16.
Wei, L. et al, Palladium-catalyzed coupling of aryl iodides with 2-alkynylbenzonitriles, Tetrahedrom Letters, 2000, vol. 42, No. 8, pp. 1215-1218.
Qian, X. et al, Syntheses and bioactivities of new trifluoromethylpyridine derivatives, Gaodeng Xuexiao Huaxue Xuebao, 1994, vol. 15, No. 2, pp. 224-226 together with English language abstract.
Notification of Reasons for Refusal dated Feb. 8, 2011 for Japanese Patent Application No. 2007-506471 together with English language translation.

* cited by examiner

*Primary Examiner* — Patricia Morris
(74) *Attorney, Agent, or Firm* — Scully, Scott, Murphy & Presser, P.C.

(57) ABSTRACT

The present invention relates to a series of 2,3,5-substituted pyridone derivatives of formula I:

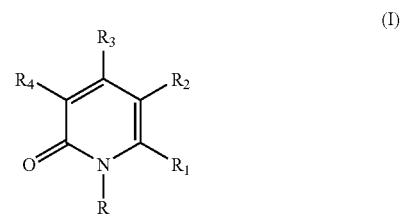

(I)

wherein R, $R_1$, $R_2$, $R_3$ and $R_4$ are as defined herein. This invention also relates to methods of making these compounds. The compounds of this invention are inhibitors of poly(adenosine 5'-diphosphate ribose) polymerase (PARP) and are therefore useful as pharmaceutical agents, especially in the treatment and/or prevention of a variety of diseases, including diseases associated with the central nervous system and cardiovascular disorders.

6 Claims, No Drawings

SUBSTITUTED PYRIDONES AS INHIBITORS OF POLY(ADP-RIBOSE) POLYMERASE (PARP)

CROSS REFERENCE TO RELATED APPLICATIONS

This application is a continuation of International application No. PCT/US2005/010,517, filed Mar. 29, 2005, which claims the benefit of U.S. Provisional Application No. 60/557,459, filed Mar. 30, 2004, both of which are incorporated herein by reference in their entirety;

BACKGROUND OF THE INVENTION

1. Field of the Invention

The present invention relates to a series of substituted pyridone compounds. More specifically, the present invention relates to a series of 2,3,5-substituted pyridone derivatives. This invention also relates to methods of making these compounds. The compounds of this invention are inhibitors of poly(adenosine 5'-diphosphate ribose) polymerase (PARP) and are, therefore, useful as pharmaceutical agents, especially in the treatment and/or prevention of a variety of diseases including diseases associated with the central nervous system and cardiovascular disorders.

2. Description of the Prior Art

Poly(adenosine 5'-diphosphate ribose) polymerase [poly (ADP-ribose) polymerase, PARP, EC 2.4.2.30] also known as poly(ADP-ribose) synthetase (PARS) is a chromatin-bound nuclear enzyme of eukaryotic cells, present at about $2 \times 10^5$ molecules/nucleus. The high degree of evolutionary conservation of PARP in multicellular organisms can be taken as an indication of the physiological importance of poly(ADP-ribosyl)ation. Activated by DNA strand breaks, PARP transfers ADP-ribose units from $NAD^+$ to nuclear proteins including histones and PARP itself. This reaction generates poly(ADP) ribose and nicotinamide, with the latter being a negative feedback inhibitor of PARP. The role of $NAD^+$ in this sequence is distinct from its role as a redox cofactor in other enzymatic processes. The poly(ADP-ribose) thus formed typically contains on the order of 200 ribose units having linear and branched connections with one branch approximately every 25 units of ADP-ribose. The links are by $\alpha$-(1"-2')ribosyl-glycosic bonds. Because of the negative charges on the ADP-ribose polymers, poly(ADP-ribosylated)proteins lose their affinity for DNA and are, therefore, inactivated. Poly(ADP-ribosyl)ation is an immediate, covalent, but transient post-translational modification. Poly(ADP-ribose) is in a dynamic state, its rapid synthesis being followed by degradation that is catalyzed by the enzyme poly(ADP) glycohydrolase (PARG). Thus, PARP and other modified proteins are returned to their native state. For reviews on PARP see: Liadet. L., "Poly(adenosine 5'-diphosphate) ribose polymerase activation as a cause of metabolic dysfunction in critical illness"; Current Opinions Clin. Nutrition Metabolic Care, 5, 175-184 (2002). Burkle, A., "Physiology and pathophysiology of poly(ADP-ribosyl)ation"; BioEssays, 23, 795-806 (2001). Hageman, G. J. and Stierum, R. H., "Niacin, Poly (ADP-ribose) polymerse-1 and genomic stability"; Mutation Res., 475, 45-56 (2001). Smith, S., "The world according to PARP"; Trends Biochem Sci., 26, 174-179 (2001). Tong, W.-M. et al., Poly(ADP-ribose) polymerase: a guardian angel protecting the genome and suppressing tumorigenisis"; Biochim. Biophys. Acta, 1552, 27-37 (2001).

In cerebral ischemia, calcium influx into neurons causes the activation of nitric oxide synthase, leading to production of nitric oxide and subsequently the reactive radical peroxynitrite. Peroxynitrite causes extensive damage to DNA and results in uncontrolled activation of PARP. Cellular NAD and ATP are quickly used up and the cell dies a necrotic death due to loss of the source of cellular energy. DNA is similarly damaged by peroxynitrite in myocardial ischemia and in inflammation.

Several studies with PARP –/– animals and with a variety of inhibitors support the role of PARP in the pathophysiology of a number of disease models. In a stroke model, for example, the infarct size in PARP-deficient animals is 80% smaller compared to control PARP +/+ animals. See, for example, Eliasson, M. J. L. et al., "Poly(ADP-ribose)polymerase gene disruption renders mice resistant to cerebral ischemia"; Nature Med., 3, 1089 (1997). In addition, many studies using various PARP inhibitors (e.g. 3-aminobenzamide, GPI 6150, PJ-34 and nicotinamide) have shown reduction in stroke-induced infarction volume and reduced behavioral deficits in post-stroke treatment paradigms. See, generally, Takahashi, K. et al., "Post-treatment with an inhibitor of poly(ADP-ribose) polymerase attenuates cerebral damage in focal ischemia"; Brain Res., 829, 46, (1999). Mokudai, T. et al., "Delayed treatment with nicotinamide (vitamin B3) improves neurological outcome and reduces infarct volume after transient focal ischemia in Wistar rats"; Stroke, 31, 1679 (2000). Abdelkarim, G. E. et al., "Protective effects of PJ34, a novel, potent inhibitor of poly(ADP ribose) polymerase (PARP) in vitro and in vivo models of stroke"; Int. J. Mol. Med., 7, 255 (2000). Ding, Y. et al., "Long-term neuroprotective effect of inhibiting poly(ADP-ribose) polymerase in rats with middle cerebral artery occlusion using a behavioral assessment"; Brain Res., 915, 210 (2001).

Other disease models in which the role of PARP has been established by using inhibitors or the knockout are streptozocin-induced diabetes (see, Mabley, J. G. et al., "Inhibition of poly(ADP-ribose) synthetase by gene disruption or inhibition with 5-iodo-6-amino-1,2-benzopyrone protects mice from multiple-low-dose-streptozotocin-induced diabetes"; Br. J. Pharmacol., 133, 909-919 (2001); Gale, E. A. et al., "Molecular mechanisms of beta-cell destruction in IDDM: the role of nicotinamide"; Horm. Res., 45, 39-43 (1996); and Heller, B. et al., "Inactivation of the poly(ADP-ribose) polymerase gene affects oxygen radical and nitric oxide toxicity in islet cells"; J. Biol. Chem., 270, 11176-11180 (1995).

PARP is also implicated in diabetic cardiomyopathy, see, Pacher, P. et al., "The role of poly(ADP-ribose) polymerase activation in the development of myocardial and endothelial dysfunction in diabetes"; Diabetes, 51, 514-521 (2002); and in head trauma, see, LaPlaca, M. C. et al., "Pharmacological inhibition of poly(ADP-ribose) polymerase is neuroprotective following traumatic brain injury in rats"; J. Neurotrauma, 18, 369-376 (2001). Also see, Verma, A., "Opportunities for neuroprotection in traumatic brain injury"; J. Head Trauma Rehabil., 15, 1149-1161 (2000).

Further diseases involving PARP include myocardial ischemia, see generally, Pieper, A. A. et al., "Myocardial postischemic injury is reduced by poly(ADP-ribose) polymerase-1 gene disruption"; Mol. Med., 6, 271-282 (2000). Also see, Grupp, I. L. et al., "Protection against hypoxia reoxygenation in the absence of poly(ADP-ribose) synthetase in isolated working hearts"; J. Mol. Cell. Cardio., 31, 297-303 (1999).

Additional diseases include experimental allergic encephalomyelitis (EAE), see for example, Scott, G. S. et al., "Role of poly(ADP-ribose) synthetase activation in the development of experimental allergic encephalomyelitis"; J. Neuroimmunology, 117, 78-86 (2001).

It has also been reported that cancer may be effectively treated with a PARP inhibitor combined with a chemotherapeutic agent or radiation therapy, see for example, Martin, N. M., "DNA repair inhibition and cancer therapy"; J. Photochem. Photobiol. B, 63, 162-170 (2001). Finally, aging related diseases also have been implicated due to PARP, see Von Zglinicki, T. et al., "Stress, DNA damage and aging—an integrative approach"; Exp. Geront., 36, 1049-1062 (2001). Also see, Rosenthal, D. S. et al., "Poly(ADP-ribose) polymerase and aging"; in "The role of DNA damage and repair in aging", Gilchrist, B. A. and Bohr, V. A., eds., Elsevier Science B. V. (2001), pp 113-133.

It is known from literature (see for example Cristina Cosi, Expert Opin. Ther. Patents, 2002, 12, 1047-1071; Southan et al., Current Medicinal Chemistry, 2003, 10, 321-340) that a few different classes of chemical compounds can be employed as PARP-inhibitors, such as derivatives of indoles, benzimidazoles, isoquinolinones or quinazolinones. It is of interest to note that most of the known PARP-inhibitors are derivatives of a bi- or polycyclic backbone.

Pyridone derivatives are known to have a potential for being used as pharmaceuticals, but none of these derivatives so far have been reported to feature any activity on the PARP enzyme. Even more importantly, the pyridone derivatives described in the literature differ significantly from those of the present invention.

For example, U.S. Pat. No. 4,699,914 discloses pyridone derivatives, which can be employed for the treatment of congestive heart failure in a patient. They differ from the compounds of the present invention in that the substitution at position 5 of the pyridone ring requires a phenylene or thienylene moiety, which in turn have to be substituted with imidazol-1-yl. In contrast, the substituent Ar of the pyridone derivatives of the present invention involve aryl, aryloyl or heteroaryl, including thienyl or phenyl. However, said aryl may not be substituted further with any other heteroaromatic residue. Instead, the pyridones of the present invention require a substitution of the Ar with a linker group Y.

U.S. Pat. No. 4,431,651 relates to 3,4-dihydro-5-(pyridinyl or phenyl)-2(1H)-pyridinones, which are used as cardiotonics. As disclosed in detail below, the pyridones of the present invention are structurally different from these compounds.

All of the references described herein are incorporated herein by reference in their entirety.

Since diseases such as myocardial infarction, which can be treated by the inhibition of PARP, are a very serious risk for the health of humans and other mammals, there is a significant demand for new pharmaceuticals having a beneficial therapeutic profile for the treatment of such diseases. Accordingly, there exists a strong need to provide further compounds having an inhibitory effect on PARP.

Therefore, it is an object of this invention to provide a series of substituted pyridone derivatives that are potent, selective inhibitors of PARP.

It is also an object of this invention to provide processes for the preparation of the substituted pyridone derivatives as disclosed herein.

Other objects and further scope of the applicability of the present invention will become apparent from the detailed description that follows.

SUMMARY OF THE INVENTION

Thus, in accordance with the practice of this invention there is provided a series of compounds, including enantiomers, stereoisomers, and tautomers of said compounds and pharmaceutically acceptable salts, solvates or derivatives thereof, with said compounds having the general structure shown in formula I:

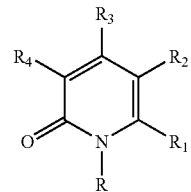

wherein
R is hydrogen or $C_{1-6}$alkyl;
$R_1$ is $C_{1-4}$alkyl, $C_{1-4}$alkenyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, wherein said alkyl or alkenyl is optionally substituted with one or more hydroxy and/or chlorine;
$R_2$ is Ar—Y, wherein
  Ar is substituted or unsubstituted aryl, aryloyl or heteroaryl wherein said substituents are selected from the group consisting of $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, —$NO_2$, —$CH_2NH_2$, —$NH_2$, —NH($C_{1-4}$alkyl), —N($C_{1-4}$alkyl)$_2$, —CN, —C(O)$R_{11}$, —NHC(O)($C_{1-4}$alkyl), —$SO_2Cl$, —$SO_2$($C_{1-4}$alkyl), halogen and hydroxy; and
  Y is hydrogen, —$SO_2NR_5R_6$, —$(CH_2)_nNR_7R_8$, —CH=N—$OR_9$, —C(O)$NR_7R_8$, —C(O)$R_9$, —CH(OH)$R_9$, —$(CH_2)_n$NHC(O)$R_9$, —NHC(O)$R_9$, —$NHSO_2R_9$ and —$(CH_2)_n$NHSO$_2R_9$;
$R_3$ is hydrogen, $C_{1-4}$alkyl, $C_{1-4}$alkenyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;
$R_4$ is $C_{1-6}$alkyl, $C_{1-6}$alkenyl, $C_{3-8}$cycloalkyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1; or
$R_3$ and $R_4$ taken together with the carbon atoms to which they are attached form a $C_{4-8}$cycloalkyl ring or a benzene ring;
$R_5$, $R_6$, $R_7$ and $R_8$ are the same or different and independently of each other selected from the group consisting of hydrogen, unsubstituted and at least monosubstituted $C_{1-10}$alkyl, $C_{3-8}$cycloalkyl, $C_{1-4}$alkoxy-$C_{1-6}$alkyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, $C_{1-6}$alkenyl, $C_{1-6}$alkynyl, aryl, heteroaryl and heterocycle;
  wherein said substituents are selected from the group consisting of: aryl, heteroaryl, heterocycle, —O-aryl, fluorine, chlorine, bromine, —$CF_3$, —$OCF_3$, —$NO_2$, —CN, —C(O)$R_{11}$, —NHC(O)($C_{1-3}$alkyl), —$NH_2$, hydroxy, $C_{1-6}$alkyl, $C_{1-3}$alkoxy, —NH($C_{1-3}$alkyl), —N($C_{1-3}$alkyl)$_2$, —SO$_2$NH$_2$, —SO$_2$($C_{1-3}$alkyl) and —NH—SO$_2$($C_1$-$C_3$-alkyl); and aryl, heterocycle and heteroaryl may optionally be at least monosubstituted with fluorine, chlorine, bromine, oxo, —CF$_3$, —OCF$_3$, —NO$_2$, —CN, heteroaryl, —NHC(O)($C_{1-3}$alkyl), —COOH, hydroxy, $C_{1-3}$alkyl, $C_{1-3}$alkoxy, —SO$_2$NH$_2$, —SO$_2$NH($C_{1-3}$alkyl), —SO$_2$N($C_{1-3}$alkyl)$_2$, —C(O)NH$_2$, —C(O)NH($C_{1-3}$alkyl), —C(O)N($C_{1-3}$alkyl)$_2$, —SO$_2$($C_{1-3}$alkyl), —NH$_2$, —NH($C_{1-3}$alkyl) or —N($C_{1-3}$alkyl)$_2$; or $R_5$ and $R_6$ taken together with the nitrogen atom to which they are attached form an unsubstituted or at least monosubstituted heterocycle; or $R_7$ and $R_8$ taken together with the nitrogen atom to which they are attached form an unsubstituted or at least monosubstituted heterocycle;

wherein said substituents are selected from: aryl, heteroaryl, heterocycle, oxo, fluorine, chlorine, bromine, —CF$_3$, —OCF$_3$, —NO$_2$, —CN, —C(O)$R_{11}$, —NHC(O)($C_{1-3}$alkyl), —NH$_2$, hydroxy, $C_{1-3}$alkyl, $C_{1-3}$alkoxy, —NH($C_{1-3}$alkyl), —N($C_{1-3}$alkyl)$_2$, —SO$_2$NH$_2$, —SO$_2$($C_{1-3}$alkyl) and —NH—SO$_2$($C_{1-3}$alkyl), and aryl, heterocycle and heteroaryl may optionally be at least monosubstituted with fluorine, chlorine, bromine, hydroxy, $C_{1-3}$alkyl or $C_{1-3}$alkoxy;

$R_9$ is hydrogen, unsubstituted or at least monosubstituted $C_{1-6}$alkyl, phenyl, heteroaryl or heterocycle;

wherein said substituents are selected from the group consisting of: fluorine, chlorine, bromine, aryl, heterocycle, heteroaryl, —CF$_3$, —OCF$_3$, —NO$_2$, —CN, —C(O)$R_{11}$, —NHC(O)($C_{1-3}$alkyl), —NH$_2$, hydroxy, $C_{1-3}$alkyl, $C_{1-3}$alkoxy, —NH($C_{1-3}$alkyl), —N($C_{1-3}$alkyl)$_2$, —SO$_2$NH$_2$, —SO$_2$($C_{1-3}$alkyl) and —NH—SO$_2$($C_{1-3}$alkyl); and aryl, heterocycle and heteroaryl may optionally be at least monosubstituted with fluorine, chlorine, bromine, hydroxy, $C_{1-3}$alkyl or $C_{1-3}$alkoxy;

$R_{11}$ is hydroxy, $C_{1-3}$alkoxy, —O-phenyl, —NH$_2$, —NH($C_{1-3}$alkyl), —N($C_{1-3}$alkyl)$_2$ or phenyl;

n is an integer from 1 to 4; and wherein heteroaryl is a 5 to 10-membered, aromatic, mono- or bicyclic heterocycle containing one or more heteroatoms selected from the group consisting of N, O and S;

aryl is a 6 to 10-membered, aromatic mono- or bicyclic ring; and heterocycle is a 3 to 10-membered, non-aromatic, mono- or bicyclic heterocycle containing one or more heteroatoms selected from the group consisting of N, O and S; and with the proviso that:

when Y and R are hydrogen, $R_3$ and $R_4$ are either hydrogen or methyl and $R_1$ is methyl, Ar is not 4-methoxyphenyl or 4-pyridinyl; and when Y and R are hydrogen, $R_3$ and $R_4$ taken together with the carbon atoms to which they are attached form a benzene ring and $R_1$ is methyl, Ar is not phenyl.

In another aspect of this invention, there is provided a method of treating a disease or a condition caused by the effects of poly(adenosine 5'-diphosphate ribose) polymerase (PARP) in a patient, comprising administering to said patient a therapeutically effective amount of a compound including enantiomers, stereoisomers, and tautomers of said compound and pharmaceutically acceptable salts, solvates or derivatives thereof, with said compound having the general structure shown in formula I, as described herein.

In a further aspect of this invention there is also provided a method of obtaining a neuronal effect in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula I, as described herein.

In an additional aspect of this invention there is also provided a method of treating a cardiovascular disorder in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula I, as disclosed herein.

These and various other aspects of this invention are apparent from the detailed description that follows.

DETAILED DESCRIPTION OF THE INVENTION

The terms as used herein have the following meanings:

As used herein, the expression "$C_{1-6}$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-4}$alkoxy", "$C_{1-4}$thioalkyl", "$C_{1-4}$alkoxy$C_{1-4}$alkyl", "hydroxy$C_{1-4}$alkyl", "$C_{1-4}$alkylcarbonyl", "$C_{1-4}$alkoxycarbonyl$C_{1-4}$alkyl", "$C_{1-4}$alkoxycarbonyl", "amino$C_{1-4}$alkyl", "$C_{1-4}$alkylamino", "$C_{1-4}$alkylcarbamoyl$C_{1-6}$alkyl", "$C_{1-4}$dialkylcarbamoyl$C_{1-4}$alkyl", "mono- or di-$C_{1-4}$alkylamino$C_{1-4}$alkyl", "amino$C_{1-4}$alkylcarbonyl", "diphenyl$C_{1-4}$alkyl", "phenyl$C_{1-4}$alkyl", "phenylcarboyl$C_{1-4}$alkyl" and "phenoxy$C_{1-4}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$alkynyl" includes ethynyl and propynyl, and straight-chained or branched butynyl, pentynyl and hexynyl groups.

As used herein the expression "$C_{1-4}$acyl" shall have the same meaning as "$C_{1-4}$alkanoyl", which also can be represented structurally as "R—CO—," where R is a $C_{1-3}$alkyl as defined herein. Additionally, "$C_{1-3}$alkylcarbonyl" shall mean same as $C_{1-4}$acyl. Specifically, "$C_{1-4}$acyl" shall mean formyl, acetyl or ethanoyl, propanoyl, n-butanoyl, etc. Derived expressions such as "$C_{1-4}$acyloxy" and "$C_{1-4}$acyloxyalkyl" are to be construed accordingly.

As used herein, the expression "$C_{1-6}$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$perfluoroalkoxy", is to be construed accordingly.

As used herein, the expression "aryl" means substituted or unsubstituted 6 to 10-membered, aromatic mono- or bicyclic ring compounds. Specific examples of aryl include without any limitation phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, such as "$C_{6-10}$arylsulfonyl," etc. are to be construed accordingly. Similarly, other derived expressions such as aryloyl means "aryl-CO." Specific examples of aryloyl include without any limitation benzoyl, naphthoyl, o-, m- or p-toluoyl, and the like.

As used herein, the expression "$C_{6-10}arylC_{1-4}alkyl$" means that the $C_{6-10}aryl$ as defined herein is further attached to $C_{1-4}alkyl$ as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Typically, heteroaryl as used herein is a 5 to 10-membered, aromatic, mono- or bicyclic heterocycle containing one or more heteroatoms selected from the group consisting of N, O and S. Representative 5-membered heteroaryl radicals include furanyl, thienyl or thiophenyl, pyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, benzimidazolyl, indazolyl, pyridofuranyl, pyridothienyl, and the like radicals.

As used herein, the expression "heterocycle" includes all of the known reduced or partially reduced heteroatom containing cyclic radicals, generally containing 3 to 10 membered, non-aromatic, mono- or bicyclic heterocycle containing one or more heteroatoms selected from the group consisting of N, O and S. Representative 3-membered heterocycle radicals include aziridinyl, oxiranyl and thiiranyl and the like. Representative 4-membered heterocycle radicals include azetidinyl, oxetanyl, thietanyl, and the like. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, imidazolidinyl, pyrazolidinyl, and the like. Representative 6-membered heterocycle radicals include piperidinyl, piperazinyl, morpholinyl, thiomorpholinyl, and the like. Various other heterocycle radicals include, without limitation, azepanyl, diazepanyl, diazabicyclo[2.2.1]hept-2-yl, and triazocanyl, and the like.

"Halogen" or "halo" means chloro, fluoro, bromo, and iodo.

As used herein, "patient" means a warm blooded animal, such as for example rats, mice, dogs, cats, guinea pigs, and primates such as humans.

As used herein, the expression "pharmaceutically acceptable carrier" means a non-toxic solvent, dispersant, excipient, adjuvant, or other material that is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, benzenesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans or E/Z). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)—(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

In a broad sense, the term "substituted" is contemplated to include all permissible substituents of organic compounds. In a few of the specific embodiments as disclosed herein, the term "substituted" means substituted with one or more substituents as specifically enumerated therein and/or independently selected from the group consisting of $C_{1-6}alkyl$, $C_{2-6}alkenyl$, $C_{1-6}perfluoroalkyl$, phenyl, hydroxy, —$CO_2H$, an ester, an amide, $C_1$-$C_6alkoxy$, $C_1$-$C_6thioalkyl$, $C_1$-$C_6perfluoroalkoxy$, —$NH_2$, Cl, Br, I, F, —NH-lower alkyl, and —N(lower alkyl)$_2$. However, it is to be understood that any of the other suitable substituents known to one skilled in the art can also be used in these embodiments unless otherwise stated.

"Therapeutically effective amount" means an amount of the compound which is effective in treating the named disease, disorder or condition.

The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

The term "ischemia" refers to localized tissue anemia due to obstruction of the inflow of arterial blood. Global ischemia occurs when blood flow to the entire organ, for example, brain, heart or kidney ceases for a period of time. Global ischemia may result from cardiac arrest. Focal ischemia occurs when a portion of the organ is deprived of its normal blood supply. Focal ischemia may result from thromboembolytic occlusion of a blood vessel, traumatic head injury, edema or brain tumor. Even if transient, both global and focal ischemia can cause widespread neuronal damage. Although nerve tissue damage occurs over hours or even days following the onset of ischemia, some permanent nerve tissue damage may develop in the initial minutes following the cessation of blood flow to the brain. Much of this damage has been attributed to glutamate toxicity (no glutamate toxicity in the heart) and to the secondary consequences of tissue reperfusion, such as the release of vasoactive products damaged endothelium and the release of cytotoxic products, such as free radicals and leukotrienes, by the damaged tissue. Ischemia can also occur in the heart in myocardial infarction and other cardiovascular disorders in which the coronary arteries have been obstructed as a result of atherosclerosis, thrombi, or spasm and in the eyes in retinal ischemia.

The term "neural tissue damage resulting from ischemia and reperfusion injury and neurodegenerative diseases" includes neurotoxicity, such as seen in vascular stroke and global and focal ischemia, as well as retinal ischemia.

The term "neurodegenerative diseases" includes Alzheimer's disease, Parkinson's disease, and Huntington's disease.

The term "nervous insult" refers to any damage to nervous tissue and any disability or death resulting therefrom. The cause of nervous insult may be metabolic, toxic, neurotoxic, thermal or chemical, iatrogenic, and includes without limitation, ischemia, hypoxia, cerebrovascular accident, trauma, surgery, pressure, mass effect, hemorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed with a neurodegenerative disease or who are at risk of developing a neurodegenerative disease. The term also encompasses preventing further neurodegeneration in patients who are already suffering from or have symptoms of a neurodegenerative disease.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

In one aspect of this invention, there is provided a compound, including enantiomers, stereoisomers, and tautomers of said compound and pharmaceutically acceptable salts, solvates or derivatives thereof, with said compound having the general structure shown in formula I:

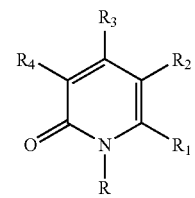

wherein
R is hydrogen or $C_{1-6}$alkyl;
$R_1$ is $C_{1-4}$alkyl, $C_{1-4}$alkenyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, wherein said alkyl or alkenyl is optionally substituted with one or more hydroxy and/or chlorine;
$R_2$ is Ar—Y, wherein
  Ar is substituted or unsubstituted aryl, aryloyl or heteroaryl wherein said substituents are selected from the group consisting of $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, —$NO_2$, —$CH_2NH_2$, —$NH_2$, —NH($C_{1-4}$alkyl), —N($C_{1-4}$alkyl)$_2$, —CN, —C(O)$R_{11}$, —NHC(O)($C_{1-4}$alkyl), —$SO_2Cl$, —$SO_2$($C_{1-4}$alkyl), halogen and hydroxy; and
  Y is hydrogen, —$SO_2NR_5R_6$, —$(CH_2)_nNR_7R_8$, —CH=N—$OR_9$, —C(O)$NR_7R_8$, —C(O)$R_9$, —CH(OH)$R_9$, —$(CH_2)_n$NHC(O)$R_9$, —NHC(O)$R_9$, —$NHSO_2R_9$ and —$(CH_2)_n$$NHSO_2R_9$;
$R_3$ is hydrogen, $C_{1-4}$alkyl, $C_{1-4}$alkenyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;
$R_4$ is $C_{1-6}$alkyl, $C_{1-6}$alkenyl, $C_{3-8}$cycloalkyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1; or
$R_3$ and $R_4$ taken together with the carbon atoms to which they are attached form a $C_{4-8}$cycloalkyl ring or a benzene ring;
$R_5$, $R_6$, $R_7$ and $R_8$ are the same or different and, independently of each other, selected from the group consisting of hydrogen, unsubstituted and at least monosubstituted $C_{1-10}$alkyl, $C_{3-8}$cycloalkyl, $C_{1-4}$alkoxy-$C_{1-6}$alkyl, fluoroalkyl or fluoroalkoxy of the formula $C_nH_xF_y$ or $OC_nH_xF_y$ respectively wherein n is an integer from 1 to 4, x is an integer from 0 to 8, y is an integer from 1 to 9 and sum of x and y is 2n+1, $C_{1-6}$alkenyl, $C_{1-6}$alkynyl, aryl, heteroaryl and heterocycle;

wherein said substituents are selected from the group consisting of: aryl, heteroaryl, heterocycle, —O-aryl, fluorine, chlorine, bromine, —$CF_3$, —$OCF_3$, —$NO_2$, —CN, —$C(O)R_{11}$, —$NHC(O)(C_{1-3}alkyl)$, —$NH_2$, hydroxy, $C_{1-6}alkyl$, $C_{1-3}alkoxy$, —$NH(C_{1-3}alkyl)$, —$N(C_{1-3}alkyl)_2$, —$SO_2NH_2$, —$SO_2(C_{1-3}alkyl)$ and —$NH—SO_2(C_1-C_3-alkyl)$; and aryl, heterocycle and heteroaryl may optionally be at least monosubstituted with fluorine, chlorine, bromine, oxo, —$CF_3$, —$OCF_3$, —$NO_2$, —CN, heteroaryl, —$NHC(O)(C_{1-3}alkyl)$, —COOH, hydroxy, $C_{1-3}alkyl$, $C_{1-3}alkoxy$, —$SO_2NH_2$, —$SO_2NH(C_{1-3}alkyl)$, —$SO_2N(C_{1-3}alkyl)_2$, —$C(O)NH_2$, —$C(O)NH(C_{1-3}alkyl)$, —$C(O)N(C_{1-3}alkyl)_2$, —$SO_2(C_{1-3}alkyl)$, —$NH_2$, —$NH(C_{1-3}alkyl)$ or —$N(C_{1-3}alkyl)_2$; or $R_5$ and $R_6$ taken together with the nitrogen atom to which they are attached form an unsubstituted or at least monosubstituted heterocycle; or $R_7$ and $R_8$ taken together with the nitrogen atom to which they are attached form an unsubstituted or at least monosubstituted heterocycle;

wherein said substituents are selected from: aryl, heteroaryl, heterocycle, oxo, fluorine, chlorine, bromine, —$CF_3$, —$OCF_3$, —$NO_2$, —CN, —$C(O)R_{11}$, —$NHC(O)(C_{1-3}alkyl)$, —$NH_2$, hydroxy, $C_{1-3}alkyl$, $C_{1-3}alkoxy$, —$NH(C_{1-3}alkyl)$, —$N(C_{1-3}alkyl)_2$, —$SO_2NH_2$, —$SO_2(C_{1-3}alkyl)$ and —$NH—SO_2(C_{1-3}alkyl)$, and aryl, heterocycle and heteroaryl may optionally be at least monosubstituted with fluorine, chlorine, bromine, hydroxy, $C_{1-3}alkyl$ or $C_{1-3}alkoxy$;

$R_9$ is hydrogen, unsubstituted or at least monosubstituted $C_{1-6}alkyl$, phenyl, heteroaryl or heterocycle;

wherein said substituents are selected from the group consisting of: fluorine, chlorine, bromine, aryl, heterocycle, heteroaryl, —$CF_3$, —$OCF_3$, —$NO_2$, —CN, —$C(O)R_{11}$, —$NHC(O)(C_{1-3}alkyl)$, —$NH_2$, hydroxy, $C_{1-3}alkyl$, $C_{1-3}alkoxy$, —$NH(C_{1-3}alkyl)$, —$N(C_{1-3}alkyl)_2$, —$SO_2NH_2$, —$SO_2(C_{1-3}alkyl)$ and —$NH—SO_2(C_{1-3}alkyl)$; and aryl, heterocycle and heteroaryl may optionally be at least monosubstituted with fluorine, chlorine, bromine, hydroxy, $C_{1-3}alkyl$ or $C_{1-3}alkoxy$;

$R_{11}$ is hydroxy, $C_{1-3}alkoxy$, —O-phenyl, —$NH_2$, —$NH(C_{1-3}alkyl)$, —$N(C_{1-3}alkyl)_2$ or phenyl;

n is an integer from 1 to 4; and wherein heteroaryl is a 5 to 10-membered, aromatic, mono- or bicyclic heterocycle containing one or more heteroatoms selected from the group consisting of N, O and S;

aryl is a 6 to 10-membered, aromatic mono- or bicyclic ring; and heterocycle is a 3 to 10-membered, non-aromatic, mono- or bicyclic heterocycle containing one or more heteroatoms selected from the group consisting of N, O and S; and with the proviso that:

when Y and R are hydrogen, $R_3$ and $R_4$ are either hydrogen or methyl and $R_1$ is methyl, Ar is not 4-methoxyphenyl or 4-pyridinyl; and when Y and R are hydrogen, $R_3$ and $R_4$ taken together with the carbon atoms to which they are attached form a benzene ring and $R_1$ is methyl, Ar is not phenyl.

In one embodiment of this invention, $R_2$ is Ar—Y, wherein Ar is substituted or unsubstituted aryl or aryloyl and Y is hydrogen. Specifically, Ar is substituted or unsubstituted aryl. Various known substituted or unsubstituted aryls as enumerated herein can be employed, and more specifically in one embodiment Ar is substituted phenyl. As further noted hereinabove, any of the permissible substituted phenyl can be employed in this embodiment. Further, the compounds of this embodiment have the following specific substituents: R is hydrogen, $R_1$ is hydrogen, methyl or ethyl, $R_3$ is hydrogen or methyl and $R_4$ is methyl, ethyl, propyl, isopropyl, isopropenyl or cyclopropyl.

Specific compounds that are within the scope of this embodiment include, without any limitation, the following:

3-(5-ethyl-2-methyl-6-oxo-1,6-dihydropyridin-3-yl)benzonitrile;

3-(2,5-dimethyl-6-oxo-1,6-dihydropyridin-3-yl)benzonitrile;

3-(5-ethyl-2,4-dimethyl-6-oxo-1,6-dihydropyridin-3-yl) benzonitrile;

5-(5-ethyl-2-methyl-6-oxo-1,6-dihydropyridin-3-yl)-2-(morpholin-4-yl)methylbenzonitrile;

3-(5-n-propyl-2-methyl-6-oxo-1,6-dihydropyridin-3-yl)benzonitrile;

3-(5-iso-propyl-2-methyl-6-oxo-1,6-dihydropyridin-3-yl) benzonitrile;

3-(5-isopropenyl-2-methyl-6-oxo-1,6-dihydro-pyridin-3-yl)-benzonitrile;

3-(5-cyclopropyl-2-methyl-6-oxo-1,6-dihydro-pyridin-3-yl)-benzonitrile;

3-ethyl-6-methyl-5-phenyl-1H-pyridin-2-one;

3-ethyl-6-methyl-5-(4-morpholin-4-ylmethyl-phenyl)-1H-pyridin-2-one hydrochloride;

3-(5-ethyl-6-oxo-1,6-dihydro-pyridin-3-yl)-benzonitrile; and 3-(2,5-diethyl-6-oxo-1,6-dihydro-pyridin-3-yl)-benzonitrile.

In another aspect of this embodiment, the compounds have the following specific substituents: R is hydrogen, $R_1$ is methyl, and $R_3$ and $R_4$ taken together form either cyclohexyl ring or benzene ring.

Specific examples of compounds within the scope of this embodiment, without any limitation, may be enumerated as follows:

3-(3-methyl-1-oxo-1,2,5,6,7,8-hexahydroisoquinolin-4-yl) benzonitrile; and 3-(3-methyl-1-oxo-1,2-dihydroisoquinolin-4-yl)benzonitrile.

In yet another embodiment, the compounds of this invention feature Ar as substituted benzoyl. The compounds of this embodiment further have the following specific substituents: R is hydrogen, $R_1$ is methyl, $R_3$ is hydrogen and $R_4$ is ethyl. A specific example of a compound of this embodiment includes, without any limitation, 3-[(5-ethyl-2-methyl-6-oxo-1,6-dihydropyridine)-3-carbonyl]benzonitrile.

In yet another embodiment, the compounds of this invention have $R_2$ as Ar—Y, wherein Ar is substituted or unsubstituted heteroaryl and Y is hydrogen. Various heteroaryl as described herein may be employed in this embodiment. Also, as noted herein, all permissible substituents on the heteroaryl can be employed in this embodiment. Specifically, the heteroaryl is selected from the group consisting of 1,2,3,-triazolyl, 1,3,4-triazolyl, 2H-1,2,4-triazolyl, 2-methyl-1,2,4-triazolyl, 2,5-dimethyl-1,2,4-triazolyl, 1,2,4-oxadiazolyl, 1,3,4-oxadiazolyl, 5-methyl-1,3,4-oxadiazolyl, 3-methyl-1,2,4-oxadiazolyl, 5-methyl-1,2,4-oxadiazolyl, pyrazolyl, imidazolyl, pyrrolyl, furanyl, thiophenyl, and pyridinyl. Further, the compounds of formula I of this embodiment have the following substituents: R is hydrogen, $R_1$ is methyl, $R_3$ is hydrogen and $R_4$ is ethyl.

Specific compounds that are within the scope of this embodiment include, without any limitation, the following:

3-ethyl-6-methyl-5-(1,2,4-triazol-1-yl)-1H-pyridin-2-one hydrochloride;
3-ethyl-6-methyl-5-(1,2,3-triazol-2-yl)-1H-pyridin-2-one;
3-ethyl-6-methyl-5-(1,2,3-triazol-1-yl)-1H-pyridin-2-one;
3-ethyl-6-methyl-5-(2H-1,2,4-triazol-3-yl)-1H-pyridin-2-one;
3-ethyl-6-methyl-5-(2-methyl-2H-1,2,4-triazol-3-yl)-1H-pyridin-2-one;
3-ethyl-6-methyl-5-(5-methyl-2H-1,2,4-triazol-3-yl)-1H-pyridin-2-one;
5-(2,5-dimethyl-2H-1,2,4-triazol-3-yl)-3-ethyl-6-methyl-1H-pyridin-2-one;
3-ethyl-2-methoxy-6-methyl-5-(1,3,4-oxadiazol-2-yl)pyridine;
3-ethyl-6-methyl-5-(1,2,4-oxadiazol-5-yl)-1H-pyridin-2-one;
3-ethyl-6-methyl-5-(1,2,4-oxadiazol-3-yl)-1H-pyridin-2-one;
3-ethyl-6-methyl-5-(5-methyl-1,3,4-oxadiazol-2-yl)-1H-pyridin-2-one;
3-ethyl-6-methyl-5-(5-methyl-1,2,4-oxadiazol-3-yl)-1H-pyridin-2-one;
3-ethyl-6-methyl-5-(3-methyl-1,2,4-oxadiazol-5-yl)-1H-pyridin-2-one;
3-ethyl-6-methyl-5-(pyrazol-1-yl)-1H-pyridin-2-one hydrochloride;
3-ethyl-5-(imidazol-1-yl)-6-methyl-1H-pyridin-2-one hydrochloride;
3-ethyl-6-methyl-5-(pyrrol-1-yl)-1H-pyridin-2-one hydrochloride;
5-(5-aminomethyl-[1,3,4]oxadiazol-2-yl)-3-ethyl-6-methyl-1H-pyridin-2-one;
3-ethyl-6-methyl-5-[5-cyanofuran-2-yl]-1H-pyridin-2-one;
3-ethyl-6-methyl-5-[5-cyanothiophen-2-yl]-1H-pyridin-2-one;
3-ethyl-6-methyl-5-[5-nitrothiophen-2-yl]-1H-pyridin-2-one; and
5-ethyl-2-methyl-1H-[3,3']bipyridinyl-6-one.

In a further embodiment of this invention there is also disclosed compounds of formula I wherein Ar is substituted or unsubstituted thienyl, phenyl or pyridinyl. Particularly, in one aspect of this embodiment of the invention the compounds of formula I contain as Ar substituted or unsubstituted thienyl which is substituted with $SO_2NR_5R_6$ as Y and wherein:

$R_5$ and $R_6$ are the same or different and independently of each other selected from the group consisting of hydrogen, $C_{1-10}$alkyl, $C_{3-8}$cycloalkyl, $C_{1-4}$alkoxy-$C_{1-6}$alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, amino-$C_{1-6}$alkyl, $C_{1-6}$alkyl-aminio-$C_{1-6}$alkyl, $C_{1-6}$dialkyl-amino-$C_{1-6}$alkyl, phenyl-$C_{0-4}$alkyl, phenoxy-$C_{1-4}$alkyl, phenyl-amino-$C_{1-4}$alkyl, pyridinyl-$C_{0-4}$alkyl, pyrazinyl-$C_{0-4}$alkyl, furanyl-$C_{0-4}$alkyl, tetrahydrofuranyl-$C_{0-4}$alkyl, pyrrolidinyl-$C_{0-4}$alkyl, morpholinyl-$C_{1-4}$alkyl, imidazolyl-$C_{0-4}$alkyl, indolyl-$C_{0-6}$alkyl, benzimidazolyl-$C_{0-4}$alkyl, piperidinyl-$C_{0-4}$alkyl, piperazinyl-$C_{0-4}$alkyl, pyrrolidinyl-$C_{0-4}$alkyl, pyrazinyl-$C_{0-4}$alkyl, dioxolanyl-$C_{0-4}$alkyl and benzodioxolanyl-$C_{0-4}$alkyl; or $R_5$ and $R_6$ taken together with the nitrogen atom to which they are attached form a $C_{3-8}$heterocycle ring optionally containing one or more heteroatoms selected from N, O or S.

In this embodiment, where appropriate any of the aforementioned groups are optionally substituted with one or more substituents selected from the group consisting of fluorine, chlorine, bromine, hydroxy, $C_{1-6}$alkyl, $C_{1-6}$alkoxy, hydroxy-$C_{1-6}$alkyl, hydroxy-$C_{1-6}$alkoxy-$C_{1-6}$alkyl, $C_{3-8}$cycloalkyl-$C_{1-4}$alkyl, trifluoromethyl, $C_{1-6}$alkoxycarbonyl, $C_{1-6}$alkylsulfonyl, amino-$C_{1-6}$alkyl, $C_{1-6}$alkyl-aminio-$C_{1-6}$alkyl, $C_{1-6}$dialkyl-amino-$C_{1-6}$alkyl, substituted or unsubstituted phenyl-$C_{0-4}$alkyl, substituted or unsubstituted pyridinyl-$C_{0-4}$alkyl, substituted or unsubstituted pyridinyl-$C_{0-4}$alkyl, substituted or unsubstituted pyrimidinyl-$C_{0-4}$alkyl, substituted or unsubstituted pyrazinyl-$C_{0-4}$alkyl, substituted or unsubstituted pyrrolidonyl-$C_{0-4}$alkyl, substituted or unsubstituted piperidinyl-$C_{0-4}$alkyl, substituted or unsubstituted pyrrolidinyl-$C_{0-4}$alkyl, substituted or unsubstituted imidazolyl-$C_{0-4}$alkyl, substituted or unsubstituted morpholinyl-$C_{0-4}$alkyl, substituted or unsubstituted dioxolanyl-$C_{0-4}$alkyl, substituted or unsubstituted bezodioxolanyl-$C_{0-4}$alkyl, substituted or unsubstituted phenyl-amino-$C_{0-4}$alkyl and substituted or unsubstituted benzoyl.

Further, in this embodiment the compounds of formula I feature the following specific substituents: R is hydrogen, $R_1$ is methyl, $R_3$ is hydrogen and $R_4$ is ethyl. Specific compounds falling within the scope of this embodiment without any limitation are the following:

3-ethyl-6-methyl-5-[5-(4-phenylpiperazine-1-sulfonyl) thiophen-2-yl]-1H-pyridin-2-one;
3-ethyl-5-{5-[4-(4-fluorophenyl)piperazine-1-sulfonyl] thiophen-2-yl}-6-methyl-1H-pyridin-2-one;
5-(5-ethyl-2-methyl-6-oxo-1,6-dihydropyridin-3-yl) thiophene-2-sulfonic acid 4-trifluoromethylbenzylamide;
5-(5-ethyl-2-methyl-6-oxo-1,6-dihydropyridin-3-yl) thiophene-2-sulfonic acid 3,5-difluorobenzylamide;
5-(5-ethyl-2-methyl-6-oxo-1,6-dihydropyridin-3-yl) thiophene-2-sulfonic acid dimethylamide;
5-(5-ethyl-2-methyl-6-oxo-1,6-dihydropyridin-3-yl) thiophene-2-sulfonic acid (3,5-difluorobenzyl)methylamide;
5-(5-ethyl-2-methyl-6-oxo-1,6-dihydro-pyridin-3-yl)-thiophene-2-sulfonic acid [3-(3-hydroxy-pyrrolidin-1-yl)-propyl]-amide hydrochloride;
5-(5-ethyl-2-methyl-6-oxo-1,6-dihydropyridin-3-yl) thiophene-2-sulfonic acid (pyridin-2-yl)methylamide hydrochloride;
5-(5-ethyl-2-methyl-6-oxo-1,6-dihydropyridin-3-yl) thiophene-2-sulfonic acid 2-phenylaminoethylamide hydrochloride;
5-(5-ethyl-2-methyl-6-oxo-1,6-dihydropyridin-3-yl) thiophene-2-sulfonic acid (2-methoxyethyl)amide;
5-(5-ethyl-2-methyl-6-oxo-1,6-dihydropyridin-3-yl) thiophene-2-sulfonic acid (3-dimethylaminopropyl)amide hydrochloride;
5-(5-ethyl-2-methyl-6-oxo-1,6-dihydropyridin-3-yl) thiophene-2-sulfonic acid (5-methylfuran-2-yl)methylamide;
5-(5-ethyl-2-methyl-6-oxo-1,6-dihydropyridin-3-yl) thiophene-2-sulfonic Acid [2-(1-methylpyrrolidin-2-yl) ethyl]amide hydrochloride;
5-(5-ethyl-2-methyl-6-oxo-1,6-dihydropyridin-3-yl) thiophene-2-sulfonic acid (2-hydroxy-2-phenylethyl)methylamide;
5-(5-ethyl-2-methyl-6-oxo-1,6-dihydropyridin-3-yl) thiophene-2-sulfonic acid (2-morpholin-4-yl)ethylamide hydrochloride;
5-(5-ethyl-2-methyl-6-oxo-1,6-dihydropyridin-3-yl) thiophene-2-sulfonic acid (1-benzylpiperidin-4-yl)amide hydrochloride;
5-(5-ethyl-2-methyl-6-oxo-1,6-dihydropyridin-3-yl) thiophene-2-sulfonic acid (2-{1-[5-(5-ethyl-2-methyl-6-oxo-1,6-dihydropyridin-3-yl)thiophene-2-sulfonyl]-1H-imidazol-4-yl}ethyl)amide hydrochloride;

5-(5-ethyl-2-methyl-6-oxo-1,6-dihydropyridin-3-yl) thiophene-2-sulfonic acid (1-tert-butyloxycarbonylpiperidin-4-yl)methylamide;
5-[5-ethyl-2-methyl-6-oxo-(1,6-dihydropyridin-3-yl)] thiophene-2-sulfonic acid (piperidin-4-yl)methylamide hydrochloride;
5-(5-ethyl-2-methyl-6-oxo-1,6-dihydro-pyridin-3-yl)-thiophene-2-sulfonic acid [3-(3,3-difluoro-pyrrolidin-1-yl)-propyl]-amide hydrochloride;
5-(5-ethyl-2-methyl-6-oxo-1,6-dihydropyridin-3-yl) thiophene-2-sulfonic acid 1-(pyridin-2-yl)ethylamide hydrochloride;
3-ethyl-6-methyl-5-{5-[4-(2-piperidin-1-yl)ethylpiperizine-1-sulfonyl]thiophen-2-yl}-1H-pyridin-2-one dihydrochloride;
3-ethyl-6-methyl-5-[5-(4-pyridin-4-yl)methylpiperizine-1-sulfonyl]thiophen-2-yl}-1H-pyridin-2-one dihydrochloride;
5-[5-ethyl-2-methyl-6-oxo-1,6-dihydropyridin-3-yl] thiophene-2-sulfonic acid (3-imidazol-1-yl)propylamide hydrochloride;
3-ethyl-6-methyl-5-{5-[4-(2-pyridin-2-yl)ethylpiperazine-1-sulfonyl]thiophen-2-yl}-1H-pyridin-2-one dihydrochloride;
3-ethyl-6-methyl-5-{5-[4-(2-pyrrolidin-1-yl)ethylpiperazine-1-sulfonyl]thiophen-2-yl}-1H-pyridin-2-one dihydrochloride;
3-ethyl-6-methyl-5-{5-[4-(3-pyrrolidin-1-yl)propylpiperazine-1-sulfonyl]thiophen-2-yl}-1H-pyridin-2-one dihydrochloride;
5-(5-ethyl-2-methyl-6-oxo-1,6-dihydro-pyridin-3-yl)-thiophene-2-sulfonic acid (3-piperidin-1-yl-propyl)-amide hydrochloride;
5-{5-[4-(2-dimethylaminoethyl)piperazine-1-sulfonyl]thiophen-2-yl}-3-ethyl-6-methyl-1H-pyridn-2-one dihydrochloride;
5-(5-ethyl-2-methyl-6-oxo-1,6-dihydropyridin-3-yl) thiophene-2-sulfonic acid 3-(4-methylpiperazin-1-yl)propylamide dihydrochloride;
3-ethyl-6-methyl-5-{5-[(4-pyrrolidin-1-yl)piperidine-1-sulfonyl]thiophen-2-yl}-1H-pyridin-2-one hydrochloride;
3-ethyl-6-methyl-5-{5-[(4-piperidin-1-yl)piperidine-1-sulfonyl]thiophen-2-yl}-1H-pyridin-2-one hydrochloride;
5-[5-ethyl-2-methyl-6-oxo-1,6-dihydropyridin-3-yl] thiophene-2-sulfonic acid [3-(2-oxopyrrolidin-1-yl)propyl]amide;
5-[5-ethyl-2-methyl-6-oxo-1,6-dihydropyridin-3-yl] thiophene-2-sulfonic acid (2-piperidin-1-yl)ethylamide hydrochloride;
3-ethyl-5-{5-[(3-imidazo-1-yl)methylpiperidine-1-sulfonyl]thiophen-2-yl}-6-methyl-1H-pyridin-2-one hydrochloride;
5-(5-ethyl-2-methyl-6-oxo-1,6-dihydropyridin-3-yl) thiophene-2-sulfonic acid (2-dimethylamino-2-pyridin-3-yl)ethylamide dihydrochloride;
5-[5-ethyl-2-methyl-6-oxo-1,6-dihydropyridin-3-yl] thiophene-2-sulfonic acid 2-(morpholin-4-yl)-2-(pyridin-3-yl)ethylamide dihydrochloride;
5-[5-ethyl-2-methyl-6-oxo-1,6-dihydropyridin-3-yl] thiophene-2-sulfonic acid (6-methylpyrazin-2-yl)methylamide hydrochloride;
5-[5-ethyl-2-methyl-6-oxo-1,6-dihydropyridin-3-yl] thiophene-2-sulfonic acid (1-cyclopropylmethylpiperidin-4-yl)amide hydrochloride;
5-(5-ethyl-2-methyl-6-oxo-1,6-dihydropyridin-3-yl) thiophene-2-sulfonic acid (1-cyclohexylmethylpiperidin-4-yl)amide hydrochloride;
5-[5-ethyl-2-methyl-6-oxo-1,6-dihydropyridin-3-yl]-thiophene-2-sulfonic acid [1-(4-chlorobenzyl)piperidin-4-yl]amide hydrochloride;
5-[5-ethyl-2-methyl-6-oxo-1,6-dihydropyridin-3-yl] thiophene-2-sulfonic acid methyl-(1-methylpiperidin-4-yl)amide hydrochloride;
5-(5-ethyl-2-methyl-6-oxo-1,6-dihydropyridin-3-yl) thiophene-2-sulfonic acid [(6-dimethylaminopyridin-3-yl)methyl]amide hydrochloride;
3-ethyl-5-[5-(4-imidazol-1-yl)piperidine-1-sulfonyl) thiophen-2-yl]-6-methyl-1H-pyridin-2-one hydrochloride;
5-[5-ethyl-2-methyl-6-oxo-1,6-dihydropyridin-3-yl] thiophene-2-sulfonic acid (1-methylimidazol-2-yl)methyl]amide hydrochloride;
5-[5-ethyl-2-methyl-6-oxo-1,6-dihydropyridin-3-yl] thiophene-2-sulfonic acid methyl(1-methylpyrrolidin-3-yl)amide hydrochloride;
5-[5-ethyl-2-methyl-6-oxo-1,6-dihydropyridin-3-yl] thiophene-2-sulfonic acid [1-(pyridin-4-yl)methyl(piperidin-4-yl)]amide dihydrochloride;
5-[5-ethyl-2-methyl-6-oxo-1,6-dihydropyridin-3-yl] thiophene-2-sulfonic acid (1-imidazol-2-yl)methyl(piperidin-4-yl)]amide dihydrochloride;
5-[5-ethyl-2-methyl-6-oxo-1,6-dihydropyridin-3-yl] thiophene-2-sulfonic acid 4-(pyridin-3-ylbutyl)]amide hydrochloride;
3-ethyl-5-[5-(3-hydroxypyrrolidine-1-sulfonyl)thiophen-2-yl]-6-methyl-1H-pyridin-2-one;
3-ethyl-6-methyl-5-[5-(4-methylpiperazine-1-sulfonyl) thiophen-2-yl]-1H-pyridin-2-one;
3-ethyl-6-methyl-5-[5-(morpholine-4-sulfonyl)thiophen-2-yl]-1H-pyridin-2-one;
3-ethyl-5-[5-(4-hydroxypiperidine-1-sulfonyl)thiophen-2-yl]-6-methyl-1H-pyridin-2-one;
5-(5-ethyl-2-methyl-6-oxo-1,6-dihydropyridin-3-yl) thiophene-2-sulfonic acid [2-(1,3-dioxolan-2-yl)ethyl]amide;
4-[5-(5-ethyl-2-methyl-6-oxo-1,6-dihydropyridin-3-yl) thiophene-2-sulfonyl]piperazine-1-carboxylic acid ethyl ester;
3-ethyl-5-[5-(3-hydroxymethylpiperidine-1-sulfonyl) thiophen-2-yl]-6-methyl-1H-pyridin-2-one;
3-ethyl-5-{5-[4-(2-hydroxyethyl)piperazine-1-sulfonyl] thiophen-2-yl}-6-methyl-1H-pyridin-2-one hydrochloride;
3-ethyl-6-methyl-5-[5-(4-methylpiperazine-1-sulfonyl) thiophen-2-yl]-1H-pyridin-2-one;
5-(5-ethyl-2-methyl-6-oxo-1,6-dihydropyridin-3-yl) thiophene-2-sulfonic acid (2-dimethylaminoethyl)amide hydrochloride;
3-ethyl-6-methyl-5-[5-(piperazine-1-sulfonyl)thiophen-2-yl]-1H-pyridin-2-one hydrochloride;
5-(5-ethyl-2-methyl-6-oxo-1,6-dihydropyridin-3-yl) thiophene-2-sulfonic acid (2-pyrrolidin-1-yl)ethylamide hydrochloride;
5-(5-ethyl-2-methyl-6-oxo-1,6-dihydropyridin-3-yl)-thiophene-2-sulfonic acid (3-diethylaminopropyl)amide hydrochloride;
5-(5-ethyl-2-methyl-6-oxo-1,6-dihydropyridin-3-yl)-thiophene-2-sulfonic acid (furan-2-ylmethyl)amide;
5-(5-ethyl-2-methyl-6-oxo-1,6-dihydropyridin-3-yl)-thiophene-2-sulfonic acid (2-phenoxyethyl)amide;
3-ethyl-5-(5-{4-[2-(2-hydroxy-ethoxy)-ethyl]-piperazine-1-sulfonyl}-thiophen-2-yl)-6-methyl-1H-pyridin-2-one hydrochloride;

5-[5-(4-benzylpiperazine-1-sulfonyl)thiophen-2-yl]-3-ethyl-6-methyl-1H-pyridin-2-one hydrochloride;

5-(5-ethyl-2-methyl-6-oxo-1,6-dihydropyridin-3-yl)-thiophene-2-sulfonic acid (pyridin-3-ylmethyl)amide hydrochloride;

5-(5-ethyl-2-methyl-6-oxo-1,6-dihydropyridin-3-yl)-thiophene-2-sulfonic acid (1-ethyl-pyrrolidin-2-ylmethyl)amide hydrochloride;

5-(5-ethyl-2-methyl-6-oxo-1,6-dihydropyridin-3-yl)-thiophene-2-sulfonic acid (1,3-benzodioxol-5-ylmethyl)amide;

5-[5-(4-1,3-benzodioxol-5-ylmethylpiperazine-1-sulfonyl)-thiophen-2-yl]-3-ethyl-6-methyl-1H-pyridin-2-one hydrochloride;

3-ethyl-6-methyl-5-[5-((S)-2-phenylaminomethylpyrrolidine-1-sulfonyl)-thiophen-2-yl]-1H-pyridin-2-one hydrochloride;

5-(5-ethyl-2-methyl-6-oxo-1,6-dihydro-pyridin-3-yl) thiophene-2-sulfonic acid furan-2-yl-methyl-methylamide;

5-(5-ethyl-2-methyl-6-oxo-1,6-dihydropyridin-3-yl) thiophene-2-sulfonic acid (2-pyridin-3-yl-ethyl)amide hydrochloride;

5-[5-(4-benzoylpiperidine-1-sulfonyl)thiophen-2-yl]-3-ethyl-6-methyl-1H-pyridin-2-one;

5-(5-ethyl-2-methyl-6-oxo-1,6-dihydropyridin-3-yl) thiophene-2-sulfonic acid (2-pyridin-4-yl-ethyl)amide hydrochloride;

5-(5-ethyl-2-methyl-6-oxo-1,6-dihydropyridin-3-yl) thiophene-2-sulfonic acid (pyridin-4-ylmethyl)amide hydrochloride;

5-(5-ethyl-2-methyl-6-oxo-1,6-dihydropyridin-3-yl) thiophene-2-sulfonic acid amide;

5-(5-ethyl-2-methyl-6-oxo-1,6-dihydropyridin-3-yl) thiophene-2-sulfonic acid (tetrahydrofuran-2-ylmethyl)amide;

5-(5-ethyl-2-methyl-6-oxo-1,6-dihydropyridin-3-yl) thiophene-2-sulfonic acid (2-hydroxypropyl)amide;

5-(5-ethyl-2-methyl-6-oxo-1,6-dihydropyridin-3-yl) thiophene-2-sulfonic acid (2-hydroxy-2-phenylethyl)amide;

5-(5-ethyl-2-methyl-6-oxo-1,6-dihydropyridin-3-yl) thiophene-2-sulfonic acid (2-hydroxyethyl)amide;

3-ethyl-6-methyl-5-{5-[(4-pyridin-2-yl)piperazine-1-sulfonyl]thiophen-2-yl}-1H-pyridin-2-one hydrochloride;

3-ethyl-6-methyl-5-[5-(4-pyrimidin-2-yl-piperazine-1-sulfonyl)thiophen-2-yl]-1H-pyridin-2-one hydrochloride;

5-(5-ethyl-2-methyl-6-oxo-1,6-dihydro-pyridin-3-yl) thiophene-2-sulfonic acid (1H-benzimidazol-2-ylmethyl)amide hydrochloride;

N-{2-[5-(5-ethyl-2-methyl-6-oxo-1,6-dihydropyridin-3-yl)thiophene-2-sulfonylamino]ethyl}acetamide;

5-(5-ethyl-2-methyl-6-oxo-1,6-dihydro-pyridin-3-yl)-thiophene-2-sulfonic acid (3,5-difluoro-phenyl)-amide;

5-(5-ethyl-2-methyl-6-oxo-1,6-dihydropyridin-3-yl) thiophene-2-sulfonic acid (1-methyl-1-pyridin-2-yl)ethylamide hydrochloride;

5-(5-ethyl-2-methyl-6-oxo-1,6-dihydropyridin-3-yl) thiophene-2-sulfonic acid cyclopropyl(1-pyridin-2-yl) ethylamide dihydrochloride;

5-(5-ethyl-2-methyl-6-oxo-1,6-dihydro-pyridin-3-yl)-thiophene-2-sulfonic acid (2-pyridin-2-yl-ethyl)-amide;

3-ethyl-6-methyl-5-[5-(4-methyl-[1,4]diazepane-1-sulfonyl)-thiophen-2-yl]-1H-pyridin-2-one;

5-(5-ethyl-2-methyl-6-oxo-1,6-dihydro-pyridin-3-yl)-thiophene-2-sulfonic acid benzylamide;

5-(5-ethyl-2-methyl-6-oxo-1,6-dihydro-pyridin-3-yl)-thiophene-2-sulfonic acid 4-methoxy-benzylamide;

5-(5-ethyl-2-methyl-6-oxo-1,6-dihydro-pyridin-3-yl)-thiophene-2-sulfonic acid 4-methanesulfonyl-benzylamide;

5-(5-ethyl-2-methyl-6-oxo-1,6-dihydro-pyridin-3-yl)-thiophene-2-sulfonic acid (1H-indol-3-ylmethyl)-amide;

5-(5-ethyl-2-methyl-6-oxo-1,6-dihydro-pyridin-3-yl)-thiophene-2-sulfonic acid {3-[(1-ethyl-pyrrolidin-2-ylmethyl)-amino]-propyl}-amide;

5-(5-ethyl-2-methyl-6-oxo-1,6-dihydro-pyridin-3-yl)-thiophene-2-sulfonic acid [3-(2R-hydroxymethyl-pyrrolidin-1-yl)-propyl]-amide hydrochloride;

5-(5-ethyl-2-methyl-6-oxo-1,6-dihydro-pyridin-3-yl)-thiophene-2-sulfonic acid [2-(2R-hydroxymethyl-pyrrolidin-1-yl)-ethyl]-amide hydrochloride;

5-(5-ethyl-2-methyl-6-oxo-1,6-dihydro-pyridin-3-yl)-thiophene-2-sulfonic acid [2-(3,3-difluoro-pyrrolidin-1-yl)-ethyl]-amide; and 1-{2-[5-(5-ethyl-2-methyl-6-oxo-1,6-dihydro-pyridin-3-yl)-thiophene-2-sulfonylamino]-ethyl}-pyrrolidine-2-carboxylic acid.

In a further embodiment of this invention, there is disclosed compounds of formula I, wherein Ar is substituted or unsubstituted furanyl, and Y is $SO_2NR_5R_6$ wherein $R_5$ and $R_6$ are as defined hereinabove. Again, in this embodiment the compounds of formula (I) feature the following specific substituents: R is hydrogen, $R_1$ is methyl, $R_3$ is hydrogen and $R_4$ is ethyl. Specific compounds falling within the scope of this embodiment without any limitation are the following:

5-(5-ethyl-2-methyl-6-oxo-1,6-dihydropyridin-3-yl)furan-2-sulfonic acid (pyridin-2-yl)methylamide hydrochloride;

3-ethyl-6-methyl-5-{5-[(4-pyridin-4-yl)piperazine-1-sulfonyl]furan-2-yl}-1H-pyridin-2-one hydrochloride;

5-(5-ethyl-2-methyl-6-oxo-1,6-dihydropyridin-3-yl)furan-2-sulfonic acid (1-benzylpiperidin-4-yl)amide hydrochloride;

5-(5-ethyl-2-methyl-6-oxo-1,6-dihydropyridin-3-yl)furan-2-sulfonic acid (2-morpholin-4-yl)ethylamide hydrochloride;

5-(5-ethyl-2-methyl-6-oxo-1,6-dihydropyridin-3-yl)furan-2-sulfonic acid (2-pyridin-3-yl)ethylamide hydrochloride;

5-(5-ethyl-2-methyl-6-oxo-1,6-dihydropyridin-3-yl)furan-2-sulfonic Acid (3-pyrrolidin-1-yl)propylamide hydrochloride;

5-(5-ethyl-2-methyl-6-oxo-1,6-dihydropyridin-3-yl)furan-2-sulfonic acid (2-piperidin-1-yl)ethylamide hydrochloride;

3-ethyl-6-methyl-5-[5-(4-piperidin-1-yl)piperidine-1-sulfonylfuran-2-yl]-1H-pyridin-2-one hydrochloride;

3-ethyl-6-methyl-5-[5-(4-methyl-1,4-diazepane-1-sulfonyl)furan-2-yl]-1H-pyridin-2-one hydrochloride;

5-(5-ethyl-2-methyl-6-oxo-1,6-dihydropyridin-3-yl)furan-2-sulfonic acid (2-pyrrolidin-1-yl)ethylamide hydrochloride;

5-(5-ethyl-2-methyl-6-oxo-1,6-dihydropyridin-3-yl)furan-2-sulfonic acid (3-imidazol-1-yl)propylamide hydrochloride;

5-(5-ethyl-2-methyl-6-oxo-1,6-dihydropyridin-3-yl)furan-2-sulfonic acid (pyridin-3-yl)methylamide hydrochloride; and 5-(5-ethyl-2-methyl-6-oxo-1,6-dihydro-pyridin-3-yl)-furan-2-sulfonic acid 3,5-difluoro-benzylamide.

In another embodiment of this invention, there is also disclosed compounds of formula I, wherein Ar is substituted or unsubstituted thienyl, phenyl or pyridinyl and Y is $(CH_2)_n NR_7R_8$, wherein:

n is an integer from 1 to 4;

$R_7$ and $R_8$ are the same or different and independently of each other selected from the group consisting of hydrogen, $C_{1-6}$alkyl, $C_{3-8}$cycloalkyl-$C_{0-4}$alkyl, $C_{3-8}$cycloalkenyl-$C_{0-4}$ alkyl, hydroxy-$C_{1-6}$alkyl, $C_{1-4}$alkoxy-$C_{1-6}$alkyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, amino-$C_{1-6}$alkyl, $C_{1-6}$alkyl-aminio-$C_{1-6}$alkyl, $C_{1-6}$dialkyl-amino-$C_{1-6}$alkyl, $C_{1-6}$dialkyl-amino-$C_{1-6}$alkylcarbonyl, phenyl-$C_{0-4}$alkyl, phenoxy-$C_{1-4}$alkyl, phenyl-amino-$C_{1-4}$ alkyl, pyridinyl-$C_{0-4}$alkyl, pyrazinyl-$C_{0-4}$alkyl, furanyl-$C_{0-4}$alkyl, tetrahydrofuranyl-$C_{0-4}$alkyl, thiophenyl-$C_{0-4}$ alkyl, pyrrolyl-$C_{0-4}$alkyl, pyrrolidinyl-$C_{0-4}$alkyl, morpholinyl-$C_{1-4}$alkyl, imidazolyl-$C_{0-4}$alkyl, pyrazolyl-$C_{0-4}$ alkyl, benzimidazolyl-$C_{0-4}$alkyl, piperidinyl-$C_{0-4}$alkyl, piperidinyl-$C_{1-4}$alkylcarbonyl, piperazinyl-$C_{0-4}$alkyl, tetrahydronaphthalenyl-$C_{0-4}$alkyl, indanyl-$C_{0-4}$alkyl, dioxolanyl-$C_{0-4}$alkyl and benzodioxolanyl-$C_{0-4}$alkyl; or $R_7$ and $R_8$ taken together with the nitrogen atom to which they are attached form a $C_{3-8}$heterocycle ring optionally containing one or more heteroatoms selected from N, O or S.

Again, in this embodiment as stated before, where appropriate any of the aforementioned groups are optionally substituted with one or more substituents selected from the group consisting of fluorine, chlorine, bromine, oxo, hydroxy, —$CF_3$, —$OCF_3$, $C_{1-6}$alkoxy, $C_{1-6}$alkyl, hydroxy-$C_{1-6}$alkyl, $C_{1-6}$alkoxy-$C_{1-6}$alkyl, $C_{3-8}$cycloalkyl-$C_{1-4}$alkyl, $C_{2-4}$alkanoyl, $C_{1-6}$alkoxycarbonyl, $C_{1-6}$alkylcarbonylamino, —$SO_2NH_2$, amino-$C_{1-6}$alkyl, $C_{1-6}$alkyl-aminio-$C_{1-6}$alkyl, $C_{1-6}$dialkyl-amino-$C_{1-6}$alkyl, substituted or unsubstituted phenyl-$C_{0-4}$alkyl, substituted or unsubstituted pyridinyl-$C_{0-4}$ alkyl, substituted or unsubstituted pyridinyl-$C_{0-4}$alkyl, substituted or unsubstituted pyrimidinyl-$C_{0-4}$alkyl, substituted or unsubstituted pyrazinyl-$C_{0-4}$alkyl, substituted or unsubstituted pyrrolidonyl-$C_{0-4}$alkyl, substituted or unsubstituted piperidinyl-$C_{0-4}$alkyl, substituted or unsubstituted pyrrolidinyl-$C_{0-4}$alkyl, substituted or unsubstituted imidazolyl-$C_{0-4}$ alkyl, substituted or unsubstituted morpholinyl-$C_{0-4}$alkyl, substituted or unsubstituted dioxolanyl-$C_{0-4}$alkyl, substituted or unsubstituted bezodioxolanyl-$C_{0-4}$alkyl, substituted or unsubstituted phenyl-amino-$C_{0-4}$alkyl and substituted or unsubstituted benzoyl.

In this embodiment, the compounds of formula I feature the following specific substituents: R is hydrogen, $R_1$ is methyl, $R_3$ is hydrogen and $R_4$ is ethyl. Specific compounds falling within the scope of this embodiment without any limitations are the following:

5-(5-aminomethylthiophen-2-yl)-3-ethyl-6-methyl-1H-pyridin-2-one hydrochloride;

3-ethyl-5-{5-[(4-hydroxycyclohexylamino)methyl]thiophen-2-yl}-6-methyl-1H-pyridin-2-one hydrochloride;

3-ethyl-5-[5-(3-hydroxypiperidin-1-ylmethyl)thiophen-2-yl]-6-methyl-1H-pyridin-2-one hydrochloride;

3-ethyl-5-[5-(4-hydroxy-piperidin-1-ylmethyl)-thiophen-2-yl]-6-methyl-1H-pyridin-2-one hydrochloride;

3-ethyl-5-{5-[(2-hydroxy-ethylamino)-methyl]thiophen-2-yl}-6-methyl-1H-pyridin-2-one hydrochloride;

5-(5-[1,4']bipiperidinyl-1'-ylmethyl-thiophen-2-yl)-3-ethyl-6-methyl-1H-pyridin-2-one dihydrochloride;

4-{[5-(5-ethyl-2-6-oxo-1,6-dyhydro-pyridin-3-yl)-thiophen-2-ylmethyl]-amino}-1-methyl-1H-pyrrole-2-carboxylic acid methyl ester dihydrochloride;

3-ethyl-5-[5-(3-hydroxymethyl-piperidin-1-ylmethyl)-thiophen-2-yl]-6-methyl-1H-pyridin-2-one hydrochloride;

5-{5-[(1-cyclohexylmethyl-piperidin-4-ylamino)-methyl]thiophen-2-yl}-3-ethyl-6-methyl-1H-pyridin-2-one dihydrochloride;

5-{5-[(1-methylpyrrolidin-3-ylamino)-methyl]thiophen-2-yl}-3-ethyl-6-methyl-1H-pyridin-2-one dihydrochloride;

3-ethyl-6-methyl-5-{5-[(1,2,3,4-tetrahydro-naphthalen-2-ylamino)-methyl]-thiophen-2-yl}-1H-pyridin-2-one hydrochloride;

3-ethyl-6-methyl-5-{5-[(1-phenyl-ethylamino)-methyl]thiophen-2-yl}-1H-pyridin-2-one hydrochloride;

3-ethyl-6-methyl-5-{5-[(1-methyl-3-phenyl-propylamino)-methyl]thiophen-2-yl}-1H-pyridin-2-one hydrochloride;

5-(5-cyclobutylaminomethyl-thiophen-2-yl)-3-ethyl-6-methyl-1H-pyridin-2-one hydrochloride;

3-ethyl-5-{5-[(2-methoxyethylamino)-methyl]thiophen-2-yl}-6-methyl-1H-pyridin-2-one hydrochloride;

3-ethyl-6-methyl-5-{5-[1-(4-trifluoromethylpyrimidin-2-yl)piperidin-4-ylamino]-thiophen-2-yl}-1H-pyridin-2-one dihydrochloride;

5-(5-{[1-(3,5-difluoro-benzyl)-)-piperidin-4-ylmethyl]-amino}methyl-thiophen-2-yl)-3-ethyl-6-methyl-1H-pyridin-2-one;

3-ethyl-6-methyl-5-{5-[(2-pyridin-2-ylethylamino)methyl]thiophen-2-yl}-1H-pyridin-2-one dihydrochloride;

5-(5-cyclopropylaminomethyl-thiophen-2-yl)-3-ethyl-6-methyl-1H-pyridin-2-one hydrochloride;

5-(5-cyclohexylmethylaminomethylthiophen-2-yl)-3-ethyl-6-methyl-1H-pyridin-2-one hydrochloride;

5-{5-[(2-cyclohex-1-enyl-ethylamino)-methyl]thiophen-2-yl}-3-ethyl-6-methyl-1H-pyridin-2-one hydrochloride;

5-{5-[(3,5-difluoro-phenylamino)-methyl]thiophen-2-yl}-3-ethyl-6-methyl-1H-pyridin-2-one hydrochloride;

3-ethyl-6-methyl-5-{5-[(2-phenoxyethylamino)-methyl]thiophen-2-yl}-1H-pyridin-2-one hydrochloride;

5-{5-[(3-methylbut-2-ylamino)methyl]thiophen-2-yl}-3-ethyl-6-methyl-1H-pyridin-2-one hydrochloride;

3-ethyl-6-methyl-5-(5-piperidin-1-ylmethy-thiophen-2-yl)-1H-pyridin-2-one hydrochloride;

5-[5-(1,4-dioxa-8-aza-spiro[4,5]dec-8-ylmethy)-thiophen-2-yl)-3-ethyl-6-methyl-1H-pyridin-2-one hydrochloride;

3-ethyl-6-methyl-5-[5-(4-oxo-piperidin-1-ylmethy)-thiophen-2-yl]-1H-pyridin-2-one hydrochloride;

5-{5-[(1-benzyl-piperidin-4-ylamino)-methyl]thiophen-2-yl}-3-ethyl-6-methyl-1H-pyridin-2-one dihydrochloride;

3-ethyl-6-methyl-5-{5-{[(pyridin-4-ylmethyl)-amino]-methyl}-thiophen-2-yl)-1H-pyridin-2-one dihydrochloride;

3-ethyl-6-methyl-5-{5-[(3-imidazol-1-yl-propylamino)-methyl]thiophen-2-yl}-1H-pyridin-2-one hydrochloride;

3-ethyl-6-methyl-5-{5-{[(2-pyrrolidin-1-ylethylamino)-methyl]thiophen-2-yl}-1H-pyridin-2-one hydrochloride;

3-ethyl-5-(5-{[(2-(3H-imidazol-4-yl)ethylamino]methyl}thiophen-2-yl)-6-methyl-1H-pyridin-2-one dihydrochloride;

3-ethyl-5-[5-(indan-2-ylaminomethyl)-thiophen-2-yl]-6-methyl-1H-pyridin-2-one hydrochloride;

5-[5-(benzylamino-methyl)-thiophen-2-yl]-3-ethyl-6-methyl-1H-pyridin-2-one hydrochloride;

5-[5-(3,5-difluorobenzylaminomethyl)thiophen-2-yl]-3-ethyl-6-methyl-1H-pyridin-2-one hydrochloride;

5-{5-[(1-benzyl-pyrrolidin-3-ylamino)-methyl]-thiophen-2-yl}-3-ethyl-6-methyl-1H-pyridin-2-one dihydrochloride;

3-ethyl-6-methyl-5-[5-(4-pyrrolidin-1-ylpiperidin-1-ylmethyl)-thiophen-2-yl]-1H-pyridin-2-one dihydrochloride;

3-ethyl-6-methyl-5-(5-{[(1-methyl-1H-imidazol-2-yl)methyl)amino]methyl}-thiophen-2-yl)-1H-pyridin-2-one dihydrochloride;
3-ethyl-6-methyl-5-{5-{[(pyridin-3-ylmethyl)amino]methyl}thiophen-2-yl)-1H-pyridin-2-one dihydrochloride;
3-ethyl-6-methyl-5-{5-{[(pyridin-3-ylethyl)amino]methyl}thiophen-2-yl)-1H-pyridin-2-one dihydrochloride;
5-{5-[(3-chlorobenzylamino)methyl]thiophen-2-y}]-3-ethyl-6-methyl-1H-pyridin-2-one hydrochloride;
5-{5-[(4-chlorobenzylamino)methyl]thiophen-2-y}]-3-ethyl-6-methyl-1H-pyridin-2-one hydrochloride;
5-{5-[(3-methylbenzylamino)methyl]thiophen-2-y}]-3-ethyl-6-methyl-1H-pyridin-2-one hydrochloride;
5-{5-[(4-methylbenzylamino)methyl]thiophen-2-y}]-3-ethyl-6-methyl-1H-pyridin-2-one hydrochloride;
5-{5-[(3-methoxybenzylamino)methyl]thiophen-2-y}]-3-ethyl-6-methyl-1H-pyridin-2-one hydrochloride;
5-{5-[(4-methoxybenzylamino)methyl]thiophen-2-y}]-3-ethyl-6-methyl-1H-pyridin-2-one hydrochloride;
3-ethyl-6-methyl-5-(5-{[(thiophen-2-ylmethyl)amino]methyl}-thiophen-2-yl)-1H-pyridin-2-one hydrochloride;
3-ethyl-6-methyl-5-(5-pyrrolidin-1-ylmethylthiophen-2-yl)-1H-pyridin-2-one hydrochloride;
5-{5-[(3,3-difluoropyrrolidin-1-ylmethyl)(thiophen-2-yl)-3-ethyl-6-methyl-1H-pyridin-2-one hydrochloride;
5-{5-[(3-fluoropyrrolidin-1-ylmethyl)(thiophen-2-yl)-3-ethyl-6-methyl-1H-pyridin-2-one hydrochloride;
3-ethyl-5-{5-[(3-methoxypyrrolidin-1-ylmethyl)(thiophen-2-yl)-6-methyl-1H-pyridin-2-one hydrochloride;
N-[5-(5-ethyl-2-methyl-6-oxo-1,6-dihydropyridin-3-yl)thiophen-2-ylmethyl]-2-(pyrrolidin-1-yl)acetamide hydrochloride;
2-dimethylamino-N-[5-(5-ethyl-2-methyl-6-oxo-1,6-dihydropyridin-3-yl)thiophen-2-ylmethyl]acetamide hydrochloride;
3-ethyl-5-{5-[(2-fluoro-3-trifluoromethylbenzylamino)methyl](thiophen-2-yl)-6-methyl-1H-pyridin-2-one hydrochloride;
5-[5-(4-benzylpiperidin-1-ylmethyl)thiophen-2-yl]-3-ethyl-6-methyl-1H-pyridin-2-one hydrochloride;
3-ethyl-6-methyl-5-[5-(4-phenylpiperidin-1-ylmethyl)thiophen-2-yl]-1H-pyridin-2-one hydrochloride;
3-ethyl-5-[5-(4-hydroxy-4-phenylpiperidin-1-ylmethyl)thiophen-2-yl]-6-methyl-1H-pyridin-2-one hydrochloride;
3-ethyl-6-methyl-5-[(5-piperidin-1-yl)methylthiophen-2-yl]-1H-pyridin-2-one hydrochloride;
3-ethyl-5-{5-[(2-methoxybenzylamino)methyl]thiophen-2-yl}-6-methyl-1H-pyridin-2-one hydrochloride;
5-{5-[(2-chlorobenzylamino)methyl]thiophen-2-yl}-3-ethyl-6-methyl-1H-pyridin-2-one hydrochloride;
5-(5-cyclopentylaminomethylthiophen-2-yl)-3-ethyl-6-methyl-1H-pyridin-2-one hydrochloride;
5-(5-cyclohexylaminomethylthiophen-2-yl)-3-ethyl-6-methyl-1H-pyridin-2-one hydrochloride;
3-ethyl-5-{5-[(S)-2-methoxymethylpyrrolidin-1-ylmethyl]thiophen-2-yl}-6-methyl-1H-pyridin-2-one hydrochloride;
3-ethyl-5-{5-[(2-fluoro-benzylamino)-methyl]-thiophen-2-yl}-6-methyl-1H-pyridin-2-one hydrochloride;
3-ethyl-5-[5-(3-fluoropiperidin-1-ylmethyl)thiophen-2-yl]-6-methyl-1H-pyridin-2-one hydrochloride;
3-ethyl-5-[5-(3-methoxypiperidin-1-ylmethyl)thiophen-2-yl]-6-methyl-1H-pyridin-2-one hydrochloride;
3-ethyl-6-methyl-5-(5-{[(pyridin-2-ylmethyl)amino]methyl}thiophen-2-yl)-1H-pyridin-2-one hydrochloride;
5-[5-(2-benzylaminoethyl)(thiophen-2-yl)-3-ethyl-6-methyl-1H-pyridin-2-one hydrochloride;
3-ethyl-6-methyl-5-[5-(2-pyrrolidin-1-ylethyl)thiophen-2-yl]-1H-pyridin-2-one hydrochloride;
5-(5-{[1-(3,5-difluoro-benzyl)-piperidin-4-ylamino]-methyl}-thiophen-2-yl)-3-ethyl-6-methyl-1H-pyridin-2-one;
3-ethyl-6-methyl-5-(3-morpholin-4-ylmethyl-phenyl)-1H-pyridin-2-one;
3-ethyl-6-methyl-5-(3-pyrrolidin-1-ylmethyl-phenyl)-1H-pyridin-2-one;
5-[3-(benzylamino-methyl)-phenyl]-3-ethyl-6-methyl-1H-pyridin-2-one;
5'-ethyl-2'-methyl-6-pyrrolidin-1-ylmethyl-1'H-[2,3']bipyridinyl-6'-one;
5'-ethyl-2'-methyl-6-{[(pyridin-2-ylmethyl)-amino]-methyl}-1'H-[2,3']bipyridinyl-6'-one;
5'-ethyl-6-(4-hydroxy-piperidin-1-ylmethyl)-2'-methyl-1'H-[2,3']bipyridinyl-6'-one;
6-(4-acetyl-piperazin-1-ylmethyl)-5'-ethyl-2'-methyl-1'H-[2,3']bipyridinyl-6'-one; and
5'-ethyl-2'-methyl-6-(4-pyrrolidin-1-yl-piperidin-1-ylmethyl)-1'H-[2,3']bipyridinyl-6'-one.

In yet another embodiment of this invention, there is disclosed compounds of formula I, wherein Ar is substituted or unsubstituted furanyl which is substituted with —(CH$_2$)$_n$NR$_7$R$_8$ as Y, wherein n, R$_7$ and R$_8$ are as defined hereinabove.

In this embodiment, the compounds of formula (I) feature the following specific substituents: R is hydrogen, R$_1$ is methyl, R$_3$ is hydrogen and R$_4$ is ethyl. Specific compounds falling within the scope of this embodiment without any limitation are the following:
5-[5-(benzylamino-methyl)-furan-2-yl]-3-ethyl-6-methyl-1H-pyridin-2-one hydrochloride;
3-ethyl-5-[5-(3-hydroxypyrrolidin-1-ylmethyl)furan-2-yl]-6-methyl-H-pyridin-2-one hydrochloride;
5-{5-[(benzyl methylamino)methyl]furan-2-yl)-3-ethyl-6-methyl-1H-pyridin-2-one;
3-ethyl-6-methyl-5-{5-[(morpholin-4-ylmethylfuran-2-yl)-1H-pyridin-2-one;
3-ethyl-6-methyl-5-{5-[(pyrolidin-1-ylmethylfuran-2-yl)-1H-pyridin-2-one;
3-ethyl-6-methyl-5-{5-[(3-fluoropyrolidin-1-ylmethylfuran-2-yl)-1H-pyridin-2-one hydrochloride;
5-(5-aminomethyl-furan-2-yl)-3-ethyl-6-methyl-1H-pyridin-2-one;
5-{5-[(benzyl-pyridin-3-ylmethyl-amino)-methyl]-furan-2-yl}-3-ethyl-6-methyl-1H-pyridin-2-one;
N-[4-({[5-(5-ethyl-2-methyl-6-oxo-1,6-dihydro-pyridin-3-yl)-furan-2-ylmethyl]-amino}-methyl)-phenyl]-acetamide;
2-chloro-5-(2-{[5-(5-ethyl-2-methyl-6-oxo-1,6-dihydro-pyridin-3-yl)-furan-2-ylmethyl]-amino}-ethyl)-benzenesulfonamide;
3-ethyl-6-methyl-5-(5-{[(1-methyl-1H-pyrazol-4-ylmethyl)-amino]-methyl}-furan-2-yl)-1H-pyridin-2-one;
3-ethyl-6-methyl-5-{5-[(2-trifluoromethoxy-benzylamino)-methyl]-furan-2-yl}-1H-pyridin-2-one;
3-ethyl-6-methyl-5-(5-pyrrolidin-1-ylmethyl-furan-3-yl)-1H-pyridin-2-one; and
3-ethyl-6-methyl-5-(5-pyrrolidin-1-ylmethyl-furan-3-yl)-1H-pyridin-2-one.

In yet another embodiment of this invention, there is disclosed compounds of formula I, wherein Ar is substituted or unsubstituted phenyl, thienyl, furanyl, pyridinyl, and Y is hydrogen, —CH=N—OR$_9$, —C(O)NR$_7$R$_8$, —C(O)R$_9$, —CH(OH)R$_9$, —(CH$_2$)$_n$NHC(O)R$_9$, or —NHSO$_2$R$_9$.
Wherein n, R$_7$ and R$_8$ are as defined herein and
R$_9$ is hydrogen, C$_{1-6}$alkyl, C$_{3-8}$cycloalkyl, amino-C$_{1-6}$alkyl, C$_{1-6}$alkyl-aminio-C$_{1-6}$alkyl, C$_{1-6}$dialkyl-amino-C$_{1-6}$alkyl, phenyl-C$_{0-4}$alkyl, phenyl-amino-C$_{1-4}$alkyl, pyridinyl-C$_{1-4}$alkyl, pyrrolyl-C$_{1-4}$alkyl, pyrrolidinyl-C$_{1-4}$alkyl, morpholinyl-C$_{1-4}$alkyl, imidazolyl-C$_{1-4}$alkyl, benzimidazolyl-C$_{1-4}$alkyl, piperidinyl-C$_{1-4}$alkyl, piperazinyl-C$_{1-4}$alkyl, pyrazinyl-C$_{1-4}$alkyl.

Again in this embodiment, where appropriate any of the aforementioned groups may optionally be substituted with one or more substituents as disclosed herein.

In this embodiment, the compounds of formula (I) feature the following specific substituents: R is hydrogen, R$_1$ is methyl, R$_3$ is hydrogen and R$_4$ is ethyl. Specific compounds falling within the scope of this embodiment without any limitation are the following:

3-ethyl-6-methyl-5-thiophen-2-yl-1H-pyridin-2-one;
3-ethyl-6-methyl-5-furan-2-yl-1H-pyridin-2-one;
5-(5-ethyl-2-methyl-6-oxo-1,6-dihydropyridin-3-yl]thiophen-2-methanol;
5-(5-ethyl-2-methyl-6-oxo-1,6-dihydropyridin-3-yl]furan-2-methanol;
3-(5-ethyl-2-methyl-6-oxo-1,6-dihydropyridin-3-yl)-benzaldehyde;
5-(5-ethyl-2-methyl-6-oxo-1,6-dihydropyridin-3-yl)thiophene-2-carbaldehyde;
5-(5-ethyl-2-methyl-6-oxo-1,6-dihydropyridin-3-yl)furan-2-carbaldehyde;
4-(5-ethyl-2-methyl-6-oxo-1,6-dihydropyridin-3-yl)furan-2-carbaldehyde;
5-[5-(ethyl-2-methyl-6-oxo-1,6-dihydropyridin-3-yl)thiophen-2-yl]acetaldehyde;
5-(5-ethyl-2-methyl-6-oxo-1,6-dihydro-pyridin-3-yl)-furan-2-carbaldehyde oxime;
5-(5-ethyl-2-methyl-6-oxo-1,6-dihydro-pyridin-3-yl)-furan-2-carbaldehyde-O-benzyl-oxime;
3-ethyl-2-methyl-6-oxo-1,6-dihydropyridin-3-yl-thiophene-2-carbaldehyde-O-(pyrrolidin-1-ylethyl)oxime hydrochloride;
3-ethyl-2-methyl-6-oxo-1,6-dihydropyridin-3-yl-furan-2-carbaldehyde-O-(pyrrolidin-1-ylethyl)oxime hydrochloride;
5'-ethyl-2'-methyl-6'-oxo-1',6'-dihydro-[2,3']bipyridinyl-4-carboxylic acid;
5'-ethyl-2'-methyl-6'-oxo-1',6'-dihydro-[3,3']bipyridinyl-5-carboxylic acid;
5'-ethyl-2'-methyl-6'-oxo-1',6'-dihydro-[2,3']bipyridinyl-5-carboxylic acid;
5'-ethyl-2'-methyl-6'-oxo-1',6'-dihydro-[2,3']bipyridinyl-6-carboxylic acid;
5'-ethyl-2'-methyl-6'-oxo-1',6'-dihydro-[2,3']bipyridinyl-6-carbaldehyde;
6-amino-5'-ethyl-2'-methyl-1'H-[2,3']bipyridinyl-6'-one;
5-(5-ethyl-2-methyl-6-oxo-1,6-dihydropyridin-3-yl)-thiophene-2-sulfonyl chloride;
5-(5-ethyl-2-methyl-6-oxo-1,6-dihydropyridin-3-yl)-furan-2-sulfonyl chloride;
3-ethyl-6-methyl-5-[5-(4-phenyl-piperazine-1-carbonyl)-furan-2-yl]-1H-pyridin-2-one;
5-(5-ethyl-2-methyl-6-oxo-1,6-dihydro-pyridin-3-yl)-furan-2-carboxylic acid cyclopropylamide;
5-(5-ethyl-2-methyl-6-oxo-1,6-dihydro-pyridin-3-yl)-thiophene-2-carboxylic acid 3,5-difluoro-benzylamide;
5-(5-ethyl-2-methyl-6-oxo-1,6-dihydro-pyridin-3-yl)-thiophene-2-carboxylic acid (pyridin-2-ylmethyl)-amide;
5'-ethyl-2'-methyl-6'-oxo-1',6'-dihydro-[2,3']bipyridinyl-6-carboxylic acid [2-(4-nitro-phenyl)-ethyl]-amide;
5'-ethyl-2'-methyl-6'-oxo-1',6'-dihydro-[2,3']bipyridinyl-6-carboxylic acid butylamide;
5'-ethyl-2'-methyl-6-(pyrrolidine-1-carbonyl)-1'H-[2,3']bipyridinyl-6'-one;
5'-ethyl-2'-methyl-6'-oxo-1',6'-dihydro-[2,3']bipyridinyl-5-carboxylic acid (pyridin-2-ylmethyl)-amide;
5'-ethyl-2'-methyl-6'-oxo-1',6'-dihydro-[2,3']bipyridinyl-5-carboxylic acid butylamide;
5'-ethyl-5-(3-hydroxy-pyrrolidine-1-carbonyl)-2'-methyl-1'H-[2,3']bipyridinyl-6'-one;
5'-ethyl-2'-methyl-5-(pyrrolidine-1-carbonyl)-1'H-[2,3']bipyridinyl-6'-one;
5'-ethyl-2'-methyl-6'-oxo-1',6'-dihydro-[2,3']bipyridinyl-5-carboxylic acid cyclopentylamide;
5'-ethyl-2'-methyl-6'-oxo-1',6'-dihydro-[2,3']bipyridinyl-4-carboxylic acid [2-(4-nitro-phenyl)-ethyl]-amide;
5'-ethyl-2'-methyl-4-(pyrrolidine-1-carbonyl)-1'H-[2,3']bipyridinyl-6'-one;
5'-ethyl-2'-methyl-6'-oxo-1',6'-dihydro-[2,3']bipyridinyl-4-carboxylic acid butylamide;
5'-ethyl-2'-methyl-6'-oxo-1',6'-dihydro-[2,3']bipyridinyl-4-carboxylic acid cyclopentylamide;
5'-ethyl-2'-methyl-6'-oxo-1',6'-dihydro-[2,3']bipyridinyl-4-carboxylic acid (2-morpholin-4-yl-ethyl)-amide;
5'-ethyl-2'-methyl-6'-oxo-1',6'-dihydro-[2,3']bipyridinyl-4-carboxylic acid (2-pyridin-4-yl-ethyl)-amide;
5'-ethyl-2'-methyl-6'-oxo-1',6'-dihydro-[3,3']bipyridinyl-5-carboxylic acid cyclopentylamide;
5'-ethyl-2'-methyl-6'-oxo-1',6'-dihydro-[3,3']bipyridinyl-5-carboxylic acid benzylamide;
5'-ethyl-2'-methyl-6'-oxo-1',6'-dihydro-[3,3']bipyridinyl-5-carboxylic acid (pyridin-2-ylmethyl)-amide;
5'-ethyl-2'-methyl-6'-oxo-1',6'-dihydro-[3,3']bipyridinyl-5-carboxylic acid (pyridin-3-ylmethyl)-amide;
5'-ethyl-2'-methyl-6'-oxo-1',6'-dihydro-[3,3']bipyridinyl-5-carboxylic acid butylamide;
5'-ethyl-2'-methyl-6'-oxo-1',6'-dihydro-[3,3']bipyridinyl-5-carboxylic acid [1-(6-methyl-pyridin-3-yl)-propyl]-amide;
5'-ethyl-2'-methyl-6'-oxo-1',6'-dihydro-[3,3']bipyridinyl-5-carboxylic acid carbamoylmethyl-amide;
5-ethyl-2-methyl-5'-(pyrrolidine-1-carbonyl)-1H-[3,3']bipyridinyl-6-one; 5'-ethyl-2'-methyl-6'-oxo-1',6'-dihydro-[3,3']bipyridinyl-5-carboxylic acid diethylamide;
5'-ethyl-2'-methyl-6'-oxo-1',6'-dihydro-[3,3']bipyridinyl-5-carboxylic acid (cyclopropyl-pyridin-3-yl-methyl)-amide;
5'-ethyl-2'-methyl-6'-oxo-1',6'-dihydro-[3,3']bipyridinyl-5-carboxylic acid (2-hydroxy-propyl)-amide;
5'-ethyl-2'-methyl-6'-oxo-1',6'-dihydro-[3,3']bipyridinyl-5-carboxylic acid [2-(4-nitro-phenyl)-ethyl]-amide;
1-(5'-ethyl-2'-methyl-6'-oxo-1',6'-dihydro-[3,3']bipyridinyl-5-carbonyl)-4-hydroxy-pyrrolidine-2-carboxylic acid methyl ester;
5'-ethyl-2'-methyl-6'-oxo-1',6'-dihydro-[3,3']bipyridinyl-5-carboxylic acid [2-(2-hydroxy-phenyl)-ethyl]-amide;
5'-ethyl-2'-methyl-6'-oxo-1',6'-dihydro-[3,3']bipyridinyl-5-carboxylic acid carbamoylmethyl-methyl-amide;
5-ethyl-2-methyl-5'-(4-oxo-piperidine-1-carbonyl)-1H-[3,3']bipyridinyl-6-one;
5'-ethyl-2'-methyl-6'-oxo-1',6'-dihydro-[3,3']bipyridinyl-5-carboxylic acid ethyl-pyridin-4-ylmethyl-amide;
5'-ethyl-2'-methyl-6'-oxo-1',6'-dihydro-[3,3']bipyridinyl-5-carboxylic acid phenethyl-amide;
5'-ethyl-2'-methyl-6'-oxo-1',6'-dihydro-[3,3']bipyridinyl-5-carboxylic acid [2-(4-sulfamoyl-phenyl)-ethyl]-amide;

5'-ethyl-2'-methyl-6'-oxo-1',6'-dihydro-[3,3']bipyridinyl-5-carboxylic acid (2-pyridin-4-yl-ethyl)-amide;
5'-ethyl-2'-methyl-6'-oxo-1',6'-dihydro-[3,3']bipyridinyl-5-carboxylic acid [2-(4-methoxy-phenyl)-ethyl]-amide;
5'-ethyl-2'-methyl-6'-oxo-1',6'-dihydro-[3,3']bipyridinyl-5-carboxylic acid [2-(3-methoxy-phenyl)-ethyl]-amide;
5'-ethyl-2'-methyl-6'-oxo-1',6'-dihydro-[3,3']bipyridinyl-5-carboxylic acid (2-morpholin-4-yl-ethyl)-amide;
5'-ethyl-2'-methyl-6'-oxo-1',6'-dihydro-[3,3']bipyridinyl-5-carboxylic acid [2-(tetrahydro-pyran-4-yl)-ethyl]-amide;
4-{2-[(5'-ethyl-2'-methyl-6'-oxo-1',6'-dihydro-[3,3']bipyridinyl-5-carbonyl)-amino]-ethyl}-benzoic acid;
5'-ethyl-2'-methyl-6'-oxo-1',6'-dihydro-[3,3']bipyridinyl-5-carboxylic acid (2-oxo-2-phenyl-ethyl)-amide;
5'-ethyl-2'-methyl-6'-oxo-1',6'-dihydro-[3,3']bipyridinyl-5-carboxylic acid [2-(1H-benzoimidazol-2-yl)-ethyl]-amide;
5'-ethyl-2'-methyl-6'-oxo-1',6'-dihydro-[3,3']bipyridinyl-5-carboxylic acid (4-acetyl-phenyl)-amide;
5'-ethyl-2'-methyl-6'-oxo-1',6'-dihydro-[3,3']bipyridinyl-5-carboxylic acid (3-[1,2,4]triazol-1-yl-propyl)-amide;
5'-ethyl-2'-methyl-6'-oxo-1',6'-dihydro-[3,3']bipyridinyl-5-carboxylic acid (3-methoxy-phenyl)-amide;
5'-ethyl-2'-methyl-6'-oxo-1',6'-dihydro-[3,3']bipyridinyl-5-carboxylic acid [2-(2-methyl-5-nitro-imidazol-1-yl)-ethyl]-amide;
5'-ethyl-2'-methyl-6'-oxo-1',6'-dihydro-[3,3']bipyridinyl-5-carboxylic acid (thiazol-2-ylmethyl)-amide;
5'-ethyl-2'-methyl-6'-oxo-1',6'-dihydro-[3,3']bipyridinyl-5-carboxylic acid (2-carbamoylmethyl-phenyl)-amide;
5'-(4-cyclopropanecarbonyl-piperazine-1-carbonyl)-5-ethyl-2-methyl-1H-[3,3']bipyridinyl-6-one;
5'-ethyl-2'-methyl-6'-oxo-1',6'-dihydro-[3,3']bipyridinyl-5-carboxylic acid (2-hydroxy-2-phenyl-ethyl)-amide;
5'-ethyl-2'-methyl-6'-oxo-1',6'-dihydro-[3,3']bipyridinyl-5-carboxylic acid [2-(2,4-dioxo-thiazolidin-3-yl)-ethyl]-amide;
5'-ethyl-2'-methyl-6'-oxo-1',6'-dihydro-[3,3']bipyridinyl-5-carboxylic acid 4-sulfamoyl-benzylamide;
5'-ethyl-2'-methyl-6'-oxo-1',6'-dihydro-[3,3']bipyridinyl-5-carboxylic acid [2-(4-methoxy-phenyl)-2-oxo-ethyl]-amide;
5'-ethyl-2'-methyl-6'-oxo-1',6'-dihydro-[3,3']bipyridinyl-5-carboxylic acid (3-pyridin-4-yl-4,5-dihydro-isoxazol-5-ylmethyl)-amide;
5'-ethyl-2'-methyl-6'-oxo-1',6'-dihydro-[3,3']bipyridinyl-5-carboxylic acid (5-tert-butyl-1H-pyrazol-3-yl)-amide;
5'-ethyl-2'-methyl-6'-oxo-1',6'-dihydro-[3,3']bipyridinyl-5-carboxylic acid (5-tert-butyl-isoxazol-3-yl)-amide;
5'-ethyl-2'-methyl-6'-oxo-1',6'-dihydro-[3,3']bipyridinyl-5-carboxylic acid((1S,6R)-6-carbamoyl-cyclohex-3-enyl)-amide;
5'-ethyl-2'-methyl-6'-oxo-1',6'-dihydro-[3,3']bipyridinyl-5-carboxylic acid (2-methoxy-ethyl)-amide;
5'-ethyl-2'-methyl-6'-oxo-1',6'-dihydro-[3,3']bipyridinyl-5-carboxylic acid (4-cyano-cyclohexylmethyl)-amide;
5'-ethyl-2'-methyl-6'-oxo-1',6'-dihydro-[3,3']bipyridinyl-5-carboxylic acid 3-methoxy-benzylamide;
5'-ethyl-2'-methyl-6'-oxo-1',6'-dihydro-[3,3']bipyridinyl-5-carboxylic acid (2-pyridin-2-yl-ethyl)-amide;
5'-ethyl-2'-methyl-6'-oxo-1',6'-dihydro-[3,3']bipyridinyl-5-carboxylic acid 4-hydroxy-3-methoxy-benzylamide;
5-(5-ethyl-2-methyl-6-oxo-1,6-dihydro-pyridin-3-yl)-furan-2-carboxylic acid 3,5-difluoro-benzylamide;
3-ethyl-6-methyl-5-[5-(2-methyl-aziridine-1-carbonyl)-furan-2-yl]-1H-pyridin-2-one;
3-ethyl-5-{5-[4-(4-fluoro-phenyl)-piperazine-1-carbonyl]-furan-2-yl}-6-methyl-1H-pyridin-2-one;
5-(5-ethyl-2-methyl-6-oxo-1,6-dihydro-pyridin-3-yl)-furan-2-carboxylic acid 4-trifluoromethyl-benzylamide;
5-(5-ethyl-2-methyl-6-oxo-1,6-dihydro-pyridin-3-yl)-furan-2-carboxylic acid dimethylamide;
5-[5-(4-benzyl-piperazine-1-carbonyl)-thiophen-2-yl]-3-ethyl-6-methyl-1H-pyridin-2-one;
5-(5-ethyl-2-methyl-6-oxo-1,6-dihydro-pyridin-3-yl)-thiophene-2-carboxylic acid dimethylamide;
5-(5-ethyl-2-methyl-6-oxo-1,6-dihydro-pyridin-3-yl)-thiophene-2-carboxylic acid 4-trifluoromethyl-benzylamide;
5-(5-ethyl-2-methyl-6-oxo-1,6-dihydro-pyridin-3-yl)-thiophene-2-carboxylic acid (pyridin-2-ylmethyl)-amide;
5-(5-ethyl-2-methyl-6-oxo-1,6-dihydro-pyridin-3-yl)-thiophene-2-carboxylic acid methoxy-methyl-amide;
3-ethyl-6-methyl-5-[5-(pyridine-2-carbonyl)-thiophen-2-yl]-1H-pyridin-2-one;
3-ethyl-5-[5-(hydroxy-pyridin-2-yl-methyl)-thiophen-2-yl]-6-methyl-1H-pyridin-2-one;
3-ethyl-5-[5-(1-hydroxy-ethyl)-furan-2-yl]-6-methyl-1H-pyridin-2-one; cyclopentanecarboxylic acid [5-(5-ethyl-2-methyl-6-oxo-1,6-dihydro-pyridin-3-yl)-furan-2-ylmethyl]-amide;
N-[5-(5-ethyl-2-methyl-6-oxo-1,6-dihydro-pyridin-3-yl)-furan-2-ylmethyl]-2-phenyl-acetamide;
N-[5-(5-ethyl-2-methyl-6-oxo-1,6-dihydro-pyridin-3-yl)-furan-2-ylmethyl]-benzamide;
N-[5-(5-ethyl-2-methyl-6-oxo-1,6-dihydro-pyridin-3-yl)-furan-2-ylmethyl]-4-methoxy-benzamide;
pyridine-2-carboxylic acid [5-(5-ethyl-2-methyl-6-oxo-1,6-dihydro-pyridin-3-yl)-furan-2-ylmethyl]-amide;
N-[5-(5-ethyl-2-methyl-6-oxo-1,6-dihydro-pyridin-3-yl)-furan-2-ylmethyl]-acetamide;
3-dimethylamino-N-[5-(5-ethyl-2-methyl-6-oxo-1,6-dihydro-pyridin-3-yl)-furan-2-ylmethyl]-benzamide;
N-[5-(5-ethyl-2-methyl-6-oxo-1,6-dihydro-pyridin-3-yl)-thiophen-2-ylmethyl]-2-pyrrolidin-1-yl-acetamide;
N-(5'-ethyl-2'-methyl-6'-oxo-1',6'-dihydro-[2,3']bipyridinyl-6-yl)-benzenesulfonamide;
N-[4-(5'-ethyl-2'-methyl-6'-oxo-1',6'-dihydro-[2,3']bipyridinyl-6-ylsulfamoyl)-phenyl]-acetamide; and
5-(5-ethyl-2-methyl-6-oxo-1,6-dihydro-pyridin-3-yl)-furan-2-carboxylic acid amide.

In an additional aspect of this invention there is also disclosed a compound, including enantiomers, stereoisomers, and tautomers of said compound and pharmaceutically acceptable salts, solvates or derivatives thereof, with said compound having the general structure shown in formula II:

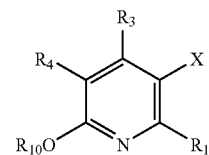

II wherein
$R_1$ is $C_{1-4}$alkyl, $C_{1-4}$alkenyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;

$R_3$ is hydrogen, $C_{1-4}$alkyl, $C_{1-4}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;

$R_4$ is $C_{1-6}$alkyl, $C_{1-6}$alkenyl, $C_{3-8}$cycloalkyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1; or $R_3$ and $R_4$ taken together with the carbon atoms to which they are attached form a $C_{4-8}$cycloalkyl ring or a benzene ring;

$R_{10}$ is $C_{1-4}$alkyl, phenyl-$C_{1-4}$alkyl, $C_{1-4}$alkenyl, fluoroalkyl of the formula $C_nH_xF_y$, wherein n is an integer from 1 to 4, x is an integer from 0 to 8, y is an integer from 1 to 9 and sum of x and y is 2n+1; and X is fluorine, chlorine, bromine, substituted or unsubstituted phenyl, thienyl, furanyl or pyridinyl, wherein the substituents are selected from the group consisting of: —CHO, —CO$_2$H, —CO$_2$C$_{1-4}$alkyl or —NH$_2$.

In an embodiment of this aspect of this invention, there is disclosed compounds of formula II, wherein $R_1$, $R_4$ and $R_{10}$ independently from each other are either methyl or ethyl and $R_3$ is hydrogen.

Specific examples of a compound of this embodiment, without any limitation include the following:

3-bromo-5-ethyl-6-methoxy-2-methylpyridine;

3-(5-ethyl-6-methoxy-2-methyl-pyridin-3-yl)-benzaldehyde;

3-ethyl-2-methoxy-6-methyl-5-thiophen-2-yl-pyridine;

3-ethyl-2-methoxy-6-methyl-5-furan-2-yl-pyridine;

5-(5-ethyl-6-methoxy-2-methyl-pyridin-3-yl)-thiophene-2-carbaldehyde;

5-(5-ethyl-6-methoxy-2-methyl-pyridin-3-yl)-furan-2-carbaldehyde;

4-(5-ethyl-6-methoxy-2-methyl-pyridin-3-yl)-furan-2-carbaldehyde;

5'-ethyl-6'-methoxy-2'-methyl-[2,3']bipyridinyl-6-carbaldehyde;

5'-ethyl-6'-methoxy-2'-methyl-[3,3']bipyridinyl-5-carboxylic acid;

5'-ethyl-6'-methoxy-2'-methyl-[2,3']bipyridinyl-4-carboxylic acid;

5'-ethyl-6'-methoxy-2'-methyl-[2,3']bipyridinyl-6-carboxylic acid;

5'-ethyl-6'-methoxy-2'-methyl-[2,3']bipyridinyl-5-carboxylic acid; and

5'-ethyl-6'-methoxy-2'-methyl-[2,3']bipyridinyl-6-ylamine.

In another aspect of this invention, there is disclosed a method of treating a disease or a condition caused by the effects of poly(adenosine 5'-diphosphate ribose) polymerase (PARP) in a patient comprising administering to said patient a therapeutically effective amount of a compound including enantiomers, stereoisomers, and tautomers of said compound and pharmaceutically acceptable salts, solvates or derivatives thereof, with said compound having the general structure shown in formula I.

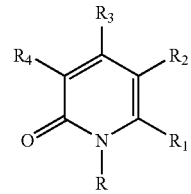

wherein

R is hydrogen or $C_{1-6}$alkyl;

$R_1$ is $C_{1-4}$alkyl, $C_{1-4}$alkenyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;

$R_2$ is Ar—Y, wherein

Ar is substituted or unsubstituted aryl, aryloyl or heteroaryl wherein said substituents are selected from the group consisting of $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, —NO$_2$, —NH$_2$, —NH(C$_{1-4}$alkyl), —N(C$_{1-4}$alkyl)$_2$, —CN, —C(O)R$_{11}$, —NHC(O)(C$_{1-4}$alkyl), —SO$_2$Cl, —SO$_2$(C$_{1-4}$alkyl), halogen and hydroxy; and Y is hydrogen, —SO$_2$NR$_5$R$_6$, —(CH$_2$)$_n$NR$_7$R$_8$, —CH=N—OR$_9$, —C(O)NR$_7$R$_8$, —C(O)R$_9$, —CH(OH)R$_9$, —(CH$_2$)$_n$NHC(O)R$_9$, —NHC(O)R$_9$, —NHSO$_2$R$_9$ and —(CH$_2$)$_n$NHSO$_2$R$_9$;

$R_3$ is hydrogen, $C_{1-4}$alkyl, $C_{1-4}$alkenyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;

$R_4$ is $C_{1-6}$alkyl, $C_{1-6}$alkenyl, $C_{3-8}$cycloalkyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1; or $R_3$ and $R_4$ taken together with the carbon atoms to which they are attached form a $C_{4-8}$cycloalkyl ring or a benzene ring;

$R_5$, $R_6$, $R_7$ and $R_8$ are the same or different and independently of each other selected from the group consisting of hydrogen, unsubstituted and at least monosubstituted $C_{1-10}$alkyl, $C_{3-8}$cycloalkyl, $C_{1-4}$alkoxy-$C_{1-6}$alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-6}$alkenyl, $C_{1-6}$alkynyl, aryl, heteroaryl and heterocycle; and wherein said substituents are selected from the group consisting of: aryl, heteroaryl, heterocycle, —O-aryl, fluorine, chlorine, bromine, —CF$_3$, —OCF$_3$, —NO$_2$, —CN, —C(O)R$_{11}$, —NHC(O)(C$_{1-3}$alkyl), —NH$_2$, hydroxy, $C_{1-6}$alkyl, $C_{1-3}$alkoxy, —NH(C$_{1-3}$alkyl), —N(C$_{1-3}$alkyl)$_2$, —SO$_2$NH$_2$, —SO$_2$(C$_{1-3}$alkyl) and —NH—SO$_2$(C$_1$-C$_3$-alkyl).

The aryl, heterocycle and heteroaryl may optionally be at least monosubstituted with fluorine, chlorine, bromine, oxo, —CF$_3$, —OCF$_3$, —NO$_2$, —CN, heteroaryl, —NHC(O)(C$_{1-3}$-alkyl), —COOH, hydroxy, C$_{1-3}$alkyl, C$_{1-3}$alkoxy, —SO$_2$NH$_2$, —SO$_2$NH(C$_{1-3}$alkyl), —SO$_2$N(C$_{1-3}$alkyl)$_2$, —C(O)NH$_2$, —C(O)NH(C$_{1-3}$alkyl), —C(O)N(C$_{1-3}$alkyl)$_2$, —SO$_2$(C$_{1-3}$alkyl), —NH$_2$, —NH(C$_{1-3}$alkyl) or —N(C$_{1-3}$alkyl)$_2$; or R$_5$ and R$_6$ taken together with the nitrogen atom to which they are attached form an unsubstituted or at least monosubstituted heterocycle; or R$_7$ and R$_8$ taken together with the nitrogen atom to which they are attached form an unsubstituted or at least monosubstituted heterocycle;

wherein said substituents are selected from: aryl, heteroaryl, heterocycle, oxo, fluorine, chlorine, bromine, —CF$_3$, —OCF$_3$, —NO$_2$, —CN, —C(O)R$_{11}$, —NHC(O)(C$_{1-3}$alkyl), —NH$_2$, hydroxy, C$_{1-3}$alkyl, C$_{1-3}$alkoxy, —NH(C$_{1-3}$alkyl), —N(C$_{1-3}$alkyl)$_2$, —SO$_2$NH$_2$, —SO$_2$(C$_{1-3}$alkyl) and —NH—SO$_2$(C$_{1-3}$alkyl), and aryl, heterocycle and heteroaryl may optionally be at least monosubstituted with fluorine, chlorine, bromine, hydroxy, C$_{1-3}$alkyl or C$_{1-3}$alkoxy;

R$_9$ is hydrogen, unsubstituted or at least monosubstituted C$_{1-6}$alkyl, phenyl, heteroaryl or heterocycle;

wherein said substituents are selected from the group consisting of: fluorine, chlorine, bromine, aryl, heterocycle, heteroaryl, —CF$_3$, —OCF$_3$, —NO$_2$, —CN, —C(O)R$_{11}$, —NHC(O)(C$_{1-3}$alkyl), —NH$_2$, hydroxy, C$_{1-3}$alkyl, C$_{1-3}$alkoxy, —NH(C$_{1-3}$alkyl), —N(C$_{1-3}$alkyl)$_2$, —SO$_2$NH$_2$, —SO$_2$(C$_{1-3}$alkyl) and —NH—SO$_2$(C$_{1-3}$alkyl); and The aryl, heterocycle and heteroaryl may optionally be at least monosubstituted with fluorine, chlorine, bromine, hydroxy, C$_{1-3}$alkyl or C$_{1-3}$alkoxy.

R$_{11}$ is hydroxy, C$_{1-3}$alkoxy, —O-phenyl, —NH$_2$, —NH(C$_{1-3}$alkyl), —N(C$_{1-3}$alkyl)$_2$ or phenyl;

n is an integer from 1 to 4.

Again in this embodiment, the heteroaryl is a 5 to 10-membered, aromatic, mono- or bicyclic heterocycle containing one or more heteroatoms selected from the group consisting of N, O and S. The aryl is a 6 to 10-membered, aromatic mono- or bicyclic ring; and the heterocycle is a 3 to 10-membered, non-aromatic, mono- or bicyclic heterocycle containing one or more heteroatoms selected from the group consisting of N, O and S.

In one aspect of this embodiment of the method of this invention, the substituents on formula I shall have the following meanings:

R is hydrogen, methyl or ethyl;
R$_1$ is methyl or ethyl;
R$_3$ is hydrogen, methyl or ethyl;
R$_4$ is methyl or ethyl; or
R$_3$ and R$_4$ taken together form either cyclohexyl ring or benzene ring;

Ar is substituted phenyl, substituted benzoyl, substituted or unsubstituted heteroaryl selected from the group consisting of 1,2,3,-triazolyl, 1,3,4-triazolyl, 2H-1,2,4-triazolyl, 2-methyl-1,2,4-triazolyl, 2,5-dimethyl-1,2,4-triazolyl, 1,2,4-oxadiazolyl, 1,3,4-oxadiazolyl, 5-methyl-1,3,4-oxadiazolyl, 3-methyl-1,2,4-oxadiazolyl, 5-methyl-1,2,4-oxadiazolyl, pyrazolyl, imidazolyl, pyrrolyl, pyridinyl, thienyl or furanyl;

Y is hydrogen, —SO$_2$NR$_5$R$_6$, —(CH$_2$)$_n$NR$_7$R$_8$, —CH=N—OR$_9$, —C(O)NR$_7$R$_8$, —C(O)R$_9$, —CH(OH)R$_9$, —(CH$_2$)$_n$NHC(O)R$_9$, and —NHSO$_2$R$_9$;

R$_5$ and R$_6$ are the same or different and independently of each other selected from the group consisting of hydrogen, C$_{1-10}$alkyl, C$_{3-8}$cycloalkyl, C$_{1-4}$alkoxy-C$_{1-6}$alkyl, fluoroalkyl or fluoroalkoxy of the formula C$_n$H$_x$F$_y$ or OC$_n$H$_x$F$_y$ wherein n is an integer from 1 to 4, x is an integer from 0 to 8, y is an integer from 1 to 9 and sum of x and y is 2n+1, amino-C$_{1-6}$alkyl, C$_{1-6}$alkyl-aminio-C$_{1-6}$alkyl, C$_{1-6}$dialkyl-amino-C$_{1-6}$alkyl, phenyl-C$_{0-4}$alkyl, phenoxy-C$_{1-4}$alkyl, phenyl-amino-C$_{1-4}$alkyl, pyridinyl-C$_{0-4}$alkyl, pyrazinyl-C$_{0-4}$alkyl, furanyl-C$_{0-4}$alkyl, tetrahydrofuranyl-C$_{0-4}$alkyl, pyrrolidinyl-C$_{0-4}$alkyl, morpholinyl-C$_{1-4}$alkyl, imidazolyl-C$_{0-4}$alkyl, indolyl-C$_{0-6}$alkyl, benzimidazolyl-C$_{0-4}$alkyl, piperidinyl-C$_{0-4}$alkyl, piperazinyl-C$_{0-4}$alkyl, pyrrolidinyl-C$_{0-4}$alkyl, pyrazinyl-C$_{0-4}$alkyl, dioxolanyl-C$_{0-4}$alkyl and benzodioxolanyl-C$_{0-4}$alkyl; or R$_5$ and R$_6$ taken together with the nitrogen atom to which they are attached form a C$_{3-8}$heterocycle ring optionally containing one or more heteroatoms selected from N, O or S;

n is an integer from 1 to 4;

R$_7$ and R$_8$ are the same or different and independently of each other selected from the group consisting of hydrogen, C$_{1-6}$alkyl, C$_{3-8}$cycloalkyl-C$_{0-4}$alkyl, C$_{3-8}$cycloalkenyl-C$_{0-4}$alkyl, hydroxy-C$_{1-6}$alkyl, C$_{1-4}$alkoxy-C$_{1-6}$alkyl, fluoroalkyl or fluoroalkoxy of the formula C$_n$H$_x$F$_y$ or OC$_n$H$_x$F$_y$, wherein n is an integer from 1 to 4, x is an integer from 0 to 8, y is an integer from 1 to 9 and sum of x and y is 2n+1, amino-C$_{1-6}$alkyl, C$_{1-6}$alkyl-aminio-C$_{1-6}$alkyl, C$_{1-6}$dialkyl-amino-C$_{1-6}$alkyl, C$_{1-6}$dialkyl-amino-C$_{1-6}$alkylcarbonyl, phenyl-C$_{0-4}$alkyl, phenoxy-C$_{1-4}$alkyl, phenyl-amino-C$_{1-4}$alkyl, pyridinyl-C$_{0-4}$alkyl, pyrazinyl-C$_{0-4}$alkyl, furanyl-C$_{0-4}$alkyl, tetrahydrofuranyl-C$_{0-4}$alkyl, thiophenyl-C$_{0-4}$alkyl, pyrrolyl-C$_{0-4}$alkyl, pyrrolidinyl-C$_{0-4}$alkyl, morpholinyl-C$_{1-4}$alkyl, imidazolyl-C$_{0-4}$alkyl, pyrazolyl-C$_{0-4}$alkyl, benzimidazolyl-C$_{0-4}$alkyl, piperidinyl-C$_{0-4}$alkyl, piperidinyl-C$_{1-4}$alkylcarbonyl, piperazinyl-C$_{0-4}$alkyl, tetrahydronaphthalenyl-C$_{0-4}$alkyl, indanyl-C$_{0-4}$alkyl, dioxolanyl-C$_{0-4}$alkyl and benzodioxolanyl-C$_{0-4}$alkyl; or R$_7$ and R$_8$ taken together with the nitrogen atom to which they are attached form a C$_{3-8}$heterocycle ring optionally containing one or more heteroatoms selected from N, O or S.

As noted above, where appropriate any of the aforementioned groups are optionally substituted with one or more substituents as described herein.

In this embodiment, a specific disease or a disorder or a condition that can be treated with the compounds of this invention include, without any limitation: tissue damage resulting from cell damage or death due to necrosis or apoptosis, neuronal mediated tissue damage or diseases, neural tissue damage resulting from ischemia and reperfusion injury, neurological disorders and neurodegenerative diseases, vascular stroke, cardiovascular disorders, age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders, muscular dystrophy, osteoarthritis, osteoporosis, chronic pain, acute pain, neuropathic pain, nervous insult, peripheral nerve injury, renal failure, retinal ischemia, septic shock and aging.

In another aspect of this embodiment, a specific disease, a disorder or a condition that can be treated with the compounds of this invention include, without any limitation: tissue damage resulting from cell damage or death due to necrosis or apoptosis, neuronal mediated tissue damage or diseases, cerebral ischemia, head trauma, stroke, reperfusion injury, neurological disorders and neurodegenerative diseases, vascular stroke, cardiovascular disorders, myocardial infarction, myocardial ischemia, experimental allergic encephalomyelitis (EAE), multiple sclerosis (MS), ischemia related to cardiac surgery, age-related macular degeneration, arthritis, atherosclerosis, cancer, degenerative diseases of skeletal muscle involving replicative senescence, diabetes and diabetic cardiomyopathy. As used herein, ischemia related to cardiac surgery refers to any brain damage occurring during open heart and other cardiac surgeries at which time the patient may be on a heart and/or a lung machine.

More specifically, multiple sclerosis (MS) is a debilitating, inflammatory, neurological illness characterized by demyelination of the central nervous system. The disease primarily affects young adults with a higher incidence in females. Symptoms of the disease include fatigue, numbness, tremor, tingling, dysesthesias, visual disturbances, dizziness, cognitive impairment, urologic dysfunction, decreased mobility, and depression. Four types classify the clinical patterns of the disease: relapsing-remitting, secondary progressive, primary-progressive and progressive-relapsing (see, S. L. Hauser and D. E. Goodkin, Multiple Sclerosis and Other Demyelinating Diseases in Harrison's Principles of Internal Medicine 14$^{th}$ Edition, vol. 2, Mc Graw-Hill, 1998, pp. 2409-2419).

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of PARP. That is, the compounds of the present invention have PARP inhibitory activity and may be effectively administered to ameliorate any disease state which is mediated all or in part by PARP.

In yet another embodiment of this invention, there is provided a method of affecting a neuronal activity in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula I as described herein. The neuronal activity as described herein may or may not be mediated by NMDA toxicity. Again, in this embodiment all of the compounds as described herein can be employed with specific definitions of the substituents as described hereinabove including all of the preferred embodiments as described above.

In this aspect of the embodiment of this invention, specific neuronal activity without any limitations may be enumerated as follows. Stimulation of damaged neurons, promotion of neuronal regeneration, prevention of neurodegeneration, and treatment of a neurological disorder. Generally, damaged neurons result from cerebral ischemia, retinal ischemia, or reperfusion injury. Thus the compounds of this invention improve neuronal activity thereby ameliorating the effects of ischemia.

In a further aspect of this embodiment, specific neurological disorders that may be enumerated without any limitation include: peripheral neuropathy caused by physical injury or disease state, traumatic brain injury, physical damage to the spinal cord, stroke associated with brain damage, neurological disorder relating to neurodegeneration.

Further, in this embodiment specific neurological disorder relating to neurodegeneration that may be enumerated without any limitation include: Alzheimer's disease, Parkinson's disease, Huntington's Disease and amyotrophic lateral sclerosis.

In still another embodiment of this invention, there is also provided a method of treating a cardiovascular disorder in a patient comprising administering to said patient a therapeutically effective amount of a compound, including enantiomers, stereoisomers, and tautomers of said compound and pharmaceutically acceptable salts, solvates or derivatives thereof, with said compound having the general structure shown in formula I as described herein. Again, in this embodiment all of the compounds as described herein can be employed with specific definitions of the substituents as described hereinabove including all of the preferred embodiments as described above.

In this embodiment of this invention specific cardiovascular disorder that may be enumerated include, without any limitation, coronary artery disease, myocardial infarction, angina pectoris, cardiogenic shock and cardiovascular tissue damage.

In yet another aspect of this invention the compounds of this invention are also effective in treating cancer. Typically, in treating cancer the compounds of this invention are used in conjunction with a chemotherapeutic agent, radiation therapy or any other therapy hitherto known or discovered in the future, to potentiate their effects. The primary objective of these therapies is to damage the DNA of a cancer cell thus resulting in cancerous cell death.

All of the various embodiments of the compounds used in the methods of this invention as disclosed herein can be used in the method of treating various disease states as described herein. As stated herein, the compounds used in the method of this invention are capable of inhibiting the effects of PARP and thereby alleviating the effects and/or conditions caused due to the activity of PARP. In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the following procedures of Schemes 1-4, wherein the R, $R_1$, $R_2$, $R_3$ and $R_4$ are as defined for Formula I unless otherwise indicated. It should also be noted that the Schemes provided below are for illustrative purposes only and various modifications can be made to these Schemes in arriving at the desired final compound of formula I, which modifications are readily appreciated by one skilled in the art of medicinal chemistry. Further, more detailed synthetic procedures that can be used in preparing a variety of compounds of this invention are illustrated by the specific examples that follow.

Scheme 1 illustrates a method for the preparation of a variety of compounds of formula I of this invention, wherein R is hydrogen, using the intermediate compound of formula II of this invention wherein $R_{10}$ and X are as defined herein.

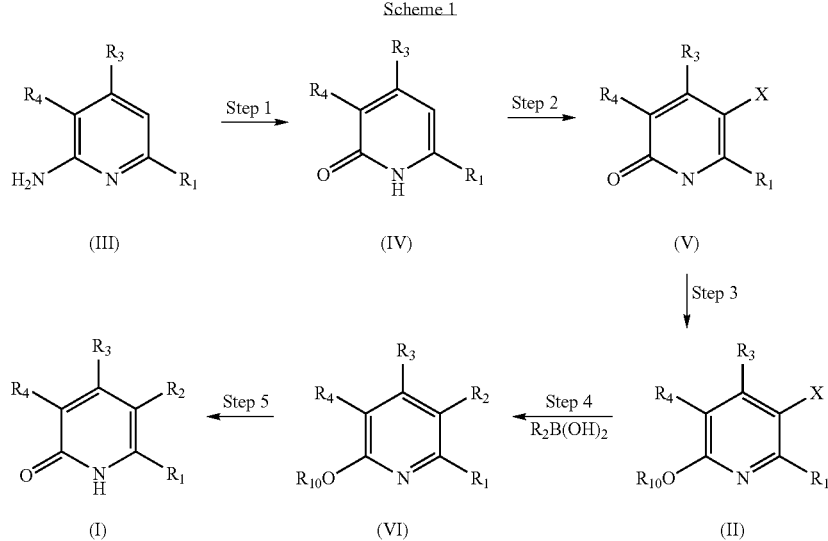

In Scheme 1, step 1, a compound of formula III is converted to a compound of formula IV using any of the known methods in the art. For instance, such conversion can be performed using any of the diazotization reactions. Typically, such a reaction is carried out under acidic conditions in the presence of a suitable nitrite salt. Examples of acids include mineral acids such as sulfuric acid or hydrochloric acid, however, any of the other inorganic or organic acids that would bring about this transformation can be employed. Examples of nitrites that can be employed include, without any limitation, ammonium nitrite; alkali metal nitrite, such as lithium nitrite, sodium nitrite, potassium nitrite; or alkaline earth metal nitrite, such as calcium nitrite and barium nitrite, etc. The diazotization reaction can be carried out at any of the desirable temperature conditions including sub-ambient, ambient or super-ambient temperatures. Typically the reaction is carried out around sub-ambient to ambient temperatures, i.e., in the temperature range of from about −20° C. to 30° C.

In Scheme 1, Step 2, the compound of formula IV is subjected to a halogenation reaction to obtain a compound of formula V. Any of the known halogenating agents that would bring about the intended transformation can be employed in this step. For example, chlorinating, brominating or iodinating reagents, such as N-chlorosuccinimide, N-bromosuccinimide, N-iodosuccinimide, or any other suitable halogenating agent can be used in the presence of suitable organic solvents such as methanol, etc. The reaction can generally be carried out at sub-ambient to ambient temperatures. More particularly, in the temperature range of from about −30° C. to about 30° C.

In Scheme 1, Step 3, the compound of formula V is converted to a compound of formula II. Typically, such reactions can be carried out using a suitable alkylating agent. Any of the known alkylating agents can be used in this step. For example, iodomethane in the presence of silver carbonate affords methylated derivative of compound of formula II. This reaction can generally be carried out at ambient conditions, however, sub-ambient to super-ambient temperature conditions can be employed depending upon the nature of the starting material as well as the alkylating agent.

In Scheme 1, Step 4, the compound of formula II is subjected to a suitable arylating, alkylating or heteroarylating agent to form the corresponding compound of formula VI. Typically this reaction can be carried out using a organoboronic acid of formula $R_2B(OH)_2$ under Suzuki coupling conditions. Thus, the reaction is generally carried out in the presence of a catalyst such as palladium tetrakis(triphenylphosphine). However, any of the other known catalysts that are suitable for this reaction can also be employed. The reaction is generally carried out at super-ambient temperatures. This reaction is particularly suitable wherein Ar is aryl. Such coupling reactions can also be carried out under other known reaction conditions. For instance, the compound of formula II can be reacted directly with ArH, wherein Ar is heteroaryl in the presence of a catalyst such as copper iodide and a base such as potassium carbonate or sodium hydroxide or a mixture thereof (see Scheme 1A). The various starting materials, such as boronic acids or boronic esters as employed herein can either be purchased or synthesized by methods known in the art.

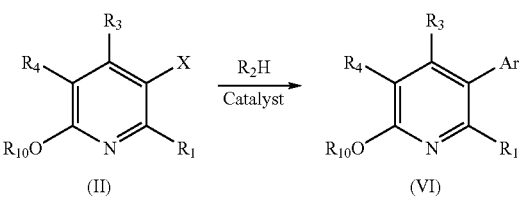

The heteroarylation reaction as described herein can also be carried out under various other reaction conditions. For instance, the heteroarylation can be carried out by subjecting a compound of formula II to suitable cyclization reaction, wherein X is a group that can be cyclyzed to form a heteroaryl ring. For instance, when X is N'-formyl-hydrizido-carbonyl, it can be cyclyzed under suitable reaction conditions to form [1,3,4]-oxadiazolyl (see, e.g., Example 14 below). Similarly, various other heteroaryl can be formed in this fashion, including without any limitation, methyl-[1,3,4]-oxadiazolyl, [1,2,4]-oxadiazolyl, methyl-[1,2,4]-oxadiazolyl, triazolyl, methyl-triazolyl, dimethyl-triazolyl, and the like.

Finally, in Scheme 1, Step 5, the compound of formula VI is converted to the compound of formula I wherein R is hydrogen. The cleavage of the $R_{10}O$-group can be carried out using any of the known procedures in the art. For example, if $R_{10}$ is benzyl the cleavage can be carried out using palladium on charcoal. If $R_{10}$ is $C_{1-4}$alkyl the cleavage can be carried out using silyl reagents such as iodotrimethylsilane or sodium iodide/chlorotrimethylsilane, etc.

Scheme 2 illustrates another method for the preparation of the compounds of formula I using a variation of the Suzuki coupling as described in Scheme 1. As illustrated herein a boronic compound of formula VII is derived from the pyridone part of the molecule which then can be reacted with a desirable halogen substituted compound of formula $R_2X$ wherein X is halogen to form a compound of formula VI that can be converted further to compound of formula I as described above. The Suzuki coupling of compound of formula VII with compound of formula $R_2X$ can be carried out under essentially similar conditions as described above or using any of the art recognized procedures. For instance, the boron compound of formula VII is formed by the reaction of compound of formula II with bis(pinacolato)diborane VIII in the presence of a suitable catalyst such as dichloro[1,1'-bis(diphenylphosphino)ferrocene]palladium. Alternatively, the boron compound can also be prepared by the reaction of pinacolborane IX with a compound of formula II. The boron compound, VII is then reacted with compound of formula $R_2X$ to form compound of formula VI.

It should be noted however that various modifications can be made to synthetic sequences in either Scheme 1 or Scheme 2 in order to prepare compound of formula I, which are readily appreciated by one of skilled in the art of medicinal chemistry. For instance, as noted in either Schemes 1 or 2, the Suzuki coupling can first be carried out on an unsubstituted pyridine derivative of formula II (i.e., wherein $R_3$ and $R_4$ are both hydrogen), and then desirable $R_3$ and $R_4$ substituents can be inserted into the resulting compound of formula VI before converting it into the desirable final compound of formula I. Again, as noted above, several of the specific modifications that can be made to these schemes are apparent from the examples that follow hereinbelow.

Scheme 3 illustrates the preparation of the compounds of formula (I) of this invention wherein $R_2$ is Ar—Y, wherein Ar is substituted or unsubstituted thienyl, furanyl, phenyl or pyridinyl and Y is $SO_2NR_5R_6$, wherein $R_5$ and $R_6$ are as defined hereinabove.

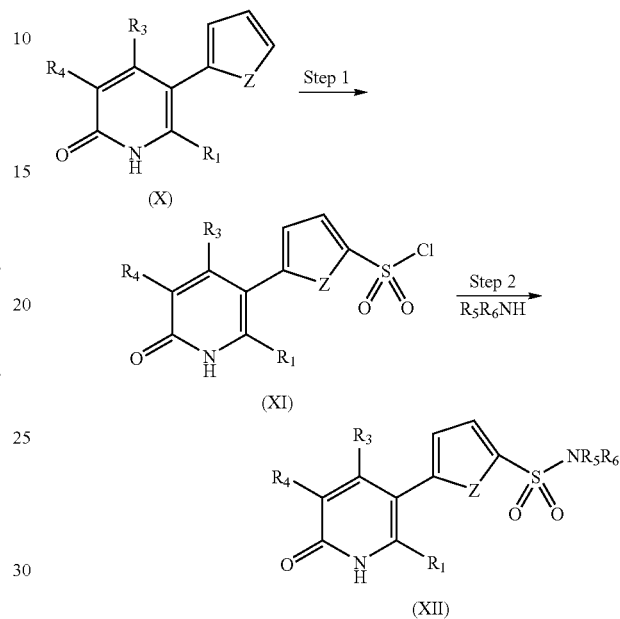

The compound of formula X is prepared in accordance with any of the procedures described in Schemes 1, 1A or 2, wherein Z is either O or S and $R_1$, $R_3$ and $R_4$ are as described hereinabove. In Scheme 3, Step 1, the compound of formula X is subjected to chlorosulfonylation reaction to form compound of formula XI. Any of the known chlorosulfonylation

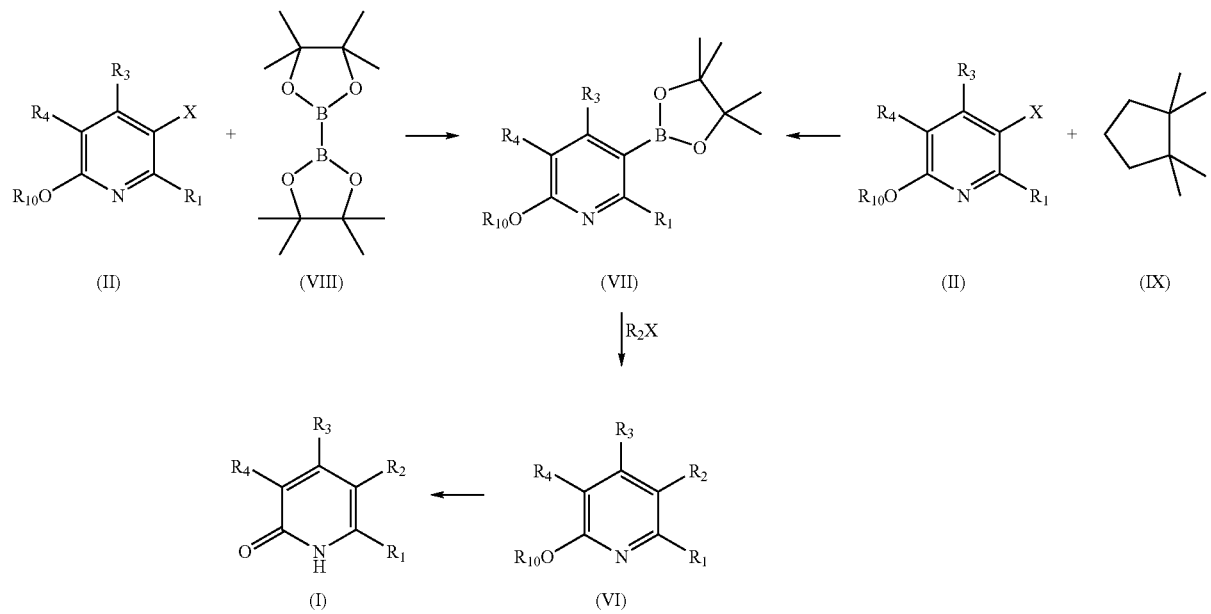

reactions that can bring about this transformation can be employed herein. For instance, without any limitation, compound of formula X can be chlorosulfonylated to compound of formula XI using chlorosulfonic acid in the presence of phosphorus pentoxide in a suitable organic solvent. The reaction can typically be carried out at sub-ambient temperatures, however, ambient to super-ambient temperatures can also be employed depending upon the nature of the starting compound of formula X.

In Scheme 3, Step 2, the compound of formula XI is then reacted with a desirable amine of formula $R_5R_6NH$ to form the sulfonamides of formula XII. This reaction can again be carried out using any of the art recognized procedures. For example, this reaction can be carried out under solid phase conditions using piperidinomethyl polystyrene. Again, various modifications can be made in forming the final sulfonamide compound of formula XII, some of which are apparent from the detailed description of the examples that follow, particularly, Examples 24 through 122.

Scheme 4 illustrates the preparation of the compounds of formula I of this invention wherein $R_2$ is Ar—Y wherein Ar is substituted or unsubstituted thienyl, furanyl, phenyl or pyridinyl and Y is $CH_2NR_7R_8$, wherein $R_7$ and $R_8$ are as described hereinabove.

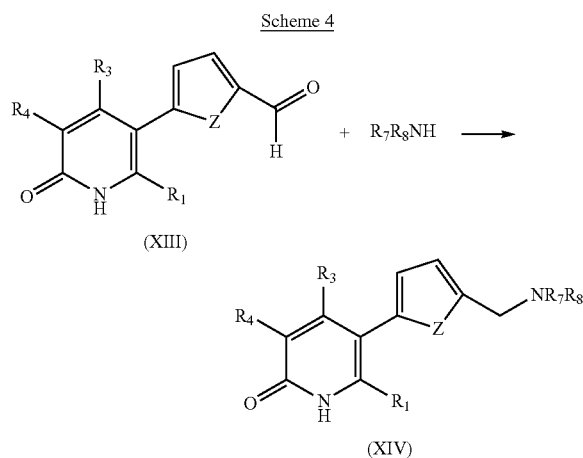

The compound of formula XIII can be prepared in accordance with any of the known procedures or using the procedures as described in Schemes 1, 1A or 2, wherein Z is either O or S and $R_1$, $R_3$ and $R_4$ are as described hereinabove. Then, the compound of formula XIII is reacted with a suitable amine of formula $R_7R_8NH$ to form the compound of formula XIV. This reaction is generally carried out under reductive conditions, for example, in the presence of a reducing agent such as sodium cyanoborohydride and acetic acid in a suitable organic solvent. The reaction is generally carried out at ambient temperature, however, it can also be carried out at higher temperatures depending upon the starting compound of formula XIII. Alternatively, this reaction can also be carried out under solid phase conditions using MP-cyanoborohydride.

Similarly, the compounds of formula I wherein $R_2$ is Ar—Y, wherein Ar is substituted or unsubstituted thienyl or furanyl and Y is $(CH_2)_nNR_7R_8$, wherein n is 2 to 4 can also be prepared using the procedures of Scheme 4, but using the appropriate starting compound of formula XIII. Again, various modifications can be made in forming the final methylamine (or alkylamine) compound of formula XIV, some of which are apparent from the detailed description of the examples that follow, particularly, Examples 123 through 197.

The compounds of formula I wherein $R_2$ is Ar—Y and wherein Y is —$CH_2OH$ can similarly be prepared from compound of formula XIII. This is effected by reacting the latter compound with, for example, sodium borohydride, or under any other reductive conditions to form compound of formula I wherein Y is —$CH_2OH$. Similarly, various other compounds of formula I wherein Y is —$CH(OH)R_9$ can be synthesized by employing the appropriate starting material XIII, wherein $R_9$ is as defined herein. Alternatively, the compounds of formula I wherein Y is —$CH(OH)R_9$ can also be prepared by lithiation of compound of formula I wherein Y is hydrogen, and then reacting the resulting product with aldehydes of formula $R_9CHO$.

The compounds of formula I wherein Y is —$(CH_2)_nNHC(O)R_9$ wherein n and $R_9$ are as described herein can be prepared by initially carrying out a reductive amination of a suitable compound of formula XIII with ammonium acetate and then coupling the resulting aminomethyl compound with appropriate carboxylic acid or its chlorides.

The compounds of formula I in which Y is —CH=$NOR_9$, wherein $R_9$ is as defied herein can similarly be prepared by reacting appropriate compound of formula XIII with a hydroxylamine of formula, $R_9ONH_2$ under suitable reaction conditions.

The compounds of formula I wherein Y is —$C(O)R_9$ are prepared by lithiation of compound of formula I wherein Y is hydrogen, and then converting it into the desirable compound by reaction with Weinreb amide $R_9CONMe(OMe)$, wherein $R_9$ is as defined herein.

The compounds of formula I wherein Y is —$C(O)NR_7R_8$ wherein $R_7$ and $R_8$ are as defined herein can be prepared by reacting compound of formula I wherein Y is —COOH with amines of formula $NHR_7R_8$. Various suitable condensing agents such as carbodiimides, fluor-N,N,N'N'-tetramethylformamidinium hexafluorophosphate (TFFH) or propanephosphonic anhydride (PPA) can be employed as condensating agents for this amidation reaction. The starting material, compounds of formula I wherein Y is —COOH can be prepared by the methods described herein and by employing the appropriate starting materials. The compounds of formula I wherein Y is —$C(O)NR_7R_8$ can also be prepared from the corresponding compounds of formula VI, as described herein. The corresponding compounds of formula VI can in turn be prepared by suitable modifications of the synthetic schemes as described herein.

The compounds of formula I wherein Y is —$NHSO_2R_9$, wherein $R_9$ is as defined herein, can be prepared by reacting compound of formula I wherein Y is —$NH_2$ with sulfonyl chlorides of formula $R_9SO_2Cl$ in the presence of a suitable base. Similarly, the compounds of formula I wherein Y is —$NHC(O)R_9$ are prepared by using corresponding compounds of formula I wherein Y is —$NH_2$, which are reacted with a suitable acid chloride in the presence of a base or with a suitable acid in the presence of a condensing agent.

Finally, in yet another embodiment of this invention, there is also provided a pharmaceutical composition comprising one or more pharmaceutically acceptable carriers, diluents, and/or excipients and one or more compounds of formula (I) of this invention, including enantiomers, stereoisomers, and tautomers of said compounds and pharmaceutically acceptable salts, solvates or derivatives thereof.

As described herein, the pharmaceutical compositions of this invention feature PARP inhibitory activity and thus are useful in treating any disease, condition or a disorder caused due to the effects of PARP in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES (GENERAL)

Reactions generally are run under a nitrogen atmosphere. Solvents are dried over magnesium sulfate and are evaporated under vacuum on a rotary evaporator. TLC analyses are generally performed with EM Science silica gel 60 F254 plates with visualization by UV irradiation. Flash chromatography is performed using Alltech prepacked silica gel cartridges. The $^1$H NMR spectra are typically run at 300 MHz on a Gemini 300 or Varian VXR 300 spectrometer and are determined in a deuterated solvent, such as DMSO-$D_6$ or $CDCl_3$ unless otherwise noted. Chemical shifts values are indicated in parts per million (ppm) with reference to tetramethylsilane (TMS) as the internal standard. The LC/MS are typically run on a Micromass Platform LCZ.

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "eq." refers to mole equivalents, "M" refers to molar, "mM" refers to millimolar, "µM" refers to micromolar, "nM" refers to nanomolar, "L" refers to liters, "mL" or "ml" refers to milliliters, "µL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "rt" refers to room temperature, "THF" refers to tetrahydrofuran, "DMF" refers to dimethylformamide, "NMP" refers to 1-methyl-2-pyrrolidinone, "DMF" refers to dimethylformamide, "$D_6$-DMSO" refers to deuterated dimethyl sulfoxide, "TMS" refers to trimethylsilyl, "TFA" refers to trifluoroacetic acid, "nBuLi" refers to n-butyllithium, "DMAP" refers to 4-dimethylaminopyridine, "NBS" refers to N-bromosuccinimide, "NIS" refers to N-iodosuccinimide, "$PdCl_2$(dppf)" refers to 1,1'-bis(diphenylphosphino)-ferrocenepalladium(II) chloride, "PPA" refers to propanephosphonic anhydride, "TFFH" refers to fluor-N,N,N',N'-tetramethylformamidinium hexafluorophosphate (from Fluka), "MP" refers to highly crosslinked macroporous polystyrene, "brine" refers to a saturated aqueous sodium chloride solution, "SCX" refers to cation exchanger (strong cation exchanger), "N" refers to normal, "TLC" refers to thin layer chromatography, "HPLC" refers to high performance liquid chromatography, "RP-HPLC" refers to reverse phase high performance liquid chromatography, "HRMS" refers to high resolution mass spectrum, "L.O.D." refers to loss on drying, "µCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets;

br=broad; LC=liquid chromatograph; MS=mass spectrograph; ESI/MS=electrospray ionization/mass spectrograph; RT=retention time; M=molecular ion.

The following examples describe the procedures used for the preparation of various starting materials employed in the preparation of the compounds of this invention.

Preparation 1

3-Bromo-5-ethyl-6-methoxy-2-methylpyridine

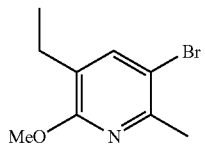

Step 1: 3-Ethyl-6-methyl-1H-pyridin-2-one: A solution of 3-ethyl-6-methyl(pyridin-2-yl)amine (also see Reimlinger, H. et al. Chem. Ber., 109, 118-124 (1976); Sawyer, J. R. H.; Wibberley, D. G. J. Chem. Soc (Perkin 1), 113801143 (1973); Childs, R. F.; Johnson, A. W. Chem. Ind. (London), 542 (1964)) (41.2 g, 0.4 mol) in sulfuric acid (817 mL) is chilled in an ice bath. To this solution is added a solution of sodium nitrite (23.81 g, 0.345 mol) in H$_2$O (200 mL). The resulting mixture is stirred at ambient temperature for 20 hr. The mixture is brought to pH 9.0 by addition of 3N sodium hydroxide (370 mL) and extracted with ethyl acetate (9×200 mL). The combined organic extract is washed with brine (300 mL), dried, filtered and concentrated. The residue is crystallized from heptane (300 mL) to afford 3-ethyl-6-methyl-1H-pyridin-2-one (also disclosed by Mistryukov, E. A. et al. Izv. Akad. Nauk SSR 512-519 (1964); Chem. Abstr. 64, 90713) (35.78 g, 87% yield) as a white, crystalline solid. The resulting product exhibited characteristic $^1$H NMR spectrum consistent with that reported in the literature.

Step 2: 5-Bromo-3-ethyl-6-methyl-1H-pyridin-2-one: A 2 neck round bottom flask, equipped with an overhead stirrer is charged with 3-ethyl-6-methyl-1H-pyridin-2-one (33.45 g, 0.26 mol) obtained from Step 1 as described above, N-bromosuccinimide (48.6 g, 0.273 mol) and methanol (867 mL) and the mixture stirred at ambient temperature for 17 hr. The mixture is then concentrated to a volume of 200 mL, diluted with water (600 mL) and the resulting suspension is chilled in an ice bath. The solids are collected by filtration, washed with water (300 mL) and dried in a vacuum oven at 64° C. for 24 hr to afford 5-bromo-3-ethyl-6-methyl-1H-pyridin-2-one (53.56 g, 95.3% yield) as an off white solid. LC/MS: MS m/e=215/217 (M+H), RT 2.64 min.

Step 3: 3-Bromo-5-ethyl-6-methoxy-2-methylpyridine: A mixture of 5-bromo-3-ethyl-6-methyl-1H-pyridin-2-one (41.8 g, 0.193 mol) obtained from Step 2 as described above, iodomethane (70 mL, 1.12 mol), silver carbonate (72 g, 0.261 mol) and dichloromethane is mechanically stirred at ambient temperature for 17 hr (The reaction vessel is wrapped in aluminum foil). An additional portion of iodomethane (70 mL, 1.12 mol) is added and stirring continued for an additional 20 hr. The reaction mixture is filtered through a pad of Celite and the filter cake is washed with dichloromethane.

The combined filtrate and wash is concentrated to afford the title compound (44.35 g, 99.9% yield) as a yellow oil.

Preparation 2

5-(5-Ethyl-2-methyl-6-oxo-1,6-dihydropyridin-3-yl)thiophene-2-carbaldehyde

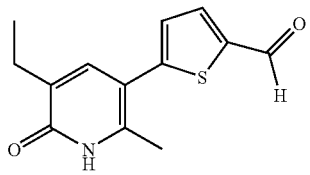

Step 1: 3-Ethyl-2-methoxy-6-methyl-5-(4,4,5,5-tetramethyl-[1,3,2-dioxaborolan-2-yl)pyridine: Under a nitrogen atmosphere, a three neck round bottom flask is charged with bis(pinacolato)diborane (9.70 g, 38.39 mmol), potassium acetate (11.25 g, 114.62 mmol), and dichloro[1,1'-bis(diphenylphosphino)ferrocene]palladium dichloromethane adduct [PdCl$_2$(dppf), 839 mg, 1.15 mmol] followed by anhyd dimethyl sulfoxide (130 mL). After stirring a short while, a solution of 5-bromo-3-ethyl-2-methoxy-6-methylpyridine (8.8 g, 38.24 mmol) in dimethyl sulfoxide (20 mL) is added. The resulting mixture is heated to 110° C. for 30 hr. The reaction is cooled, poured into ethyl acetate (200 mL) and washed with water, with brine, dried over sodium sulfate, filtered and concentrated. The dark residue is purified by flash chromatography eluting with heptane-10% ethyl acetate to afford 3-ethyl-2-methoxy-6-methyl-5-(4,4,5,5-tetramethyl-[1,3,2-dioxaborolan-2-yl)pyridine as a pale green solid (78% yield). MS: m/e=278 (M+H); $^1$H-NMR (CDCl$_3$, δ ppm) 7.96 (1H, s), 3.95 (3H, s), 2.62 (3H, s), 2.57 (2H, q), 1.33 (12H, s), 1.19 (3H, t).

Alternatively, this material is also prepared as follows. A mixture of 5-bromo-3-ethyl-2-methoxy-6-methylpyridine (20 g, 86.91 mmol), pinacolborane (14.5 g, 113.3 mmol), dichloro[1,1'-bis(diphenylphosphino)ferrocene]palladium dichloromethane adduct (3.4 g, 4.64 mmol), triethylamine (40 mL, 286 mmol) and dioxane (200 mL) under a nitrogen atmosphere is heated to 90° C. for 1.5 d. The reaction is cooled, diluted with ethyl acetate and filtered through a pad of silica gel. The filtrate is cooled to 0° C. and carefully ice cold water is added (CAUTION, EXOTHERMIC). After the foaming has ceased, the mixture is washed with water, dried over sodium sulfate, filtered and concentrated. The residue is purified by flash chromatography eluting with heptane-20% ethyl acetate to afford 3-ethyl-2-methoxy-6-methyl-5-(4,4,5,5-tetramethyl-[1,3,2-dioxaborolan-2-yl)pyridine (82% yield) as a white solid.

Step 2: 5-(5-Ethyl-6-methoxy-2-methylpyridin-3-yl)thiophene-2-carbaldehyde: To a mixture of 5-bromothiophene-2-carbaldehyde (1.25 g, 7.14 mmol), 3-ethyl-2-methoxy-6-methyl-5-(4,4,5,5-tetramethyl-[1,3,2-dioxaborolan-2-yl)pyridine (1.32 g, 4.76 mmol) prepared in accordance with one of the procedures of Step 1, potassium carbonate (2.63 g, 7.14 mmol) and dimethylformamide (30 mL) under a nitrogen atmosphere is added dichloro[1,1'-bis(diphenylphosphino)ferrocene]-palladium dichloromethane adduct (0.2 g, 6 mol %) and the mixture is stirred at 90° C. for 2 hr. The reaction is cooled, diluted with water and washed with water. The organic layer is separated, dried, filtered and concentrated. The residue is purified by flash chromatography eluting with heptane-30% ethyl acetate to afford 5-(5-ethyl-6-methoxy-2-methylpyridin-3-yl)thiophene-2-carbaldehyde (1.2 g, 103% yield).

Step 3: 5-(5-Ethyl-2-methyl-6-oxo-1,6-dihydropyridin-3-yl)thiophene-2-carbaldehyde: To a mixture of 5-(5-ethyl-6-methoxy-2-methylpyridin-3-yl)thiophene-2-carbaldehyde (0.7 g, 2.9 mmol) prepared in accordance with the procedures of Step 2 as described above, potassium iodide (1.43 g, 8.6 mmol) and acetonitrile (15 mL) is added chlorotrimethylsilane (1.1 mL, 8.6 mmol) at room temperature then the reaction is heated at 60° C. for 0.5 hr. Solid product begins to form so more solvent is added to facilitate stirring. The solids are collected by filtration, washed with water, with ether and dried to afford 5-(5-ethyl-2-methyl-6-oxo-1,6-dihydropyridin-3-yl)thiophene-2-carbaldehyde (1.2 g, 61% yield). MS: m/e=248 (M+H).

Preparation 2A 3-(5-Ethyl-6-methoxy-2-methyl-pyridin-3-yl)-benzaldehyde

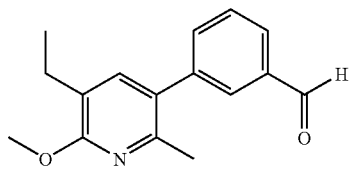

Preparation 2, Steps 1 and 2 are substantially repeated in Preparation 2A except for utilizing the respective starting materials to obtain the title compound: MS: m/e=256 (M+H).

Preparation 3

5-(5-Ethyl-2-methyl-6-oxo-1,6-dihydropyridin-3-yl)furan-2-carbaldehyde

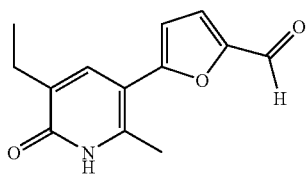

Step 1: 5-(5-Ethyl-6-methoxy-2-methylpyridin-3-yl)furan-2-carbaldehyde: To a mixture of 5-bromofuran-2-carbaldehyde (1.25 g, 7.14 mmol), 3-ethyl-2-methoxy-6-methyl-5-(4,4,5,5-tetramethyl-[1,3,2-dioxaborolan-2-yl)pyridine (1.32 g, 4.76 mmol), prepared in accordance with one of the procedures of Step 1, PREPARATION 2, potassium carbonate (2.63 g, 7.14 mmol) and dimethylformamide (30 mL) under a nitrogen atmosphere is added dichloro[1,1'-bis (diphenylphosphino)ferrocene]-palladium dichloromethane adduct (0.2 g, 6 mol %) and the mixture is stirred at 90° C. for 2 hr. The reaction is cooled, diluted with water and washed with water. The organic layer is separated, dried, filtered and concentrated. The residue is purified by flash chromatography eluting with heptane-30% ethyl acetate to afford 5-(5-ethyl-6-methoxy-2-methylpyridin-3-yl)furan-2-carbaldehyde (1.2 g, 103% yield). MS: m/e=246 (M+H). $^1$H-NMR (CDCl$_3$, δ ppm) 9.64 (s, 1H), 7.79 (s, 1H), 7.33 (d, 1H, J=3.8 Hz), 6.67 (d, 1H, J=3.8 Hz); 3.99 (s, 3H); 2.64 (s, 3H); 2.61 (q, 2H, J=7.6 Hz), 1.21 (t, 3H, J=7.6 Hz).

Step 2: 5-(5-Ethyl-2-methyl-6-oxo-1,6-dihydropyridin-3-yl)furan-2-carbaldehyde: To a mixture of 5-(5-ethyl-6-methoxy-2-methylpyridin-3-yl)furan-2-carbaldehyde (0.7 g, 2.9 mmol) prepared in accordance with the procedures of Step 1 as described above, potassium iodide (1.43 g, 8.6 mmol) and acetonitrile (15 mL) is added chlorotrimethylsilane (1.1 mL, 8.6 mmol) at room temperature then the reaction is heated at 60° C. for 0.5 hr. Solid product begins to form so more solvent is added to facilitate stirring. The solids are collected by filtration, washed with water, with ether and dried to afford 5-(5-ethyl-2-methyl-6-oxo-1,6-dihydropyridin-3-yl)furan-2-carbaldehyde (1.2 g, 61% yield). MS: m/e=232 (M+H).

Preparation 3A 4-(5-Ethyl-2-methyl-6-oxo-1,6-dihydropyridin-3-yl)-furan-2-carbaldehyde

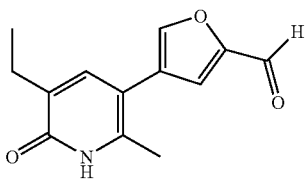

Step 1: 4-(5-Ethyl-6-methoxy-2-methyl-pyridin-3-yl)-furan-2-carbaldehyde: Step 1 of PREPARATION 3 is substantially repeated in this preparation except for utilizing the appropriate starting material, 160 mg of 3-ethyl-2-methoxy-6-methyl-5-(4,4,5,5-tetramethyl-[1,3,2-dioxaborolan-2-yl) pyridine and appropriate amounts of reagents to afford 62 mg (44% yield) of the title compound. MS: m/e=246 (M+H); $^1$H-NMR (CDCl$_3$, δ ppm) 9.71 (s, 1H), 7.72 (s, 1H), 7.35 (d, 1H, J=1.0 Hz), 7.26 (d, 1H, J=1.0 Hz); 3.97 (s, 3H); 2.58 (q, 2H, J=7.6 Hz), 2.48 (s, 3H); 1.20 (t, 3H, J=7.6 Hz).

Step 2: 4-(5-Ethyl-2-methyl-6-oxo-1,6-dihydropyridin-3-yl)-furan-2-carbaldehyde: Step 2 of PREPARATION 3 is substantially repeated in this preparation except for utilizing 72 mg of 4-(5-ethyl-6-methoxy-2-methyl-pyridin-3-yl)-furan-2-carbaldehyde and appropriate amounts of other reagents to afford 53 mg of the title compound; MS: m/e=232 (M+H).

Preparation 4

5-[5-(Ethyl-2-methyl-6-oxo-1,6-dihydropyridin-3-yl)thiophen-2-yl]acetaldehyde

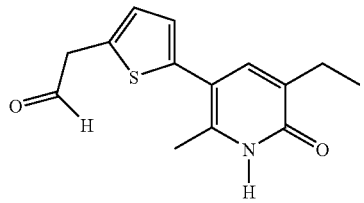

Step 1: 3-Ethyl-5-[5-(2-hydroxyethyl)thiophen-2-yl]-6-methyl-1H-pyridin-2-one: Steps 1 and 2 of PREPARATION 3 are substantially repeated in this preparation except for utilizing the appropriate starting materials to afford the title compound; m/e 264 (M+H).

Step 2: 5-[5-(Ethyl-2-methyl-6-oxo-1,6-dihydropyridin-3-yl)thiophen-2-yl]acetaldehyde: 3-Ethyl-5-[5-(2-hydroxyethyl)thiophen-2-yl]-6-methyl-1H-pyridin-2-one is oxidized using a suitable oxidizing agent to afford the title compound; m/e 262 (M+H).

Preparation 5

N-(3,5-difluorobenzyl)-5-(5-ethyl-6-methoxy-2-methylpyridin-3-yl)thiophene-2-carboxamide

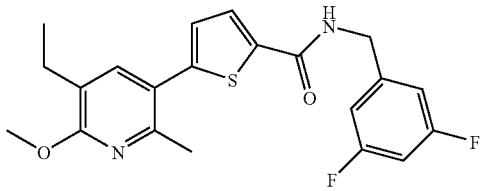

Step 1: 5-Bromo-thiophene-2-carboxylic acid 3,5-difluoro-benzylamide: Thionyl chloride (35 ml) is added dropwise to 5-bromo-2-thiophenecarboxylic acid (4.92 g, 23.77 mmol) at 0° C., and the mixture is then heated at 90° C. overnight. After the mixture has cooled to room temperature, the solvent is removed in vacuo, and the residue is washed with cold heptane. 5-Bromothiophene-2-carbonyl chloride is obtained as an almost white solid. 3,5-Difluorobenzylamine (209 mg, 1.46 mmol) is added to a mixture of 5-bromothiophene-2-carbonyl chloride (300 mg, 1.33 mmol), piperidinomethylpolystyrene (410 mg, 3.5 mmol/g, 1.44 mmol) in anhydrous dichloromethane (5 mL) and stirred for 2.5 hr. The reaction mixture is diluted with dichloromethane and filtered through silica gel. The filtrate is concentrated to afford 5-bromo-thiophene-2-carboxylic acid 3,5-difluoro-benzylamide as a white solid (400 mg, 90% yield).

Step 2: N-(3,5-difluorobenzyl)-5-(5-ethyl-6-methoxy-2-methylpyridin-3-yl)thiophene-2-carboxamide: Step 1 of PREPARATION 3 is substantially repeated utilizing 5-bromo-thiophene-2-carboxylic acid 3,5-difluoro-benzylamide (276 mg) as prepared above, 3-ethyl-2-methoxy-6-methyl-5-(4,4,5,5-tetramethyl-[1,3,2-dioxaborolan-2-yl)pyridine (230 mg) and appropriate amounts of other reagents to afford 126 mg (38% yield) of the title compound as a yellow solid; MS: m/e=403 (M+H)

Preparation 6

[5-(5-Ethyl-6-methoxy-2-methylpyridin-3-yl)-furan-2-yl]-(4-phenylpiperazin-1-yl)-methanone

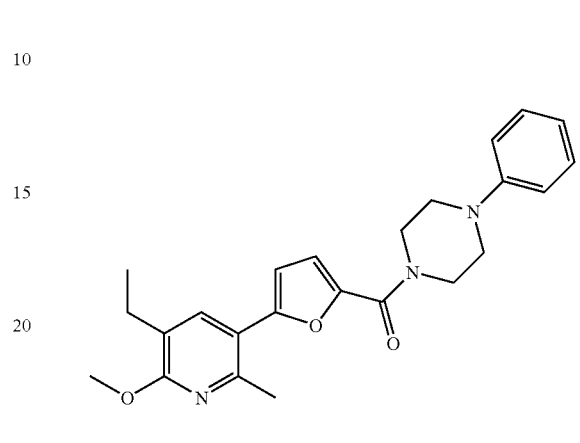

Step 1: (5-Bromo-furan-2-yl)-(4-phenyl-piperazin-1-yl)-methanone: A mixture of 5-bromo-2-furancarboxylic acid (7.17 g, 37.54 mmol) and thionyl chloride (55 ml) is heated at 90° C. overnight. After the mixture has cooled to room temperature, the solvent is removed in vacuo, and the residue is washed with heptane. 5-Bromofuran-2-carbonyl chloride is obtained as a pale beige solid.

N-Phenylpiperazine (1.3 ml, 8.51 mmol) is added to a mixture of 5-bromofuran-2-carbonyl chloride (1.5 g, 7.16 mmol), piperidinomethylpolystyrene (2.2 g, 3.5 mmol/g, 7.7 mmol) in anhydrous dichloromethane (30 mL) and stirred for 2.5 hr. The reaction mixture is diluted with dichloromethane and filtered through silica gel. The filtrate is concentrated to afford (5-bromo-furan-2-yl)-(4-phenyl-piperazin-1-yl)-methanone as a white solid (1.85 g, 77% yield); MS: m/e=336 (M+H). $^1$H-NMR (CDCl$_3$, δ ppm) 7.03 (m, 6H); 6.45 (d, 1H); 3.96 (s, 4H); 3.28 (m, 4H).

Step 2: [5-(5-Ethyl-6-methoxy-2-methylpyridin-3-yl)-furan-2-yl]-(4-phenylpiperazin-1-yl)-methanone: Step 1 of PREPARATION 3 is substantially repeated utilizing (5-Bromo-furan-2-yl)-(4-phenyl-piperazin-1-yl)-methanone (425 mg) as prepared above, 3-ethyl-2-methoxy-6-methyl-5-(4,4,5,5-tetramethyl-[1,3,2-dioxaborolan-2-yl)pyridine (318 mg) and appropriate amounts of other reagents to afford 350 mg (75% yield) of the title compound as a yellow oil; MS: m/e=406 (M+H).

Preparation 7

5'-Ethyl-2'-methyl-6'-oxo-1',6'-dihydro-[3,3']bipyridinyl-5-carboxylic acid

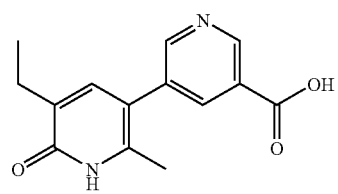

Step 1: 5'-Ethyl-6'-methoxy-2'-methyl-[3,3']bipyridinyl-5-carboxylic acid: Step 1 of PREPARATION 3 is substantially repeated utilizing the respective starting material in appropriate quantities, 3-ethyl-2-methoxy-6-methyl-5-(4,4,5,5-tetramethyl-[1,3,2-dioxaborolan-2-yl)pyridine (5 g) and appropriate amounts of other reagents to afford 3.76 g (77% yield) of the title compound (with the additional step of acidification of the reaction mixture to pH 4 with 1N HCl solution). MS: m/e=273 (M+H). $^1$H-NMR (CDCl$_3$, δ ppm) 9.33 (d, 1H, J=2.0 Hz); 8.88 (d, 1H, J=2.0 Hz); 8.60 (t, 1H, J=2.0 Hz), 7.28 (s, 1H); 4.02 (s, 3H); 2.62 (q, 2H, J=7.6 Hz); 2.43 (s, 3H); 1.21 (t, 3H, J=7.6 Hz).

Step 2: 5'-Ethyl-2'-methyl-6'-oxo-1',6'-dihydro-[3,3']bipyridinyl-5-carboxylic acid: Step 2 of PREPARATION 3 is substantially repeated utilizing 4.88 g of 5'-ethyl-6'-methoxy-2'-methyl-[3,3']bipyridinyl-5-carboxylic acid and appropriate amounts of other reagents to afford 1.99 g (47% yield) of the title compound. MS: m/e=259 (M+H). $^1$H-NMR (D6-DMSO, δ ppm) 9.03 (d, 1H, J=2.0 Hz); 8.80 (d, 1H, J=2.0 Hz); 8.21 (t, 1H, J=2.0 Hz); 7.30 (s, 1H); 2.42 (q, 2H, J=7.3 Hz), 2.18 (s, 3H); 1.11 (t, 3H, J=7.3 Hz).

Preparation 8

5'-Ethyl-2'-methyl-6'-oxo-1',6'-dihydro-[2,3']bipyridinyl-4-carboxylic acid

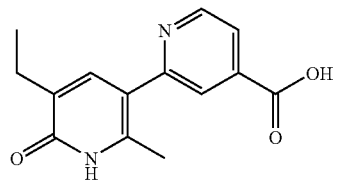

Step 1: 5'-Ethyl-6'-methoxy-2'-methyl-[2,3']bipyridinyl-4-carboxylic acid: Step 1 of PREPARATION 3 is substantially repeated utilizing the respective starting material in appropriate quantities, 3-ethyl-2-methoxy-6-methyl-5-(4,4,5,5-tetramethyl-[1,3,2-dioxaborolan-2-yl)pyridine (1 g) and appropriate amounts of other reagents to afford 0.30 g (30% yield) of the title compound (with the additional step of acidification of the reaction mixture to pH 4 with 1N HCl solution). MS: m/e=273 (M+H).

Step 2: 5'-Ethyl-2'-methyl-6'-oxo-1',6'-dihydro-[2,3']bipyridinyl-4-carboxylic acid: Step 2 of PREPARATION 3 is substantially repeated utilizing 283 mg of 5'-ethyl-6'-methoxy-2'-methyl-[2,3']bipyridinyl-4-carboxylic acid and appropriate amounts of other reagents to afford 206 mg (80% yield) of the title compound. MS: m/e=259 (M+H). $^1$H-NMR (D6-DMSO, δ ppm) 13.70 (s, 1H); 11.68 (s, 1H); 8.80 (d, 1H, J=5.0 Hz); 7.85 (s, 1H); 7.70 (dd, 1H, J=5.0 and 1.2 Hz); 7.52 (s, 1H); 2.42 (q, 2H, J=7.3 Hz), 2.32 (s, 3H); 1.11 (t, 3H, J=7.3 Hz).

Preparation 9

5'-Ethyl-2'-methyl-6'-oxo-1',6'-dihydro-[2,3']bipyridinyl-6-carboxylic acid

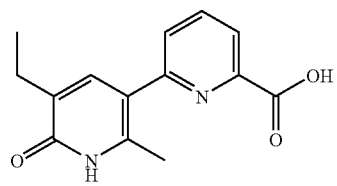

Step 1: 5'-Ethyl-6'-methoxy-2'-methyl-[2,3']bipyridinyl-6-carboxylic acid ethyl ester: Step 1 of PREPARATION 3 is substantially repeated utilizing ethyl 6-bromopicolinate (1.06 g, 4.6 mmol), 3-ethyl-2-methoxy-6-methyl-5-(4,4,5,5-tetramethyl-[1,3,2-dioxaborolan-2-yl)pyridine (1.66 g, 6 mmol) and appropriate amounts of other reagents to afford 0.75 g (54% yield) of the title compound. MS: m/e=301 (M+H).

Step 2: 5'-Ethyl-2'-methyl-6'-oxo-1',6'-dihydro-[2,3']bipyridinyl-6-carboxylic acid: 5'-Ethyl-6'-methoxy-2'-methyl-[2,3']bipyridinyl-6-carboxylic acid ethyl ester (750 mg, 2.5 mmol) is suspended in acetonitrile and, after addition of KI (1.04 g, 6.25 mmol) and trimethylsilyl chloride, heated to 80° C. under argon for 3 h. This is followed by cooling to room temperature, concentration, addition of 50 ml of water and filtration with suction. The resulting ester (710 mg) is dissolved in MeOH/THF (4/1, 10 ml) and stirred with 1N LiOH solution (7.5 ml) at RT. After 1.5 h, 2N KHSO4 solution is used to acidify, and the precipitate is filtered off with suction. The mother liquor is concentrated and dried in vacuo overnight. The precipitate and the residue are combined and purified by chromatography on silica gel with ethyl acetate/methanol (1/1); yield: 630 mg (98%). MS: m/e=259 (M+H). $^1$H-NMR (D6-DMSO, δ ppm) 11.65 (s, 1H); 7.91 (t, 1H, J=7.7 Hz); 7.84 (d, 1H, J=7.7 Hz); 7.60 (d, 1H, J=7.7 Hz); 7.51 (s, 1H); 2.42 (q, 2H, J=7.4 Hz); 2.33 (s, 3H); 1.11 (t, 3H, J=7.4 Hz).

Preparation 10

5'-Ethyl-2'-methyl-6'-oxo-1',6'-dihydro-[2,3']bipyridinyl-5-carboxylic acid

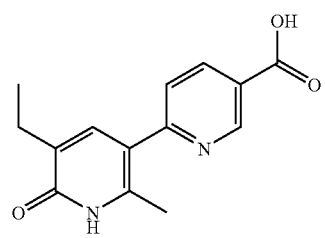

Step 1: 5'-Ethyl-6'-methoxy-2'-methyl-[2,3']bipyridinyl-5-carboxylic acid: Step 1 of PREPARATION 3 is substantially repeated utilizing the respective starting material in appropriate quantities, 3-ethyl-2-methoxy-6-methyl-5-(4,4,5,5-tetramethyl-[1,3,2-dioxaborolan-2-yl)pyridine (2.85 g) and appropriate amounts of other reagents to afford 2.80 g (100% yield) of the title compound (with the additional step of acidification of the reaction mixture to pH 4 with 1N HCl solution). MS: m/e=273 (M+H).

Step 2: 5'-Ethyl-2'-methyl-6'-oxo-1',6'-dihydro-[2,3']bipyridinyl-5-carboxylic acid: Step 2 of PREPARATION 3 is substantially repeated utilizing 2.8 g of 5'-ethyl-6'-methoxy-2'-methyl-[2,3']bipyridinyl-5-carboxylic acid and appropriate amounts of other reagents to afford 373 mg (23% yield) of the title compound. MS: m/e=259 (M+H). $^1$H-NMR (D6-DMSO, δ ppm) 11.75 (s, 1H) 9.09 (dd, 1H, J=2.4 and 0.7 Hz); 8.26 (dd, 1H, J=8.3 and 2.4 Hz); 7.65 (dd, 1H, J=8.3 and 0.7 Hz); 7.56 (s, 1H); 2.42 (q, 2H, J=7.4 Hz), 2.36 (s, 3H); 1.11 (t, 3H, J=7.4 Hz).

Preparation 11

5'-Ethyl-2'-methyl-6'-oxo-1',6'-dihydro-[2,3']bipyridinyl-6-carbaldehyde

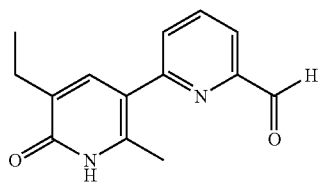

Step 1: 5'-Ethyl-6'-methoxy-2'-methyl-[2,3']bipyridinyl-6-carbaldehyde: Step 1 of PREPARATION 3 is substantially repeated utilizing the respective starting material in appropriate quantities, 3-ethyl-2-methoxy-6-methyl-5-(4,4,5,5-tetramethyl-[1,3,2-dioxaborolan-2-yl)pyridine (1.1 g) and appropriate amounts of other reagents to afford 0.66 g (65% yield) of the title compound. MS: m/e=257 (M+H). $^1$H-NMR (CDCl$_3$, δ ppm) 10.13 (s, 1H); 7.92 (m, 2H); 7.64 (dd, 1H, J=6.1 and 2.9 Hz); 7.54 (s, 1H); 4.01 (s, 3H); 2.63 (q, 3H, J=7.6 Hz); 2.53 (s, 3H); 1.22 (t, 3H, J=7.6 Hz).

Step 2: 5'-Ethyl-2'-methyl-6'-oxo-1',6'-dihydro-[2,3']bipyridinyl-6-carbaldehyde: Step 2 of PREPARATION 3 is substantially repeated utilizing 665 mg of 5'-ethyl-6'-methoxy-2'-methyl-[2,3']bipyridinyl-6-carbaldehyde and appropriate amounts of other reagents to afford 280 mg (45% yield) of the title compound. MS: m/e=243 (M+H)

Preparation 12

6-Amino-5'-ethyl-2'-methyl-1'H-[2,3']bipyridinyl-6'-one

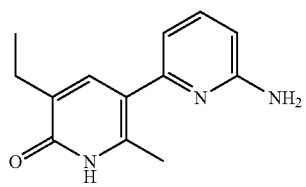

Step 1: 5'-Ethyl-6'-methoxy-2'-methyl-[2,3']bipyridinyl-6-ylamine: Step 1 of PREPARATION 3 is substantially repeated utilizing the respective starting material in appropriate quantities, 3-ethyl-2-methoxy-6-methyl-5-(4,4,5,5-tetramethyl-[1,3,2-dioxaborolan-2-yl)pyridine (0.28 g) and appropriate amounts of other reagents to afford 116 mg (48% yield) of the title compound. MS: m/e=244 (M+H).

Step 2: 6-Amino-5'-ethyl-2'-methyl-1'H-[2,3']bipyridinyl-6'-one: Step 2 of PREPARATION 3 is substantially repeated utilizing 116 mg of 5'-ethyl-6'-methoxy-2'-methyl-[2,3']bipyridinyl-6-ylamine and appropriate amounts of other reagents to afford 62 mg (57% yield) of the title compound. MS: m/e=230 (M+H).

Example 1

3-(5-Ethyl-2-methyl-6-oxo-1,6-dihydropyridin-3-yl)benzonitrile

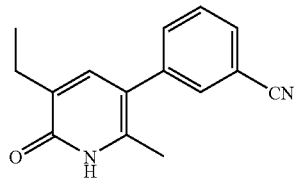

A stirred mixture of 5-bromo-3-ethyl-6-methyl-1H-pyridin-2-one, prepared in accordance with the procedures of PREPARATION 1, Step 2, (100 mg, 0.46 mmol), 3-cyanophenylboronic acid (88 mg, 0.6 mmol), 2M aq sodium carbonate (0.69 mL, 1.38 mmol), palladium tetrakis(triphenylphosphine) (16 mg, 0.014 mmol) and toluene (5 mL) is heated at reflux under a nitrogen atmosphere. After 2 hr, more catalyst (16 mg) is added and heating is continued overnight. The reaction is cooled and the mixture is partitioned between water and dichloromethane. The organic layer is separated and the solvents are removed. The residue is purified by chromatography eluting with ethyl acetate and with dichloromethane-5% methanol. Fractions containing product are combined, concentrated and the residue is triturated with hot ether to afford 3-(5-ethyl-2-methyl-6-oxo-1,6-dihydropyridin-3-yl)benzonitrile (40 mg, 36%) as a white solid. LC/MS: MS m/e=239 (M+H); RT 2.83 min.

Example 1A 3-(5-n-Propyl-2-methyl-6-oxo-1,6-dihydropyridin-3-yl)benzonitrile

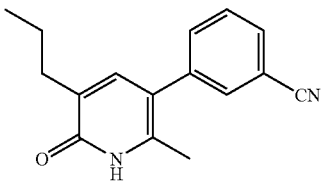

Example 1 is substantially repeated in this example except for utilizing the appropriate starting materials to afford the title compound.

Example 1B 3-(5-iso-Propyl-2-methyl-6-oxo-1,6-dihydropyridin-3-yl)benzonitrile

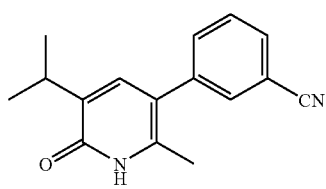

Example 1 is substantially repeated in this example except for utilizing the appropriate starting materials to afford the title compound.

Example 1C 3-(5-Isopropenyl-2-methyl-6-oxo-1,6-dihydro-pyridin-3-yl)-benzonitrile

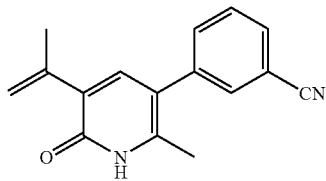

Example 1 is substantially repeated in this example except for utilizing the appropriate starting materials to afford the title compound.

Example 1D 3-(5-Cyclopropyl-2-methyl-6-oxo-1,6-dihydro-pyridin-3-yl)-benzonitrile

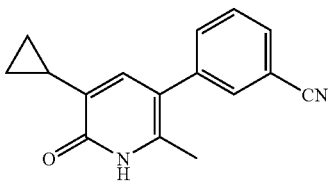

Example 1 is substantially repeated in this example except for utilizing the appropriate starting materials to afford the title compound.

Example 2

5-(5-Ethyl-2-methyl-6-oxo-1,6-dihydropyridin-3-yl)-2-(morpholin-4-yl)methylbenzonitrile

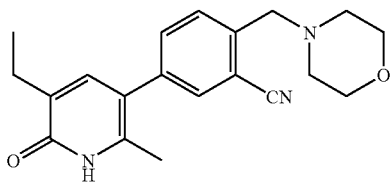

Step 1: 6-Benzyloxy-5-Ethyl-2-methyl-3-(4,4,5,5-tetramethyl-[1,3,2]dioxaborolan-2-yl)pyridine: The title compound is prepared in accordance with the procedures as set forth in PREPARATION 2, Step 1 starting from 3-bromo-6-benzyloxy-5-ethyl-2-methylpyridine.

Step 2: 5-Amino-2-methylbenzonitrile: A mixture of 2-methyl-5-nitrobenzonitrile (25.0 g, 154 mmol), 10% palladium on charcoal (2.5 g) ethyl acetate (150 mL) and ethanol (150 mL) is stirred under an atmosphere of hydrogen. The catalyst is removed by filtration through a pad of celite and the filtrate is concentrated to give 5-amino-2-methylbenzonitrile (also see, Scholz, D. et al. *J. Med. Chem.*, 41, 1050-1059 (1998)) (19.6 g, 96%) as a tan solid. MS: m/e=133 (M+H).

Step 3: 5-Bromo-2-methylbenzonitrile: Conc. sulfuric acid (60 mL) is added to sodium nitrite (5.75 g, 83.4 mmol). The temperature rises to 70° C. and solution is effected. After cooling to 20-40° C., the above solution is added dropwise to a mechanically stirred solution of 5-amino-2-methylbenzonitrile (10.0 g, 75.8 mmol) in acetic acid (150 mL). The temperature is maintained at 20-40° C. throughout the addition. The reaction mixture is cooled to 16-20° C. and a solution of cuprous bromide (24 g, 167 mmol) in conc. hydrobromic acid (150 mL) is added keeping the temperature between 16-20° C. After 45 min, the reaction mixture is poured onto ice (500 g) and the solids are collected by filtration then dissolved in dichloromethane (600 mL), washed with brine, dried, filtered and concentrated to give 5-bromo-2-methylbenzonitrile (see also, Dressler, J. et al. EP 0 594 019) (11.5 g, 77%) as a brown solid. $^1$H NMR (CDCl$_3$, δ ppm): 7.72 (1H, s), 7.60 (1H, dd), 7.20 (1H, dd), 2.50 (3H, s).

Step 4: 5-Bromo-2-bromomethylbenzonitrile: A mixture of 5-bromo-2-methylbenzonitrile (5.0 g, 25.5 mmol), N-bromosuccinimide (4.54 g, 25.5 mmol), 2',2'-azobis(2-methylpropionitrile) (0.05 g) and carbon tetrachloride (25 mL) is heated at reflux for 75 min. After cooling to room temperature, the solids are removed by filtration. The filtrate is concentrated and the residue purified by chromatography eluting with cyclohexane-20% ethyl acetate. Product containing fractions are combined and concentrated to afford 5-bromo-2-bromomethylbenzonitrile (2.69 g, 38%). LC/MS: MS showed no parent molecular ion peak; RT 3.52 min.

Step 5: 5-Bromo-2-(morpholin-4-yl)methylbenzonitrile: 5-Bromo-2-bromomethylbenzonitrile (2.50 g, 9.1 mmol) is added portionwise to a stirred solution of morpholine (828 μL, 9.5 mmol) and triethylamine (1.27 mL, 9.1 mmol) in methanol (2 mL). After 4 hr, the solvent is removed and the residue is suspended in water that is made basic with sodium hydroxide and then extracted with ethyl acetate. The extract is dried, filtered, and concentrated to give 5-bromo-2-(morpholin-4-yl)methylbenzonitrile (1.90 g, 74%) as a cream solid.

Step 6: 5-(6-Benzyloxy-5-ethyl-2-methylpyridin-3-yl)-2-(morpholin-4-yl)methyl-benzonitrile: A nitrogen purged stirred mixture of 5-bromo-2-(morpholin-4-yl)methylbenzonitrile (500 mg, 1.78 mmol) from Step 5,6-benzyloxy-5-ethyl-2-methyl-3-(4,4,5,5-tetramethyl-[1,3,2]dioxaborolan-2-yl)pyridine (572 mg, 1.62 mmol) from Step 1, potassium carbonate (673 mg, 4.86 mmol), dimethylformamide (15 mL), and $PdCl_2(dppf)CH_2Cl_2$ (82 mg) is heated overnight at 80° C. The reaction mixture is cooled to room temperature and the solvent is removed. The residue is suspended in ethyl acetate and washed with water, with brine, dried, filtered and concentrated. The residue is purified by chromatography eluting with cyclohexane-20 to 50% ethyl acetate. Product containing fractions are combined and concentrated to afford 5-(6-benzyloxy-5-ethyl-2-methylpyridin-3-yl)-2-(morpholin-4-yl)methylbenzonitrile (460 mg, 66%) as a pale yellow oil. LC/MS: MS m/e=428 (M+H); RT 3.38 min.

Step 7: 5-(5-Ethyl-2-methyl-6-oxo-1,6-dihydropyridin-3-yl)-2-(morpholin-4-yl)methylbenzonitrile: A mixture of 5-(6-benzyloxy-5-ethyl-2-methylpyridin-3-yl)-2-(morpholin-4-yl)methylbenzonitrile (460 mg, 1.08 mmol), 5% palladium on charcoal (30 mg) and ethanol (15 mL) is stirred under an atmosphere of hydrogen. After 2.5 hr, the catalyst is separated by filtration through a pad of Hi-Flo. The filtrate is concentrated and the residue is stirred with ethereal hydrochloric acid. The solvent is removed to give a foam that is dissolved in ether and the solvent removed. This procedure is repeated twice more to afford 5-(5-ethyl-2-methyl-6-oxo-1,6-dihydropyridin-3-yl)-2-(morpholin-4-yl)methylbenzonitrile (280 mg, 77%) as a pale yellow solid. LC/MS: MS m/e=338 (M+H); RT 0.38 min.

Example 3

3-(2,5-Dimethyl-6-oxo-1,6-dihydropyridin-3-yl)benzonitrile

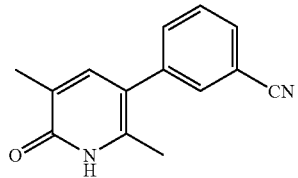

Step 1: 3-Bromo-6-methoxy-2-methylpyridine: A mixture of 5-bromo-6-methyl-1H-pyridin-2-one (5.5 g, 29 mmol), silver carbonate (10.89 g, 39 mmol), iodomethane (13.6 mL, 217 mmol) and chloroform (115 mL) is stirred overnight in the dark at room temperature. Triethylamine (10 mL) is added and stirring continued for 1.5 hr. The reaction mixture is filtered through a pad of Hi-Flo and the filtrate is washed with water (100 mL), dried, filtered and concentrated. The residue is purified by filtration through a pad of silica gel washing with cyclohexane-20% ethyl acetate. The solvent is concentrated to afford 3-bromo-6-methoxy-2-methylpyridine (3.7 g, 63% yield) as an oil. LC/MS RT 3.76 min; MS m/e=202/204 (M); NMR ($CDCl_3$) 7.6 (1H, d), 6.43 (1H, d), 3.89 (3H, s), 2.57 (3H, s).

Step 2: 3-(6-Methoxy-2-methylpyridin-3-yl)benzonitrile: To a nitrogen flushed mixture of 3-cyanophenylboronic acid (5.0 g, 34 mmol), 3-bromo-6-methoxy-2-methylpyridine (4.6 g, 22.7 mmol) and palladium tetrakis(triphenylphosphine) (789 mg, 0.68 mmol) is added toluene (150 mL), methanol (12 mL) and sodium carbonate (22.7 mmol) and the mixture is heated overnight at reflux. The cooled reaction is concentrated and the residue is purified by chromatography eluting with cyclohexane-3.2 to 9% ethyl acetate. Product containing fractions are combined and concentrated to afford 3-(6-methoxy-2-methylpyridin-3-yl)benzonitrile (3.09 g, 61% yield) as a white solid. LC/MS: MS m/e=225 (M+H); RT 3.58 min; $^1$H NMR ($CDCl_3$, δ ppm) 7.65 (1H, m), 7.60 (1H, m), 7.56 (2H, m), 7.40 (1H, d), 6.63 (1H, d), 3.98 (3H, s), 2.40 (3H, s).

Step 3: 3-(5-bromo-6-methoxy-2-methylpyridin-3-yl)benzonitrile: A mixture of 3-(6-methoxy-2-methylpyridin-3-yl)benzonitrile (3.00 g, 13.4 mmol), N-bromosuccinimide (2.89 g, 16.08 mmol) and methanol (150 mL) is stirred 66 hr at room temperature. The solids are collected by filtration to give 3-(5-bromo-6-methoxy-2-methylpyridin-3-yl)benzonitrile (1.20 g, 30%) as a white solid. LC/MS RT 4.19 min; MS m/e=303/305 (M); NMR ($CDCl_3$) 7.65 (2H, m), 7.60 (1H, s), 7.56 (2H, m), 4.02 (3H, s), 2.37 (3H, s).

Step 4: 3-(2,5-Dimethyl-6-oxo-1,6-dihydropyridin-3-yl)benzonitrile: The title compound is prepared by subjecting 3-(5-bromo-6-methoxy-2-methylpyridin-3-yl)benzonitrile as prepared above to a methylation reaction and then cleaving the methoxy group by following the procedures as set forth in PREPARATION 2, Step 3.

Example 4

3-(3-methyl-1-oxo-1,2-dihydroisoquinolin-4-yl)benzonitrile

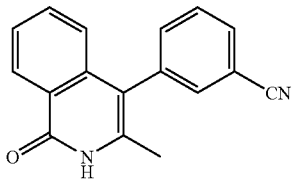

Step 1: 3-Methylisoquinoline oxide (also see Robison, Robison, J. Org. Chem. 21, 1337-1341, 1957): A mixture of 3-methyisoquinoline (1.0 g, 7 mmol), acetic acid (2 mL) and 27% hydrogen peroxide (0.7 mL) is heated at 60-70° C. More (0.5 mL) peroxide is added after 3 hr. After stirring overnight the volatiles are removed. Water (3 mL) is added to the residue and removed. The process is repeated and the residue is dissolved in chloroform (70 mL), solid potassium carbonate is added and a small amount of water. The mixture is stirred for 1 hr, the aqueous layer is separated and washed with chloroform (40 mL). The combined chloroform layer and wash is dried, filtered and concentrated to give 3-methylisoquinoline oxide (0.78 g, 70% yield) as a cream solid, mp 132-135° C. LC/MS: MS m/e=160 (M+H); RT 2.01 min.

Step 2: 3-Methyl-2H-isoquinolin-1-one: 3-Methyisoquinoline oxide (3.60 g, 22.6 mmol) and acetic anhydride (38 mL) are heated at reflux for 6 hr. After cooling the volatiles are removed and the residue is distilled at 220° C. under 0.5 mbar using a Kugelrohr distillation apparatus to afford 3-methyl-2H-isoquinolin-1-one (900 mg, 27% yield). LC/MS: MS m/e=160 (M+H); RT 2.45 min.

Step 3: 4-bromo-3-methyl-2H-isoquinolin-1-one: A solution of bromine 491 mL, 9.58 mmol) in acetic acid (10 mL) is added to a stirred solution of 3-methyl-2H-isoquinolin-1-one (1.45 g, 9.12 mmol) in acetic acid (1 mL). After 3 hr, water (60 mL) is added and the resulting solids are collected by filtration to afford 4-bromo-3-methyl-2H-isoquinolin-1-one (1.90 g, 88% yield) as a white solid. LC/MS: MS m/e=238/240 (M+H); RT 2.97 min.

Step 4: 4-bromo-1-methoxyisoquinoline: To a stirred suspension of 4-bromo-3-methyl-2H-isoquinolin-1-one (1.86 g, 7.81 mmol), silver carbonate (2.92 g, 10.6 mmol) and chloroform (150 mL) is added dropwise over 10 min iodomethane (7.3 mL, 117 mmol) and the mixture is stirred in the dark for 3 d. Triethylamine is added and the solids are removed by filtration through a pad of Celite. The filtrate is concentrated and the residue is purified by chromatography eluting with dichloromethane. Product containing fractions are combined and concentrated to afford 4-bromo-1-methoxyisoquinoline (1.19 g, 60% yield) as an oil that solidified on standing. LC/MS: MS m/e=252/254 (M+H); RT 4.68; $^1$H NMR (CDCl$_3$, δ ppm) 8.19 (1H, d), 8.09 (1H, d), 7.71 (1H, t), 7.50 (1H, t), 4.10 (3H, s); 2.71 (3H, s).

Step 5: 4-(3-cyanophenyl)-1-methoxyisoquinoline: A stirred mixture of 4-bromo-1-methoxyisoquinoline (1.19 g, 4.72 mmol), 3-cyanophenylboronic acid (1.04 g, 7.08 mmol), palladium tetrakis(triphenylphosphine) (0.33 g. 0.28 mmol), 2 m aq sodium carbonate (4.72 mmol) and toluene (30 mL) is heated 42 hr at reflux under a nitrogen atmosphere. After cooling, the solvent is removed and the residue is purified by chromatography eluting with cyclohexane-2.5 to 6% ethyl acetate. Product containing fractions are combined and concentrated to afford 4-(3-cyanophenyl)-1-methoxyisoquinoline (200 mg, 15.5% yield). LC/MS: MS m/e=275 (M+H); RT 4.38; $^1$H NMR (δ ppm): 8.22 (1H, d), 7.98 (1H, d), 7.83 (1H, s); 7.78 (1H, t), 7.65 (2H, m), 7.58 (1H, t), 7.18 (1H, d); 4.11 (3H, s), 2.23 (3H, s).

Step 6: 3-(3-methyl-1-oxo-1,2-dihydroisoquinolin-4-yl)benzonitrile: To a solution of 4-(3-cyanophenyl)-1-methoxyisoquinoline (200 mg, 0.73 mmol) in acetonitrile (6 mL) is added sodium iodide (219 mg, 1.46 mmol) followed by chlorotrimethylsilane (186 μL, 1.46 mmol) and the mixture is heated at reflux for 1.5 hr. The cooled reaction is diluted with water (15 mL) and the solids are collected by filtration, washed with water and dried to give 3-(3-methyl-1-oxo-1,2-dihydroisoquinolin-4-yl)benzonitrile (157 mg, 83% yield). $^1$H NMR (δ ppm) 11.55 (1H, s), 8.22 (1H, d), 7.95 (1H, d), 7.82 (1H, s), 7.72 (1H, t), 7.66 (1H, m), 7.60 (1H, m), 7.47 (1H, t), 6.94 (1H, d), 1.99 (3H, s).

Example 5

3-(3-Methyl-1-oxo-1,2,5,6,7,8-hexahydroisoquinolin-4-yl)benzonitrile

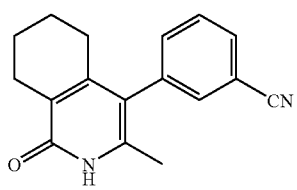

Step 1: 3-Methyl-5,6,7,8-tetrahydro-2H-isoquiloin-1-one: A mixture of 3-methyl-2H-isoquinolin-1-one (1.45 g, 9.12 mmol) and platinum oxide (300 mg) in acetic acid (30 mL) is stirred under an atmosphere of hydrogen. After 8 hr, more catalyst (150 mg) is added and stirring continued for an additional period of 8 hr. The catalyst is removed by filtration through a pad of Celite and the filtrate is diluted with water (50 mL), made basic with aq sodium hydroxide and extracted with dichloromethane. The extract is dried, filtered and concentrated to give 3-methyl-5,6,7,8-tetrahydro-2H-isoquiloin-1-one (1.14 g, 77%) as a white solid. LC/MS: MS m/e=164 (M+H); RT 2.39 min; $^1$H NMR (δ ppm) 5.69 (1H, s), 2.41 (2H, m), 2.24 (2H, m), 2.04 (2H, s), 1.62 (4H, m).

Step 2: 4-Bromo-3-methyl-5,6,7,8-tetrahydro-2H-isoquiloin-1-one: A solution of bromine (297 mL, 5.80 mmol) in acetic acid (5 mL) is added to a solution of 3-methyl-5,6,7,8-tetrahydro-2H-isoquiloin-1-one (900 mg, 5.52 mmol) in acetic acid (5 mL) and the reaction is stirred 2 hr at room temperature. The reaction is diluted with water (70 mL), stirred 30 min and the solids collected by filtration, washed with water and dried to give 4-bromo-3-methyl-5,6,7,8-tetrahydro-2H-isoquiloin-1-one (1.05 g, 78% yield) as a cream solid. LC/MS: MS m/e=242/244 (M+H); $^1$H NMR (CDCl$_3$, δ ppm) 2.59 (2H, m), 2.55 (2H, m), 2.41 (2H, m), 1.75 (4H, br m).

Step 3: 4-Bromo-1-methoxy-3-methyl-5,6,7,8-tetrahydroisoquinoline: A suspension of 3-methyl-5,6,7,8-tetrahydro-2H-isoquinolin-1-one (1.0 g, 4.13 mmol), silver carbonate (1.54 g, 5.58 mmol), iodomethane (3.86 mL, 62 mmol) and chloroform (120 mL) is stirred at room temperature in the dark for 3 d. Triethylamine (10 mL) is added and the reaction mixture is stirred for 1 hr. The solids are removed by filtration and the filtrate is washed with water (100 mL), dried, filtered and concentrated to give 4-bromo-1-methoxy-3-methyl-5,6,7,8-tetrahydroisoquinoline (ca 1.06 g, 100%).

Step 4: 3-(1-Methoxy-3-methyl-5,6,7,8-tetrahydroisoquinolin-4-yl)benzonitrile: The above bromide (1.00 g, 3.91 mmol), 3-cyanophenylboronic acid (863 mg, 5.87 mmol) palladium tetrakis(triphenylphosphine) (273 mg, 0.235 mmol), 2M aq sodium carbonate (3.91 mL), toluene (30 nL0 and methanol (2.5 mL) are heated at reflux under a nitrogen atmosphere for 42 hr. The reaction is cooled and the solvents removed. The residue is purified by chromatography eluting with cyclohxane-2 to 10% ethyl acetate. Fractions containing only the product are combined and concentrated. Product containing fractions mixed with starting material are combined, concentrated and rechromatographed. Fractions containing only the product are combined with material from the first column and concentrated to afford 3-(1-methoxy-3-methyl-5,6,7,8-tetrahydroisoquinolin-4-yl)benzonitrile (156 mg, 14% yield). LC/MS: MS m/e=279 (M+H); RT 4.48 min.

Step 5: 3-(3-Methyl-1-oxo-1,2,5,6,7,8-hexahydroisoquinolin-4-yl)benzonitrile: A stirred mixture of 3-(1-methoxy-3-methyl-5,6,7,8-tetrahydroisoquinolin-4-yl)benzonitrile (56 mg, 0.2 mmol), sodium iodide (60 mg, 0.4 mmol), chlorotrimethylsilane (51 μL, 0.4 mL) and acetonitrile (3 mL) is heated at reflux temperature for 1.5 hr. The cooled reaction mixture is diluted with water (5 mL) and the solids are collected by filtration to give 3-(3-methyl-1-oxo-1,2,5,6,7,8-hexahydroisoquinolin-4-yl)benzonitrile (45 mg, 87%) as a beige solid. LC/MS: MS m/e=265 (M+H); RT 2.97 min.

Example 6

3-(5-Ethyl-2,4-dimethyl-6-oxo-1,6-dihydropyridin-3-yl)benzonitrile

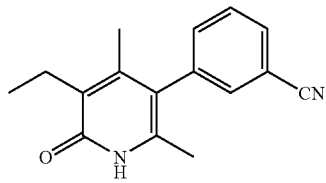

Step 1: 2-Chloro-3-cyano-4,6-dimethylpyridine: A stirred mixture of 3-cyano-4,6-dimethyl-2-hydroxypyridine (4.35 g, 29.39 mmol) and phosphorous pentachloride (6.92 g, 33.21 mmol) is heated to 120° C. The reaction mixture becomes clear and is stirred for an additional 1 hr. It is then poured onto ice/water (250 mL) and allowed to stand for 30 min. The solution is neutralized with sodium bicarbonate (pH 6) and extracted with dichloromethane (400 mL). The separated organic layer is dried, filtered and concentrated to yield 2-chloro-3-cyano-4,6-dimethylpyridine (4.60 g, 94% yield) as a tan solid containing ca 15% impurity. LC/MS: MS m/e=167/169 (M+H); RT 2.98 min; NMR (CDCl$_3$, δ ppm) 7.08 (1H, s), 2.57 (3H, s), 2.55 (3H, s).

Step 2: 3-Cyano-4,6-dimethyl-2-methoxypyridine: A solution of 2-chloro-3-cyano-4,6-dimethylpyridine (4.60 g, 27.7 mmol) in methanol (30 mL) is added to a stirred solution of sodium methoxide (2.09 g, 38.78 mmol) in methanol (20 mL) and the reaction mixture is heated at 60° C. for 4 hr. After cooling, the reaction is diluted with water (150 mL) and the solids are collected by filtration, washed with water and dried to yield 3-cyano-4,6-dimethyl-2-methoxypyridine (2.90 g, 65%) as an off-white solid containing the same impurity as the starting material. LC/MS: MS m/e=163 (M+H); RT 3.29 min; $^1$H NMR (CDCl$_3$, δ ppm) 6.69, (1H, s), 4.00 (3H, s), 2.43 (6H, s).

Step 3: 2-Methoxy-4,6-dimethylpyridine-3-carbaldehyde: DIBAL (1.5 M in toluene, 12.2 mL, 18.30 mmol) is added dropwise over 10 min to a stirred solution of 3-cyano-4,6-dimethyl-2-methoxypyridine (2.85 g, 17.60 mmol) in toluene (50 mL) cooled to −50° C. The reaction is stirred at −50 to −78° C. for 2 hr, then quenched by careful addition of sat. aq ammonium chloride (30 mL) and stirring at room temperature for 30 min. The 5% sulfuric acid is added and stirring maintained for 5 min. The mixture is adjusted to pH 9 with aq sodium hydroxide and extracted with toluene. The organic layer is dried, filtered, concentrated and the residue purified by chromatography eluting with cyclohexane-5% ethyl acetate. Product containing fractions are combined and concentrated to afford 2-methoxy-4,6-dimethylpyridine-3-carbaldehyde (1.22 g. 42% yield). LC/MS: MS m/e=166 (M+H); RT 3.28 min; $^1$H NMR (CDCl$_3$, δ ppm) 10.49 (1H, s), 6.61 (1H, s), 4.01 (3H, s), 2.56 (3H, s), 2.42 (3H, s).

Step 4: 2-Methoxy-4,6-dimethyl-3-vinylpyridine: Potassium tert-butoxide (1.63 g, 14.54 mmol) is added to a suspension of methyl triphenylphosphine (5.20 g, 14.54 mmol) in toluene (70 mL) and the mixture is stirred at room temperature of 0.5 hr. To this yellow-orange mixture is added a solution of 4,6-dimethyl-2-methoxypyridine-3-carbaldehyde (1.20 g, 7.27 mmol) in toluene (10 mL). After 1.5 hr. the reaction mixture is washed with water (150 mL), with brine (150 mL), dried, filtered and concentrated and the residue is purified by chromatography eluting with cyclohexane-5% ethyl acetate. Product containing fractions are combined and concentrated to afford 2-methoxy-4,6-dimethyl-3-vinylpyridine (0.66 g, 55.5% yield) as an oil containing triphenylphosphine oxide.

Step 5: 3-Ethyl-2-methoxy-4,6-dimethylpyridine: A mixture of the above 2-methoxy-4,6-dimethyl-3-vinylpyridine (0.66 g, 4.05 mmol), 5% palladium on charcoal and ethyl alcohol (10 mL) is stirred under an atmosphere of hydrogen for 4 hr. The catalyst is removed by filtration through a pad of Hi-Flo and the filtrate is concentrated. The residue is purified by chromatography eluting with dichloromethane. Product containing fractions are combined and concentrated to afford 3-ethyl-2-methoxy-4,6-dimethylpyridine (265 mg, 22.4% yield for two steps). LC/MS: MS m/e=166 (M+H); RT 3.76 min; $^1$H NMR (CDCl$_3$, δ ppm) 6.50 (1H, s), 3.90 (3H, s); 2.58 (2H, q), 2.38 (3H, s); 2.21 (3H, s), 1.07 (3H, t).

Step 6: 5-Bromo-3-ethyl-2-methoxy-4,6-dimethylpyridine: A mixture of 3-ethyl-2-methoxy-4,6-dimethylpyridine (265 mg, 1.61 mmol), N-bromosuccinimide (346 mg, 1.93 mmol) and methanol (5 mL) is stirred at room temperature for 5 hr. The solvent is removed and the residue is purified by chromatography eluting with dichloromethane. Product containing fractions are combined and concentrated to afford 5-bromo-3-ethyl-2-methoxy-4,6-dimethylpyridine (285 mg, 73%) as a white semi-solid. LC/MS: MS m/e=244/246 (M+H); RT 4.78 min.

Step 7: 3-(5-Ethyl-6-methoxy-2,4-dimethylpyridin-3-yl)benzonitrile: A mixture of 5-bromo-3-ethyl-2-methoxy-4,6-dimethylpyridine (254 mg, 1.75 mmol), 3-cyanophenylboronic acid (254 mg, 1.75 mmol), palladium tetrakis (triphenylphosphine) (81.2 mg, 0.07 mmol), 2M aq sodium carbonate (1.15 mL), toluene (10 mL) and methanol (0.7 mL) is reacted following the procedures of Step 4, Example 5. The crude product is purified by HPLC in two runs eluting with a gradient of acetonitrile-20 to 5% water ramping @ 0.5% per min. Product containing fractions from both runs are combined and concentrated to afford 3-(5-ethyl-6-methoxy-2,4-dimethylpyridin-3-yl)benzonitrile (44 mg, 14%) as an oil. LC/MS: MS m/e=267 (M+H); RT 4.41 min.

Step 8: 3-(5-Ethyl-2,4-dimethyl-6-oxo-1,6-dihydropyridin-3-yl)benzonitrile: A stirred mixture of 3-(5-ethyl-6-methoxy-2,4-dimethylpyridin-3-yl)benzonitrile (44 mg, 0.165 mmol), sodium iodide (50 mg, 0.33 mmol), chlorotrimethylsilane (58.4 µL, 0.33 mL) and acetonitrile (2 mL) is heated at reflux temperature for 3 hr. The cooled reaction mixture is diluted with water (10 mL) and extracted with dichloromethane. The extract is dried, filtered, concentrated and the residue is purified by chromatography eluting with cyclohexane-ethyl acetate then with dichloromethane-5% methanol. Product containing fractions are combined and concentrated to afford 3-(5-ethyl-2,4-dimethyl-6-oxo-1,6-dihydropyridin-3-yl)benzonitrile (13 mg, 32%) as a beige solid. LC/MS: MS m/e=253 (M+H); RT 2.92 min.; $^1$H NMR (CDCl$_3$, δ ppm) 7.69 (1H, d), 7.59 (1H, t), 7.45 (1H, s), 7.41 (1H, d), 2.63 (2H, q), 2.02 (3H, s), 1.84 (3H, s), 1.11 (3H, t).

Example 7

3-[(5-Ethyl-2-methyl-6-oxo-1,6-dihydropyridine)-3-carbonyl]benzonitrile

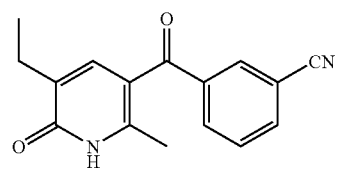

Step 1: 3-[(5-Ethyl-6-methoxy-2-methylpyridin3-yl)hydroxymethyl]benzonitrile: Butyl lithium (2.5M in hexane, 2.09 mL, 5.22 mmol) is added to a solution of 3-bromo-5-ethyl-6-methoxy-2-methylpyridine (1.0 g, 4.35 mmol) in tetrahydrofuran (10 mL) cooled to −50° C. and the reaction mixture is stirred for 45 min after which 3-cyanobenzaldehyde (0.71 g, 5.44 mmol) is added in two portions. After 1 hr at −50° C., the dry ice/acetone bath is removed, the reaction is warmed to room temperature, quenched with sat. aq ammonium chloride (30 mL) and extracted with ether (40 mL). The extract is dried, filtered, concentrated and the residue is purified by chromatography eluting with cyclohexane and 10 to 15% ethyl acetate. Product containing fractions are combined and concentrated to afford 3-[(5-ethyl-6-methoxy-2-methylpyridin3-yl)hydroxymethyl]benzonitrile (0.69 g, 56% yield).

Step 2: 3-[(5-Ethyl-6-methoxy-2-methylpyridin-3-yl)-3-carbonyl]benzonitrile: A stirred mixture of 3-[(5-ethyl-6-methoxy-2-methylpyridin3-yl)hydroxymethyl]benzonitrile (0.69 g, 2.45 mmol) as prepared above, activated manganese dioxide (2.13 g, 24.5 mmol) and toluene (35 mL) is heated at reflux under a Dean-Stark water separator for 5 hr. The reaction is cooled to room temperature and stirred overnight. The solids are removed by filtration through a pad of Celite and the filtrate is concentrated. The residue is purified by chromatography eluting with cyclohexane-8% ethyl acetate. Product containing fractions are combined and concentrated to afford 3-[(5-ethyl-6-methoxy-2-methylpyridin-3-yl)-3-carbonyl]benzonitrile (330 mg, 48% yield) as an oil that solidified to a white solid.

Step 3: 3-[(5-Ethyl-2-methyl-6-oxo-1,6-dihydropyridine)-3-carbonyl]benzonitrile: A stirred mixture of 3-[(5-ethyl-6-methoxy-2-methylpyridin-3-yl)-3-carbonyl]benzonitrile (330 mg, 1.18 mmol), sodium iodide (354 mg, 2.36 mmol), chlorotrimethylsilane (301 μL, 2.30 mL) and acetonitrile (10 mL) is heated at reflux temperature for 2 hr. The cooled reaction mixture is diluted with water and the solids are collected by filtration to give of 3-[(5-ethyl-2-methyl-6-oxo-1,6-dihydropyridine)-3-carbonyl]benzonitrile (163 mg, 52%) as a white solid. LC/MS: MS m/e=267 (M+H); RT 2.75 min; $^1$H NMR (CDCl$_3$, δ ppm) 11.83 (1H, br s), 8.01 (1H, m), 7.95 (1H, dd), 7.79 (1H, dd), 7.63 (1H, t), 7.30 (1H, s), 2.58 (5H, m), 1.16 (3H, t).

Example 7A

3-Ethyl-6-methyl-5-(3-morpholin-4-ylmethyl-phenyl)-1H-pyridin-2-one

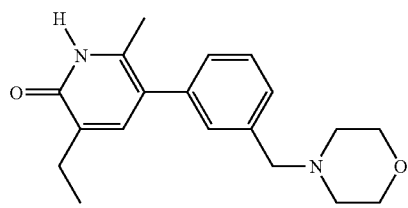

Example 7 is substantially repeated except for utilizing suitable starting materials and reagents such that the title compound is formed; MS: m/e=313 (M+H).

Example 7B

3-Ethyl-6-methyl-5-(3-pyrrolidin-1-ylmethyl-phenyl)-1H-pyridin-2-one

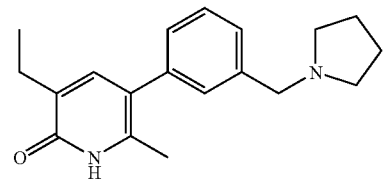

Example 7 is substantially repeated except for utilizing suitable starting materials and reagents such that the title compound is formed; MS: m/e=297 (M+H).

Example 7C

5-[3-(Benzylamino-methyl)-phenyl]-3-ethyl-6-methyl-1H-pyridin-2-one

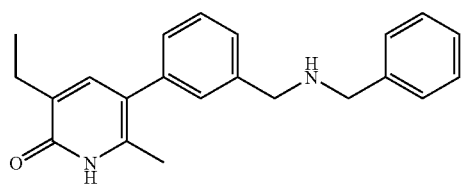

Example 7 is substantially repeated except for utilizing suitable starting materials and reagents such that the title compound is formed; MS: m/e=333 (M+H).

Example 7D

3-Ethyl-6-methyl-5-phenyl-1H-pyridin-2-one

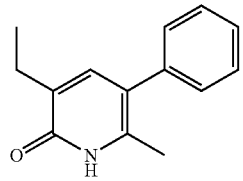

Example 7 is substantially repeated except for utilizing suitable starting materials and reagents such that the title compound is formed.

Example 7E

3-Ethyl-6-methyl-5-(4-morpholin-4-ylmethyl-phenyl)-1H-pyridin-2-one hydrochloride

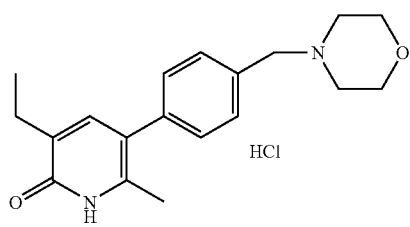

Example 7 is substantially repeated except for utilizing suitable starting materials and reagents such that the title compound is formed.

Example 7F 3-(5-Ethyl-6-oxo-1,6-dihydro-pyridin-3-yl)-benzonitrile

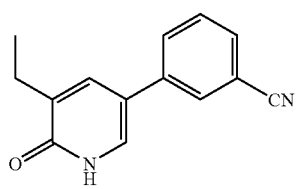

Example 7 is substantially repeated except for utilizing suitable starting materials and reagents such that the title compound is formed.

Example 7G 3-(2,5-Diethyl-6-oxo-1,6-dihydro-pyridin-3-yl)-benzonitrile

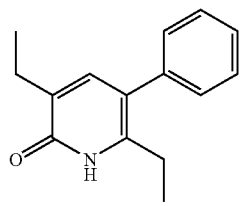

Example 7 is substantially repeated except for utilizing suitable starting materials and reagents such that the title compound is formed.

Example 8

3-Ethyl-6-methyl-5-(pyrazol-1-yl)-1H-pyridin-2-one hydrochloride

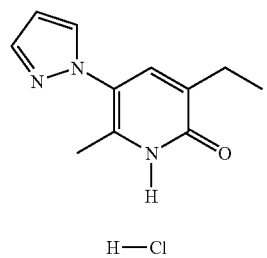

Step 1: 3-Ethyl-2-methoxy-6-methyl-5-(pyrazol-1-yl)pyridine: Into each of 2 microwave vials is added 3-bromo-5-ethyl-6-methoxy-2-methylpyridine (200 mg, 0.869 mmol), potassium carbonate (180 mg, 1.30 mmol), copper iodide (16 mg, 0.084 mmol) and pyrazole (59 mg, 0.869 mmol). The vials are flushed with $N_2$ before anhydrous dimethylformamide (5.5 mL) is added and then sealed. The first reaction is heated in the CEM Discover microwave at 160° C. for 20 minutes. LC/MS shows the reaction is incomplete. The reaction is re-microwaved to 180° C. for 20 min and LC/MS suggests that the reaction is approximately 50% complete. The reaction is re-microwaved at 185° C. for 20 min then 185° C. for 30 min and LC/MS shows the reaction is largely complete. Reaction 2 is heated in the microwave to 185° C. for 1.5 hr and LC/MS shows the reaction is almost complete. The 2 reactions are combined and diluted with water and extracted with 3 portions of dichloromethane. The combined organic layers are washed with 2 portions of aqueous sodium hydroxide (1M), then dried over magnesium sulfate and evaporated to give a dark oil. The crude product is purified by flash chromatography on a 5-gram silica gel cartridge by elution with dichloromethane. Fractions containing the product are combined and the solvent evaporated. The residue is further purified by flash chromatography on a 5-gram silica gel cartridge by elution with heptane:ethyl acetate (19:1) then dichloromethane:heptane (1:1, increasing to 1:0). Clean fractions containing the product are combined and evaporated to give 3-ethyl-2-methoxy-6-methyl-5-(pyrazol-1-yl)pyridine as a yellow oil (102 mg, 27% yield). MS: m/e=218 (M+H); NMR (CDCl$_3$): 7.70 (1H, d), 7.53 (1H, d), 7.37 (1H, s), 6.44 (1H, t), 3.99 (3H, s), 2.59 (2H, q), 2.29 (3H, s), 1.10 (3H, t)

Step 2: 3-Ethyl-6-methyl-5-(pyrazol-1-yl)-1H-pyridin-2-one Hydrochloride: To a mixture of 3-ethyl-2-methoxy-6-methyl-5-pyrazol-1-yl-pyridine (98 mg, 0.452 mmol) and sodium iodide (203 mg, 1.35 mmol) under a N$_2$ atmosphere is added anhydrous acetonitrile (3 mL) followed by dropwise addition of chlorotrimethylsilane (170 μL, 1.35 mmol). The reaction mixture is stirred at 65° C. under nitrogen for 13 h. The reaction mixture is allowed to cool, diluted with water and the resulting mixture is extracted with 3 portions of dichloromethane. The combined extracts are dried over magnesium sulfate and evaporated to leave an orange residue. The crude product is triturated with ether/heptane to give 3-ethyl-6-methyl-5-pyrazol-1-yl-1H-pyridin-2-one as a light orange solid (75 mg, 82% yield). This material (30 mg) is dissolved in dichloromethane (2 mL) and treated with ethereal hydrochloric acid (2.0 M, 0.444 mL). The mixture is stirred for 1.5 h, evaporated and triturated with ether to give 3-ethyl-6-methyl-5-pyrazol-1-yl-1H-pyridin-2-one hydrochloride (29 mg) as a white powder. LC/MS: RT: 2.15 min, MS: m/e=204 (M+H); $^1$H NMR (CDCl$_3$, δ ppm): 7.73 (1H, d), 7.55 (1H, d), 7.47 (1H, s), 6.47 (1H, t), 2.62 (2H, q), 2.33 (3H, s), 1.22 (3H, t).

Example 9

3-Ethyl-6-methyl-5-(1,2,4-triazol-1-yl)-1H-pyridin-2-one Hydrochloride

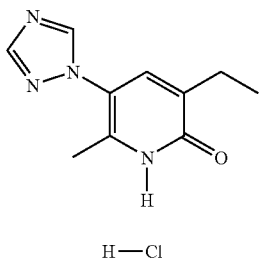

Into a microwave vial is added 3-bromo-5-ethyl-6-methoxy-2-methyl-pyridine (400 mg, 1.74 mmol), potassium carbonate (360 mg, 2.61 mmol), copper iodide (50 mg, 0.263 mmol) and 1,2,4-triazole (240 mg, 3.47 mmol). The vial is flushed with N$_2$ before anhydrous dimethylformamide (5 mL) is added and then sealed. The reaction is heated in the CEM Discover microwave at 180° C. for 40 minutes. LC/MS shows the reaction is incomplete. Further 1,2,4-triazole (120 mg) and copper iodide (30 mg) are added, the reaction flushed with N$_2$ and is re-microwaved to 180° C. Initially the pressure limit of 20 bar is reached and the process is aborted. The residual pressure is released and the reaction is re-microwaved to 180° C. for 40 min with a maximum pressure of 9-11 bar attained. LC/MS shows the reaction to be complete. The reaction is diluted and extracted with 11 portions of dichloromethane. The combined extracts are then dried over magnesium sulfate and evaporated to give a dark oil. The crude product is purified by flash chromatography on a 5-gram silica gel cartridge by elution with dichloromethane:methanol (19:1). Clean fractions containing the product are combined, the solvent evaporated, and the residue is further purified by flash chromatography on a 5-gram silica gel cartridge by elution with heptane:ethyl acetate (19:1) then dichloromethane:heptane (1:1, increasing to 1:0). Clean fractions containing the product are combined and evaporated to give an orange residue. The product is triturated with ether/heptane to give 3-ethyl-6-methyl-5-(1,2,4-triazol-1-yl)-1H-pyridin-2-one as an orange powder (67 mg, 19% yield). This material (57 mg) is suspended in dichloromethane (2 mL) and treated with ethereal hydrochloric acid (2.0 M, 0.444 mL). The mixture is stirred for 1.5 h and then evaporated to give 3-ethyl-6-methyl-5-1,2,4-triazol-1-yl-1H-pyridin-2-one hydrochloride (70 mg) as a cream-orange solid. LC/MS: RT: 1.79 min, MS: m/e=205 (M+H).

$^1$H NMR (δ ppm): 8.78 (1H, s), 8.19 (1H, s), 7.29 (1H, s), 2.40 (2H, q), 2.01 (3H, s), 1.09 (3H, t).

Example 10

3-Ethyl-5-(imidazol-1-yl)-6-methyl-1H-pyridin-2-one Hydrochloride

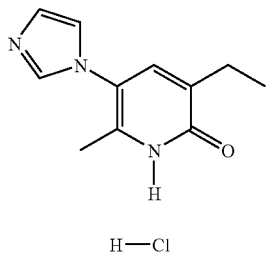

Step 1: 3-Ethyl-5-(imidazol-1-yl)-2-methoxy-6-methylpyridine: Into each of 2 microwave vials is added 3-bromo-5-ethyl-6-methoxy-2-methylpyridine (200 mg, 0.869 mmol), potassium carbonate (180 mg, 1.30 mmol), copper iodide (16 mg, 0.084 mmol), sodium hydroxide (84 mg, 2.10 mmol) and imidazole (59 mg, 0.869 mmol). The vials are flushed with N$_2$ before anhydrous dimethylformamide (5.5 mL) is added and then sealed. Each reaction is heated in the CEM Discover microwave at 185° C. for 1 hr. The 2 reactions are combined diluted with water and extracted with 3 portions of dichloromethane. The combined dichloromethane layers are washed with 2 portions of 1 M aqueous sodium hydroxide, dried over magnesium sulfate and evaporated to give a dark oil. The crude product is purified by flash chromatography on a 5-gram silica gel cartridge by elution with dichloromethane:ethyl acetate (1:1). Fractions containing the product are combined. The solvent evaporated, and the residue is further purified by flash chromatography on a 5-gram silica gel cartridge by elution with dichloromethane:ethyl acetate (3:1, increasing to 2:1). Clean fractions containing the product are combined and evaporated to give 3-ethyl-5-(imidazol-1-yl)-2-methoxy-6-methyl-pyridine (53 mg, 14% yield) as a yellow oil. MS: m/e=218 (M+H); $^1$H NMR (300 MHz, CDCl$_3$, δ ppm): 7.54 (1H, s) 7.22 (1H, s), 7.21 (1H, s), 7.00 (1H, s), 3.98 (3H, s), 2.59 (2H, q), 2.25 (3H, s), 1.10 (3H, t).

Step 2: 3-Ethyl-5-(imidazol-1-yl)-6-methyl-1H-pyridin-2-one Hydrochloride: To a mixture of 3-ethyl-5-imidazol-1-yl-2-methoxy-6-methyl-pyridine (76 mg, 0.350 mmol) and sodium iodide (158 mg, 1.05 mmol) under a N$_2$ atmosphere is added anhydrous acetonitrile (4 mL) followed by drop-wise addition of chlorotrimethylsilane (132 μL, 1.05 mmol). The reaction mixture is stirred at 65° C. under nitrogen for 17 h. LC/MS shows the reaction is incomplete. Further sodium iodide (158 mg) and chlorotrimethylsilane (132 μL) are added and the heating is continued for 2 h. Further sodium iodide (158 mg) and chlorotrimethylsilane (132 μL) are added and heating is continued for 45 min. LC/MS indicates the reaction is complete. The reaction mixture is allowed to cool, diluted with water, treated with solid sodium bicarbonate and the resulting mixture is extracted with 10 portions of dichloromethane. The combined extracts are dried over magnesium sulfate and evaporated to leave an orange residue. The crude product is triturated with ether/acetonitrile, then the solid is suspended in dichloromethane:ethyl acetate (1:1) and filtered. The filtrate is evaporated and the residue is triturated with ether to give 3-ethyl-5-imidazol-1-yl-6-methyl-1H-pyridin-2-one (52 mg, 73% yield) as a light orange powder. This material (38 mg) is suspended in dichloromethane (2 mL) and treated with ethereal hydrochloric acid (2.0M, 0.38 mL). The heterogeneous mixture is stirred for 1.5 h, evaporated and the residue is triturated with ether to give 3-ethyl-5-(imidazol-1-yl)-6-methyl-1H-pyridin-2-one hydrochloride (29 mg) as an orange solid. LC/MS: RT: 0.45 min, MS: m/e=204 (M+H); $^1$H NMR (δ ppm): 12.09 (1H, s), 9.36 (1H, d), 7.91 (1H, t), 7.88 (1H, d), 7.40 (1H, s), 2.40 (2H, q), 2.06 (3H, s), 1.10 (3H, t).

Example 11

3-Ethyl-6-methyl-5-(pyrrol-1-yl)-1H-pyridin-2-one Hydrochloride

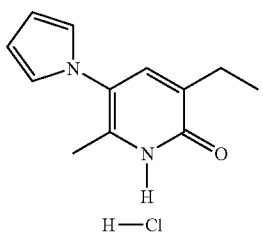

Step 1: 3-Ethyl-2-methoxy-6-methyl-5-(pyrrol-1-yl)pyridine: Into each of 2 microwave vials is added 3-bromo-5-ethyl-6-methoxy-2-methyl-pyridine (200 mg, 0.869 mmol), potassium carbonate (180 mg, 1.30 mmol), copper iodide (16 mg, 0.084 mmol), sodium hydroxide (84 mg, 2.10 mmol) and pyrrole (72 μL, 1.04 mmol). The vials are flushed with $N_2$ before anhydrous dimethylformamide (5 mL) is added then sealed. The first reaction is heated in the CEM Discover microwave at 185° C. (max wattage set to 150 W) for 1 hr. LC/MS shows the reaction is incomplete. The reaction is re-microwaved at 185° C. for a further 1 hr but LC/MS shows no further apparent product formation. The second reaction is microwaved at 185° C. for 1 hr. Further copper iodide (150 mg) is added, the reaction is flushed with $N_2$ and re-microwaved at 185° C. for a further 1 hr. LC/MS shows the reaction is largely complete. The two reactions are combined, diluted with water and extracted with three portions of dichloromethane. The combined organic layers are washed with two portions of 1 M aqueous sodium hydroxide, dried over magnesium sulfate and evaporated to give a black oil. The crude product is purified by flash chromatography on a 5-gram silica gel cartridge by elution with ethyl acetate:heptane (1:49, increasing to 1:1). Clean fractions containing the product are combined and evaporated to give 3-ethyl-2-methoxy-6-methyl-5-pyrrol-1-yl-pyridine (68 mg, 18% yield) as a yellow-orange oil. MS: m/e=217 (M+H); $^1$H NMR (CDCl$_3$, δ ppm): 7.26 (1H, s, obscured by CHCl$_3$ in CDCl$_3$), 6.73 (2H, m), 6.30 (2H, m), 3.98 (3H, s), 2.58 (2H, q), 2.27 (3H, s), 1.10 (3H, t).

Step 2: 3-Ethyl-6-methyl-5-(pyrrol-1-yl)-1H-pyridin-2-one Hydrochloride: To a mixture of 3-ethyl-2-methoxy-6-methyl-5-pyrrol-1-yl-pyridine (68 mg, 0.315 mmol) and sodium iodide (141 mg, 0.94 mmol) under a $N_2$ atmosphere is added anhydrous acetonitrile (4 mL) followed by dropwise addition of chlorotrimethylsilane (118 μL, 0.940 mmol). The reaction mixture is stirred at 65° C. under nitrogen for 17 hr. The reaction mixture is allowed to cool, diluted with water and extracted with three portions of dichloromethane. The combined extracts are dried over magnesium sulfate and evaporated to leave an orange residue. The crude product is purified by flash chromatography on a 5-gram silica gel cartridge by elution with dichloromethane:methanol (49:1). Clean fractions containing the product are combined and evaporated to give 3-ethyl-6-methyl-5-(pyrrol-1-yl)-1H-pyridin-2-one (59 mg, 93% yield) as a white solid. This material (49 mg) is dissolved in dichloromethane (2 mL) and treated with ethereal hydrochloric acid (2.0M, 0.49 mL). The solution is stirred for 1.5 hr and then evaporated to give 3-ethyl-6-methyl-5-pyrrol-1-yl-1H-pyridin-2-one hydrochloride (54 mg) as an off-white solid. LC/MS: RT: 2.70 min, MS: m/e=203 (M+H); $^1$H NMR (δ ppm): 11.75 (1H, s), 7.16 (1H, s), 6.80 (2H, t), 6.16 (2H, t), 2.38 (2H, q), 1.97 (3H, s), 1.08 (3H, t).

Examples 12 and 13

3-Ethyl-6-methyl-5-(1,2,3-triazol-2-yl)-1H-pyridin-2-one and 3-ethyl-6-methyl-5-(1,2,3-triazol-1-yl)-1H-pyridin-2-one

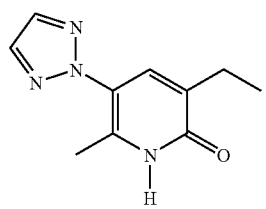

Example 12 and

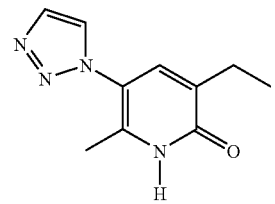

Example 13

Example 12: 3-Ethyl-6-methyl-5-(1,2,3-triazol-2-yl)-1H-pyridin-2-one: Into a microwave vial is added 3-bromo-5-ethyl-6-methoxy-2-methyl-pyridine (400 mg, 1.74 mmol), potassium carbonate (360 mg, 2.61 mmol), copper iodide (50 mg, 0.263 mmol) and 1,2,3-triazole (201 μL, 3.47 mmol). The vial is flushed with nitrogen before anhydrous dimethylformamide (4 mL) is added then sealed. The reaction is heated in the CEM Discover microwave at 185° C. for 20 min (4 bar pressure attained). LC/MS shows the reaction is incomplete. The reaction is re-microwaved to 180° C. for 20 min. Further copper iodide (50 mg) is added, the reaction flushed with nitrogen and is re-microwaved to 180° C. for 20 min. LC/MS shows the reaction is complete with the formation of 2 materials. The reaction is diluted with water and extracted with six portions of dichloromethane. The combined extracts are then dried over magnesium sulfate and evaporated to give a dark oil. The crude product is purified by flash chromatography on a 5-gram silica gel cartridge by elution with dichloromethane:ethyl acetate (3:1, increasing to 2:1 then 1:1). Fractions containing the higher $R_f$ product are combined, the solvent evaporated and the residue is triturated twice with heptane and twice with ether to give 3-ethyl-6-methyl-5-(1,2,3-triazol-2-yl)-1H-pyridin-2-one (40 mg, 11% yield) as a white powder. LC/MS: RT: 2.19 min, MS: m/e=205 (M+H); $^1$H NMR (δ, ppm): 11.93 (1H, s), 8.04 (2H, s), 7.40 (1H, s), 2.41 (2H, q), 2.06 (3H, s), 1.09 (3H, t).

Example 13: 3-Ethyl-6-methyl-5-(1,2,3-triazol-1-yl)-1H-pyridin-2-one: Evaporation of fractions containing the lower $R_f$ product are combined, the solvent evaporated and residue is triturated once with heptane and twice with ether to give 3-ethyl-6-methyl-5-1,2,3-triazol-1-yl-1H-pyridin-2-one (35 mg, 9% yield) as a white solid. LC/MS: RT: 1.87 min, MS: m/e=205 (M+H); $^1$H NMR (400 MHz, $d_6$-DMSO, δ, ppm): 12.01 (1H, s), 8.37 (1H, s), 7.92 (1H, s), 7.31 (1H, s), 2.40 (2H, q), 1.98 (3H, s), 1.04 (3H, t).

Example 14

3-Ethyl-2-methoxy-6-methyl-5-(1,3,4-oxadiazol-2-yl)pyridine

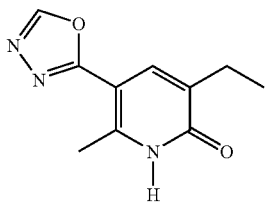

Step 1: 5-Ethyl-6-methoxy-2-methyl-nicotinic acid methyl ester: An oven dried round-bottom flask is charged with toluene (35 mL) and cooled to −15° C. in a dry ice/acetone bath. A solution of butyl lithium in hexane (1.6M, 11.22 mL, 18.0 mmol) is added in one portion. To this mixture is added a solution of butylmagnesium bromide in tetrahydrofuran (2 M, 4.5 mL, 9.0 mmol) drop-wise over 1.25 hr to give a suspension. The reaction is stirred at −10° C. for 1 hr after which a solution of 3-bromo-5-ethyl-6-methoxy-2-methylpyridine (5 g, 21.7 mmol) in anhydrous toluene (10 mL) is added drop-wise over 1.25 hr. The resulting suspension is stirred at −10° C. for 30 min. The bath is cooled to −30° C. and allowed to warm slowly to 0° C. over 12 hr. The reaction is allowed to stir at −10° C. for 5 hr before diluting with anhydrous tetrahydrofuran (15 mL) to give a cloudy cream solution. This solution is added drop-wise over 1.5 hr to a cold solution of dimethyl carbonate (9.14 mL, 108 mmol) in anhydrous toluene (10 mL) stirring under a nitrogen atmosphere at −20° C. The resulting mixture is allowed to warm slowly to 0° C. After 5.5 hr, the reaction is quenched with saturated aqueous ammonium chloride (20 mL) and then partitioned between water and ethyl acetate. The ethyl acetate layer is washed with a further portion of water, and the combined aqueous washes are extracted with seven portions of ethyl acetate and two portions of dichloromethane. The combined organic extract is dried over magnesium sulfate, filtered and evaporated to give crude 5-ethyl-6-methoxy-2-methyl-nicotinic acid methyl ester (5.58 g) as an orange oil. This material is used without further purification. MS: m/e=210 (M+H); $^1$H NMR (CDCl$_3$, δ, ppm): 7.94 (1H, s), 4.02 (3H, s), 3.90 (3H, s), 2.77 (3H, s), 2.59 (2H, q), 1.23 (3H, t).

Step 2: 5-Ethyl-6-methoxy-2-methylnicotinic acid: Water (30 mL) is added to a mixture of the above 5-ethyl-6-methoxy-2-methyl-nicotinic acid methyl ester and sodium hydroxide (3 g, 75 mmol) in methanol (150 mL). The reaction mixture is stirred at 50° C. for 36 hr. The reaction mixture is allowed to cool and is acidified to pH 3 with concentrated hydrochloric acid, then the mixture is treated with excess solid sodium hydrogen carbonate. The resulting suspension is concentrated under vacuum and washed with a portion of dichloromethane. The dichloromethane wash is back extracted with three portions of saturated aqueous sodium hydrogen carbonate, and the combined aqueous layers are acidified to pH 3. The resulting mixture is extracted with six portions of dichloromethane, the combined organic extract is dried over magnesium sulfate, filtered and evaporated to give 5-ethyl-6-methoxy-2-methyl-nicotinic acid (3.49 g, 82% yield over 2 steps) as a white solid. MS: m/e=196 (M+H); $^1$H NMR (CDCl$_3$, δ, ppm): 8.01 (1H, s), 4.00 (3H, s), 3.77 (3H, s), 2.77 (3H, s), 2.58 (2H, q), 1.20 (3H, t).

Step 3: 5-Ethyl-6-methoxy-2-methyl-nicotinic acid N'-formylhydrazide: Under a nitrogen atmosphere in a round bottom flask, 5-ethyl-6-methoxy-2-methyl-nicotinic acid (500 mg, 2.56 mmol) is dissolved in dichloromethane (30 mL). O-(1,2-dihydro-2-oxo-1-pyridyl)-N,N,N',N'-tetramethyluronium tetrafluoroborate (990 mg, 3.33 mmol) is added, followed by hydroxybenzotriazole hydrate (510 mg, 3.33 mmol). The resulting mixture is stirred at rt for 40 min to give a suspension, which is treated with formyl hydrazide (231 mg, 3.85 mmol) followed by N-ethyl-diisopropylamine (1.16 mL, 6.66 mmol) to give a solution. After stirring at rt for 23 hr, LC/MS shows the reaction to be incomplete. The reaction is allowed to stir for a further 97 hr at room temperature. The reaction is diluted with water and the mixture is extracted with six portions of dichloromethane, the combined extract is dried over magnesium sulfate, filtered and evaporated. The crude product is purified by flash chromatography on a 10-gram silica gel cartridge by elution with dichloromethane:ethyl acetate (1:1, increasing to 1:2). Fractions containing the product are combined, and the product triturated with ether to give 5-ethyl-6-methoxy-2-methyl-nicotinic acid N'-formylhydrazide (361 mg) as a white solid that was used without further purification. MS: m/e=238 (M+H); $^1$H NMR (300 MHz, CDCl$_3$, δ, ppm): 9.05 (1H, br.s), 8.71 (1H, br.s), 8.20 (1H, s), 7.49 (1H, s), 3.97 (3H, s), 2.58 (3H, s), 2.56 (2H, q), 1.16 (3H, t).

Step 4: 3-Ethyl-2-methoxy-6-methyl-5-(1,3,4-oxadiazol-2-yl)pyridine: Into a microwave vial is added 5-ethyl-6-methoxy-2-methyl-nicotinic acid N'-formylhydrazide (132 mg), tosyl chloride (64 mg, 0.336 mmol), and 2-t-butylimino-2-diethylamino-1,3-dimethyl-perhydro-1,3,2-diazaphosphorine on polystyrene (2.2 mmol/g, 634 mg, 1.39 mmol) and anhydrous tetrahydrofuran (6 mL). The vial is flushed with nitrogen, sealed and heated in the CEM Discover microwave at 145° C. holding at that temperature for 3 min, with a maximum pressure of 6 bar. The reaction is evaporated and the residue is directly purified by flash chromatography on a 5-gram silica gel cartridge by elution with dichloromethane. Fractions containing the product are combined and the solvent evaporated, and further purified by flash chromatography on a 5-gram silica gel cartridge by elution with dichloromethane. Fractions containing the product are combined, evaporated and re-purified by flash chromatography on a 5-gram silica gel cartridge by elution with dichloromethane:methanol (1:0 increasing to 99:1). Fractions containing the product are combined, evaporated and re-purified by flash chromatography on a 5-gram silica gel cartridge by elution with dichloromethane:ethyl acetate (6:1). Fractions containing the product are combined and the solvent evaporated. The clean fraction containing the product is evaporated to give 3-ethyl-2-methoxy-6-methyl-5-[1,3,4]oxadiazol-2-yl-pyridine (10 mg, 8% yield). MS: m/e=220 (M+H); $^1$H NMR (CDCl$_3$, δ, ppm): 8.45 (1H, d), 7.91 (1H, s), 4.01 (3H, s), 2.81 (3H, s), 2.61 (2H, q), 1.13 (3H, t).

Step 5: 3-Ethyl-6-methyl-5-(1,3,4-oxadiazol-2-yl)-1H-pyridin-2-one: To a mixture of 3-ethyl-2-methoxy-6-methyl-5-[1,3,4]oxadiazol-2-yl-pyridine (10 mg, 0.0457 mmol) and sodium iodide (19 mg, 0.127 mmol) under a nitrogen atmosphere is added anhydrous acetonitrile (2 mL) followed by chlorotrimethylsilane (16.4 μL, 0.131 mmol). The reaction mixture is stirred at 50° C. under nitrogen for 2.5 hr. The reaction mixture is allowed to cool and then quenched with water (0.1 mL). After stirring for 30 min, the mixture is evaporated. The crude residue is purified by flash chromatography on a 2-gram silica gel cartridge by elution with dichloromethane:methanol (49:1). The fraction containing the product is evaporated to give 3-ethyl-6-methyl-5-(1,3,4-oxadiazol-2-yl)-1H-pyridin-2-one (2 mg, 21% yield) as a white solid. LC/MS: RT: 1.98 min, MS: m/e=206 (M+H).

Example 15

3-Ethyl-6-methyl-5-(5-methyl-1,3,4-oxadiazol-2-yl)-1H-pyridin-2-one

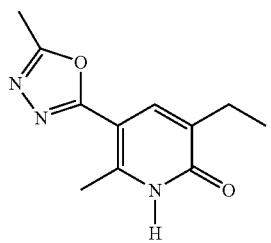

Step 1: 5-Ethyl-6-methoxy-2-methyl-nicotinic acid N'-acetylhydrazide: Under a nitrogen atmosphere in a round bottom flask, 5-ethyl-6-methoxy-2-methyl-nicotinic acid (500 mg, 2.56 mmol) of Step 2, Example 14 is dissolved in dichloromethane (30 mL). O-(1,2-dihydro-2-oxo-1-pyridyl)-N,N,N',N'-tetramethyluronium tetrafluoroborate (990 mg, 3.33 mmol) is added, followed by hydroxybenzotriazole hydrate (510 mg, 3.33 mmol). The resulting mixture is stirred at rt for 45 min to give a suspension, which is treated with acetic hydrazide (285 mg, 3.85 mmol) followed by N-ethyldiisopropylamine (1.16 mL, 6.66 mmol). The resulting solution is stirred at rt for 32 hr, LC/MS shows the reaction to be complete. The reaction is diluted with water and the mixture is extracted with six portions of dichloromethane, the combined extract is dried over magnesium sulfate, filtered and evaporated. The crude product is purified by flash chromatography on a 10-gram silica gel cartridge by elution with dichloromethane:ethyl acetate (1:1, increasing to 1:2). Fractions containing the product are combined and evaporated to obtain 5-ethyl-6-methoxy-2-methyl-nicotinic acid N'-acetylhydrazide (give 923 mg) as a white solid. MS: m/e=252 (M+H); $^1$H NMR (300 MHz, CDCl$_3$, δ, ppm): 8.72 (1H, d), 8.50 (1H, d), 7.49 (1H, s), 3.96 (3H, s), 2.59 (3H, s), 2.54 (2H, q), 2.12 (3H, s), 1.17 (3H, t).

Step 2: 3-Ethyl-2-methoxy-6-methyl-5-(5-methyl-[1,3,4]oxadiazol-2-yl)-pyridine: Into each of two microwave vials is added 5-ethyl-6-methoxy-2-methyl-nicotinic acid N'-acetylhydrazide (100 mg), tosyl chloride (64 mg, 0.336 mmol), and 2-t-butylimino-2-diethylamino-1,3-dimethyl-perhydro-1,3,2-diazaphosphorine on polystyrene (2.2 mmol/g, 634 mg, 1.39 mmol) and anhydrous tetrahydrofuran (6 mL). Each vial is flushed with nitrogen, sealed and heated in the CEM Discover microwave at 145° C. holding at that temperature for 3 min, with a maximum pressure of 6.5 bar. LC/MS shows the reaction is complete. The product from both the vials are combined and evaporated, and the residue is purified by flash chromatography on a 5-gram silica gel cartridge by elution with dichloromethane:methanol (49:1). Fractions containing the product are combined and the solvent evaporated and further purified by flash chromatography on a 5-gram silica gel cartridge by elution with dichloromethane. Fractions containing the product are combined, evaporated and re-purified by flash chromatography on a 5-gram silica gel cartridge by elution with dichloromethane:ethyl acetate (3:1). Fractions containing the product are combined again and evaporated to give 3-ethyl-2-methoxy-6-methyl-5-(5-methyl-[1,3,4]oxadiazol-2-yl-pyridine (95 mg, 73% yield, 2 steps). MS: m/e=234 (M+H); $^1$H NMR (CDCl$_3$, δ, ppm): 7.86 (1H, s), 4.00 (3H, s), 2.79 (3H, s), 2.55-2.65 (5H, m), 1.21 (3H, t).

Step 3: 3-Ethyl-6-methyl-5-(5-methyl-1,3,4-oxadiazol-2-yl)-1H-pyridin-2-one: To a mixture of 3-ethyl-2-methoxy-6-methyl-5-(5-methyl-[1,3,4]oxadiazol-2-yl)pyridine (95 mg, 0.408 mmol) and sodium iodide (182 mg, 1.21 mmol) under a nitrogen atmosphere is added anhydrous acetonitrile (3 mL) followed by chlorotrimethylsilane (156 μL, 1.24 mmol). The reaction mixture is stirred at 50° C. under nitrogen for 2.5 hr. The reaction mixture is allowed to cool and then quenched with water (0.5 mL). After stirring for 30 min the mixture is evaporated. The residue is partitioned between water and dichloromethane and the mixture treated with a little sodium bisulfite to decolorize. The dichloromethane layer is separated and the aqueous layer is extracted with five portions of dichloromethane. The combined dichloromethane layer is washed with two portions of aqueous sodium hydroxide (1M), then dried over magnesium sulfate and evaporated to give an orange residue. The crude product is purified by flash chromatography on a 5-gram silica gel cartridge by elution with dichloromethane:methanol (30:1). The clean fractions containing the product are combined and evaporated to give 3-ethyl-6-methyl-5-(5-methyl-1,3,4-oxadiazol-2-yl)-1H-pyridin-2-one (38 mg, 43% yield) as a white solid. LC/MS: RT: 2.10 min, MS: m/e=220 (M+H); $^1$H NMR (300 MHz, CDCl$_3$, δ, ppm): 12.24 (1H, s), 7.76 (1H, s), 2.76 (3H, s), 2.61 (2H, q), 2.61 (3H, s), 1.25 (3H, t).

Example 16

3-Ethyl-6-methyl-5-(2H-1,2,4-triazol-3-yl)-1H-pyridin-2-one

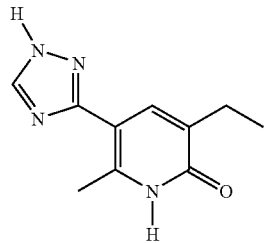

Step 1: 5-Ethyl-6-methoxy-2-methyl-nicotinamide: A round bottom flask under a nitrogen atmosphere is charged with 5-ethyl-6-methoxy-2-methyl-nicotinic acid (1.00 g, 5.13 mmol) of Step 2, Example 14 dissolved in dichloromethane (50 mL). To this is added O-(1,2-dihydro-2-oxo-1-pyridyl)-N,N,N',N'-tetramethyluronium tetrafluoroborate (1.676 g, 5.64 mmol) followed by hydroxybenzotriazole hydrate (785 mg, 5.13 mmol). The resulting mixture is stirred at rt for 30 min then treated with a solution of ammonia in 1,4-dioxane (0.5 M, 10.3 mL, 5.15 mmol) followed by N-ethyl-diisopropylamine (2.32 mL, 13.3 mmol) to give a suspension. After stirring at rt for 23 hr, LC/MS shows the reaction to be incomplete. A solution of ammonia in 1,4-dioxane (0.5 M, 10 mL, 5.00 mmol) is added and stirred for an additional period of 24 hr. LC/MS shows the reaction is still incomplete and so more ammonia (0.5 M, 5 mL, 2.5 mmol) is added and allowed to stir for 68 hr to give a solution. LC/MS shows the reaction to be complete. The reaction is diluted with water and the mixture is extracted with seven portions of dichloromethane. The combined extract is dried over magnesium sulfate, filtered and evaporated. The crude product is purified by flash chromatography on a 10-gram silica gel cartridge by elution with dichloromethane:ethyl acetate (1:0, increasing to 1:2). Fractions containing the product are combined and re-purified by flash chromatography on a 10-gram silica gel cartridge by elution with dichloromethane:ethyl acetate (1:0, increasing to 1:2). Fractions containing the product are combined, the solvent evaporated and the residue triturated with ether to give 5-ethyl-6-methoxy-2-methyl-nicotinamide (1.22 g) as a fluffy, pink solid. MS: m/e=195 (M+H); $^1$H NMR (CDCl$_3$, δ, ppm): 7.50 (1H, s), 5.77 (2H, s), 3.96 (3H, s), 2.61 (3H, s), 2.56 (2H, q), 1.18 (3H, t).

Step 2: N-Dimethylaminomethylene-5-ethyl-6-methoxy-2-methylnicotinamide: In a round bottom flask under a nitrogen atmosphere, 5-ethyl-6-methoxy-2-methyl-nicotinamide (60 mg, 0.309 mmol) is treated with dimethylformamide dimethylacetal (0.5 mL). The resulting mixture is stirred at 100° C. for 1.25 hr to give a yellow solution. LC/MS shows the complete consumption of the starting material. The reaction mixture is evaporated to give N-dimethylaminomethylene-5-ethyl-6-methoxy-2-methyl-nicotinamide directly as a cream solid that is used without purification. MS: m/e=250 (M+H); $^1$H NMR (CDCl$_3$, δ, ppm): 8.57 (1H, s), 8.19 (1H, s), 5.77 (2H, s), 3.98 (3H, s), 3.19 (6H, s), 2.58 (3H, s), 2.56 (2H, q), 1.20 (3H, t).

Step 3: 3-Ethyl-2-methoxy-6-methyl-5-(1H-1,2,4-triazol-3-yl)pyridine: In a round bottom flask under a nitrogen atmosphere N-dimethylaminomethylene-5-ethyl-6-methoxy-2-methylnicotinamide (synthesized on 0.309 mmol scale) is treated with glacial acetic acid (1 mL) followed by hydrazine hydrate (16.5 µL, 0.340 mmol). The resulting mixture is stirred at 90° C. for 3.75 hr. The reaction mixture is evaporated, then partitioned between water and dichloromethane and the pH adjusted to 6-7 by treating with solid sodium bicarbonate. The aqueous layer is separated and then further extracted with five portions of dichloromethane. The combined extract is dried over magnesium sulfate, filtered and evaporated to give 3-ethyl-2-methoxy-6-methyl-5-(1H-1,2,4-triazol-3-yl)-pyridine (35 mg, 52% yield, 2 steps) as a white solid. MS: m/e=219 (M+H); $^1$H NMR (300 MHz, CDCl$_3$, δ, ppm): 11.52 (1H, s), 8.18 (1H, s), 7.78 (1H, s), 3.98 (3H, s), 2.68 (3H, s), 2.57 (2H, q), 1.19 (3H, t).

Step 4: 3-Ethyl-6-methyl-5-(2H-1,2,4-triazol-3-yl)-1H-pyridin-2-one: To a mixture of 3-ethyl-2-methoxy-6-methyl-5-(1H-1,2,4-triazol-3-yl-pyridine (90 mg, 0.413 mmol) and sodium iodide (186 mg, 1.24 mmol) under a nitrogen atmosphere is added anhydrous acetonitrile (5 mL) followed by chlorotrimethylsilane (156 µL, 1.24 mmol) drop-wise. The reaction mixture is stirred at 60° C. under nitrogen for 12 hr. The reaction mixture is allowed to cool and then quenched with water (0.75 mL). After stirring for 30 min, the reaction mixture is evaporated to dryness. The residue is purified by flash chromatography on a 5-gram silica gel cartridge by elution with dichloromethane:methanol (9:1). Fractions containing the product are combined and evaporated and re-purified by flash chromatography on a 5-gram silica gel cartridge by elution with dichloromethane:methanol (9:1). Fractions containing the product are combined and the solvent evaporated. The resulting residue is extracted with hot 2-propanol and the extract evaporated. The residue is re-purified by flash chromatography on a 5-gram silica gel cartridge by elution with 2-propanol:heptane (1:1, then 1:0). Fractions containing the product are combined, the solvent evaporated and triturated with acetonitrile to give 3-ethyl-6-methyl-5-(2H-1,2,4-triazol-3-yl)-1H-pyridin-2-one (18.6 mg, 22% yield) as a light orange solid. LC/MS: RT: 1.77 min, MS: m/e=205 (M+H); $^1$H NMR (δ, ppm):13.99 (1H, s), 11.82 (0.3H, br.s), 11.63 (0.7H, s), 8.57 (0.7H, s), 7.98 (0.3H, br.s), 7.82 (0.7H, s), 7.58 (0.3H, s), 2.41 (2H, q), 1.12 (3H, t).

Example 17

3-Ethyl-6-methyl-5-(2-methyl-2H-1,2,4-triazol-3-yl)-1H-pyridin-2-one

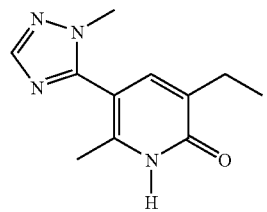

Step 1: 3-Ethyl-2-methoxy-6-methyl-5-(2-methyl-2H-1,2,4-triazol-3-yl)pyridine: In a round bottom flask under a nitrogen atmosphere N-dimethylaminomethylene-5-ethyl-6-methoxy-2-methyl-nicotinamide (synthesized on 0.567 mmol scale) of Step 2, Example 16 is treated with glacial acetic acid (1 mL) followed by methylhydrazine (50 µL, 0.94 mmol). The resulting mixture is stirred at 90° C. for 12 hr. The reaction mixture is evaporated to dryness and the residue is purified by flash chromatography on a 5-gram silica gel cartridge by elution with dichloromethane:methanol (49:1). Fractions containing the product are combined, evaporated and re-purified by flash chromatography on a 5-gram silica gel cartridge by elution with dichloromethane:methanol (99:1). Fractions containing the product are combined and the solvent evaporated to give 3-ethyl-2-methoxy-6-methyl-5-(2-methyl-2H-[1,2,4]triazol-3-yl)-pyridine (80 mg, 61% yield) as a light yellow oil. MS: m/e=233 (M+H); $^1$H NMR (δ, ppm): 7.96 (1H, s), 7.29 (1H, s), 3.99 (3H, s), 3.74 (3H, s), 2.59 (2H, q), 2.30 (3H, s), 1.19 (3H, t).

Step 2: 3-Ethyl-6-methyl-5-(2-methyl-2H-1,2,4-triazol-3-yl)-1H-pyridin-2-one: To a mixture of 3-ethyl-2-methoxy-6-methyl-5-(2-methyl-2H-1,2,4-triazol-3-yl)-pyridine (76 mg, 0.328 mmol) and sodium iodide (148 mg, 0.987 mmol) under a nitrogen atmosphere is added anhydrous acetonitrile (5 mL) followed by drop-wise addition of chlorotrimethylsilane (123 µL, 0.979 mmol). The reaction mixture is stirred at 60° C. under nitrogen for 12 hr. The reaction mixture is allowed to cool and then quenched with water (0.75 mL). After stirring for 30 min, the mixture is partitioned between water and dichloromethane. The dichloromethane layer is separated and the aqueous layer is extracted with ten further portions of dichloromethane. The combined organic layer is dried over magnesium sulfate and evaporated. The crude product is purified by flash chromatography on a 5-gram silica gel cartridge by elution with dichloromethane:methanol (9:1). Fractions containing the product are combined and the solvent evaporated to give 3-ethyl-6-methyl-5-(2-methyl-2H-1,2,4-triazol-3-yl)-1H-pyridin-2-one (73 mg, 100% yield) as a cream solid. LC/MS: RT: 1.85 min, MS: m/e=219 (M+H); $^1$H NMR (400 MHz, $d_6$-DMSO, δ, ppm): 11.92 (1H, s), 7.98 (1H, s), 3.74 (3H, s), 2.39 (2H, q), 1.09 (3H, t).

Example 18

3-Ethyl-6-methyl-5-(1,2,4-oxadiazol-5-yl)-1H-pyridin-2-one

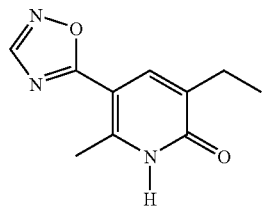

Step 1: 3-Ethyl-2-methoxy-6-methyl-5-(1,2,4-oxadiazol-5-yl)pyridine: In a round bottom flask under a nitrogen atmosphere a mixture of N-dimethylaminomethylene-5-ethyl-6-methoxy-2-methylnicotinamide (synthesized on 1.13 mmol scale) of Step 2, Example 16, hydroxylamine hydrochloride (103 mg, 1.48 mmol) and sodium hydroxide (59.4 mg, 1.48 mmol) and glacial acetic acid (1.7 mL) is treated with water (0.85 mL) and 1,4-dioxane (1.24 mL). The resulting dark mixture is stirred at 90° C. for 45 min. The reaction mixture is evaporated and the residue is partitioned between water and dichloromethane. The mixture is treated with excess solid sodium bicarbonate, the dichloromethane layer is separated and the aqueous layer is extracted with 2 further portions of dichloromethane. The combined organic layer is dried over magnesium sulfate and evaporated. The crude product is purified by flash chromatography on a 5-gram silica gel cartridge by elution with dichloromethane. Fractions containing the product are combined, evaporated and re-purified by flash chromatography on a 5-gram silica gel cartridge by elution with dichloromethane. Fractions containing the product are combined and the solvent evaporated to give 3-ethyl-2-methoxy-6-methyl-5-(1,2,4-oxadiazol-5-yl)pyridine as a white solid (138 mg, 56% yield, 2 steps). NMR (CDCl$_3$, δ ppm): 8.45 (1H, s), 8.05 (1H, s), 4.02 (3H, s), 2.82 (3H, s), 2.62 (2H, q), 1.23 (3H, t).

Step 2: 3-Ethyl-6-methyl-5-(1,2,4-oxadiazol-5-yl)-1H-pyridin-2-one: To a mixture of 3-ethyl-2-methoxy-6-methyl-5-(1,2,4-oxadiazol-5-yl)pyridine (36 mg, 0.164 mmol) and sodium iodide (74 mg, 0.493 mmol) under a nitrogen atmosphere is added anhydrous acetonitrile (3 mL) followed by chlorotrimethylsilane (62 μL, 0.494 mmol) drop-wise. The reaction mixture is stirred at 60° C. under nitrogen for 12 hr. The reaction mixture is allowed to cool and then quenched with water (0.5 mL). After stirring for 30 min the mixture is diluted with water and extracted with five portions of dichloromethane. The combined dichloromethane layer is dried over magnesium sulfate and evaporated. The crude product is purified by flash chromatography on a 5-gram silica gel cartridge by elution with dichloromethane:methanol (49:1, increasing to 19:1). Fractions containing the product are combined, the solvent evaporated and the residue triturated with heptane to give 3-ethyl-6-methyl-5-(1,2,4-oxadiazol-5-yl)-1H-pyridin-2-one (24 mg, 71% yield) as a white solid. LC/MS: RT: 2.37 min, MS: m/e=206 (M+H); $^1$H NMR (CDCl$_3$, δ, ppm): 12.56 (1H, s), 8.44 (1H, s), 7.96 (1H, s), 2.82 (3H, s), 2.62 (2H, q), 1.26 (3H, t).

Example 19

3-Ethyl-6-methyl-5-(3-methyl-1,2,4-oxadiazol-5-yl)-1H-pyridin-2-one

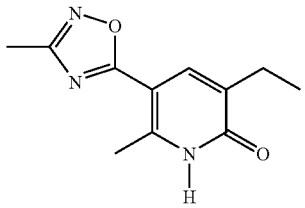

Step 1: N-(1-Dimethylaminoethylidene)-5-ethyl-6-methoxy-2-methylnicotinamide: In a round bottom flask under a nitrogen atmosphere 5-ethyl-6-methoxy-2-methyl-nicotinamide (195 mg, 1.00 mmol) of Step 1, Example 16 is treated with dimethylacetamide dimethylacetal (2 mL). The mixture is stirred at 100° C. for 65 min to give a dark solution. The reaction mixture is evaporated to give N-(1-dimethylaminoethylidene)-5-ethyl-6-methoxy-2-methylnicotinamide directly as a black oil that is used without purification. MS: m/e=264 (M+H).

Step 2: 3-Ethyl-2-methoxy-6-methyl-5-(3-methyl-1,2,4-oxadiazol-5-yl)pyridine: In a round bottom flask under a nitrogen atmosphere a mixture of N-(1-dimethylaminoethylidene)-5-ethyl-6-methoxy-2-methylnicotinamide (synthesized on 1.00 mmol scale), hydroxylamine hydrochloride (83.4 mg, 1.2 mmol), sodium hydroxide (48 mg, 1.2 mmol) and glacial acetic acid (1.4 mL) is treated with water (0.7 mL) and 1,4-dioxane (1 mL). The resulting dark mixture is stirred at 90° C. for 35 min. The reaction mixture is partitioned between water and ethyl acetate. The mixture is treated with excess solid sodium bicarbonate, the ethyl acetate layer is separated and the aqueous layer is extracted with 4 further portions of ethyl acetate. The combined ethyl acetate layer is dried over magnesium sulfate and evaporated to give a black residue that is purified by flash chromatography on a 5-gram silica gel cartridge by elution with dichloromethane. Fractions containing the product are combined, evaporated and re-purified by flash chromatography on a 5-gram silica gel cartridge by elution with heptane:dichloromethane (49:1). Fractions containing the product are combined and the solvent evaporated to give 3-ethyl-2-methoxy-6-methyl-5-(3-methyl-1,2,4-oxadiazol-5-yl)pyridine (189 mg, 81% yield, from Steps 1 and 2 above) as a white solid. MS: m/e=234 (M+H); $^1$H NMR (CDCl$_3$, δ, ppm): 8.01 (1H, s), 4.01 (3H, s), 2.81 (3H, s), 2.60 (2H, q), 2.46 (3H, s), 1.23 (3H, t).

Step 3: 3-Ethyl-6-methyl-5-(3-methyl-1,2,4-oxadiazol-5-yl)-1H-pyridin-2-one: To a mixture of 3-ethyl-2-methoxy-6-methyl-5-(3-methyl-1,2,4-oxadiazol-5-yl) pyridine (50 mg, 0.215 mmol) and sodium iodide (96 mg, 0.64 mmol) under a nitrogen atmosphere is added anhydrous acetonitrile (4 mL)

followed by drop-wise chlorotrimethylsilane (82 μL, 0.653 mmol). The reaction mixture is stirred at 65° C. under nitrogen for 7 hr. The reaction mixture is allowed to cool and then quenched with water (0.5 mL). After stirring for 30 min the mixture is partitioned between water and dichloromethane and the mixture treated with a little sodium bisulfite to decolorize. The dichloromethane layer is separated and the aqueous layer is extracted with four further portions of dichloromethane. The combined organic layer is dried over magnesium sulfate and evaporated. The crude product is purified by flash chromatography on a 5-gram silica gel cartridge by elution with dichloromethane:methanol (49:1). Fractions containing the product are combined and the solvent evaporated to give 3-ethyl-6-methyl-5-(3-methyl-1,2,4-oxadiazol-5-yl)-1H-pyridin-2-one (41 mg, 88% yield) as a white solid. LC/MS: RT: 2.44 min, MS: m/e=220 (M+H); $^1$H NMR (CDCl$_3$, δ, ppm): 12.49 (1H, s), 7.92 (1H, s), 2.79 (3H, s), 2.61 (2H, q), 2.45 (3H, s), 1.25 (3H, t).

Example 20

5-(2,5-Dimethyl-2H-1,2,4-triazol-3-yl)-3-ethyl-6-methyl-1H-pyridin-2-one

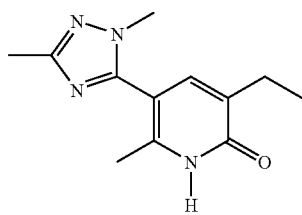

Step 1: 3-(2,5-Dimethyl-2H-1,2,4-triazol-3-yl)-5-ethyl-6-methoxy-2-methylpyridine: In a round bottom flask under a nitrogen atmosphere N-(1-dimethylaminoethylidene)-5-ethyl-6-methoxy-2-methyl-nicotinamide (synthesized on 0.567 mmol scale) prepared in accordance with the procedures of Step 1, Example 19 is treated with glacial acetic acid (1 mL), followed by methylhydrazine (50 μL, 0.94 mmol). The resulting mixture is stirred at 90° C. for 12 hr. The reaction mixture is evaporated to dryness and the residue is purified by flash chromatography on a 5-gram silica gel cartridge by elution with dichloromethane:methanol (99:1). Fractions containing the product are combined, evaporated and re-purified by flash chromatography on a 5-gram silica gel cartridge by elution with dichloromethane:methanol (199:1). Fractions containing the product are combined and the solvent evaporated to give 3-(2,5-dimethyl-2H-1,2,4-triazol-3-yl)-5-ethyl-6-methoxy-2-methyl-pyridine (80 mg, 57% yield). MS: m/e 247 (M+H); $^1$H NMR (CDCl$_3$, δ, ppm): 7.29 (1H, s), 3.98 (3H, s), 3.66 (3H, s), 2.58 (2H, q), 2.42 (3H, s), 2.31 (3H, s), 1.19 (3H, t).

Step 2: 5-(2,5-Dimethyl-2H-1,2,4-triazol-3-yl)-3-ethyl-6-methyl-1H-pyridin-2-one: To a mixture of 3-(2,5-dimethyl-2H-1,2,4-triazol-3-yl)-5-ethyl-6-methoxy-2-methylpyridine (76 mg, 0.309 mmol) and sodium iodide (139 mg, 0.927 mmol) under a nitrogen atmosphere is added anhydrous acetonitrile (5 mL) followed by drop-wise addition of chlorotrimethylsilane (116 μL, 0.924 mmol). The reaction mixture is stirred at 60° C. under nitrogen for 12 hr. LC/MS shows the reaction is incomplete. A further amount of chlorotrimethylsilane (100 μL) is added and the reaction is reheat at 60° C. for 9 hr. The reaction mixture is allowed to cool and then quenched with water (0.7 mL). After stirring for 30 min the mixture is partitioned between water and dichloromethane and the mixture treated with little sodium bisulfite to decolorize. The dichloromethane layer is separated and the aqueous layer is extracted with six further portions of dichloromethane. The combined dichloromethane layer is dried over magnesium sulfate and evaporated. The crude product is purified by flash chromatography on a 5-gram silica gel cartridge by elution with dichloromethane:methanol (1:0, increasing to 19:1). Fractions containing the product are combined, the solvent evaporated and triturated with ether to give 5-(2,5-dimethyl-2H-1,2,4-triazol-3-yl)-3-ethyl-6-methyl-1H-pyridin-2-one (47 mg, 66% yield) as a cream solid. LC/MS: RT: 1.88 min, MS: m/e=233 (M+H); $^1$H NMR (400 MHz, d$_6$-DMSO, δ, ppm): 11.85 (1H, s), 7.20 (1H, s), 3.61 (3H, s), 2.36 (2H, q), 2.20 (3H, s), 2.07 (3H, s), 1.07 (3H, t).

Example 21

3-Ethyl-6-methyl-5-(5-methyl-2H-1,2,4-triazol-3-yl)-1H-pyridin-2-one

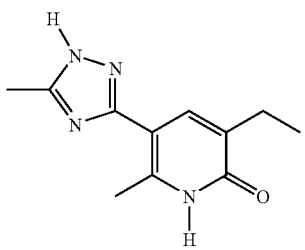

Step 1: 3-Ethyl-2-methoxy-6-methyl-5-(5-methyl-1H-1,2,4-triazol-3-yl)pyridine: In a round bottom flask under a nitrogen atmosphere N-(1-dimethylaminoethylidene)-5-ethyl-6-methoxy-2-methyl-nicotinamide (synthesized on 0.567 mmol scale) prepared in accordance with the procedures of Step 1, Example 19 is treated with glacial acetic acid (1 mL), followed by hydrazine hydrate (36 μL, 0.742 mmol). The resulting mixture is stirred at 90° C. for 12 hr. The reaction mixture is evaporated and the residue is purified by flash chromatography on a 5-gram silica gel cartridge by elution with dichloromethane:methanol (49:1). Fractions containing the product are combined, evaporated and re-purified by flash chromatography on a 5-gram silica gel cartridge by elution with dichloromethane:methanol (99:1). Fractions containing the product are combined and the solvent evaporated to give 3-ethyl-2-methoxy-6-methyl-5-(5-methyl-1H-1,2,4-triazol-3-yl)pyridine (105 mg, 80% yield, 2 steps) as a orange-red. MS: m/e=233 (M+H); $^1$H NMR (CDCl$_3$, δ, ppm): 9.8-11.6 (1H, br.s), 7.81 (1H, s), 3.97 (3H, s), 2.69 (3H, s), 2.59 (2H, q), 2.52 (3H, s), 1.19 (3H, t).

Step 2: 3-Ethyl-6-methyl-5-(5-methyl-2H-1,2,4-triazol-3-yl)-1H-pyridin-2-one: To a mixture of 3-ethyl-2-methoxy-6-methyl-5-(5-methyl-1H-1,2,4-triazol-3-yl)pyridine (90 mg, 0.413 mmol) and sodium iodide (194 mg, 1.29 mmol) under a nitrogen atmosphere is added anhydrous acetonitrile (5 mL) followed by drop-wise addition of chlorotrimethylsilane (162 μL, 1.29 mmol). The reaction mixture is stirred at 60° C. under nitrogen for 12 hr. LC/MS shows the reaction is incomplete. Further chlorotrimethylsilane (100 μL) is added and heating continued for 6 hr. The reaction mixture is allowed to cool and then quenched with water (0.7 mL). After stirring for 30 min the reaction mixture is evaporated to dryness. The residue is purified by flash chromatography on a 5-gram silica gel cartridge by elution with 2-propanol. Fractions containing the product are combined, evaporated, triturated with acetonitrile and re-purified by flash chromatography on a 5-gram silica gel cartridge by elution with 2-propanol. Fractions containing the product are combined and the solvent evaporated. The resulting residue is triturated with acetonitrile to give 3-ethyl-6-methyl-5-(5-methyl-2H-1,2,4-triazol-3-yl)-1H-pyridin-2-one (47 mg, 50% yield) as a cream solid. LC/MS: RT: 1.77 min, MS: m/e=219 (M+H); $^1$H NMR ($\delta$, ppm): 13.99 (1H, s), 11.59 (1, br.s), 7.78 (1H, s), 2.41 (2H, q), 2.37 (3H, s), 1.10 (3H, t).

Example 22

3-Ethyl-6-methyl-5-(5-methyl-1,2,4-oxadiazol-3-yl)-1H-pyridin-2-one

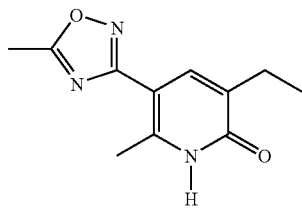

Step 1: 5-Ethyl-6-methoxy-2-methylnicotinonitrile: Into each of six microwave vials is added zinc cyanide (204 mg, 1.74 mmol), 3-bromo-5-ethyl-6-methoxy-2-methylpyridine (400 mg, 1.74 mmol), and tetrakis(triphenylphosphine)palladium(0) (60 mg, 0.519 mmol). The vials are flushed with nitrogen before anhydrous dimethylformamide (5.5 mL) is added and the vials sealed. Each of the six vials is heated in the Smith Synthesizer Microwave oven for 2 min with a set temperature of 175° C. A temperature of 165° C. is reached within 60 sec and the pressure of the reaction reaches a maximum of 0.3 bar. The six reactions are combined and partitioned between ethyl acetate and water. The ethyl acetate layer is separated and washed with three further portions of water and is dried over magnesium sulfate, filtered and evaporated to leave a brown semi-solid. This material is purified by flash chromatography on a 10-gram silica gel cartridge by elution with heptane:ethyl acetate (19:1). Fractions containing the product are combined, the solvent evaporated, and re-purified by flash chromatography on a 10-gram silica gel cartridge by elution with heptane:ethyl acetate (19:1). Clean fractions containing the product are combined and evaporated to give 5-ethyl-6-methoxy-2-methylnicotinonitrile (1.04 g) as a crystalline, white solid. Impure fractions are combined, evaporated and further purified by flash chromatography on a 10-gram silica gel cartridge by elution with heptane:ethyl acetate (19:1). Clean fractions containing the product are combined and evaporated to give additional 5-ethyl-6-methoxy-2-methylnicotinonitrile as a crystalline white solid (636 mg, 92% total yield). MS: m/e=177 (M+H); $^1$H NMR (CDCl$_3$, $\delta$, ppm): 7.49 (1H, s), 3.99 (3H, s), 2.62 (3H, s), 2.56 (2H, q), 1.18 (3H, t).

Step 2: 5-Ethyl-N-hydroxy-6-methoxy-2-methylnicotinamidine: To a mixture of 5-ethyl-6-methoxy-2-methylnicotinonitrile (300 mg, 1.705 mmol), potassium carbonate (1.174 g, 8.51 mmol) and hydroxylamine hydrochloride (591 mg, 8.50 mmol) is added absolute ethanol (15 mL). The reaction mixture is heated at 90° C. under a reflux condenser for 22 hr. LC/MS shows the reaction is incomplete, and 2 products are observed, one consistent with the desired compound and the other consistent with the corresponding primary nicotinamide. More potassium carbonate (1.174 g, 8.51 mmol) and hydroxylamine hydrochloride (591 mg, 8.50 mmol) are added and the reaction is heated at 90° C. for a further 15 hr. The mixture is allowed to cool, filtered and the filtrate is evaporated to give a sticky, cream colored residue that is used in the next step without purification.

Step 3: 3-Ethyl-2-methoxy-6-methyl-5-(5-methyl-1,2,4-oxadiazol-3-yl)-pyridine: Acetyl chloride (121 µL, 1.70 mmol) is added drop-wise to a mixture of 5-ethyl-N-hydroxy-6-methoxy-2-methylnicotinamidine (formed on 1.705 mmol scale) in pyridine (5 mL) under a nitrogen atmosphere. After the vigorous reaction has ceased, the mixture is heated at 98° C. for 22 hr. LC/MS indicates the reaction is incomplete and a further amount of acetyl chloride (50 µL) is added and the reaction mixture is heated for an additional 40 min. The reaction mixture is allowed to cool, then evaporated to dryness. The residue is suspended in water and extracted with three portions of ethyl acetate. The combined ethyl acetate layer is washed with saturated aqueous sodium bicarbonate, dried over magnesium sulfate, filtered and evaporated to leave a sticky, orange residue. The residue is extracted with five portions of heptane and the combined extract is evaporated. The residue is purified by flash chromatography on a 10-gram silica gel cartridge by elution with heptane:dichloromethane (9:1, increasing to 4:1). Clean fractions containing the product are combined and the solvent evaporated to give 3-ethyl-2-methoxy-6-methyl-5-(5-methyl-1,2,4-oxadiazol-3-yl)pyridine (47 mg, 20% combined yield from Steps 3 and 4) as an off-white solid. MS: m/e=234 (M+H); $^1$H NMR (CDCl$_3$, $\delta$, ppm): 7.94 (1H, s), 4.00 (3H, s), 2.74 (3H, s), 2.64 (3H, s), 2.60 (2H, q), 1.10 (3H, t).

Step 4: 3-Ethyl-6-methyl-5-(5-methyl-1,2,4-oxadiazol-3-yl)-1H-pyridin-2-one: To a mixture of 3-ethyl-2-methoxy-6-methyl-5-(5-methyl-1,2,4-oxadiazol-3-yl)-pyridine (47 mg, 0.202 mmol) and sodium iodide (91 mg, 0.607 mmol) under a nitrogen atmosphere is added anhydrous acetonitrile (4 mL) followed by drop-wise addition of chlorotrimethylsilane (76 µL, 0.605 mmol). The reaction mixture is stirred at 65° C. under nitrogen for 15 hr. The reaction mixture is allowed to cool, diluted with water and the resulting mixture is extracted with four portions of dichloromethane. The combined extracts are dried over magnesium sulfate and evaporated to leave an orange residue. The crude product is purified by flash chromatography on a 2-gram silica gel cartridge by elution with heptane:dichloromethane: (1:1). Fractions containing the product are combined, the solvent evaporated and the residue triturated with ether to 3-ethyl-6-methyl-5-(5-methyl-1,2,4-oxadiazol-3-yl)-1H-pyridin-2-one (25 mg, 58% yield) as a light yellow powder. LC/MS: RT: 2.39 min, MS: m/e=220 (M+H); $^1$H NMR (CDCl$_3$, $\delta$, ppm): 12.14 (1H, s), 7.89 (1H, s), 2.70 (3H, s), 2.64 (3H, s), 2.61 (2H, q), 1.24 (3H, t).

Example 23

3-Ethyl-6-methyl-5-(1,2,4-oxadiazol-3-yl)-1H-pyridin-2-one

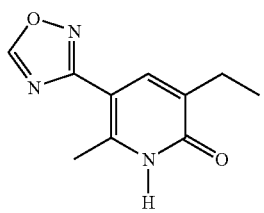

Step 1: 3-Ethyl-2-methoxy-6-methyl-5-(1,2,4-oxadiazol-3-yl)-pyridine: To a crude mixture of 5-ethyl-N-hydroxy-6-methoxy-2-methylnicotinamidine (formed on 1.705 mmol scale following the procedures of Step 3, Example 22), under a nitrogen atmosphere, is added triethylorthoformate (2 mL), followed by boron trifluoride etherate (42.6 µL, 0.336 mmol). The resulting solution mixture is heated at 100° C. for 3.25 hr. The mixture is allowed to cool, concentrated under vacuum, then treated with aqueous hydrochloric acid (1M, 2 mL). The resulting mixture is allowed to stand for 30 min before making basic with excess solid sodium bicarbonate. The mixture is extracted with five portions of ethyl acetate, dried over magnesium sulfate, filtered and evaporated to leave an oily, brown residue that is purified by flash chromatography on a 5-gram silica gel cartridge by elution with heptane:dichloromethane (1:1, increasing to 4:1). Fractions containing the product are combined, the solvent evaporated and re-purified by flash chromatography on a 5-gram silica gel cartridge by elution with heptane:dichloromethane (9:1, increasing to 17:3 then 1:1). Fractions containing the product are combined, the solvent evaporated and further purified by flash chromatography on a 5-gram silica gel cartridge by elution with heptane:dichloromethane (87:13, then 1:1). Clean fractions containing the product are combined, evaporated and triturated with heptane to give 3-ethyl-2-methoxy-6-methyl-5-(1,2,4-oxadiazol-3-yl)-pyridine (57 mg, 15% yield, 2 steps). MS: m/e=220 (M+H); $^1$H NMR (300 MHz, CDCl$_3$, δ, ppm): 8.72 (1H, s), 7.99 (1H, s), 4.00 (3H, s), 2.76 (3H, s), 2.61 (2H, q), 1.11 (3H, t)

Step 2: 3-Ethyl-6-methyl-5-(1,2,4-oxadiazol-3-yl)-1H-pyridin-2-one: To a mixture of 3-ethyl-2-methoxy-6-methyl-5-(1,2,4-oxadiazol-3-yl)pyridine (56 mg, 0.256 mmol) and sodium iodide (117 mg, 0.78 mmol) under a nitrogen atmosphere is added anhydrous acetonitrile (4 mL) followed by drop-wise addition of chlorotrimethylsilane (97.5 µL, 0.776 mmol). The reaction mixture is stirred at 65° C. under nitrogen for 16 hr. The reaction mixture is allowed to cool, diluted with water and the resulting mixture is extracted with five portions of dichloromethane. The combined extract is dried over magnesium sulfate and evaporated to leave a brown residue. This material is purified by flash chromatography on a 5-gram silica gel cartridge by elution with dichloromethane:methanol (49:1). Fractions containing the product are combined and the solvent evaporated, to give 3-ethyl-6-methyl-5-(1,2,4-oxadiazol-3-yl)-1H-pyridin-2-one (38 mg, 73% yield) as a off-white solid. LC/MS: RT: 2.27 min, m/e=206 (M+H); $^1$H NMR (400 MHz, δ, ppm): 12.02 (1H, s), 9.64 (1H, s), 7.74 (1H, s), 2.52 (3H, s), 2.41 (2H, q), 1.10 (3H, t).

Example 23A 5-(5-Aminomethyl-[1,3,4]oxadiazol-2-yl)-3-ethyl-6-methyl-1H-pyridin-2-one

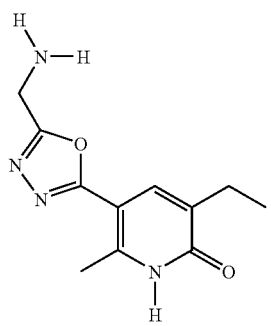

Step 1: Hydrazinocarbonylmethyl-carbamic acid tert-butyl ester: The title compound was prepared essentially in accordance with the procedures of Tetrahedron Letters, Vol 36, No. 37 P6591-6594 as set forth herein. Under a nitrogen atmosphere in a round bottom flask, tert-butoxycarbonylamino-acetic acid methyl ester (2.0 mL, 13.5 mmol) is dissolved in absolute ethanol (50 mL) and anhydrous hydrazine (0.45 mL, 14.3 mmol) is added. The resulting mixture is heated in an oil bath at 60° C. for 3 hours then 80° C. for 5.5 hours. The reaction mixture is evaporated and the residue partitioned between water (50 mL) and dichloromethane (50 mL). The aqueous layer is extracted with dichloromethane (2×10 mL). The combined dichloromethane extracts are washed with water (2×30 mL). The dichloromethane layer is dried over magnesium sulfate and evaporated to give a solid that is triturated with diethyl ether to give hydrazinocarbonylmethyl-carbamic acid tert-butyl ester (1.94 g, 76% yield).

Step 2: {2-[N'-(5-Ethyl-2-methyl-6-oxo-1,6-dihydro-pyridine-3-carbonyl)-hydrazino]-2-oxo-ethyl}-carbamic acid tert-butyl ester: Under a nitrogen atmosphere in a round bottom flask, 5-ethyl-6-methoxy-2-methyl-nicotinic acid (500 mg, 2.56 mmol) of Step 2, Example 14 is dissolved in dichloromethane (60 mL). O-(1,2-dihydro-2-oxo-1-pyridyl)-N,N,N',N'-tetramethyluronium tetrafluoroborate (838 mg, 2.82 mmol) is added, followed by hydroxybenzotriazole hydrate (392 mg, 2.56 mmol). The resulting mixture is stirred at rt for 30 min to give a suspension, which is treated with hydrazinocarbonylmethyl-carbamic acid tert-butyl ester (509 mg, 2.69 mmol) followed by N-ethyl-diisopropylamine (1.16 mL, 6.66 mmol). The resulting solution is stirred at rt for 135 hr, LC/MS shows the reaction to be complete. The reaction is diluted with water and the mixture is extracted with five portions of dichloromethane, the combined extract is washed with saturated aqueous sodium bicarbonate (30 mL), then dried over magnesium sulfate, filtered and evaporated. The crude product is purified by flash chromatography on a 10-gram silica gel cartridge by elution with dichloromethane:ethyl acetate (3:1). Fractions containing the product are combined and evaporated and repurified by flash chromatography on a 10-gram silica gel cartridge by elution with dichloromethane:ethyl acetate (3:1 increasing to 1:1) to obtain {2-[N'-(5-ethyl-2-methyl-6-oxo-1,6-dihydro-pyridine-3-carbonyl)-hydrazino]-2-oxo-ethyl}-carbamic acid tert-butyl ester (686 mg, 73% yield) as a white solid. MS: m/e 755 (100%) (2M+Na), 367 (70%) (M+H); $^1$H NMR (300 MHz, CDCl$_3$, δ, ppm): 8.97 (1H, br.s), 8.22 (1H, br.s), 7.44 (1H, s), 5.21 (1H, br.t), 3.96 (5H, m), 2.59 (3H, s), 2.53 (2H, q), 1.48 (9H, s), 1.18 (3H, t).

Step 3: [5-(5-Ethyl-6-methoxy-2-methyl-pyridin-3-yl)-[1,3,4]oxadiazol-2-ylmethyl]-carbamic acid tert-butyl ester: Into each of three microwave vials is added {2-[N'-(5-ethyl-2-methyl-6-oxo-1,6-dihydro-pyridine-3-carbonyl)-hydrazino]-2-oxo-ethyl}-carbamic acid tert-butyl ester (190 mg, 0.519 mmol), tosyl chloride (119 mg, 0.624 mmol), and 2-t-butylimino-2-diethylamino-1,3-dimethyl-perhydro-1,3,2-diazaphosphorine on polystyrene (2.2 mmol/g, 1.18 g, 2.6 mmol) and anhydrous tetrahydrofuran (6 mL). Each vial is flushed with nitrogen, sealed and heated in the CEM Discover microwave at 145° C. holding at that temperature for 3 min, with a maximum pressure of 7.3 bar. LC/MS shows the reaction is complete. The product from all three vials are filtered and washed with THF. The filtrate is evaporated, and the residue is purified by flash chromatography on a 5-gram silica gel cartridge by elution with dichloromethane:ethyl acetate (3:1). Fractions containing the product are combined again and evaporated to give [5-(5-ethyl-6-methoxy-2-methyl-pyridin-3-yl)-[1,3,4]oxadiazol-2-ylmethyl]-carbamic acid tert-butyl ester (329 mg, 61% yield). MS: m/e 719 (95%) (2M+Na), 249 (100%) (M+H); $^1$H NMR (CDCl$_3$, δ, ppm): 7.87 (1H, s), 5.15 (1H, br.), 4.61 (2H, br.d), 4.00 (3H, s), 2.79 (3H, s), 2.60 (2H, q), 1.49 (9H, s), 1.21 (3H, t).

Step 4: 5-(5-Aminomethyl-[1,3,4]oxadiazol-2-yl)-3-ethyl-6-methyl-1H-pyridin-2-one: To a mixture of [5-(5-ethyl-6-methoxy-2-methyl-pyridin-3-yl)-[1,3,4]oxadiazol-2-ylmethyl]-carbamic acid tert-butyl ester (358 mg, 1.03 mmol) and sodium iodide (463 mg, 3.09 mmol) under a nitrogen atmosphere is added anhydrous acetonitrile (4 mL) followed by chlorotrimethylsilane (388 μL, 3.09 mmol). The reaction mixture is stirred at 50° C. under nitrogen for 8 hr. The black/dark brown reaction mixture is allowed to cool and then quenched with water (0.7 mL). After stirring for 20 min the mixture is evaporated. Isopropanol is added and the black suspension treated with triethylamine to give a yellow orange mixture. This crude suspension is purified by flash chromatography on a 2-gram silica gel cartridge by elution with dichloromethane:methanol (19:1 increasing to 9:1). The fractions containing the product are combined and evaporated to give an orange oil. This oil is treated with 10% trifluoroacetic acid in dichloromethane and a ixture forms. Diethyl ether is added and the resulting suspension is filtered off to give 5-(5-aminomethyl-[1,3,4]oxadiazol-2-yl)-3-ethyl-6-methyl-1H-pyridin-2-one as its trifluoroacetic acid salt (196 mg, 55% yield) as a beige solid. LC/MS: RT: 2.10 min, m/e 235 (M+H); $^1$H NMR (300 MHz, d$_6$-DMSO, δ, ppm): 12.19 (1H, s), 8.70 (3H, br.s), 7.66 (1H, s), 4.46 (2H, s), 2.58 (3H, s), 2.44 (2H, q), 1.12 (3H, t).

Example 23B

3-Ethyl-6-methyl-5-[5-cyanofuran-2-yl]-1H-pyridin-2-one

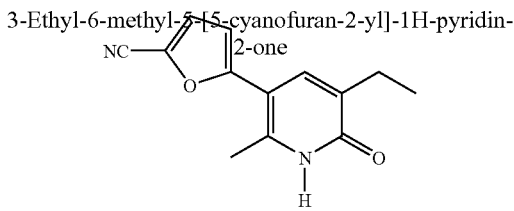

The title compound is prepared from appropriate starting materials and using suitable procedure.

Example 23C

3-Ethyl-6-methyl-5-[5-cyanothiophen-2-yl]-1H-pyridin-2-one

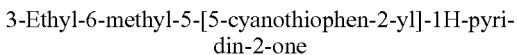
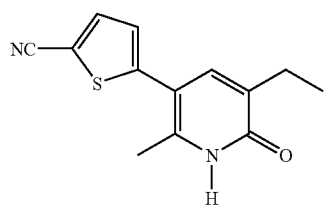

The title compound is prepared from appropriate starting materials and using suitable procedure.

Example 23D

3-Ethyl-6-methyl-5-[5-nitrothiophen-2-yl]-1H-pyridin-2-one

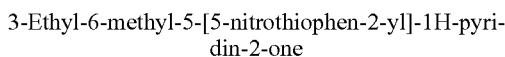
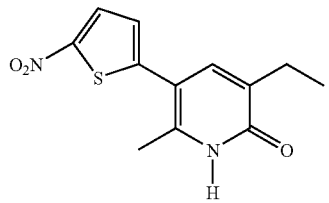

The title compound is prepared from appropriate starting materials and using suitable procedure.

Example 23E

5-Ethyl-2-methyl-1H-[3,3']bipyridinyl-6-one

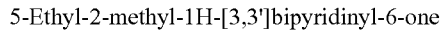
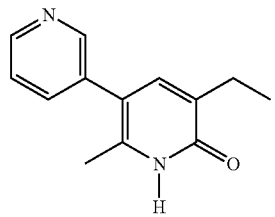

The title compound is prepared from appropriate starting materials and using suitable procedure.

Example 24

3-Ethyl-6-methyl-5-[5-(4-phenylpiperazine-1-sulfonyl)thiophen-2-yl]-1H-pyridin-2-one

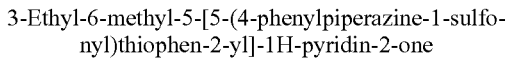
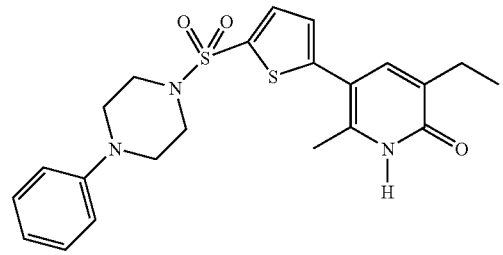

Step 1: 3-Ethyl-2-methoxy-6-methyl-5-(4,4,5,5-tetramethyl-[1,3,2-dioxaborolan-2-yl)-pyridine: The title compound is prepared in accordance with one of the procedures as set forth in PREPARATION 2, Step 1.

Step 2: 3-Ethyl-2-methoxy-6-methyl-5-(thiophen-2-yl)pyridine: Under a nitrogen atmosphere, a three neck round bottom flask is charged with 3-ethyl-2-methoxy-6-methyl-5-(4,4,5,5-tetramethyl-[1,3,2-dioxaborolan-2-yl)pyridine (7.8 g, 28.14 mmol) as prepared above, potassium carbonate (9.72 g, 70.33 mmol), and dichloro[1,1'-bis(diphenylphosphino) ferrocene]-palladium dichloromethane (1.23 mg, 1.68 mmol) followed by anhyd dimethylformamide (100 mL). To this is added a solution of 2-bromothiophene (9.2 g, 56.44 mmol) in dimethylformamide (10 mL) and the resulting mixture is heated to 105-110° C. for 16 hr. The reaction is cooled, diluted with ethyl acetate and washed with water, with brine, dried (sodium sulfate), filtered and concentrated. The residue is purified by flash chromatography eluting with heptane, then heptane-5% ethyl acetate to afford 3-ethyl-2-methoxy-6-methyl-5-(thiophen-2-yl)pyridine as a yellow oil (94% yield).

Step 3: 3-ethyl-6-methyl-5-(thiophen-2-yl)-1H-pyridin-2-one: To a solution of 3-ethyl-2-methoxy-6-methyl-5-(thiophen-2-yl)pyridine (6.15 g, 26.36 mmol) of the above reaction, potassium iodide (8.75 g, 52.71 mmol) and acetonitrile (80 mL) is added chlorotrimethylsilane (6.69 mL, 52.71 mmol) and the resulting cloudy mixture is heated to 80° C. for 2 hr. The reaction is cooled, poured into water and the solids collected by filtration, washed with water, with ethyl acetate and dried giving 3-ethyl-6-methyl-5-(thiophen-2-yl)-1H-pyridin-2-one as a yellow solid (90% yield).

Step 4: 5-(5-Ethyl-2-methyl-6-oxo-1,6-dihydropyridin-3-yl)thiophene-2-sulfonyl chloride: Phosphorus pentachloride (4.67 g, 22.4 mmol) is placed in a three neck round bottom flask and cooled to 0° C. Chlorosulfonic acid (6.53 g, 56.0 mmol) is added slowly. The reaction is stirred until the fuming action stops and the reaction mixture becomes clear. Then a solution of 3-ethyl-6-methyl-5-(thiophen-2-yl)-1H-pyridin-2-one (4.92 g, 22.4 mmol) of the above reaction in chloroform (35 mL) is added dropwise, and stirring at 0° C. is maintained for 5 min, then at room temperature. After 30 min, the reaction is poured into ice water (200 mL) and extracted with dichloromethane. The organic layer is washed with water, dried (sodium sulfate), filtered and concentrated and the residue is triturated with hepatane-30% ethyl acetate to afford the title compound (6.88 g, 97% yield) as a yellow solid. MS: m/e=318 (M+H). $^1$H-NMR (D6-DMSO, δ ppm) 13.2 (br s, 1H); 7.25 (s, 1H); 7.05 (d, 1H, J=3.2 Hz); 6.82 (d, 1H, J=3.2 Hz); 2.39 (q, 2H, J=7.4 Hz); 2.27 (s, 3H); 1.10 (t, 3H, J=7.4 Hz).

Step 5: 3-Ethyl-6-methyl-5-[5-(4-phenylpiperazine-1-sulfonyl)thiophen-2-yl]-1H-pyridin-2-one: To a solution of 5-(5-ethyl-2-methyl-6-oxo-1,6-dihydropyridin-3-yl) thiophene-2-sulfonyl chloride (70 mg, 0.22 mmol) in methylene chloride (5 mL) is added 1-phenylpiperazine (30 mg, 0.22 mmol), piperidinomethyl polystyrene (75 mg, 0.262 mmol) and the mixture is stirred overnight at room temperature under a nitrogen atmosphere. After the reaction is completed (determined by TLC) it is filtered and the filtrate concentrated. The residue is purified by chromatography on a 5 g silica gel cartridge (eluting with ethyl acetate-50% heptane then 100% ethyl acetate) affording the corresponding sulfonamide as a solid (95% yield). LC/MS: RT 3.79 min; m/e 444 (M+H); $^1$H NMR (δ, ppm): 11.83 (1H, s), 7.65 (1H, d); 7.38 (1H, s); 7.28 (1H, d), 7.21 (2H, m), 6.94 (2H, d), 6.81 (1H, t), 3.26 (4H, br d), 3.12 (4H, br d), 2.38 (2H, q), 2.32 (3H, s), 1.09 (3H, t).

Step 6: Hydrochloric Acid Salt Formation: The above sulfonamide in methanol (2 mL) is treated with 2M ethereal Hydrochloric acid (0.1 mL). The methanol is partially removed and more ether added to precipitate the product that is collected by filtration.

Example 25

3-Ethyl-5-{5-[4-(4-fluorophenyl)piperazine-1-sulfonyl]thiophen-2-yl}-6-methyl-1H-pyridin-2-one

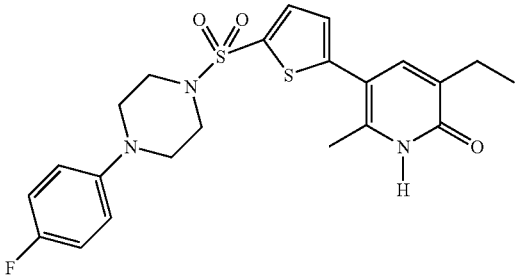

5-(5-Ethyl-2-methyl-6-oxo-1,6-dihydropyridin-3-yl) thiophene-2-sulfonyl chloride is reacted with 1-(4-fluorophenyl)piperazine as described in Step 5, Example 24 to give the title compound as a solid (99% yield). LC/MS: RT 3.92 min; m/e 462 (M+H); $^1$H NMR (δ, ppm): 11.84 (1H, s), 7.65 (1H, d); 7.38 (1H, s); 7.30 (1H, d), 6.94 (4H, m), 3.12 (8H, m), 2.39 (2H, q), 2.33 (3H, s), 1.07 (3H, t); $^{19}$F NMR −123.8.

Example 26

5-(5-Ethyl-2-methyl-6-oxo-1,6-dihydropyridin-3-yl) thiophene-2-sulfonic acid 4-trifluoromethylbenzylamide

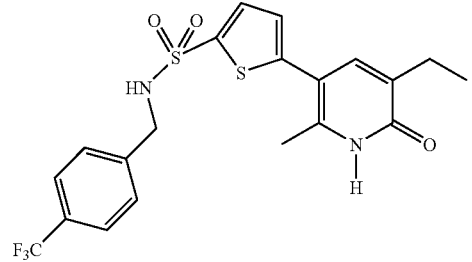

5-(5-Ethyl-2-methyl-6-oxo-1,6-dihydropyridin-3-yl) thiophene-2-sulfonyl chloride is reacted with 4-trifluoromethylbenzylamine as described in Step 5, Example 24 to give the title compound as a solid (44% yield). LC/MS: RT 3.80 min; m/e 457 (M+H).

Example 27

5-(5-Ethyl-2-methyl-6-oxo-1,6-dihydropyridin-3-yl) thiophene-2-sulfonic acid 3,5-difluorobenzylamide

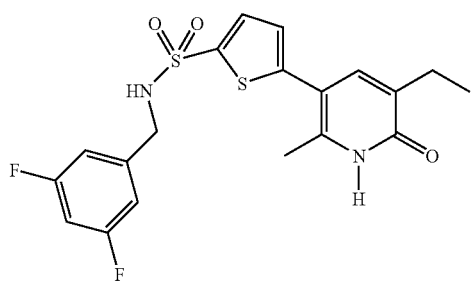

5-(5-Ethyl-2-methyl-6-oxo-1,6-dihydropyridin-3-yl)thiophene-2-sulfonyl chloride is reacted with 3,5-difluorobenzylamine as described in Step 5, Example 24 to give the title compound as a solid (26% yield). LC/MS: RT 3.67 min; m/e 425 (M+H); $^1$H NMR (δ, ppm): 11.82 (1H, s), 8.58 (1H, t), 7.49 (1H, s); 7.25 (1H, s); 7.08 (2H, m), 6.96 (2H, m), 4.20 (2H, d), 2.49 (2H, q), 2.27 (3H, s), 1.10 (3H, t); $^{19}$F NMR −110.

Example 28

5-(5-Ethyl-2-methyl-6-oxo-1,6-dihydropyridin-3-yl)thiophene-2-sulfonic acid dimethylamide

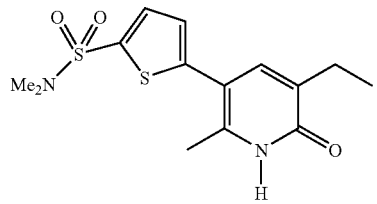

5-(5-Ethyl-2-methyl-6-oxo-1,6-dihydropyridin-3-yl)thiophene-2-sulfonyl chloride is reacted with dimethylamine as described in Step 5, Example 24 to give the title compound as a solid (61% yield). LC/MS: RT 3.68 min; m/e 327 (M+H); $^1$H NMR (δ, ppm): 11.84 (1H, s), 7.61 (1H, d), 7.38 (1H, s); 7.28 (1H, d); 2.69 (6H, s), 2.39 (2H, q), 2.33 (3H, s), 1.07 (3H, t).

Example 29

5-(5-Ethyl-2-methyl-6-oxo-1,6-dihydropyridin-3-yl)thiophene-2-sulfonic acid (3,5-difluorobenzyl)methylamide

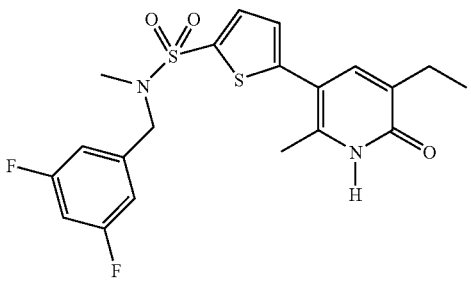

5-(5-Ethyl-2-methyl-6-oxo-1,6-dihydropyridin-3-yl)thiophene-2-sulfonyl chloride is reacted with (3,5-difluorobenzyl)methylamide as described in Step 5, Example 24 to give the title compound as a solid (15% yield). LC/MS: RT 3.30 min; m/e 439 (M+H); $^1$H NMR (δ, ppm): 11.82 (1H, s), 7.72 (1H, d), 7.37 (1H, s); 7.28 (1H, d); 7.03 (3H, m), 4.26 (2H, s), 2.71 (3H, s), 2.37 (2H, q), 2.34 (3H, s), 1.11 (3H, t); $^{19}$F NMR −109.

Example 30

5-(5-Ethyl-2-methyl-6-oxo-1,6-dihydro-pyridin-3-yl)-thiophene-2-sulfonic acid [3-(3-hydroxy-pyrrolidin-1-yl)-propyl]-amide hydrochloride

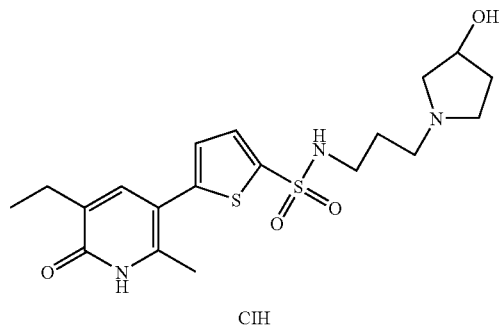

5-(5-Ethyl-2-methyl-6-oxo-1,6-dihydropyridin-3-yl)thiophene-2-sulfonyl chloride is reacted with [3-(3-hydroxy-pyrrolidin-1-yl)-propyl]-amine as described in Step 5, Example 24 to give the title compound (40% yield). LC/MS: RT 2.25 min; m/e 426 (M+H).

Example 31

5-(5-Ethyl-2-methyl-6-oxo-1,6-dihydropyridin-3-yl)thiophene-2-sulfonic acid (pyridin-2-yl)methylamide hydrochloride

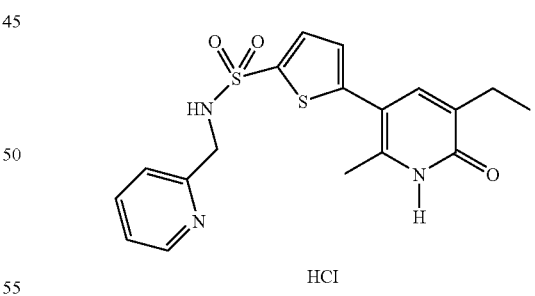

5-(5-Ethyl-2-methyl-6-oxo-1,6-dihydropyridin-3-yl)thiophene-2-sulfonyl chloride is reacted with (pyridin-2-yl)methylamine as described in Step 5, Example 24 and the resulting sulfonamide is converted to hydrochloride following the procedures as set forth in Step 6, Example 24 to give the title compound as a solid (38% yield). LC/MS: RT 2.28 min; me 390 (M+H).

Example 32

5-(5-Ethyl-2-methyl-6-oxo-1,6-dihydropyridin-3-yl)thiophene-2-sulfonic acid 2-phenylaminoethylamide hydrochloride

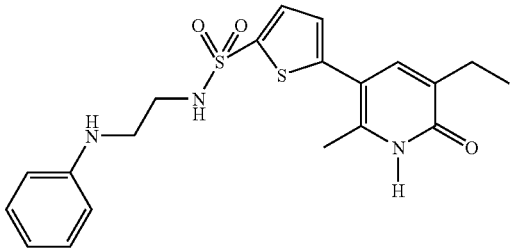

5-(5-Ethyl-2-methyl-6-oxo-1,6-dihydropyridin-3-yl)thiophene-2-sulfonyl chloride is reacted with (2-phenylamino)ethylamine as described in Step 5, Example 24 to give the title compound as a solid (40% yield). LC/MS: RT 2.91 min; m/e 418 (M+H); $^1$H NMR ($\delta$, ppm): 11.84 (1H, br s), 8.12 (1H, t), 7.57 (1H, d), 7.15 (4H, m); 6.96 (3H); 3.22 (2H), 3.10 (2H), 2.38 (2H, q), 2.32 (3H, s), 1.09 (3H, t).

Example 33

5-(5-Ethyl-2-methyl-6-oxo-1,6-dihydropyridin-3-yl)thiophene-2-sulfonic acid (2-methoxyethyl)amide

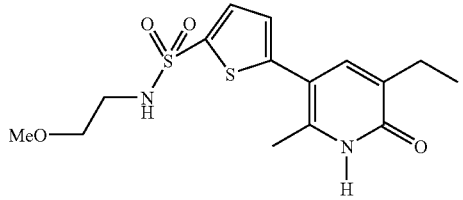

5-(5-Ethyl-2-methyl-6-oxo-1,6-dihydropyridin-3-yl)thiophene-2-sulfonyl chloride is reacted with (2-methoxyethyl)amide as described in Step 5, Example 24 to give the title compound as a solid (26% yield). LC/MS: RT 2.51 min; m/e 357 (M+H); $^1$H NMR ($\delta$, ppm): 11.82 (1H, s), 7.97 (1H, t), 7.54 (1H, d), 7.33 (1H, s); 7.16 (1H, d), 3.34 (2H), 3.32 (3H, s), 3.01 (2H), 2.39 (2H, q), 2.31 (3H, s), 1.07 (3H, t).

Example 34

5-(5-Ethyl-2-methyl-6-oxo-1,6-dihydropyridin-3-yl)thiophene-2-sulfonic acid (3-dimethylaminopropyl)amide hydrochloride

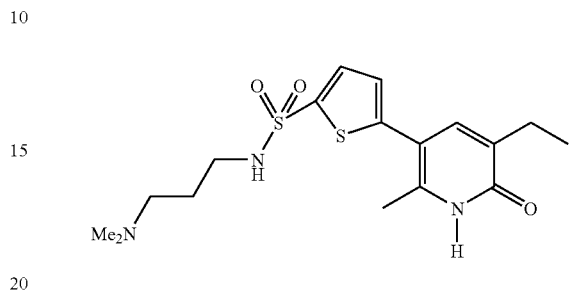

5-(5-Ethyl-2-methyl-6-oxo-1,6-dihydropyridin-3-yl)thiophene-2-sulfonyl chloride is reacted with 3-dimethylaminopropylamine as described in Step 5, Example 24 to give the title compound as a solid (64% yield). LC/MS: RT 1.98 min; m/e 384 (M+H); $^1$H NMR ($\delta$, ppm): 11.84 (1H, br s), 8.06 (1H, t), 7.57 (1H, d), 7.34 (1H, s); 7.17 (1H, d), 2.94 (4H, m), 2.70 (6H), 2.36 (2H, q), 2.32 (3H, s), 1.82 (2H), 1.07 (3H, t).

Example 35

5-(5-Ethyl-2-methyl-6-oxo-1,6-dihydropyridin-3-yl)thiophene-2-sulfonic acid (5-methylfuran-2-yl)methylamide

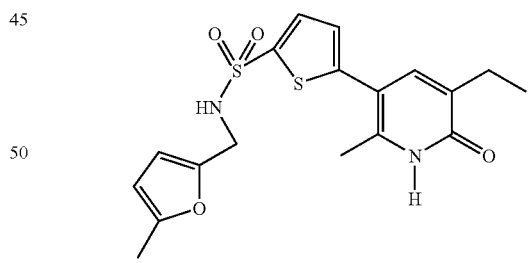

5-(5-Ethyl-2-methyl-6-oxo-1,6-dihydropyridin-3-yl)thiophene-2-sulfonyl chloride is reacted with (5-methylfuran-2-yl)methylamine as described in Step 5, Example 24 to give the title compound as a solid (93% yield). LC/MS: RT 2.90 min; m/e 393 (M+H); $^1$H NMR ($\delta$, ppm): 11.75 (1H, br s), 8.32 (1H, br s), 7.48 (1H, d), 729 (1H, s); 7.10 (1H, d); 6.07 (1H, d), 5.92 (1H, d), 4.05 (2H, s), 2.41 (2H, q), 2.30 (3H, s), 2.15 (3H, s), 1.10 (3H, t).

Example 36

5-(5-Ethyl-2-methyl-6-oxo-1,6-dihydropyridin-3-yl)thiophene-2-sulfonic Acid [2-(1-methylpyrrolidin-2-yl)ethyl]amide hydrochloride

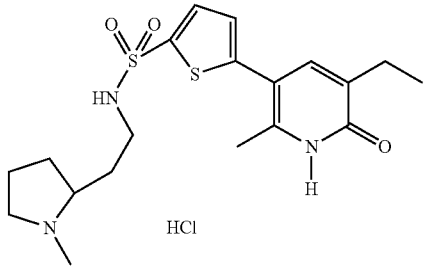

5-(5-Ethyl-2-methyl-6-oxo-1,6-dihydropyridin-3-yl)thiophene-2-sulfonyl chloride is reacted with [2-(1-methylpyrrolidin-2-yl)ethyl]amine as described in Step 5, Example 24 and the resulting product is subsequently converted to hydrochloride to give the title compound as a solid (70% yield). LC/MS: RT 2.03 min; m/e 410 (M+H); $^1$H NMR (δ, ppm): 11.84 (1H, s), 8.05 (1H, t), 7.58 (1H, d), 7.33 (1H, s); 7.17 (1H, d), 3.37 (1H), 3.01 (4H), 2.75 (3H), 2.39 (2H, q), 2.32 (3H, s), 1.60 (6H, m), 1.10 (3H, t).

Example 37

5-(5-Ethyl-2-methyl-6-oxo-1,6-dihydropyridin-3-yl)thiophene-2-sulfonic acid (2-hydroxy-2-phenylethyl)methylamide

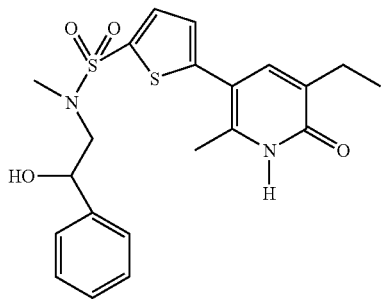

5-(5-Ethyl-2-methyl-6-oxo-1,6-dihydropyridin-3-yl)thiophene-2-sulfonyl chloride is reacted with (2-hydroxy-2-phenylethyl)methylamine as described in Step 5, Example 24 to give the title compound as a solid (58% yield). LC/MS: RT 2.93 min; m/e 433 (M+H); $^1$H NMR (δ, ppm): 11.81 (1H, s), 7.59 (1H, d), 7.34 (6H, m); 7.19 (1H, d), 5.61 (1H, d), 4.78 (1H, q), 3.12 (2H), 2.78 (3H, s), 2.38 (2H), 2.31 (3H, s), 1.09 (3H, t).

Example 38

5-(5-Ethyl-2-methyl-6-oxo-1,6-dihydropyridin-3-yl)thiophene-2-sulfonic acid (2-morpholin-4-yl)ethylamide hydrochloride

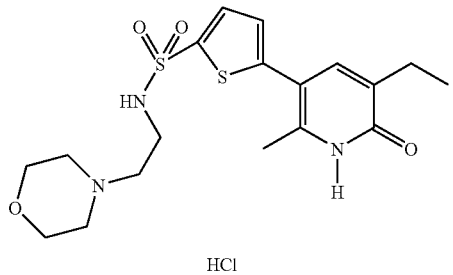

5-(5-Ethyl-2-methyl-6-oxo-1,6-dihydropyridin-3-yl)thiophene-2-sulfonyl chloride is reacted with (2-morpholin-4-yl)ethylamine as described in Steps 5 and 6, Example 24 to give the title compound as a solid (71% yield). LC/MS: RT 1.97 min; m/e 412 (M+H); $^1$H NMR (δ, ppm): 11.85 (1H, br s), 8.36 (1H, t), 7.65 (1H, d); 7.34 (1H, s), 7.20 (1H, d), 3.93 (4H, m), 3.44 (4H, m), 3.23 (4H, m), 2.41 (2H, q), 2.33 (3H, s), 1.10 (3H, t).

Example 39

5-(5-Ethyl-2-methyl-6-oxo-1,6-dihydropyridin-3-yl)thiophene-2-sulfonic acid (1-benzylpiperidin-4-yl)amide hydrochloride

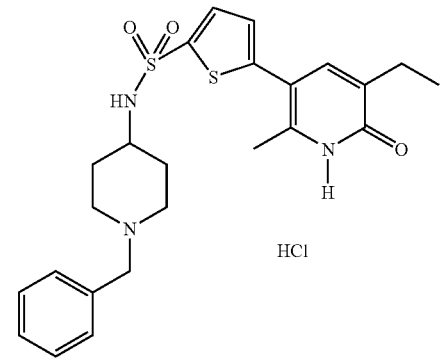

5-(5-Ethyl-2-methyl-6-oxo-1,6-dihydropyridin-3-yl)thiophene-2-sulfonyl chloride was reacted with (1-benzylpiperidin-4-yl)amine as described in Step 5, Example 24 to give the title compound as a solid (80% yield). LC/MS: RT 2.27 min; m/e 472 (M+H).

Example 40

5-(5-Ethyl-2-methyl-6-oxo-1,6-dihydropyridin-3-yl)thiophene-2-sulfonic acid (2-1'-[5-(5-ethyl-2-methyl-6-oxo-1,6-dihydropyridin-3-yl)thiophene-2-sulfonyl]-1H-imidazol-4-yl}ethyl)amide hydrochloride

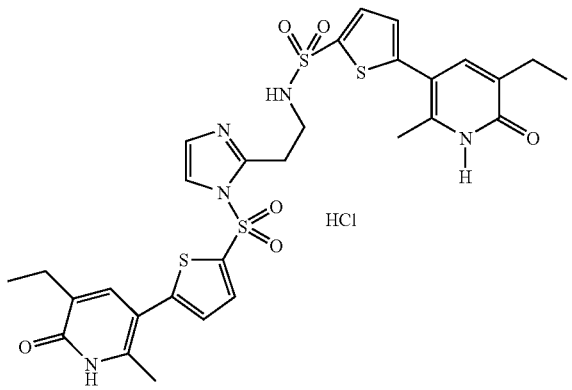

5-(5-Ethyl-2-methyl-6-oxo-1,6-dihydropyridin-3-yl)thiophene-2-sulfonyl chloride is reacted with (1H-imidazol-4-yl)ethylamine as described in Steps 5 and 6, Example 24 to give the title compound as a solid (62% yield). LC/MS: RT 2.85 min; m/e 674 (M+H); $^1$H NMR (δ, ppm): 14.4 (2H, br s), 8.33 (1H, s), 7.93 (2H); 7.53 (2H, dd), 7.30 (3H, m), 7.11 (1H, d), 3.11 (2H), 2.63 (2H), 2.48 (4H, m), 2.28 (6H), 1.07 (6H, t).

Example 41

5-[5-Ethyl-2-methyl-6-oxo-(1,6-dihydropyridin-3-yl)]thiophene-2-sulfonic acid (piperidin-4-yl)methylamide hydrochloride

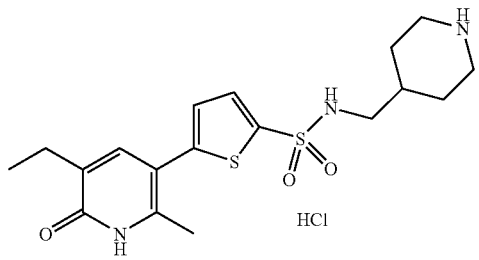

Step 1: 5-(5-Ethyl-2-methyl-6-oxo-1,6-dihydropyridin-3-yl)thiophene-2-sulfonic acid (1-tert-butyloxycarbonylpiperidin-4-yl)methylamide: 5-(5-Ethyl-2-methyl-6-oxo-1,6-dihydropyridin-3-yl)thiophene-2-sulfonyl chloride is reacted with (1-tert-butyloxycarbonylpiperidin-4-yl)methylamide as described in Step 5, Example 24 to give the title compound as a solid (54% yield). LC/MS: RT 3.09 min; m/e 496 (M+H); $^1$H NMR (CDCl$_3$, δ, ppm): 12.19 (1H, br s), 7.56 (1H, d), 7.29 (1H, s), 6.94 (1H, d); 5.15 (1H, t); 4.16 (2H, br t), 3.00 (2H, t), 2.71 (2H, br m), 2.58 (2H, q), 2.45 (3H, s), 1.66 (2H, br m), 1.45 (9H, s), 1.24 (3H, t).

Step 2: 5-[5-Ethyl-2-methyl-6-oxo-(1,6-dihydropyridin-3-yl)]thiophene-2-sulfonic acid (piperidin-4-yl)methylamide hydrochloride: The above (1-tert-butyloxycarbonylpiperidin-4-yl)methylamide (35 mg, 0.071 mmol) is dissolved in dichloromethane (1 mL) and treated with trifluoroacetic acid (0.2 mL), then stirred at room temperature for 1 hr. The reaction is concentrated to oil. Methanol is added and concentrated to oil again. The oil then is dried under high vacuum to obtain 5-[5-ethyl-2-methyl-6-oxo-(1,6-dihydropyridin-3-yl)]thiophene-2-sulfonic acid (piperidin-4-yl)methylamide (41 mg) as beige foam.

The 5-[5-ethyl-2-methyl-6-oxo-(1,6-dihydropyridin-3-yl)]thiophene-2-sulfonic acid (piperidin-4-yl)methylamide is basified with 20% aq sodium hydroxide and extracted with ether and with ethyl acetate. The ethyl acetate layer is evaporated, the residue is dissolved in methanol and treated with 2M ethereal hydrochloric acid. The solids are collected by filtration, washed with ether and dried to afford the title compound (10.5 mg, 38% yield) as beige solid. MS: m/e=396 (M+H); RT=2.00 min.

Example 42

5-(5-Ethyl-2-methyl-6-oxo-1,6-dihydro-pyridin-3-yl)-thiophene-2-sulfonic acid [3-(3,3-difluoro-pyrrolidin-1-yl)-propyl]-amide hydrochloride

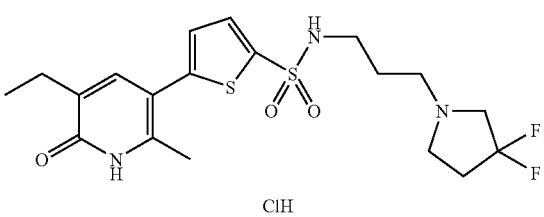

5-(5-Ethyl-2-methyl-6-oxo-1,6-dihydropyridin-3-yl)thiophene-2-sulfonyl chloride is reacted with [3-(3,3-difluoro-pyrrolidin-1-yl)-propyl]-amine as described in Step 5, Example 24 to give the title compound (39% yield). LC/MS: RT 1.69 min; m/e=446 (M+H).

Example 43

5-(5-Ethyl-2-methyl-6-oxo-1,6-dihydropyridin-3-yl)thiophene-2-sulfonic acid 1-(pyridin-2-yl)ethylamide hydrochloride

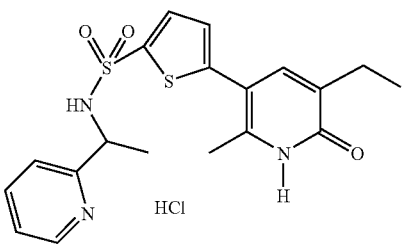

5-(5-Ethyl-2-methyl-6-oxo-1,6-dihydropyridin-3-yl)thiophene-2-sulfonyl chloride is reacted with (1-pyridin-2-yl)ethylamine as described in Step 5, Example 24 to give the title compound as a solid (40% yield). LC/MS: RT 2.40 min; m/e 404 (M+H); $^1$H NMR (δ, ppm): 11.82 (1H, br s), 8.81

(1H, d), 8.60 (1H, d), 8.06 (1H); 7.66 (3H, m); 7.23 (1H, s), 7.04 (1H, d), 4.64 (1H, m), 2.38 (2H, q), 2.30 (3H, s), 1.37 (3H, d), 1.10 (3H, t).

Example 43A 5-(5-Ethyl-2-methyl-6-oxo-1,6-dihydropyridin-3-yl) thiophene-2-sulfonic acid 2-(pyridin-2-yl)ethylamide

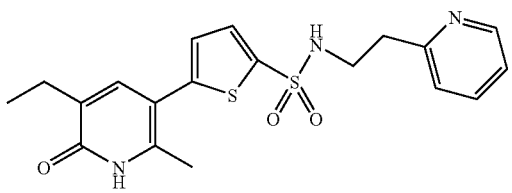

5-(5-Ethyl-2-methyl-6-oxo-1,6-dihydropyridin-3-yl) thiophene-2-sulfonyl chloride is reacted with (2-pyridin-2-yl)ethylamine as described in Step 5, Example 24 to give the title compound. MS: m/e 404 (M+H).

Example 44

5-(5-Ethyl-2-methyl-6-oxo-1,6-dihydropyridin-3-yl) furan-2-sulfonic acid (pyridin-2-yl)methylamide hydrochloride

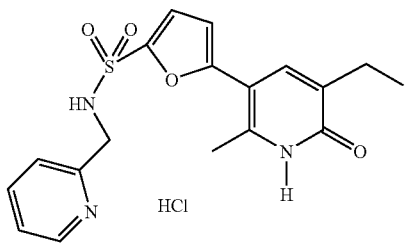

Step 1: 3-Ethyl-2-methoxy-6-methyl-5-furan-2-yl-pyridine: Steps 1 and 2 of Example 24 is substantially repeated utilizing 2.01 g of 3-ethyl-2-methoxy-6-methyl-5-(4,4,5,5-tetramethyl-[1,3,2-dioxaborolan-2-yl])-pyridine and various other appropriate materials in order to obtain 1.26 g of 3-ethyl-2-methoxy-6-methyl-5-furan-2-yl-pyridine; MS m/e=218 (M+H).
Step 2: 3-Ethyl-6-methyl-5-furan-2-yl-1H-pyridin-2-one: Example 24, Step 3 is substantially repeated utilizing appropriate amounts of 3-ethyl-2-methoxy-6-methyl-5-furan-2-yl-pyridine as prepared above and various other reagents in order to obtain 3-ethyl-6-methyl-5-furan-2-yl-1H-pyridin-2-one. MS: m/e=204 (M+H).
Step 3: 5-(5-Ethyl-2-methyl-6-oxo-1,6-dihydropyridin-3-yl)furan-2-sulfonyl chloride: Example 24, Step 4 is substantially repeated utilizing appropriate amounts of 3-ethyl-6-methyl-5-furan-2-yl-1H-pyridin-2-one as prepared above and various other reagents in order to obtain 5-(5-ethyl-2-methyl-6-oxo-1,6-dihydropyridin-3-yl)furan-2-sulfonyl chloride. MS: m/e=302 (M+H).
Step 4: 5-(5-Ethyl-2-methyl-6-oxo-1,6-dihydropyridin-3-yl)furan-2-sulfonic acid (pyridin-2-yl)methylamide hydrochloride: 5-(5-Ethyl-2-methyl-6-oxo-1,6-dihydropyridin-3-yl)furan-2-sulfonyl chloride as prepared above is reacted with (pyridin-2-yl)methylamine as described in Step 5, Example 24 to give the title compound as a solid (78% yield). LC/MS: RT 2.21 min; m/e 374 (M+H).

Example 45

3-Ethyl-6-methyl-5-{5-[(4-pyridin-4-yl)piperazine-1-sulfonyl]furan-2-yl}-1H-pyridin-2-one hydrochloride

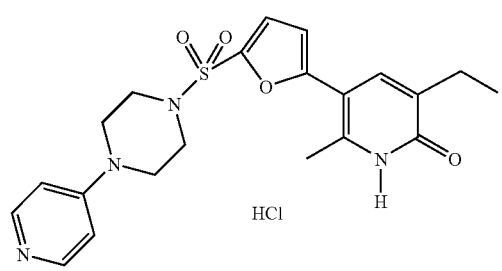

5-(5-Ethyl-2-methyl-6-oxo-1,6-dihydropyridin-3-yl)furan-2-sulfonyl chloride is reacted with 1-(pyridin-4-yl)piperazine as described in Step 5, Example 24 to give the title compound as a solid (72% yield). LC/MS: RT 2.13 min; m/e 429 (M+H).

Example 46

5-(5-Ethyl-2-methyl-6-oxo-1,6-dihydropyridin-3-yl) furan-2-sulfonic acid (1-benzylpiperidin-4-yl)amide hydrochloride

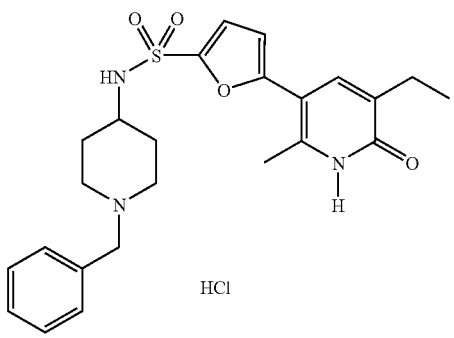

5-(5-Ethyl-2-methyl-6-oxo-1,6-dihydropyridin-3-yl)furan-2-sulfonyl chloride is reacted with (1-benzylpiperidin-4-yl)amine as described in step 5, Example 24 to give the title compound as a solid (38% yield). LC/MS: RT 2.20 min; m/e 456 (M+H).

Example 47

5-(5-Ethyl-2-methyl-6-oxo-1,6-dihydropyridin-3-yl)furan-2-sulfonic acid (2-morpholin-4-yl)ethylamide hydrochloride

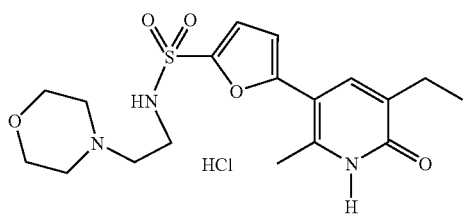

5-(5-Ethyl-2-methyl-6-oxo-1,6-dihydropyridin-3-yl)furan-2-sulfonyl chloride is reacted with (2-morpholin-4-yl)ethylamine as described in Step 5, Example 24 to give the title compound as a solid (51% yield). LC/MS: RT 1.93 min; m/e 396 (M+H); $^1$H NMR (δ, ppm): 11.85 (1H, s), 8.46 (1H, t), 7.52 (1H, s), 7.24 (1H, d); 6.73 (1H, d), 3.85 (4H, m), 3.12 (8H, m), 2.49 (5H), 1.11 (3H, t).

Example 48

5-(5-Ethyl-2-methyl-6-oxo-1,6-dihydropyridin-3-yl)furan-2-sulfonic acid (2-pyridin-3-yl)ethylamide hydrochloride

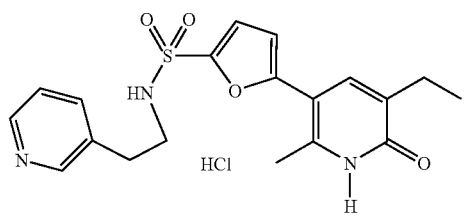

5-(5-Ethyl-2-methyl-6-oxo-1,6-dihydropyridin-3-yl)furan-2-sulfonyl chloride is reacted with (2-pyridin-3-yl)ethylamine as described in Step 5, Example 24 to give the title compound as a solid (34% yield). LC/MS: RT 2.00 min; m/e 388 (M+H); $^1$H NMR (δ, ppm): 8.75 (2H), 7.90-8.36 (3H), 7.45 (1H, s), 7.13 (1H, d); 6.68 (1H, d), 3.27 (2H), 2.96 (2H), 2.36 (3H, s), 2.40 (2H), 1.11 (3H, t).

Example 49

5-(5-Ethyl-2-methyl-6-oxo-1,6-dihydropyridin-3-yl)furan-2-sulfonic Acid (3-pyrrolidin-1-yl)propylamide hydrochloride

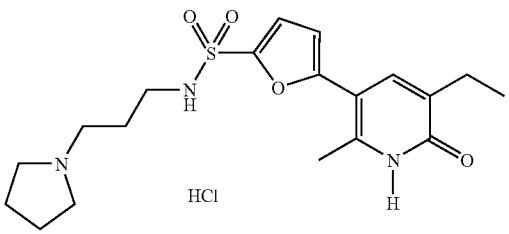

5-(5-Ethyl-2-methyl-6-oxo-1,6-dihydropyridin-3-yl)furan-2-sulfonyl chloride is reacted with (3-pyrrolidin-1-yl)propylamine as described in Step 5, Example 24 to give the title compound as a solid (15% yield). LC/MS: RT 1.98 min; m/e 394 (M+H).

Example 50

5-(5-Ethyl-2-methyl-6-oxo-1,6-dihydropyridin-3-yl)furan-2-sulfonic acid (2-piperidin-1-yl)ethylamide hydrochloride

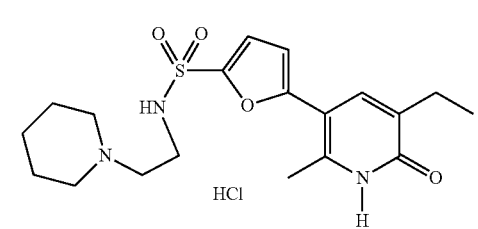

5-(5-Ethyl-2-methyl-6-oxo-1,6-dihydropyridin-3-yl)furan-2-sulfonyl chloride is reacted with (2-piperidin-1-yl)ethylamine as described in Steps 5 and 6, Example 24 to give the title compound as a solid (84% yield). LC/MS: RT 2.02 min; m/e 394 (M+H).

Example 51

3-Ethyl-6-methyl-5-[5-(4-piperidin-1-yl)piperidine-1-sulfonylfuran-2-yl]-1H-pyridin-2-one hydrochloride

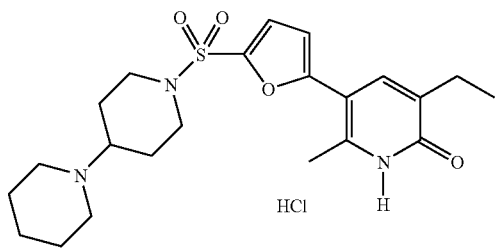

5-(5-Ethyl-2-methyl-6-oxo-1,6-dihydropyridin-3-yl)furan-2-sulfonyl chloride is reacted with 4-(piperidin-1-yl)piperidine as described in Steps 5 and 6, Example 24 to give the title compound as a solid (55% yield). LC/MS: RT 2.13 min; m/e 434 (M+H); $^1$H NMR (CDCl$_3$, δ, ppm): 7.63 (1H, s), 7.23 (1H, d), 6.73 (1H, d), 4.05 (2H, br d); 3.33 (5H), 2.78 (2H, br t), 2.52 (2H), 2.50 (3H, s), 2.21 (2H, br d), 1.84 (8H, m), 1.22 (3H, t).

Example 52

3-Ethyl-6-methyl-5-[5-(4-methyl-1,4-diazepane-1-sulfonyl)furan-2-yl]-1H-pyridin-2-one hydrochloride

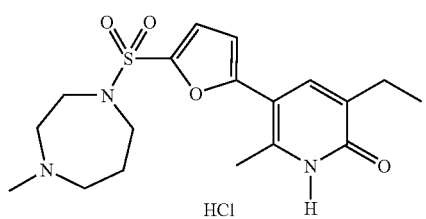

5-(5-Ethyl-2-methyl-6-oxo-1,6-dihydropyridin-3-yl)furan-2-sulfonyl chloride is reacted with 1-methyl-1,4-diazepane as described in Steps 5 and 6, Example 1 to give the title compound as a solid (73% yield). LC/MS: RT 2.00 min; m/e 380 (M+H); $^1$H NMR (CDCl$_3$, δ, ppm): 11.81 (1H), 7.51 (1H), 7.29 (1H), 6.78 (1H); 3.85 (2H), 3.46 (6H), 3.19 (2H), 2.78 (3H), 2.40 (5H), 1.09 (3H, t).

Example 52A

3-Ethyl-6-methyl-5-[5-(4-methyl-1,4-diazepane-1-sulfonyl)thiophen-2-yl]-1H-pyridin-2-one hydrochloride

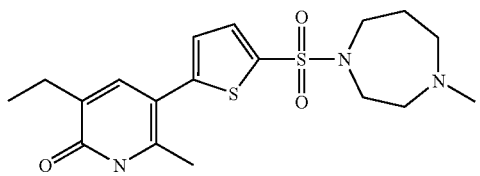

5-(5-Ethyl-2-methyl-6-oxo-1,6-dihydropyridin-3-yl)thiophene-2-sulfonyl chloride is reacted with 1-methyl-1,4-diazepane as described in Steps 5 and 6, Example 1 to give the title compound. MS: m/e 396 (M+H)

Example 53

5-(5-Ethyl-2-methyl-6-oxo-1,6-dihydropyridin-3-yl) furan-2-sulfonic acid (2-pyrrolidin-1-yl)ethylamide hydrochloride

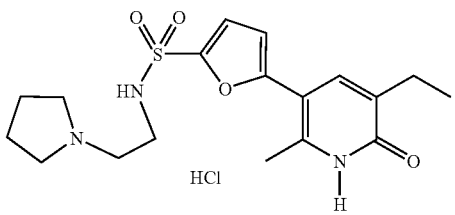

5-(5-Ethyl-2-methyl-6-oxo-1,6-dihydropyridin-3-yl)furan-2-sulfonyl chloride is reacted with (2-pyrolidin-1-yl) ethylamine as described in Steps 5 and 6, Example 24 to give the title compound as a solid (97% yield). LC/MS: RT 1.95 min; m/e 380 (M+H); $^1$H NMR (δ, ppm): 11.86 (1H, s), 8.44 (1H, br t), 7.53 (1H, s), 7.24 (1H, d); 6.74 (1H, d), 3.0-3.89 (8H), 2.39 (5H), 1.85 (4H), 1.09 (3H, t).

Example 54

5-(5-Ethyl-2-methyl-6-oxo-1,6-dihydropyridin-3-yl)furan-2-sulfonic acid (3-imidazol-1-yl)propylamide hydrochloride

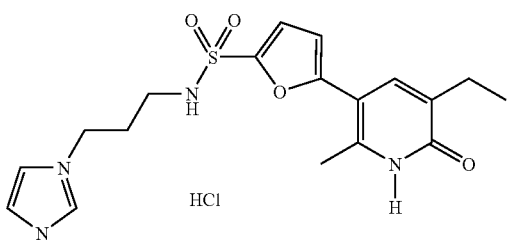

5-(5-Ethyl-2-methyl-6-oxo-1,6-dihydropyridin-3-yl)furan-2-sulfonyl chloride is reacted with (3-imidazol-1-yl)propylamine as described in Steps 5 and 6, Example 24 to give the title compound as a solid (41% yield). LC/MS: RT 1.54 min; m/e 391 (M+H).

Example 55

5-(5-Ethyl-2-methyl-6-oxo-1,6-dihydropyridin-3-yl)furan-2-sulfonic acid (pyridin-3-yl)methylamide hydrochloride

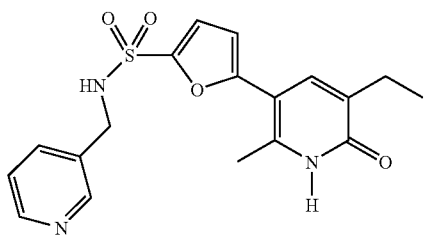

5-(5-Ethyl-2-methyl-6-oxo-1,6-dihydropyridin-3-yl)furan-2-sulfonyl chloride is reacted with (pyridin-3-yl)methylamine as described in Steps 5 and 6, Example 24 to give the title compound as a solid (10% yield). LC/MS: RT 2.05 min; m/e 374 (M+H).

Example 55A

5-(5-Ethyl-2-methyl-6-oxo-1,6-dihydro-pyridin-3-yl)-furan-2-sulfonic acid 3,5-difluoro-benzylamide

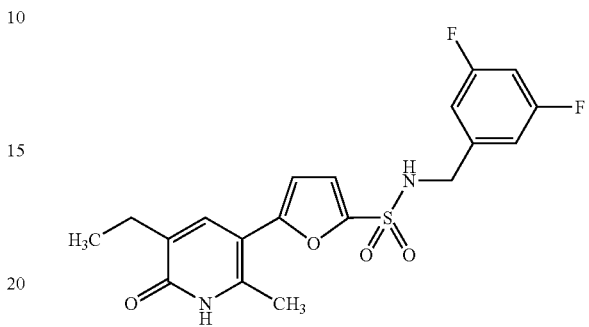

5-(5-Ethyl-2-methyl-6-oxo-1,6-dihydropyridin-3-yl)furan-2-sulfonyl chloride is reacted with 3,5-difluoro-benzylamine as described in Steps 5 and 6, Example 24 to give the title compound as a solid (10% yield). MS: m/e 409 (M+H).

Example 56

3-Ethyl-6-methyl-5-{5-[4-(2-pyridin-1-yl)ethylpiperizine-1-sulfonyl]thiophen-2-yl}-1H-pyridin-2-one dihydrochloride

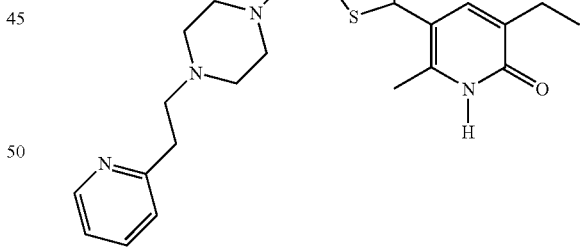

5-(5-Ethyl-2-methyl-6-oxo-1,6-dihydropyridin-3-yl)thiophene-2-sulfonyl chloride is reacted with 1-(2-pyridin-2-yl)ethylpiperazine as described in Steps 5 and 6, Example 24 to give the title compound as a yellow solid (95% yield). LC/MS: RT 1.90 min; m/e 473 (M+H); $^1$H NMR (δ, ppm): 11.96 (1H, br), 8.90 (1H, s), 8.02 (2H, s), 7.70 (1H, s), 7.36 (2H, d), 7.16 (1H, s), 3.00-4.00 (8H, m), 2.20-2.40 (9H, m), 1.10 (3H, t).

Example 57

3-Ethyl-6-methyl-5-{5-[4-(2-piperidin-1-yl)ethylpiperizine-1-sulfonyl]thiophen-2-yl}-1H-pyridin-2-one dihydrochloride

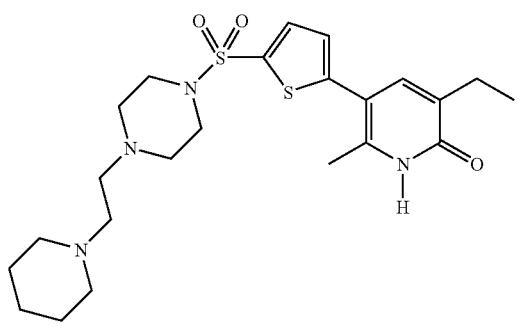

2 HCl 5-(5-Ethyl-2-methyl-6-oxo-1,6-dihydropyridin-3-yl) thiophene-2-sulfonyl chloride is reacted with 1-(2-piperidin-1-yl)ethylpiperazine as described in steps 5 and 6, Example 24 to give the title compound as a beige solid (94% yield). LC/MS: RT 2.20 min; m/e 478 (M+H).

Example 58

3-Ethyl-6-methyl-5-[5-(4-pyridin-4-yl)methylpiperizine-1-sulfonyl]thiophen-2-yl}1H-pyridin-2-one dihydrochloride

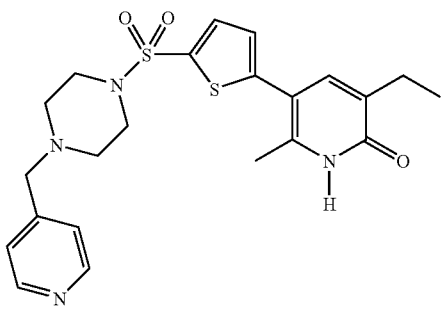

2 HCl 5-(5-Ethyl-2-methyl-6-oxo-1,6-dihydropyridin-3-yl) thiophene-2-sulfonyl chloride is reacted with 1-(pyridin-4-yl)methylpiperazine as described in Steps 5 and 6, Example 24 to give the title compound as a beige solid (90% yield). LC/MS: RT 2.20 min; m/e 459 (M+H); $^1$H NMR ($\delta$, ppm): 11.94 (1H, br), 8.87 (2H, s), 7.98 (2H, s), 7.66 (1H, s), 7.35 (2H, s), 7.16 (1H, s), 4.6-3.8 (m), 2.25-2.60 (m), 1.11 (3H, t).

Example 59

5-[5-Ethyl-2-methyl-6-oxo-1,6-dihydropyridin-3-yl] thiophene-2-sulfonic acid (3-imidazol-1-yl)propylamide hydrochloride

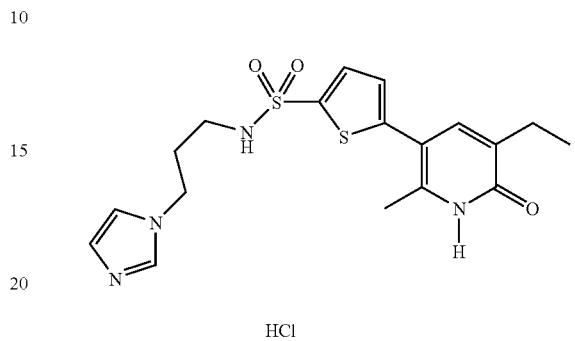

HCl 5-(5-Ethyl-2-methyl-6-oxo-1,6-dihydropyridin-3-yl) thiophene-2-sulfonyl chloride is reacted with 3-(imidaol-1-yl)propylamine as described in Steps 5 and 6, Example 24 to give the title compound as a yellow solid (18% yield). LC/MS: RT 2.00 min; m/e 407; $^1$H NMR ($\delta$, ppm): 11.84 (1H, br), 7.08-8.80 (6H, m), 3.29 (2H, m), 2.88 (2H, m), 2.42 (2H, q), 2.31 (3H, s), 2.00 (2H, m), 1.11 (3H, t).

Example 60

3-Ethyl-6-methyl-5-{5-[4-(2-pyridin-2-yl)ethylpiperazine-1-sulfonyl]thiophen-2-yl}-1H-pyridin-2-one dihydrochloride

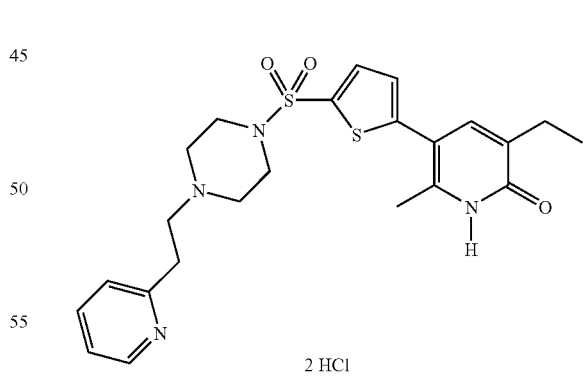

2 HCl 5-(5-Ethyl-2-methyl-6-oxo-1,6-dihydropyridin-3-yl) thiophene-2-sulfonyl chloride is reacted with 1-(2-pyridin-2-yl)ethylpiperazine as described in Steps 5 and 6, Example 24 to give the title compound as a yellow solid (95% yield). LC/MS: RT 2.00 min; m/e 473; $^1$H NMR ($\delta$, ppm): 11.83 (1H, br), 8.73 (1H, s), 8.30 (1H, s), 7.56-7.90 (3H, t), 7.20-7.44 (2H, t), 3.05-4.70 (12H, m), 2.20-2.60 (5H, m), 1.10 (3H, t).

Example 61

3-Ethyl-6-methyl-5-{5-[4-(2-pyrrolidin-1-yl)eth-ylpiperazine-1-sulfonyl]thiophen-2-yl}-1H-pyridin-2-one dihydrochloride

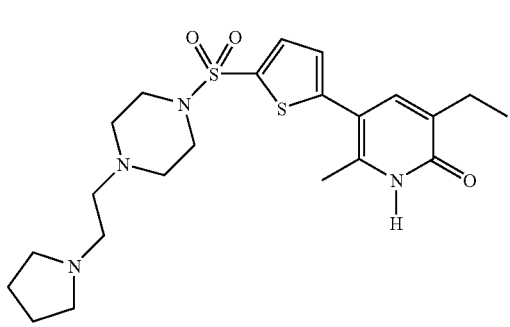

2 HCl 5-(5-Ethyl-2-methyl-6-oxo-1,6-dihydropyridin-3-yl) thiophene-2-sulfonyl chloride is reacted with 1-(2-pyrrolidin-1-yl)ethylpiperazine as described in Steps 5 and 6, Example 24 to give the title compound as a yellow solid (70% yield). LC/MS: RT 2.15 min; m/e 465.

Example 62

3-Ethyl-6-methyl-5-{5-[4-(3-pyrrolidin-1-yl)propy-lpiperazine-1-sulfonyl]thiophen-2-yl}-1H-pyridin-2-one dihydrochloride

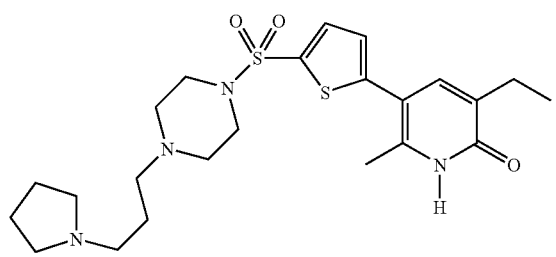

2 HCl 5-(5-Ethyl-2-methyl-6-oxo-1,6-dihydropyridin-3-yl) thiophene-2-sulfonyl chloride is reacted with 1-(3-pyrrolidin-1-yl)propylpiperazine as described in Steps 5 and 6, Example 24 to give the title compound as a yellow solid (67% yield). LC/MS: RT 1.95 min; m/e 479.

Example 63

5-(5-Ethyl-2-methyl-6-oxo-1,6-dihydro-pyridin-3-yl)-thiophene-2-sulfonic acid (3-piperidin-1-yl-pro-pyl)-amide hydrochloride

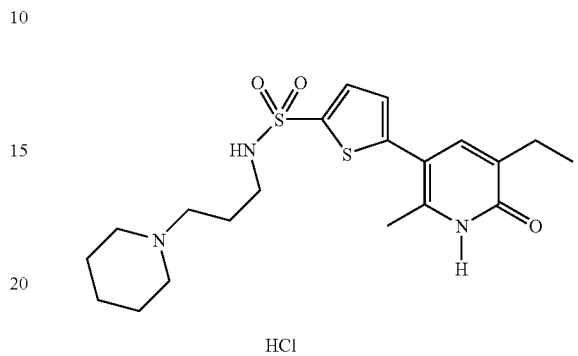

HCl 5-(5-Ethyl-2-methyl-6-oxo-1,6-dihydropyridin-3-yl) thiophene-2-sulfonyl chloride is reacted with 1-(3-piperidin-1-yl)propylamine as described in Steps 5 and 6, Example 24 to give the title compound as a brown solid (72% yield). LC/MS: RT 2.03 min; m/e 424.

Example 64

5-{5-[4-(2-Dimethylaminoethyl)piperazine-1-sulfo-nyl]thiophen-2-yl}-3-ethyl-6-methyl-1H-pyridn-2-one dihydrochloride

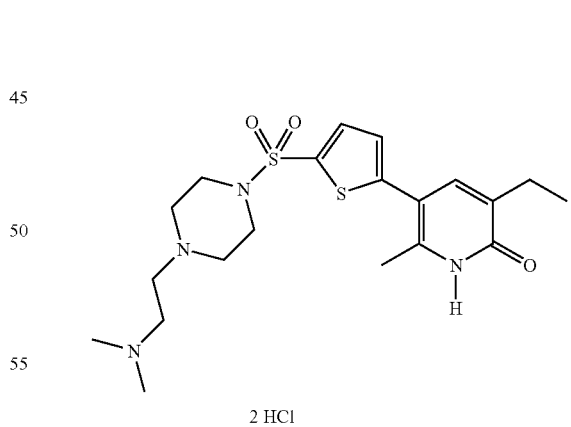

2 HCl 5-(5-Ethyl-2-methyl-6-oxo-1,6-dihydropyridin-3-yl) thiophene-2-sulfonyl chloride is reacted with dimethylami-noethylpiperazine as described in Steps 5 and 6, Example 24 to give the title compound as a brown solid (36% yield). LC/MS: RT 2.14 min; m/e 439.

Example 65

5-(5-Ethyl-2-methyl-6-oxo-1,6-dihydropyridin-3-yl)thiophene-2-sulfonic acid 3-(4-methylpiperazin-1-yl)propylamide dihydrochloride

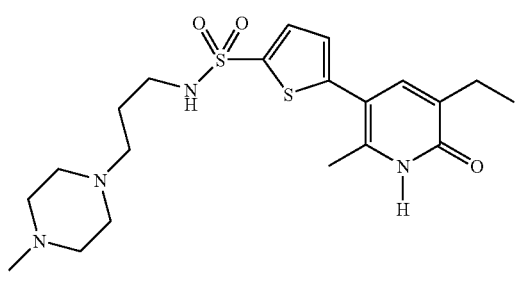

2 HCl 5-(5-Ethyl-2-methyl-6-oxo-1,6-dihydropyridin-3-yl)thiophene-2-sulfonyl chloride is reacted with 3-(4-methylpiperazin-1-yl)propylamine as described in Steps 5 and 6, Example 24 to give the title compound as a white solid (80% yield). LC/MS: RT 1.82 min; m/e 439; $^1$H NMR ($\delta$, ppm): 8.01 (1H, s), 7.56 (1H, d), 7.35 (1H, s), 7.18 (1H, d), 2.70-3.60 (m), 2.40 (2H, q), 2.33 (3H, s), 2.50-2.10 (6H, m), 1.89 (2H, m), 1.09 (3H, t).

Example 66

3-Ethyl-6-methyl-5-{5-[(4-pyrrolidin-1-yl)piperidine-1-sulfonyl]thiophen-2-yl}-1H-pyridin-2-one hydrochloride

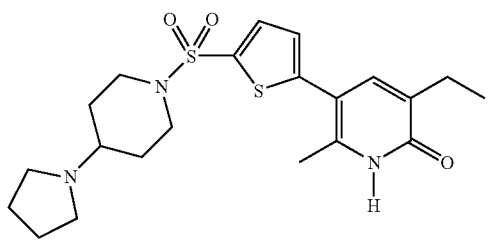

HCl 5-(5-Ethyl-2-methyl-6-oxo-1,6-dihydropyridin-3-yl)thiophene-2-sulfonyl chloride is reacted with 4-(pyrrolidin-1-yl)piperidine as described in Steps 5 and 6, Example 24 to give the title compound as a yellow solid (58% yield). LC/MS: RT 2.12 min; m/e 436; $^1$H NMR ($\delta$, ppm): 11.89 (1H, br), 10.87 (1H, br), 7.64 (1H, d), 7.36 (1H, s), 7.29 (1H, d), 3.75 (2H, d), 3.46 (2H, m), 3.08-3.28 (2H, s), 2.87-3.08 (2H, s), 2.35-2.60 (2H, q), 2.35 (3H, s), 2.08-2.24 (2H, m), 1.69-2.03 (6H, m), 1.10 (3H, t).

Example 67

3-Ethyl-6-methyl-5-{5-[(4-piperidin-1-yl)piperidine-1-sulfonyl]thiophen-2-yl}-1H-pyridin-2-one hydrochloride

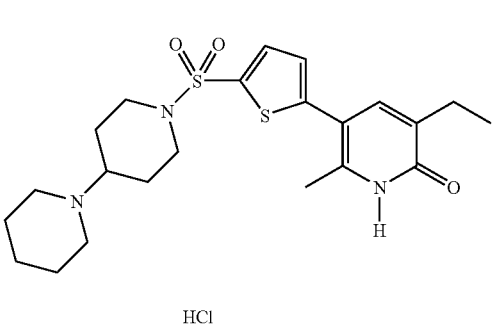

HCl 5-(5-Ethyl-2-methyl-6-oxo-1,6-dihydropyridin-3-yl)thiophene-2-sulfonyl chloride is reacted with 4-(piperidin-1-yl)piperidine as described in Steps 5 and 6, Example 24 to give the title compound as a white solid (93% yield). LC/MS: RT 2.17 min; m/e 450; $^1$H NMR ($\delta$, ppm): 11.89 (1H, br), 10.44 (1H, br), 7.64 (1H, d), 7.37 (1H, s), 7.29 (1H, d), 3.78 (2H, d), 3.50 (2H, d), 2.78-2.98 (2H, m), 2.35-2.58 (2H, q), 2.34 (3H, s), 2.20 (2H, d), 1.60-1.96 (8H, m), 1.20-1.50 (2H, m), 1.10 (3H, t).

Example 68

5-[5-Ethyl-2-methyl-6-oxo-1,6-dihydropyridin-3-yl]thiophene-2-sulfonic acid [3-(2-oxopyrrolidin-1-yl)propyl]amide

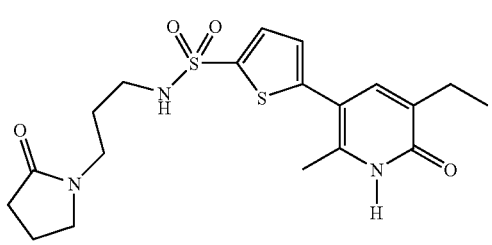

5-(5-Ethyl-2-methyl-6-oxo-1,6-dihydropyridin-3-yl)thiophene-2-sulfonyl chloride is reacted with 1-(3-aminopropyl)pyrrolidin-2-one as described in Step 5, Example 24 to give the title compound as a white solid (69% yield). LC/MS: RT 2.42 min; m/e 424.

Example 69

5-[5-Ethyl-2-methyl-6-oxo-1,6-dihydropyridin-3-yl]thiophene-2-sulfonic acid (2-piperidin-1-yl)ethylamide hydrochloride

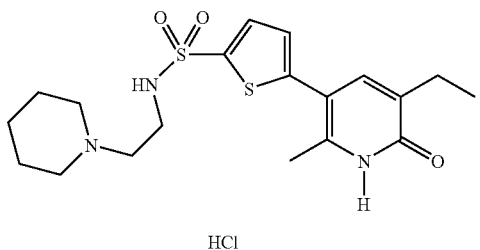

5-(5-Ethyl-2-methyl-6-oxo-1,6-dihydropyridin-3-yl)thiophene-2-sulfonyl chloride is reacted with 2-(piperidin-1-yl)ethylamine as described in Steps 5 and 6, Example 24 to give the title compound as a white solid (60% yield). LC/MS: RT 2.07 min; m/e 410; $^1$H NMR (δ, ppm): 10.68 (1H, br), 8.39 (1H, s), 7.64 (1H, s), 7.35 (1H, s), 7.20 (1H, s), 3.25-3.50 (4H, m), 2.80-3.00 (2H, m), 2.10-2.60 (7H, m), 1.60-2.00 (4H, m), 1.20-1.40 (2H, m), 1.10 (3H, t).

Example 70

3-Ethyl-5-{5-[(3-imidazo-1-yl)methylpiperidine-1-sulfonyl]thiophene-2-yl}-6-methyl-1H-pyridin-2-one hydrochloride

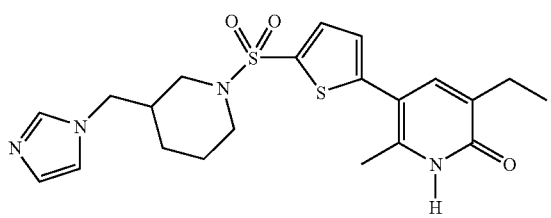

5-(5-Ethyl-2-methyl-6-oxo-1,6-dihydropyridin-3-yl)thiophene-2-sulfonyl chloride is reacted with 3-(imidazol-1-yl)piperidine as described in Steps 5 and 6, Example 24 to give the title compound as a yellow (66% yield). LC/MS: RT 2.15 min; m/e 447; $^1$H NMR (δ, ppm): 14.66 (1H, br), 11.88 (1H, br), 9.17 (1H, s), 7.79 (1H, s), 7.74 (1H, s), 7.60 (1H, d), 7.36 (1H, s), 7.28 (1H, d), 4.08-4.35 (2H, m), 3.00-3.60 (4H, m), 2.25-2.75 (6H, m), 1.20-1.84 (4H, m), 1.10 (3H, t).

Example 71

5-(5-Ethyl-2-methyl-6-oxo-1,6-dihydropyridin-3-yl)thiophene-2-sulfonic acid (2-dimethylamino-2-pyridin-3-yl)ethylamide dihydrochloride

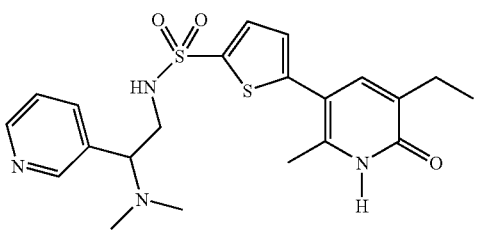

5-(5-Ethyl-2-methyl-6-oxo-1,6-dihydropyridin-3-yl)thiophene-2-sulfonyl chloride is reacted with 2-dimethylamino-2-(3-pyridyl)ethylamine as described in Steps 5 and 6, Example 24 to give the title compound as a purple solid (59% yield). LC/MS: RT 1.94 min; m/e 447; $^1$H NMR (δ, ppm): 11.88 (1H, br), 8.9 (1H, s), 8.79 (1H, d), 8.33 (2H, br), 7.75 (1H, br), 7.61 (1H, q), 7.32 (1H, s), 7.17 (1H, q), 3.63-3.90 (2H, m), 2.20-2.90 (12H, m), 1.11 (3H, t).

Example 72

5-[5-Ethyl-2-methyl-6-oxo-1,6-dihydropyridin-3-yl]thiophene-2-sulfonic acid 2-(morpholin-4-yl)-2-(pyridin-3-yl)ethylamide dihydrochloride

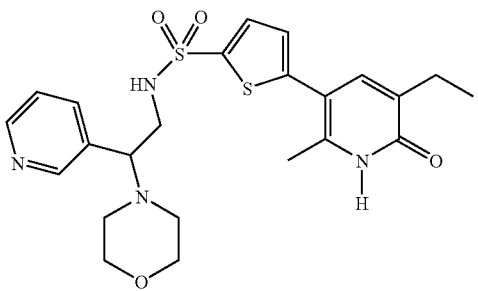

5-(5-Ethyl-2-methyl-6-oxo-1,6-dihydropyridin-3-yl)thiophene-2-sulfonyl chloride is reacted with 2-(morpholin-4-yl)-2-(pyridin-3-yl)ethylamine as described in Steps 5 and 6, Example 24 to give the title compound as a white solid (55% yield). LC/MS: RT 2.06 min; m/e 489; $^1$H NMR (δ, ppm): 11.85 (1H, br), 8.98 (1H, s), 8.86 (1H, d), 8.54 (1H, d), 7.90 (2H, t), 7.58 (1H, t), 7.34 (1H, s), 7.1.7 (1H, d), 4.65 (1H, br), 3.6-4.10 (8H, br), 2.8-3.1 (2H, br), 2.40 (2H, q), 2.33 (3H, s), 1.10 (3H, t).

Example 73

5-[5-Ethyl-2-methyl-6-oxo-1,6-dihydropyridin-3-yl]
thiophene-2-sulfonic acid (6-methylpyrazin-2-yl)
methylamide hydrochloride

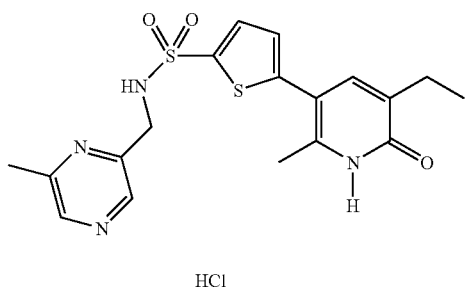

5-(5-Ethyl-2-methyl-6-oxo-1,6-dihydropyridin-3-yl) thiophene-2-sulfonyl chloride is reacted with (6-methylpyrazin-2-yl)methylamine as described in Steps 5 and 6, Example 24 to give the title compound as a white solid (33% yield). LC/MS: RT 2.40 min; m/e 405; $^1$H NMR ($\delta$, ppm): 11.83 (1H, br), 8.63 (1H, t), 8.42 (2H, d), 7.49 (1H, d), 7.29 (1H, s), 7.09 (1H, d), 4.25 (2H, d), 2.34-2.58 (5H, m), 2.29 (3H, s), 1.10 (3H, t).

Example 74

5-[5-Ethyl-2-methyl-6-oxo-1,6-dihydropyridin-3-yl]
thiophene-2-sulfonic acid (1-cyclopropylmethylpiperidin-4-yl)amide hydrochloride

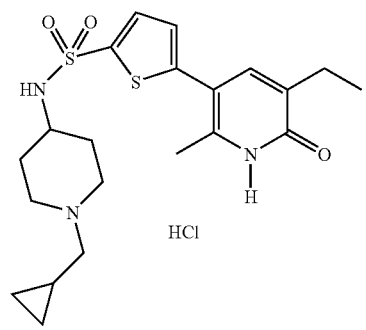

5-(5-Ethyl-2-methyl-6-oxo-1,6-dihydropyridin-3-yl) thiophene-2-sulfonyl chloride is reacted with (1-cyclopropylmethylpiperidin-4-yl)amine as described in Steps 5 and 6, Example 24 to give the title compound as a white solid (58% yield). LC/MS: RT 2.07 min; m/e 436; $^1$H NMR ($\delta$, ppm): 11.85 (1H, br), 10.18 (1H, br), 8.30 (1H, d), 7.57 (1H, d), 7.34 (1H, s), 7.17 (1H, d), 3.30-3.58 (2H, m), 2.80-3.08 (2H, m), 2.40 (2H, q), 2.33 (3H, s), 1.72-2.18 (4H, m), 1.00-1.20 (4H, m), 0.60 (2H, m), 0.35 (2H, m).

Example 75

5-(5-Ethyl-2-methyl-6-oxo-1,6-dihydropyridin-3-yl)
thiophene-2-sulfonic acid (1-cyclohexylmethylpiperidin-4-yl)amide hydrochloride

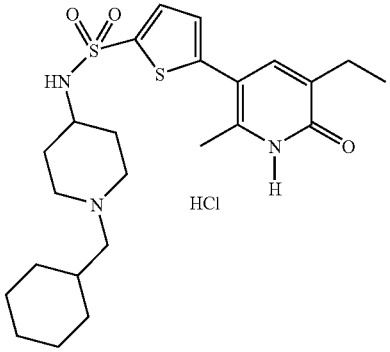

5-(5-Ethyl-2-methyl-6-oxo-1,6-dihydropyridin-3-yl) thiophene-2-sulfonyl chloride is reacted with (1-cyclohexylmethylpiperidin-4-yl)amine as described in Steps 5 and 6, Example 24 to give the title compound as a white solid (73% yield). LC/MS: RT 2.28 min; m/e 478; $^1$H NMR ($\delta$, ppm): 11.85 (1H, br), 9.80 (1H, br), 8.18-8.37 (1H, m), 7.54-7.65 (1H, m), 7.34 (1H, s), 7.17 (1H, d), 2.70-3.75 (7H, m), 2.40 (2H, q), 2.32 (3H, s), 1.50-2.08 (10H, m), 0.80-1.35 (8H, m).

Example 76

5-[5-Ethyl-2-methyl-6-oxo-1,6-dihydropyridin-3-yl]-
thiophene-2-sulfonic acid 1-(4-chlorobenzyl)piperidin-4-yl]amide hydrochloride

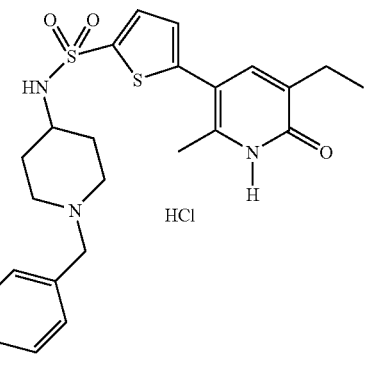

5-(5-Ethyl-2-methyl-6-oxo-1,6-dihydropyridin-3-yl) thiophene-2-sulfonyl chloride is reacted with [1-(4-chlorobenzyl)piperidin-4-yl]amine as described in Steps 5 and 6, Example 24 to give the title compound as a yellow solid (55% yield). LC/MS: RT 2.30 min; m/e 506; $^1$H NMR ($\delta$, ppm): 11.80 (1H, br), 10.94 (1H, br), 8.13-8.30 (1H, m), 7.42-7.70 (5H, m), 7.32 (1H, s), 7.14 (1H, m), 2.80-3.53 (7H, m), 2.38 (2H, q), 2.28 (3H, s), 1.68-2.15 (4H, m), 1.09 (3H, t).

Example 77

5-[5-Ethyl-2-methyl-6-oxo-1,6-dihydropyridin-3-yl]thiophene-2-sulfonic acid methyl-(1-methylpiperidin-4-yl]amide hydrochloride

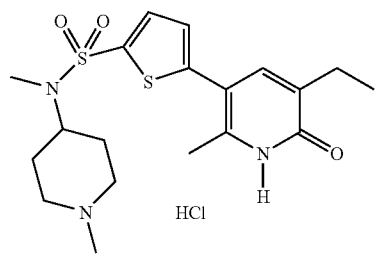

5-(5-Ethyl-2-methyl-6-oxo-1,6-dihydropyridin-3-yl)thiophene-2-sulfonyl chloride is reacted with methyl 1-(methylpiperidin-4-yl]amine as described in Steps 5 and 6, Example 24 to give the title compound as a yellow solid (41% yield). LC/MS: RT 2.05 min; m/e 410; $^1$H NMR (δ, ppm): 11.86 (1H, br), 10.70 (1H, br), 7.65 (1H, d), 7.36 (1H, s), 7.23 (1H, d), 3.30-3.50 (5H, m), 2.75 (3H, s), 2.65 (3H, s), 2.40 (2H, q), 2.34 (3H, s), 2.08 (2H, q), 1.53 (2H, d), 1.10 (3H, t).

Example 78

5-(5-Ethyl-2-methyl-6-oxo-1,6-dihydropyridin-3-yl)thiophene-2-sulfonic acid [(6-dimethylaminopyridin-3-yl)methyl]amide hydrochloride

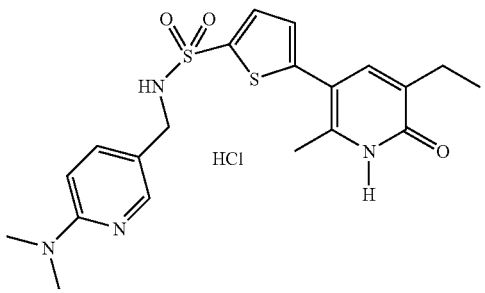

5-(5-Ethyl-2-methyl-6-oxo-1,6-dihydropyridin-3-yl)thiophene-2-sulfonyl chloride is reacted with [(6-dimethylaminopyridin-3-yl)methyl]amine as described in Steps 5 and 6, Example 24 to give the title compound as a yellow solid (55% yield). LC/MS: RT 2.07 min; m/e 433; $^1$H NMR (δ, ppm): 11.86 (1H, br), 8.57 (1H, t), 7.80-7.95 (2H, m), 7.54 (1H, d), 7.43 (1H, s), 7.21 (1H, d), 7.14 (1H, d), 4.03 (2H, d), 3.17 (6H, d), 2.41 (2H, q), 2.30 (3H, s), 1.10 (3H, t).

Example 79

3-Ethyl-5-[5-(4-imidazol-1-yl)piperidine-1-sulfonyl)thiophen-2-yl]-6-methyl-1H-pyridin-2-one hydrochloride

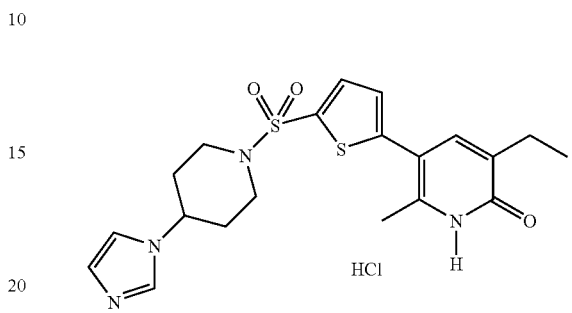

5-(5-Ethyl-2-methyl-6-oxo-1,6-dihydropyridin-3-yl)thiophene-2-sulfonyl chloride is reacted with 4-(imidazol-1-yl)piperidine as described in Steps 5 and 6, Example 24 to give the title compound as a yellow solid (90% yield). LC/MS: RT 2.17 min; m/e 433; $^1$H NMR (δ, ppm): 9.22 (1H, s), 7.90 (1H, s), 7.73 (1H, s), 7.66 (1H, d), 7.57 (1H, s), 7.29 (1H, d), 4.47 (1H, s), 3.80 (2H, d), 2.00-2.75 (9H, m), 1.10 (3H, t).

Example 80

5-[5-Ethyl-2-methyl-6-oxo-1,6-dihydropyridin-3-yl]thiophene-2-sulfonic acid (1-methylimidazol-2-yl)methyl]amide hydrochloride

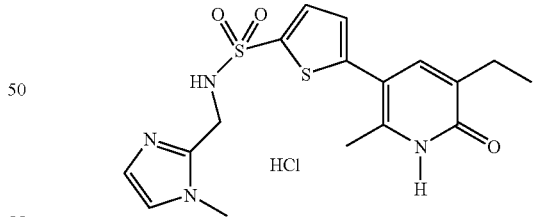

5-(5-Ethyl-2-methyl-6-oxo-1,6-dihydropyridin-3-yl)thiophene-2-sulfonyl chloride is reacted with (1-methylimidazol-2-yl)methylamine as described in Steps 5 and 6, Example 24 to give the title compound as a white solid (29% yield). LC/MS: RT 2.00 min; m/e 393; $^1$H NMR (δ, ppm): 11.82 (1H, br), 8.35 (1H, br), 7.51 (1H, d), 7.31 (1H, s), 7.14 (1H, d), 7.06 (1H, s), 6.76 (1H, s), 4.05 (2H, d), 3.58 (3H, s), 2.40 (2H, q), 2.31 (3H, s), 1.10 (3H, t).

Example 81

5-[5-Ethyl-2-methyl-6-oxo-1,6-dihydropyridin-3-yl]
thiophene-2-sulfonic acid methyl (1-methylpyrrolidin-3-yl)amide hydrochloride

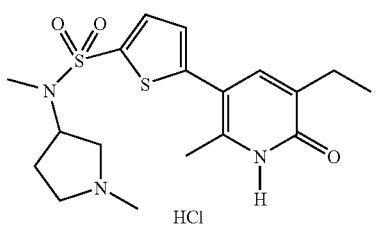

5-(5-Ethyl-2-methyl-6-oxo-1,6-dihydropyridin-3-yl)thiophene-2-sulfonyl chloride is reacted with methyl(1-methylpyrrolidin-3-yl)amine as described in Steps 5 and 6, Example 24 to give the title compound as a yellow solid (90% yield). LC/MS: RT 2.12 min; m/e 396; $^1$H NMR (δ, ppm): 11.82 (1H, br), 7.61 (1H, d), 7.37 (1H, s), 7.22 (1H, d), 4.08 (1H, m), 2.76 (3H, s), 2.20-2.69 (m), 1.94 (1H, m), 1.55 (1H, m), 1.10 (3H, t).

Example 82

5-[5-Ethyl-2-methyl-6-oxo-1,6-dihydropyridin-3-yl]
thiophene-2-sulfonic acid [1-(pyridin-4-yl)methyl(piperidin-4-yl)]amide dihydrochloride

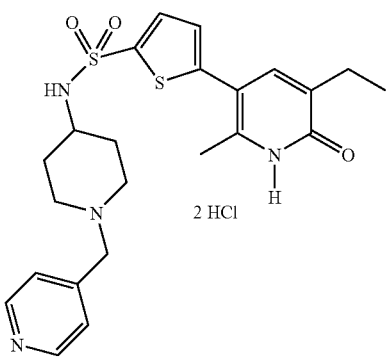

5-(5-Ethyl-2-methyl-6-oxo-1,6-dihydropyridin-3-yl)thiophene-2-sulfonyl chloride is reacted with [1-pyridin-4-yl)methyl](piperidin-4-yl)amine as described in Steps 5 and 6, Example 24 to give the title compound as a yellow solid (31% yield). LC/MS: RT 2.00 min; m/e 473; $^1$H NMR (δ, ppm): 11.80 (1H, br), 8.49 (2H, d), 7.97 (1H, d), 7.54 (1H, d), 7.34 (1H, s), 7.27 (2H, d), 7.14 (1H, d), 4.10 (1H, m), 3.44 (2H, s), 3.00-3.14 (4H, m), 2.40 (2H, q), 2.30 (3H, s), 1.90-2.10 (2H, m), 1.38-1.73 (2H, m), 1.10 (3H, t).

Example 83

5-[5-Ethyl-2-methyl-6-oxo-1,6-dihydropyridin-3-yl]
thiophene-2-sulfonic acid (1-imidazol-2-yl)methyl(piperidin-4-yl)]amide dihydrochloride

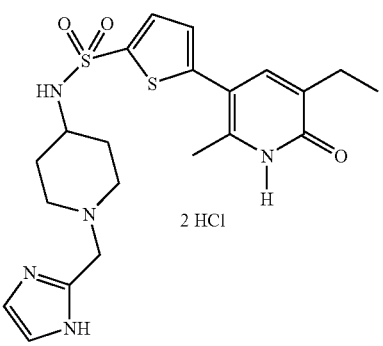

5-(5-Ethyl-2-methyl-6-oxo-1,6-dihydropyridin-3-yl)thiophene-2-sulfonyl chloride is reacted with 1-(imidazol-2-yl)methyl(piperidin-4-yl)amine as described in Steps 5 and 6, Example 24 to give the title compound as a yellow solid (30% yield). LC/MS: RT 1.98 min; m/e 462; $^1$H NMR (δ, ppm): 11.83 (1H, br), 6.80-8.20 (6H, m), 4.11 (1H, m), 2.60-3.50 (6H, m), 2.26-2.46 (5H, m), 1.36-2.20 (4H, m), 1.10 (3H, t).

Example 84

5-[5-Ethyl-2-methyl-6-oxo-1,6-dihydropyridin-3-yl]
thiophene-2-sulfonic acid 4-(pyridin-3-ylbutyl)]
amide hydrochloride

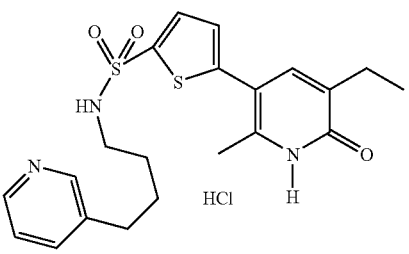

5-(5-Ethyl-2-methyl-6-oxo-1,6-dihydropyridin-3-yl)thiophene-2-sulfonyl chloride is reacted with 4-(pyridin-3-yl)butylamine as described in Steps 5 and 6, Example 24 to give the title compound as a yellow solid (22% yield). LC/MS: 2.23 min; m/e 432 (M+H).

Example 85

3-Ethyl-5-[5-(3-hydroxypyrrolidine-1-sulfonyl)thiophen-2-yl]-6-methyl-1H-pyridin-2-one

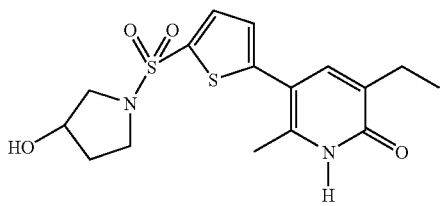

5-(5-Ethyl-2-methyl-6-oxo-1,6-dihydropyridin-3-yl)thiophene-2-sulfonyl chloride is reacted with 3-hydroxypyrrolidine as described in Step 5, Example 24 to give the title compound as a solid (48.8% yield). LC/MS: RT 2.42 min; m/e 369 (M+H); $^1$H NMR ($\delta$, ppm): 11.8 (1H, s), 7.6 (1H, d); 7.38 (1H, d); 7.2 (1H, d), 4.92 (1H, br s), 4.2 (1H, s), 3.38 (4H, m), 3.07 (1H, d), 2.4 (2H, q), 2.32 (3H, s), 1.8 (2H, m), 1.08 (3H, t).

Example 86

3-Ethyl-6-methyl-5-[5-(morpholine-4-sulfonyl)thiophen-2-yl]-1H-pyridin-2-one

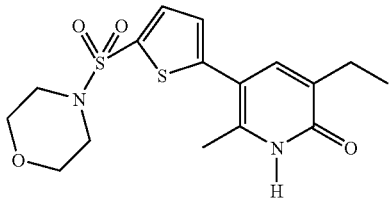

5-(5-Ethyl-2-methyl-6-oxo-1,6-dihydropyridin-3-yl)thiophene-2-sulfonyl chloride is reacted with morpholine as described in Step 5, Example 24 to give the title compound as a solid (57.4% yield). LC/MS: RT 2.72 min; m/e 369 (M+H); $^1$H NMR ($\delta$, ppm): 11.8 (1H, s), 7.6 (1H, d); 7.4 (1H, d); 7.3 (1H, d), 3.7 (4H, m), 2.95 (4H, s), 2.4 (2H, q), 2.36 (3H, s), 1.05 (3H, t).

Example 87

3-Ethyl-5-[5-(4-hydroxypiperidine-1-sulfonyl)thiophen-2-yl]-6-methyl-1H-pyridin-2-one

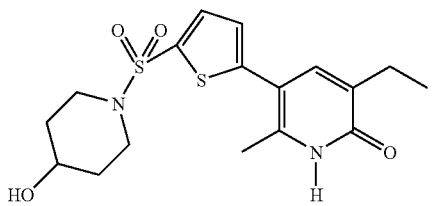

5-(5-Ethyl-2-methyl-6-oxo-1,6-dihydropyridin-3-yl)thiophene-2-sulfonyl chloride is reacted with 4-hydroxypiperidine as described in Step 5, Example 24 to give the title compound as a solid (63.6% yield). LC/MS: RT 2.48 min; m/e 383 (M+H); $^1$H NMR ($\delta$, ppm): 11.8 (1H, s), 7.6 (1H, d); 7.4 (1H, s); 7.3 (1H, d), 3.6 (1H, s), 3.2 (2H, m), 2.8 (2H, m), 2.4 (2H, q), 2.36 (3H, s), 1.8 (2H, m), 1.5 (2H, m), 1.05 (3H, t).

Example 88

5-(5-Ethyl-2-methyl-6-oxo-1,6-dihydropyridin-3-yl)thiophene-2-sulfonic acid [2-(1,3-dioxolan-2-yl)ethyl]amide

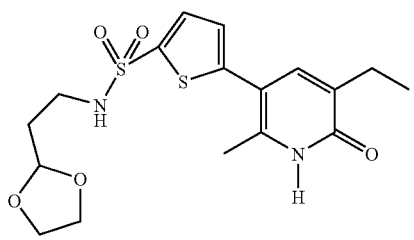

5-(5-Ethyl-2-methyl-6-oxo-1,6-dihydropyridin-3-yl)thiophene-2-sulfonyl chloride is reacted with 2-(1,3-dioxolan-2-yl)ethylamine as described in Step 5, Example 24 to give the title compound as a solid (50.5% yield). LC/MS: RT 2.58 min; m/e 399 (M+H); $^1$H NMR ($\delta$, ppm): 11.8 (1H, s), 7.8 (1H, br s); 7.56 (1H, d); 7.35 (1H, s), 7.18 (1H, d), 4.8 (1H, t), 3.8 (2H, m), 3.75 (2H, m), 2.95 (2H, m), 2.4 (2H, q), 2.36 (3H, s), 1.75 (2H, m), 1.08 (3H, t).

Example 89

4-[5-(5-Ethyl-2-methyl-6-oxo-1,6-dihydropyridin-3-yl)thiophene-2-sulfonyl]piperazine-1-carboxylic acid ethyl ester

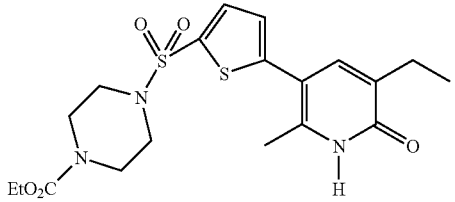

5-(5-Ethyl-2-methyl-6-oxo-1,6-dihydropyridin-3-yl)thiophene-2-sulfonyl chloride is reacted with ethyl piperazine-1-carboxylate as described in Step 5, Example 24 to give the title compound as a solid (60.2% yield). LC/MS: RT 2.93 min; m/e 440 (M+H); $^1$H NMR ($\delta$, ppm): 11.8 (1H, s), 7.6 (1H, d); 7.4 (1H, s); 7.3 (1H, d), 4.0 (2H, t), 3.5 (4H, m), 3.0 (4H, m), 2.4 (2H, q), 2.36 (3H, s), 1.08 (6H, m).

Example 90

3-Ethyl-5-[5-(3-hydroxymethylpiperidine-1-sulfonyl)thiophen-2-yl]-6-methyl-1H-pyridin-2-one

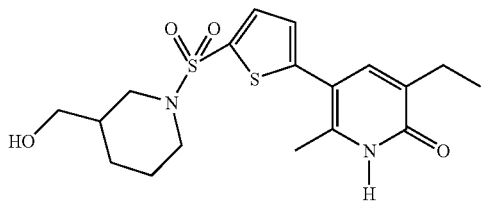

5-(5-Ethyl-2-methyl-6-oxo-1,6-dihydropyridin-3-yl)thiophene-2-sulfonyl chloride is reacted with 3-hydroxymethylpiperidine as described in Step 5, Example 24 to give the title compound as a solid (54.7% yield). LC/MS: RT 2.63 min; m/e 397 (M+H); $^1$H NMR ($\delta$, ppm): 11.8 (1H, s), 7.6 (1H, d); 7.4 (1H, s); 7.24 (1H, d), 4.6 (1H, br s), 3.6 (21H, m), 3.2 (1H, m), 2.4 (2H, q), 2.36 (3H, s), 2.1 (1H, t), 1.8-1.4 (5H, m), 1.1 (3H, t), 0.94 (1H, m).

Example 91

3-Ethyl-5-{5-[4-(2-hydroxyethyl)piperazine-1-sulfonyl]thiophen-2-yl}-6-methyl-1H-pyridin-2-one hydrochloride

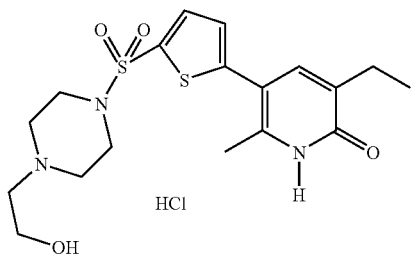

5-(5-Ethyl-2-methyl-6-oxo-1,6-dihydropyridin-3-yl)thiophene-2-sulfonyl chloride is reacted with 4-(2-hydroxyethyl)piperidine as described in Steps 5 and 6, Example 24 to give the title compound as a solid (50.8% yield). LC/MS: RT 2.07 min; m/e 412 (M+H); $^1$H NMR ($\delta$, ppm): 11.8 (1H, s), 10.7 (1H, s), 7.7 (1H, d); 7.4 (1H, s); 7.32 (1H, d), 4.8-3.6 (6H, m), 3.2 (4H, m), 3.0 (2H, t), 2.4 (2H, q), 2.36 (3H, s), 1.1 (3H, t).

Example 92

3-Ethyl-6-methyl-5-[5-(4-methylpiperazine-1-sulfonyl)thiophen-2-yl]-1H-pyridin-2-one

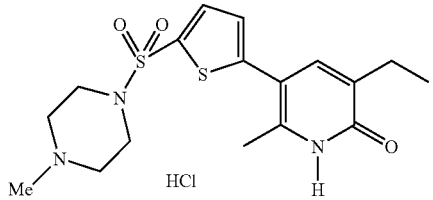

5-(5-Ethyl-2-methyl-6-oxo-1,6-dihydropyridin-3-yl)thiophene-2-sulfonyl chloride is reacted with 1-methylpiperazine as described in Steps 5 and 6, Example 24 to give the title compound as a solid (63.3% yield). LC/MS: RT 2.07 min; m/e 382 (M+H); 1H NMR ($\delta$, ppm): 11.8 (1H, s), 11.3 (1H, s), 7.7 (1H, d); 7.4 (1H, s); 7.32 (1H, d), 4.8 (2H, m), 3.5 (2H, d), 3.2 (2H, m), 2.9 (2H, t), 2.75 (3H, s), 2.4 (2H, q), 2.36 (3H, s), 1.1 (3H, t).

Example 93

5-(5-Ethyl-2-methyl-6-oxo-1,6-dihydropyridin-3-yl)thiophene-2-sulfonic acid (2-dimethylaminoethyl)amide hydrochloride

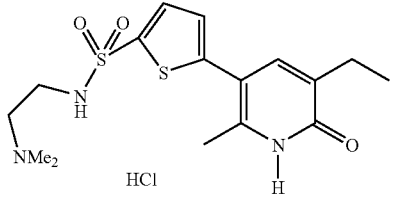

5-(5-Ethyl-2-methyl-6-oxo-1,6-dihydropyridin-3-yl)thiophene-2-sulfonyl chloride is reacted with 2-(dimethylamino)ethylamine as described in Steps 5 and 6, Example 24 to give the title compound as a solid (44.3% yield). LC/MS: RT 1.97 min; m/e 370 (M+H); $^1$H NMR ($\delta$, ppm): 11.8 (1H, s), 10.3 (1H, s), 8.3 (1H, t); 7.65 (1H, d); 7.35 (1H, s), 7.2 (1H, d), 4.2 (2H, m), 3.8 (6H, m), 2.4 (2H, q), 2.36 (3H, s), 1.1 (3H, t).

Example 94

3-Ethyl-6-methyl-5-[5-(piperazine-1-sulfonyl)thiophen-2-yl]-1H-pyridin-2-one hydrochloride

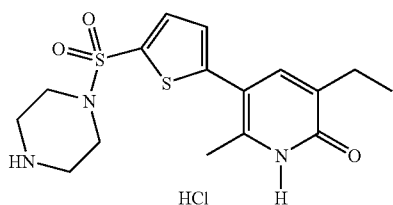

5-(5-Ethyl-2-methyl-6-oxo-1,6-dihydropyridin-3-yl)thiophene-2-sulfonyl chloride is reacted with piperazine as described in Steps 5 and 6, Example 24 to give the title compound as a solid (73.3% yield). LC/MS: RT 2.07 min; m/e 368 (M+H); $^1$H NMR (δ, ppm): 11.8 (1H, br s), 9.5 (1H, s), 7.65 (1H, d); 7.35 (1H, s); 7.3 (1H, d), 3.2 (8H, m), 2.4 (2H, q), 2.36 (3H, s), 1.1 (3H, t).

Example 95

5-(5-Ethyl-2-methyl-6-oxo-1,6-dihydropyridin-3-yl)thiophene-2-sulfonic acid (2-pyrrolidin-1-yl)ethylamide hydrochloride

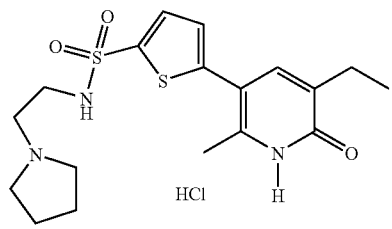

5-(5-Ethyl-2-methyl-6-oxo-1,6-dihydropyridin-3-yl)thiophene-2-sulfonyl chloride is reacted with 1-(2-aminoethyl)pyrrolidine as described in Steps 5 and 6, Example 24 to give the title compound as a solid (36.7% yield). LC/MS: RT 2.02 min; m/e 396 (M+H); $^1$H NMR (δ, ppm): 11.8 (1H, br s), 10.6 (1H, s), 8.3 (1H, m), 7.6 (1H, d); 7.35 (1H, s); 7.2 (1H, d), 3.2 (5H, s), 3.0 (2H, m), 2.4 (2H, q), 2.36 (3H, s), 1.9 (4H, m), 1.1 (3H, t).

Example 96

5-(5-Ethyl-2-methyl-6-oxo-1,6-dihydropyridin-3-yl)-thiophene-2-sulfonic acid (3-diethylaminopropyl)amide hydrochloride

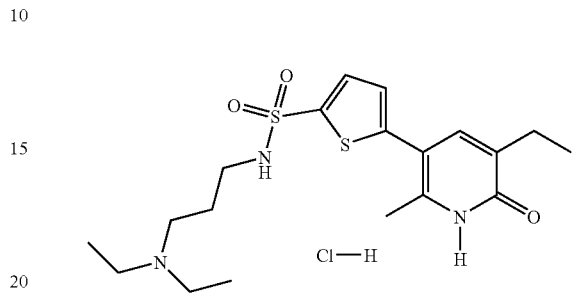

5-(5-Ethyl-2-methyl-6-oxo-1,6-dihydropyridin-3-yl)thiophene-2-sulfonyl chloride is reacted with N,N-diethylpropane-1,3-diamine as described in Steps 5 and 6, Example 24 to give the title compound as an orange solid (50% yield). LC/MS: RT: 2.03 min; m/e 412 (M+H); $^1$H NMR (δ, ppm): 11.86 (1H, s), 10.07 (1H, s), 8.05 (1H, t), 7.56 (1H, d), 7.34 (1H, s), 7.19 (1H, d), 2.93-3.58 (8H, m), 2.40 (2H, q), 2.32 (3H, s), 1.82 (2H, m), 1.19 (6H, t), 1.10 (3H, t).

Example 97

5-(5-Ethyl-2-methyl-6-oxo-1,6-dihydropyridin-3-yl)-thiophene-2-sulfonic acid (furan-2-ylmethyl)amide

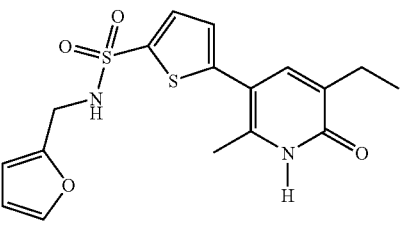

5-(5-Ethyl-2-methyl-6-oxo-1,6-dihydropyridin-3-yl)thiophene-2-sulfonyl chloride is reacted with (furan-2-yl)methylamine as described in Step 5, Example 24 to give the title compound as a light orange solid (78% yield). LC/MS: RT 2.75 min; m/e 379 (M+H); $^1$H NMR (δ, ppm): 11.3 (1H, s), 8.42 (1H, t), 7.54 (1H, s), 7.50 (1H, t), 7.30 (1H, s), 7.11 (1H, d), 6.35 (1H, d), 6.22 (1H, s), 4.12 (2H, d), 2.41 (2H, q), 2.30 (3H, s), 1.10 (3H, t).

Example 98

5-(5-Ethyl-2-methyl-6-oxo-1,6-dihydropyridin-3-yl)-thiophene-2-sulfonic acid (2-phenoxyethyl)amide

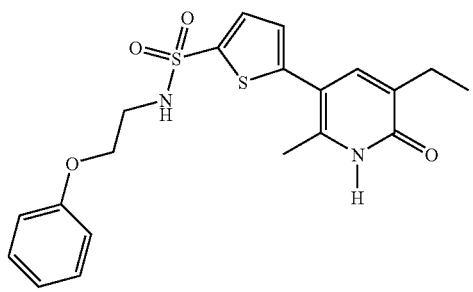

5-(5-Ethyl-2-methyl-6-oxo-1,6-dihydropyridin-3-yl) thiophene-2-sulfonyl chloride is reacted with 2-phenoxyethylamine as described in Step 5, Example 24 to give the title compound as a yellow-orange solid (78% yield). LC/MS: RT 3.00 min; m/e 419 (M+H); $^1$H NMR ($\delta$, ppm): 11.82 (1H, s), 8.18 (1H, m), 7.58 (1H, dd), 7.23-7.29 (3H, m), 7.15 (1H, dd), 6.86-6.94 (3H, m), 3.99 (2H, t), 3.28 (2H, t), 2.40 (2H, q), 2.29 (3H, s), 1.09 (3H, t).

Example 99

3-Ethyl-5-(5-{4-[2-(2-hydroxy-ethoxy)-ethyl]-piperazine-1-sulfonyl}-thiophen-2-yl)-6-methyl-1H-pyridin-2-one hydrochloride

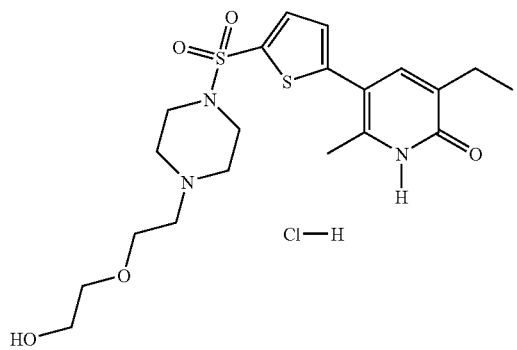

5-(5-Ethyl-2-methyl-6-oxo-1,6-dihydropyridin-3-yl) thiophene-2-sulfonyl chloride (70 mg, 0.220 mmol) is reacted with 2-(2-piperazin-1-yl-ethoxy)-ethanol (41.7 μL, 0.242 mmol) as described in Steps 5 and 6, Example 24 to give the title compound as an orange solid (90% yield). LC/MS: RT 2.03 min, m/e 456 (M+H); $^1$H NMR ($\delta$, ppm): 11.89 (1H, s), 10.6 (1H, s), 7.69 (1H, d), 7.37 (1H, s), 7.34 (1H, d), 3.71-3.76 (4H, m), 3.60-3.64 (2H, m), 3.45-3.50 (4H, m), 3.32-3.31 (4H, m), 2.92-3.00 (2H, m), 2.41 (2H, q), 2.35 (3H, s), 1.10 (3H, t).

Example 100

5-[5-(4-Benzylpiperazine-1-sulfonyl)thiophen-2-yl]-3-ethyl-6-methyl-1H-pyridin-2-one hydrochloride

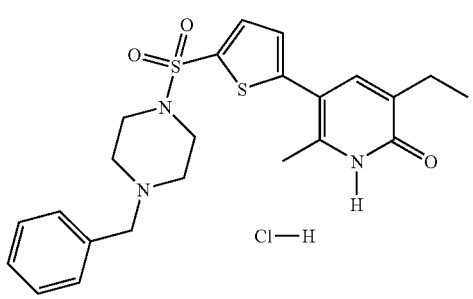

5-(5-Ethyl-2-methyl-6-oxo-1,6-dihydropyridin-3-yl) thiophene-2-sulfonyl chloride is reacted with 1-benzyl-piperazine as described in Steps 5 and 6, Example 24 to give the title compound as an orange solid (82% yield). LC/MS: RT 2.32 min, m/e 458 (M+H); $^1$H NMR ($\delta$, ppm): 11.88 (1H, s), 11.08 (1H, s), 7.65 (1H, d), 7.55 (2H, br s), 7.45 (3H, m), 7.35 (1H, d), 7.31 (1H, d), 4.33 (2H, s), 3.36-3.40 (2H, m), 3.22 (2H, m), 2.90-2.97 (2H, m), 2.40 (2H, q), 2.33 (3H, s), 1.09 (3H, t).

Example 101

5-(5-Ethyl-2-methyl-6-oxo-1,6-dihydropyridin-3-yl)-thiophene-2-sulfonic acid (pyridin-3-ylmethyl)amide hydrochloride

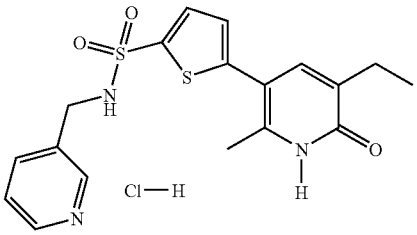

5-(5-Ethyl-2-methyl-6-oxo-1,6-dihydropyridin-3-yl) thiophene-2-sulfonyl chloride is reacted with pyridin-3-ylmethylamine as described in Steps 5 and 6, Example 24 to give the title compound as a yellow-orange solid (31% yield). LC/MS: RT 2.07 min, m/e 390 (M+H); $^1$H NMR ($\delta$, ppm): 11.86 (1H, s), 8.78-8.80 (3H, m), 8.43 (1H, d), 7.96 (1H, dd), 7.58 (1H, d), 7.30 (1H, s), 7.13 (1H, d), 4.37 (2H, d), 2.41 (2H, q), 2.29 (3H, s), 1.10 (3H, t).

Example 102

5-(5-Ethyl-2-methyl-6-oxo-1,6-dihydropyridin-3-yl)-thiophene-2-sulfonic acid (1-ethyl-pyrrolidin-2-ylmethyl)amide hydrochloride

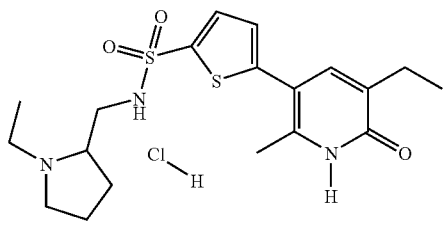

5-(5-Ethyl-2-methyl-6-oxo-1,6-dihydropyridin-3-yl)thiophene-2-sulfonyl chloride is reacted with (1-ethyl-pyrrolidin-2-yl)-methylamine as described in Steps 5 and 6, Example 24 to give the title compound as a yellow oil (47% yield). LC/MS: RT 1.98 min, m/e 410 (M+H); $^1$H NMR (δ, ppm): 11.85 (1H, s), 10.26 (1H, s), 8.39 (1H, t), 7.63 (1H, d), 7.34 (1H, s), 7.21 (1H, d), 3.43-3.55 (2H, m), 3.33-3.39 (2H, m), 3.20-3.31 (1H, m), 2.99-3.12 (2H, m), 2.40 (2H, q), 2.32 (3H, s), 2.09-2.17 (1H, m), 1.74-1.98 (3H, m), 1.25 (3H, t), 1.10 (3H, t).

Example 103

5-(5-Ethyl-2-methyl-6-oxo-1,6-dihydropyridin-3-yl)-thiophene-2-sulfonic acid (1,3-benzodioxol-5-ylmethyl)amide

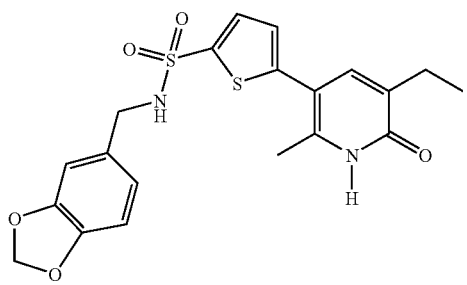

5-(5-Ethyl-2-methyl-6-oxo-1,6-dihydropyridin-3-yl)thiophene-2-sulfonyl chloride is reacted with benzo[1,3]dioxol-5-yl-methylamine as described in Step 5, Example 24 to give the title compound as a crystalline cream-yellow solid (86% yield). LC/MS: RT 2.87 min, m/e 433 (M+H); $^1$H NMR (δ, ppm): 11.91 (1H, s), 7.55 (1H, dd), 7.28 (1H, s), 6.92 (1H, dd), 6.68-6.74 (3H, m), 5.93 (2H, s), 5.03 (1H, br. t), 4.19 (2H, d), 2.58 (2H, q), 2.44 (3H, s), 1.22 (3H, t).

Example 104

5-[5-(4-1,3-Benzodioxol-5-ylmethylpiperazine-1-sulfonyl)-thiophen-2-yl]-3-ethyl-6-methyl-1H-pyridin-2-one hydrochloride

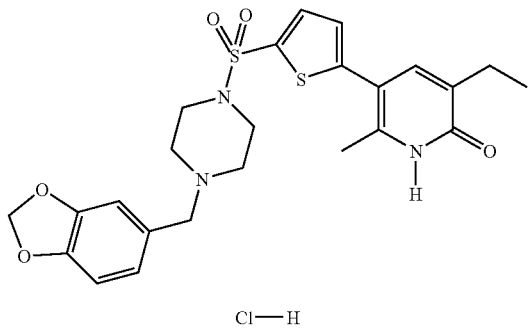

5-(5-Ethyl-2-methyl-6-oxo-1,6-dihydropyridin-3-yl)thiophene-2-sulfonyl chloride is reacted with 1-benzo[1,3]dioxol-5-ylmethyl-piperazine as described in Steps 5 and 6, Example 24 to give the title compound as a yellow glass (61% yield). LC/MS: RT 2.33 min, m/e 502 (M+H); $^1$H NMR (δ, ppm): 11.88 (1H, s), 10.79 (1H, s), 7.66 (1H, d), 7.36 (1H, s), 7.32 (1H, d), 7.16 (1H, s), 6.98 (2H, s), 6.05 (2H, s), 4.24 (2H, s), 3.69-3.77 (2H, m), 3.37-3.40 (2H, m), 3.14-3.17 (2H, m), 2.86-2.94 (2H, m), 2.40 (2H, q), 2.33 (3H, s), 1.10 (3H, t).

Example 105

3-Ethyl-6-methyl-5-[5-((S)-2-phenylaminomethylpyrrolidine-1-sulfonyl)-thiophen-2-yl]-1H-pyridin-2-one hydrochloride

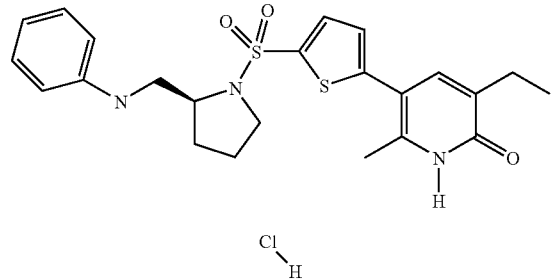

5-(5-Ethyl-2-methyl-6-oxo-1,6-dihydropyridin-3-yl)thiophene-2-sulfonyl chloride is reacted with (S)-phenyl-pyrrolidin-2-ylmethyl-amine as described in Steps 5 and 6, Example 24 to give the title compound as a yellow glass (77% yield). LC/MS: RT 3.29 min, m/e 458 (M+H); $^1$H NMR (δ, ppm): 11.84 (1H, s), 7.65 (1H, d), 7.35 (1H, s), 7.25 (1H, d), 7.14 (2H, t), 6.74 (2H, d), 6.62 (1H, t), 3.76 (1H, m), 3.34-3.45 (2H, m), 3.06-3.20 (2H, m), 2.39 (2H, q), 2.30 (3H, s), 1.86 (2H, m), 1.51-1.58 (2H, m), 1.09 (3H, t).

Example 106

5-(5-Ethyl-2-methyl-6-oxo-1,6-dihydro-pyridin-3-yl)thiophene-2-sulfonic acid furan-2-yl-methyl-methylamide

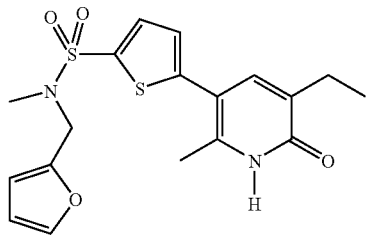

5-(5-Ethyl-2-methyl-6-oxo-1,6-dihydropyridin-3-yl)thiophene-2-sulfonyl chloride is reacted with furan-2-ylmethyl-methyl-amine as described in Step 5, Example 24 to give the title compound as a cream solid (78% yield). LC/MS: RT 3.03 min, n/e 393 (M+H); $^1$H NMR (δ, ppm): 11.85 (1H, s), 7.62 (2H, m), 7.35 (1H, s), 7.23 (1H, d), 6.40 (2H, dd), 4.27 (2H, s), 2.70 (3H, s), 2.41 (2H, q), 2.32 (3H, s), 1.10 (3H, t).

Example 107

5-(5-Ethyl-2-methyl-6-oxo-1,6-dihydropyridin-3-yl)thiophene-2-sulfonic acid (2-pyridin-3-yl-ethyl)amide hydrochloride

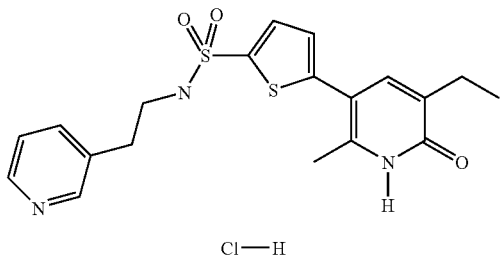

5-(5-Ethyl-2-methyl-6-oxo-1,6-dihydropyridin-3-yl)thiophene-2-sulfonyl chloride is reacted with 2-pyridin-3-yl-ethylamine as described in Steps 5 and 6, Example 24 to give the title compound as a cream-yellow solid (31% yield). LC/MS: RT 2.02 min, m/e 404 (M+H); $^1$H NMR (δ, ppm): 11.85 (1H, s), 8.79-8.82 (2H, m), 8.47 (1H, d), 7.98-8.08 (2H, m), 7.52 (1H, dd), 7.33 (1H, s), 7.15 (1H, dd), 3.25 (2H, dt), 2.98 (2H, t), 2.41 (2H, q), 2.31 (3H, s), 1.10 (3H, t).

Example 108

5-[5-(4-Benzoylpiperidine-1-sulfonyl)thiophen-2-yl]-3-ethyl-6-methyl-1H-pyridin-2-one

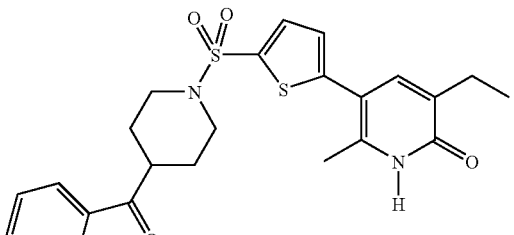

5-(5-Ethyl-2-methyl-6-oxo-1,6-dihydropyridin-3-yl)thiophene-2-sulfonyl chloride is reacted with phenyl-piperidin-4-yl-methanone hydrochloride as described in Step 5, Example 24 to give the title compound as a yellow solid (85% yield). LC/MS: RT 3.27 min, m/e 471 (M+H); $^1$H NMR (CDCl$_3$, δ, ppm): 11.95 (1H, s), 7.89 (2H, dd), 7.55-7.60 (1H, m), 7.44-7.52 (3H, m), 7.33 (1H, s), 7.01 (1H, d), 3.79-3.84 (2H, m), 3.27-3.36 (1H, m), 2.73-2.82 (2H, m), 2.60 (2H, q), 2.48 (3H, s), 1.89-2.05 (4H, m), 1.24 (3H, t).

Example 109

5-(5-Ethyl-2-methyl-6-oxo-1,6-dihydropyridin-3-yl)thiophene-2-sulfonic acid (2-pyridin-4-yl-ethyl)amide hydrochloride

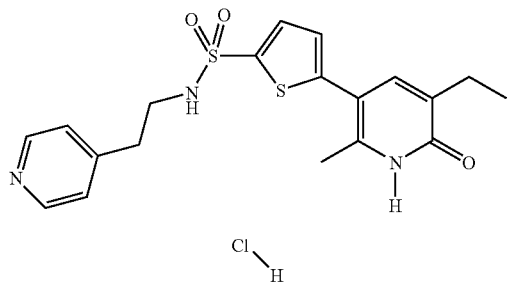

5-(5-Ethyl-2-methyl-6-oxo-1,6-dihydropyridin-3-yl)thiophene-2-sulfonyl chloride is reacted with 2-pyridin-4-yl-ethylamine as described in Steps 5 and 6, Example 24 to give the title compound as a yellow-orange solid (40% yield). LC/MS: RT 2.02 min, m/e 404 (M+H); $^1$H NMR (δ, ppm): 11.86 (1H, s), 8.84 (2H, s), 8.07 (1H, t), 7.95 (2H, d), 7.54 (1H, d), 7.33 (1H, s), 7.16 (1H, d), 3.29 (2H, dt), 3.06 (2H, t), 2.41 (2H, q), 2.31 (3H, s), 1.10 (3H, t).

Examples 110 and 111

5-(5-Ethyl-2-methyl-6-oxo-1,6-dihydropyridin-3-yl)thiophene-2-sulfonic acid (pyridin-4-ylmethyl)amide hydrochloride and 5-(5-Ethyl-2-methyl-6-oxo-1,6-dihydropyridin-3-yl)thiophene-2-sulfonic acid amide

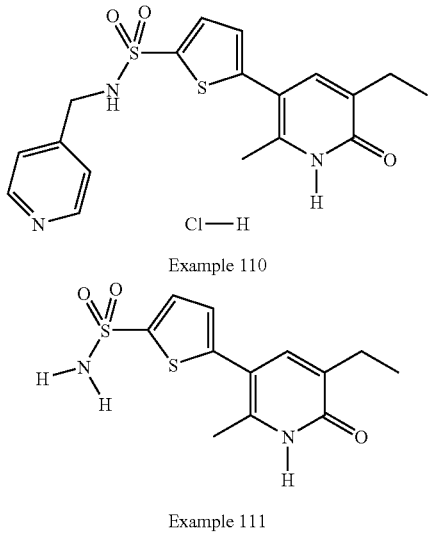

Example 110

Example 111

5-(5-Ethyl-2-methyl-6-oxo-1,6-dihydropyridin-3-yl)thiophene-2-sulfonyl chloride is reacted with pyridin-4-ylmethylamine as described in Steps 5 and 6, Example 24 to obtain 5-(5-ethyl-2-methyl-6-oxo-1,6-dihydropyridin-3-yl)thiophene-2-sulfonic acid (pyridin-4-ylmethyl)amide hydrochloride (Example 110) as a gray solid (30% yield). LC/MS: RT 2.03 min, m/e 390 (M+H); $^1$H NMR (δ, ppm): 11.86 (1H, s), 8.90-8.96 (1H, m), 8.85 (2H, d), 7.97 (2H, d), 7.59 (1H, d), 7.31 (1H, s), 7.15 (1H, d), 4.48 (2H, d), 2.41 (2H, q), 2.30 (3H, s), 1.10 (3H, t).

Evaporation of fractions containing a higher eluting material gave 5-(5-ethyl-2-methyl-6-oxo-1,6-dihydro-pyridin-3-yl)-thiophene-2-sulfonic acid amide (Example 111) as a yellow-orange solid (52% yield). LC/MS: RT 2.18 min, m/e 299 (M+H); $^1$H NMR (δ, ppm): 11.82 (1H, s), 7.69 (2H, s), 7.50 (1H, d), 7.31 (1H, s), 7.11 (1H, d), 2.40 (2H, q), 2.30 (3H, s), 1.89-2.05 (4H, m), 1.10 (3H, t).

Example 112

5-(5-Ethyl-2-methyl-6-oxo-1,6-dihydropyridin-3-yl)thiophene-2-sulfonic acid (tetrahydrofuran-2-ylmethyl)amide

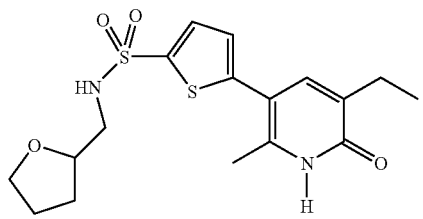

5-(5-Ethyl-2-methyl-6-oxo-1,6-dihydropyridin-3-yl)thiophene-2-sulfonyl chloride is reacted with (tetrahydrofuran-2-yl)methylamine as described in Step 5, Example 24 to give the title compound as a yellow solid (39.5% yield). LC/MS: RT 2.63 min; m/e 383 (M+H); $^1$H NMR (CDCl$_3$, δ, ppm): 11.21 (H, br), 7.50 (1H, d), 7.23 (1H, s), 6.90 (1H, d), 4.98 (1H, t), 4.00 (1H, q), 3.80 (2H, m), 3.30 (1H, m), 3.05 (1H, m), 2.6 (2H, dd), 2.40 (3H, s), 1.87 (3H, m), 1.23 (3H, t).

Example 113

5-(5-Ethyl-2-methyl-6-oxo-1,6-dihydropyridin-3-yl)thiophene-2-sulfonic acid (2-hydroxypropyl)amide

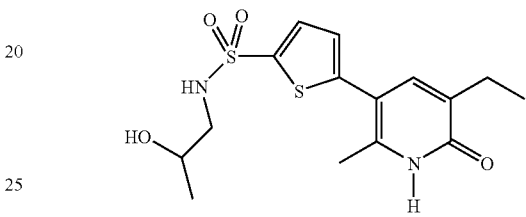

5-(5-Ethyl-2-methyl-6-oxo-1,6-dihydropyridin-3-yl)thiophene-2-sulfonyl chloride is reacted with 1-aminopropan-2-ol as described in Step 5, Example 24 to give the title compound as a yellow solid (59% yield). LC/MS: RT 2.33 min; m/e 357 (M+H); $^1$H NMR (CDCl$_3$, δ, ppm): 11.13 (1H, br), 7.52 (1H, d), 7.23 (1H, s), 6.91 (1H, d), 5.27 (1H, m), 4.00 (1H, m), 3.20 (1H, m), 2.90 (1H, m), 2.53 (2H, q), 2.40 (3H, s), 2.01 (1H, s), 1.20 (6H, m).

Example 114

5-(5-Ethyl-2-methyl-6-oxo-1,6-dihydropyridin-3-yl)thiophene-2-sulfonic acid (2-hydroxy-2-phenylethyl)amide

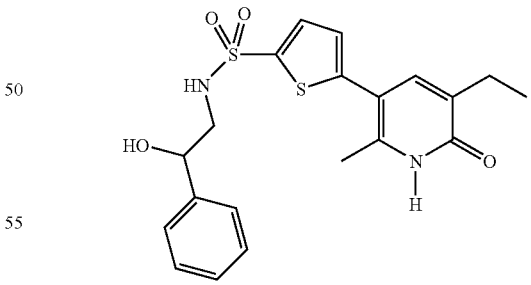

5-(5-Ethyl-2-methyl-6-oxo-1,6-dihydropyridin-3-yl)thiophene-2-sulfonyl chloride is reacted with 2-amino-1-phenylethanol as described in Step 5, Example 24 to give the title compound as a yellow solid (58% yield). LC/MS: RT 2.68 min; m/e 419 (M+H); $^1$H NMR (CDCl$_3$, δ, ppm): 11.30 (1H, br), 7.58 (1H, d), 7.40 (5H, m), 6.90 (1H, d), 5.33 (1H, br), 4.90 (1H, m), 3.47 (1H, m), 3.22 (1H, m), 2.60 (2H, q), 2.44 (3H, s), 1.22 (3H, t).

Example 115

5-(5-Ethyl-2-methyl-6-oxo-1,6-dihydropyridin-3-yl)thiophene-2-sulfonic acid (2-hydroxyethyl)amide

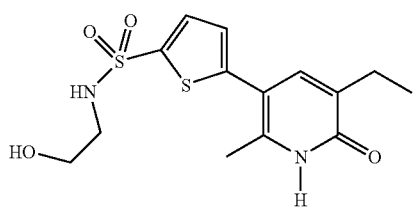

5-(5-Ethyl-2-methyl-6-oxo-1,6-dihydropyridin-3-yl)thiophene-2-sulfonyl chloride is reacted with 2-aminoethanol as described in Step 5, Example 24 to give the title compound as a yellow solid (38% yield). LC/MS: RT 2.20 min; m/e 343 (M+H); $^1$H NMR (δ, ppm): 11.80 (1H, br), 7.80 (1H, s), 7.53 (1H, d), 7.32 (1H, s), 7.13 (1H, d), 4.72 (1H, t), 3.26-3.42 (2H, m), 2.90 (2H, t), 2.30-2.60 (3H, s), 2.4 (2H, q), 1.10 (3H, t).

Example 116

3-Ethyl-6-methyl-5-{5-[(4-pyridin-2-yl)piperazine-1-sulfonyl]thiophen-2-yl}-1H-pyridin-2-one hydrochloride

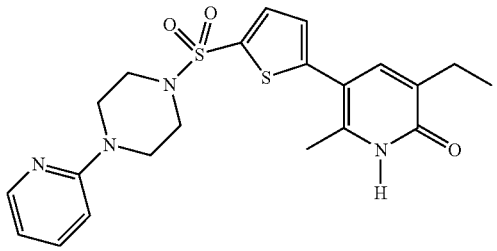

ClH 5-(5-Ethyl-2-methyl-6-oxo-1,6-dihydropyridin-3-yl)thiophene-2-sulfonyl chloride is reacted with 1-(pyridin-2-yl)piperazine as described in Step 5, Example 24 to give the title compound as a yellow solid (37% yield). LC/MS: RT 2.32 min; m/e 445 (M+H).

Example 117

3-Ethyl-6-methyl-5-[5-(4-pyrimidin-2-yl-piperazine-1-sulfonyl)thiophen-2-yl]-1H-pyridin-2-one hydrochloride

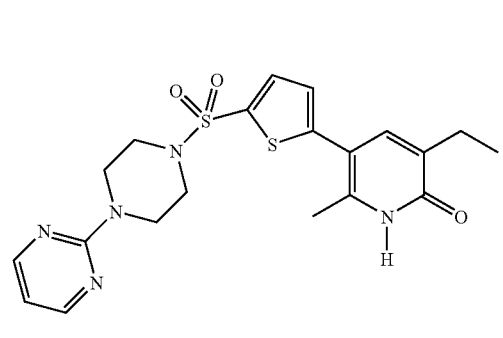

ClH 5-(5-Ethyl-2-methyl-6-oxo-1,6-dihydropyridin-3-yl)thiophene-2-sulfonyl chloride is reacted with 2-(piperazin-1-yl)pyrimidine as described in Step 5, Example 24 to give the title compound as a yellow solid (18% yield). LC/MS: RT 2.98 min; m/e 446 (M+H).

Example 118

5-(5-Ethyl-2-methyl-6-oxo-1,6-dihydro-pyridin-3-yl)thiophene-2-sulfonic acid (1H-benzoimidazol-2-ylmethyl)amide hydrochloride

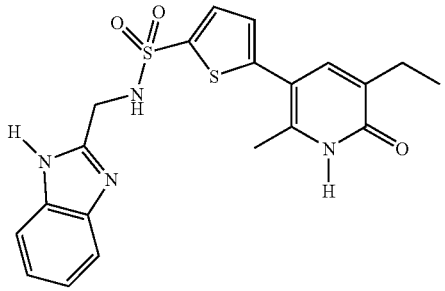

5-(5-Ethyl-2-methyl-6-oxo-1,6-dihydropyridin-3-yl)thiophene-2-sulfonyl chloride is reacted with (1H-benzoimidazol-2-yl)methylamine as described in Step 5, Example 24 to give the title compound as a yellow solid (44% yield). LC/MS: RT 2.10 min; m/e 429 (M+H); $^1$H NMR (δ, ppm): 11.80 (1H, br), 9.17 (1H, t), 7.80 (2H, m), 7.70 (1H, d), 7.50 (2H, m), 7.21 (1H, s), 7.12 (1H, d), 4.65 (3H, m), 2.40 (2H, q), 2.28 (3H, s), 1.10 (3H, t).

Example 119

N-{2-[5-(5-Ethyl-2-methyl-6-oxo-1,6-dihydropyridin-3-yl)thiophene-2-sulfonylamino]ethyl}acetamide

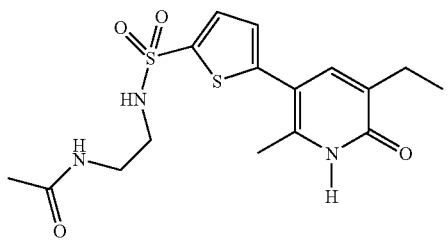

5-(5-Ethyl-2-methyl-6-oxo-1,6-dihydropyridin-3-yl)thiophene-2-sulfonyl chloride is reacted with N-(2-aminoethyl)acetamide as described in Step 5, Example 24 to give the title compound as a yellow solid (71% yield). LC/MS: RT 3.60 min; m/e 384 (M+H); $^1$H NMR (CDCl$_3$, δ, ppm): 11.53 (1H, br), 7.50 (1H, d), 7.25 (1H, s), 6.90 (1H, d), 6.13 (1H, br), 5.90 (1H, br), 3.42 (31H, m), 3.20 (2H, m), 2.40-2.60 (5H, m), 2.00 (3H, m), 1.20 (3H, t).

Example 120

5-(5-Ethyl-2-methyl-6-oxo-1,6-dihydro-pyridin-3-yl)-thiophene-2-sulfonic acid (3,5-difluoro-phenyl)-amide

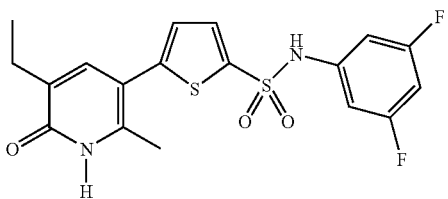

To a 3-neck round bottom flask under nitrogen atmosphere is added 3-ethyl-2-methoxy-6-methyl-5-(4,4,5,5-tetramethyl-[1,3,2-dioxaborolan-2-yl)pyridine (81 mg, 0.292 mmol), 5-bromo-thiophene-2-sulfonic acid (3,5-difluoro-phenyl)-amide (103 mg, 0.291 mmol), dichloro[1,1'-bis(diphenylphosphino)ferrocene]-palladium dichloromethane (13 mg, 0.1078 mmol), potassium carbonate (88 mg, 0.637 mmol) and dimethylformamide (15 mL) and the whole is refluxed overnight. The reaction is cooled to room temperature, diluted with ethyl acetate, washed with water, with brine, dried over sodium sulfate and concentrated. The resulting dark residue is purified by chromatography on a silica gel cartridge eluting with heptane-10% ethyl acetate affording the corresponding biaryl sulfonamide, 5-(5-ethyl-6-methoxy-2-methyl-pyridin-3-yl)-thiophene-2-sulfonic acid (3,5-difluoro-phenyl)-amide.

The above biaryl sulfonamide (0.0489 mmol) is dissolved in acetonitrile (1 mL). Potassium iodide (24 mg, 0.144 mmol) and chlorotrimethylsilane (19 μL) is added to this solution and the resulting mixture is heated to 80° C. for 1 hr. The reaction is cooled to room temperature, water is added and the resulting solid is collected, washed with water, with ethyl acetate and vacuum dried affording the title compound. LC/MS: RT 3.05 min; m/e 411 (M+H).

Example 121

5-(5-Ethyl-2-methyl-6-oxo-1,6-dihydropyridin-3-yl)thiophene-2-sulfonic acid (1-methyl-1-pyridin-2-yl)ethylamide hydrochloride

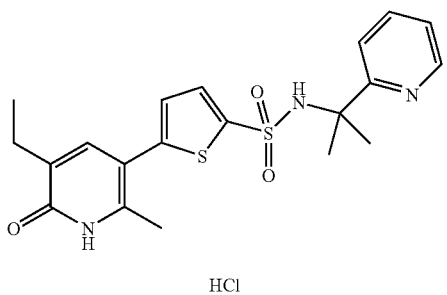

Step 1: 1-methyl-1-pyridin-2-yl)ethylamine: Anhydrous cerium chloride (5.10 g, 20.69 mmol) is placed in a flask and vacuum dried for 15 min while being heated with a heat gun, then it is cooled to 0° C. and tetrahydrofuran (45 mL) is added. After stirring at room temperature for 2 hr, the mixture is cooled to −70° C. and treated with 2.0 M methyl lithium in diethyl ether (10.5 mL, 21 mmol). After stirring for an additional period of 0.5 hrs, 2-cyanopyridine (720 mg, 6.91 mmol) in tetrahydrofuran (1 mL) is added. The reaction temperature is kept below −60° C. for 0.5 hr, then the temperature is raised to 23° C. while stirring for 2 hr. The reaction is quenched with isopropanol (3 mL), filtered through a pad of Celite that is washed thoroughly with dichloromethane. The combined filtrate and wash is concentrated and the residue is purified by flash chromatography on an ISCO Redisep 35 g cartridge eluting with dichloromethane-10% methanol to afford 1-methyl-1-pyridin-2-yl)ethylamine (688 mg, 73% yield) as an oil that solidified on standing to yellow solid. $^1$H NMR (δ, ppm): 1.6 (6H, s), 7.42 (1H), 7.64 (1H), 7.90 (1H), 8.2 (2H, br s), 8.65 (1H).

Step 2: 5-(5-ethyl-6-methoxy-2-methylpyridin-3-yl)thiophene-2-sulfonic acid (1-methyl-1-pyridin-2-yl)ethylamide: 5-(5-Ethyl-2-methyl-6-oxo-1,6-dihydropyridin-3-yl)thiophene-2-sulfonyl chloride (232 mg, 0.699 mmol) is added to a mixture of 1-methyl-1-pyridin-2-yl)ethylamine (114 mg, 0.837 mmol), piperidinomethyl polystyrene (PS) (567 mg, 2.09 mmol, beads) in dichloromethane (20 mL) and stirred at room temperature for 48 hr. The reaction is filtered through a silica gel pad and the silica gel rinsed with dichloromethane (2×20 mL). The combined filtrate and wash is evaporated to afford 5-(5-ethyl-6-methoxy-2-methylpyridin-3-yl)thiophene-2-sulfonic acid (1-methyl-1-pyridin-2-yl)ethylamide (250 mg, 83%) as yellow oil that is used directly in the next step. MS: 431 (M$^+$).

Step 3: 5-(5-ethyl-2-methyl-6-oxo-1,6-dihydropyridin-3-yl)thiophene-2-sulfonic acid (1-methyl-1-pyridin-2-yl)ethylamide: To a mixture of 5-(5-ethyl-6-methoxy-2-methylpyridin-3-yl)thiophene-2-sulfonic acid (1-methyl-1-pyridin-2-yl)ethylamide (230 mg, 0.533 mmol), potassium iodide (265 mg, 1.59 mmol) in acetonitrile (10 mL) is added chlorotrimethylsilane (0.2 mL, 1.57 mmol) and the resulting mixture is heated to 80° C. for 4 hr. The reaction is cooled, diluted with water and extracted with dichloromethane The combined organic layer is washed with water, with brine, dried over Na₂SO₄, filtered and concentrated. The residue is purified by flash chromatography using an ISCO Redisep 10 g cartridge eluting with ethyl acetate to afford 5-(5-ethyl-2-methyl-6-oxo-1,6-dihydropyridin-3-yl)thiophene-2-sulfonic acid (1-methyl-1-pyridin-2-yl)ethylamide (150 mg, 68% yield) as a beige solid.

Step 4: 5-(5-ethyl-2-methyl-6-oxo-1,6-dihydropyridin-3-yl)thiophene-2-sulfonic acid (1-methyl-1-pyridin-2-yl)ethylamide hydrochloride: 5-(5-ethyl-2-methyl-6-oxo-1,6-dihydropyridin-3-yl)thiophene-2-sulfonic acid (1-methyl-1-pyridin-2-yl)ethylamide from the above reaction is dissolved in methanol (5 mL) and treated with 1 M ethereal hydrochloride (1.0 mL). The methanol is partially removed and more ether added. The solids are collected by filtration to afford 5-(5-ethyl-2-methyl-6-oxo-1,6-dihydropyridin-3-yl) thiophene-2-sulfonic acid (1-methyl-1-pyridin-2-yl)ethylamide hydrochloride (145 mg, 60% yield) as brown solid. RT=2.03 min; MS 418 (M+1); ¹H NMR (δ, ppm): 11.80 (1H, br s), 8.54 (2H), 7.94 (1H, br t), 7.71 (1H, d), 7.26-7.40 (3H, m), 6.97 (1H, d), 2.37 (2H, q), 2.28 (3H, s), 1.61 (6H, s), 1.13 (3H, t).

Example 122

5-(5-Ethyl-2-methyl-6-oxo-1,6-dihydropyridin-3-yl)thiophene-2-sulfonic acid cyclopropyl (1-pyridin-2-yl)ethylamide hydrochloride

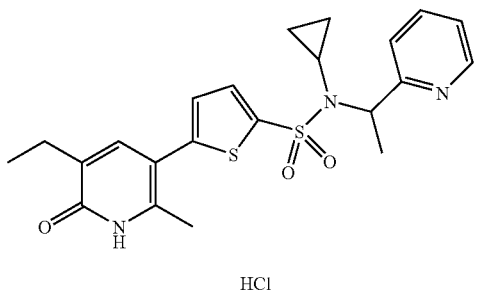

HCl

Step 1: Cyclopropyl(1-pyridin-2-yl)ethylamine: A mixture of 2-acetylpyridine (250 mg, 2.06 mmol), cyclopropylamine (111 mg, 1.94 mmol), anhyd tetrahydrofuran (15 mL) and acetic acid (1.5 mL) is stirred at room temperature for 10 min. MP-cyanoborohydride (1.2 g, 2.82 mmol) is added and the mixture is stirred overnight. The reaction is filtered through a Varian mega bond elut SCX and the resin washed with methanol (20 mL). The resin is then washed with 7 N methanolic ammonia (60 mL) and the eluent is evaporated. The residue is purified by chromatography on an ISCO Redisep 10 g cartridge eluting with ethyl acetate to afford cyclopropyl(1-pyridin-2-yl)ethylamine (245 mg, 73% yield) as oil. A hydrochloride salt is prepared by dissolving the amine (50 mg, 0.308 mmol) in methanol (2 mL), adding 1 M ethereal hydrochloric acid (0.8 mL), some methanol is removed, more ether added and the hydrochloride salt is collected by filtration (50 mg, 69% yield as gray solid). RT=1.69 min; MS 163 (M+1); ¹H NMR (δ, ppm): 9.5 (2H, br s), 8.69 (1H, d), 7.94 (1H, dd), 7.69 (1H, d), 7.47 (1H, m), 4.59 (1H, q), 1.58 (3H, d), 0.6-0.96 (4H, m).

Step 2: 5-(5-Ethyl-2-methyl-6-oxo-1,6-dihydropyridin-3-yl)thiophene-2-sulfonic acid cyclopropyl(1-pyridin-2-yl)ethylamide hydrochloride: A mixture of cyclopropyl(1-pyridin-2-yl)ethylamine (73.5 mg, 0.453 mmol), 5-(5-ethyl-2-methyl-6-oxo-1,6-dihydropyridin-3-yl)thiophene-2-sulfonyl chloride (144 mg, 0.453 mmol), PS-piperidinomethyl (155 mg, 0.542 mmol, beads) and dichloromethane (5 mL) is stirred at room temperature overnight. The reaction mixture is filtered and the filtrate is evaporated. The residue is purified by chromatography on an ISCO Redisep 10 g cartridge eluting with ethyl acetate-5% methanol to afford 5-(5-ethyl-2-methyl-6-oxo-1,6-dihydropyridin-3-yl)thiophene-2-sulfonic acid cyclopropyl(1-pyridin-2-yl)ethylamide (85 mg, 43% yield) as a white solid. A hydrochloride salt is prepared by dissolving the amine (85 mg, 0.192 mmol) in methanol (2 mL), adding 1 M ethereal hydrochloric acid (0.3 mL), some methanol is removed, more ether added and the hydrochloride salt is collected by filtration (50 mg, 54% yield as an off white solid). RT=2.93 min; m/e=444; ¹H NMR (δ, ppm): 11.84 (1H, br s), 8.6 (1H, d), 8.02 (1H, m), 7.69 (1H, d), 7.61 (1H, d), 7.50 (1H, m), 7.37 (1H, s), 5.24 (1H, d), 5.27 (2H, m), 2.40 (2H, m), 2.33 (3H, s), 1.53 (3H, d), 1.13 (3H, t), 0.6-0.96 (4H, m).

Example 122A 5-(5-Ethyl-2-methyl-6-oxo-1,6-dihydro-pyridin-3-yl)-thiophene-2-sulfonic acid benzylamide

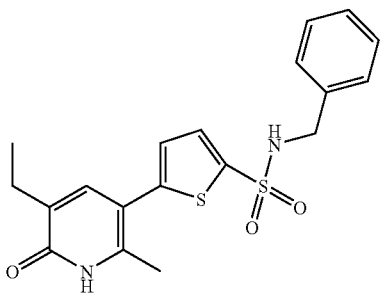

5-(5-Ethyl-2-methyl-6-oxo-1,6-dihydropyridin-3-yl)thiophene-2-sulfonyl chloride is reacted with benzyl amine as described in Step 5, Example 24 to give the title compound. MS: m/e 389 (M+H).

Example 122B 5-(5-Ethyl-2-methyl-6-oxo-1,6-dihydro-pyridin-3-yl)-thiophene-2-sulfonic acid 4-methoxy-benzylamide

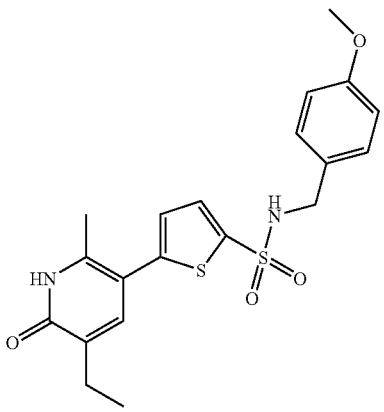

5-(5-Ethyl-2-methyl-6-oxo-1,6-dihydropyridin-3-yl)thiophene-2-sulfonyl chloride is reacted with 4-methoxybenzyl amine as described in Step 5, Example 24 to give the title compound. MS: m/e 419 (M+H). $^1$H NMR (δ ppm): 11.83 (s, 1H); 8.33 (t, 1H, J=6.3 Hz); 7.49 (d, 1H, J=3.7 Hz); 7.28 (s, 1H); 7.16 (d, 2H, J=8.6 Hz); 7.10 (d, 1H, J=3.7 Hz); 6.84 (d, 1H; J=8.6 Hz); 4.05 (d, 2H, J=6.3 Hz); 3.70 (s, 3H); 2.40 (q, 2H, J=7.4 Hz); 2.28 (s, 3H); 1.10 (t, 3H, J=7.4 Hz).

Example 122C 5-(5-Ethyl-2-methyl-6-oxo-1,6-dihydro-pyridin-3-yl)-thiophene-2-sulfonic acid 4-methanesulfonyl-benzylamide

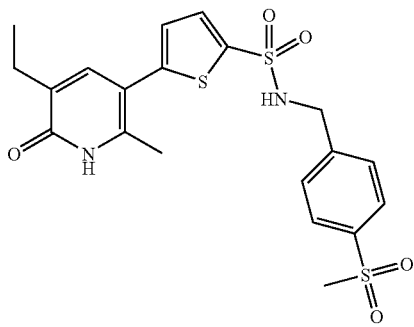

5-(5-Ethyl-2-methyl-6-oxo-1,6-dihydropyridin-3-yl)thiophene-2-sulfonyl chloride is reacted with 4-methanesulfonyl-benzyl amine as described in Step 5, Example 24 to give the title compound. MS: m/e 467 (M+H).

Example 122D 5-(5-Ethyl-2-methyl-6-oxo-1,6-dihydro-pyridin-3-yl)-thiophene-2-sulfonic acid (1H-indol-3-ylmethyl)-amide

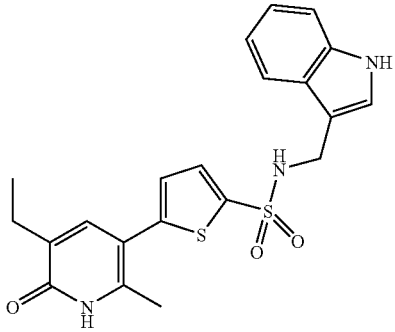

5-(5-Ethyl-2-methyl-6-oxo-1,6-dihydropyridin-3-yl)thiophene-2-sulfonyl chloride is reacted with 1H-indol-3-ylmethyl amine as described in Step 5, Example 24 to give the title compound. MS: m/e 428 (M+H).

Example 122E 5-(5-Ethyl-2-methyl-6-oxo-1,6-dihydro-pyridin-3-yl)-thiophene-2-sulfonic acid {3-[(1-ethyl-pyrrolidin-2-ylmethyl)-amino]-propyl}-amide

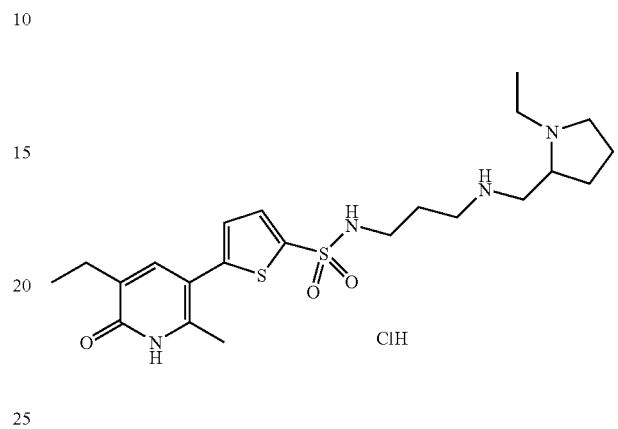

5-(5-Ethyl-2-methyl-6-oxo-1,6-dihydropyridin-3-yl)thiophene-2-sulfonyl chloride is reacted with 3-[(1-ethyl-pyrrolidin-2-ylmethyl)-amino]-propyl amine as described in Step 5, Example 24 to give the title compound (19% yield). LC/MS: RT 2.19 min; m/e 467 (M+H).

Example 122F 5-(5-Ethyl-2-methyl-6-oxo-1,6-dihydro-pyridin-3-yl)-thiophene-2-sulfonic acid [3-(2R-hydroxymethyl-pyrrolidin-1-yl)-propyl]-amide hydrochloride

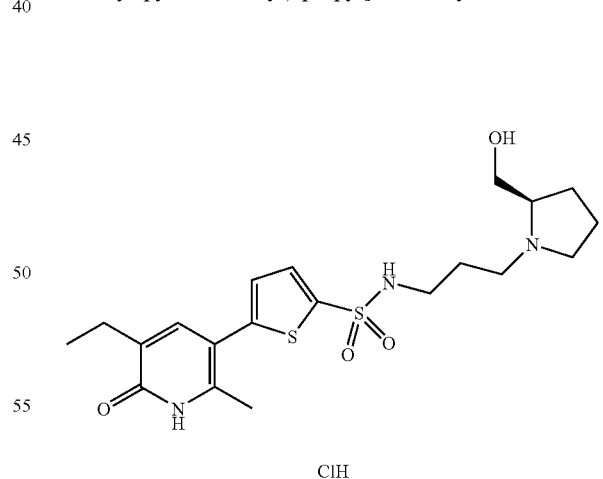

5-(5-Ethyl-2-methyl-6-oxo-1,6-dihydropyridin-3-yl)thiophene-2-sulfonyl chloride is reacted with 3-(2R-hydroxymethyl-pyrrolidin-1-yl)-propylamine as described in Step 5, Example 24 to give the title compound (59% yield). LC/MS: RT 2.28 min; m/e 440 (M+H).

Example 122G 5-(5-Ethyl-2-methyl-6-oxo-1,6-dihydro-pyridin-3-yl)-thiophene-2-sulfonic acid [2-(2R-hydroxymethyl-pyrrolidin-1-yl)-ethyl]-amide hydrochloride

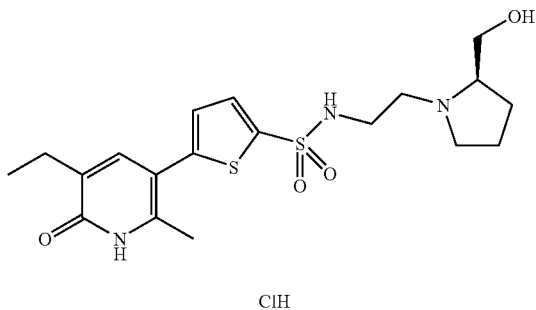

5-(5-Ethyl-2-methyl-6-oxo-1,6-dihydropyridin-3-yl)thiophene-2-sulfonyl chloride is reacted with 2-(2R-hydroxymethyl-pyrrolidin-1-yl)-ethylamine as described in Step 5, Example 24 to give the title compound (45% yield). LC/MS: RT 2.03 min; m/e 426 (M+H).

Example 122H 5-(5-Ethyl-2-methyl-6-oxo-1,6-dihydro-pyridin-3-yl)-thiophene-2-sulfonic acid [2-(3,3-difluoro-pyrrolidin-1-yl)-ethyl]-amide

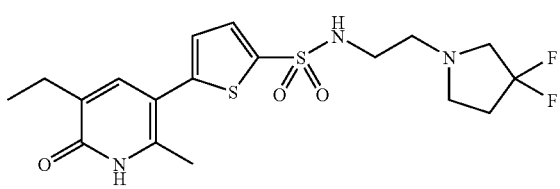

5-(5-Ethyl-2-methyl-6-oxo-1,6-dihydropyridin-3-yl)thiophene-2-sulfonyl chloride is reacted with 2-(3,3-difluoro-pyrrolidin-1-yl)-ethylamine as described in Step 5, Example 24 to give the title compound (43% yield). LC/MS: RT 1.32 min; m/e 432 (M+H).

Example 122I

1-{2-[5-(5-Ethyl-2-methyl-6-oxo-1,6-dihydro-pyridin-3-yl)-thiophene-2-sulfonylamino]-ethyl}-pyrrolidine-2-carboxylic acid

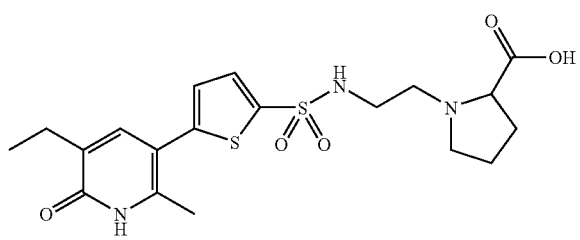

5-(5-Ethyl-2-methyl-6-oxo-1,6-dihydropyridin-3-yl)thiophene-2-sulfonyl chloride is reacted with 1-(2-aminoethyl)-pyrrolidine-2-carboxylic acid as described in Step 5, Example 24 to give the title compound (88% yield). LC/MS: RT 2.04 min; m/e 440 (M+H).

Example 123

5-[5-(Benzylamino-methyl)-furan-2-yl]-3-ethyl-6-methyl-1H-pyridin-2-one hydrochloride

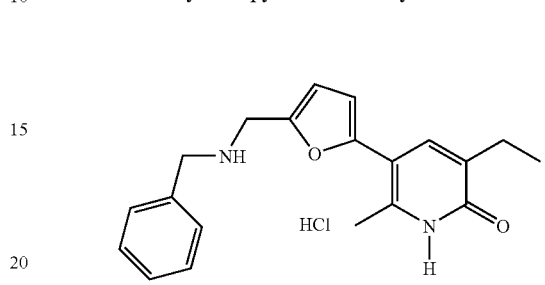

Method A: A mixture of 5-(5-ethyl-2-methyl-6-oxo-1,6-dihydropyridin-3-yl)furan-2-carbaldehyde (60 mg, 0.24 mmol), prepared in accordance with the procedures of PREPARATION 3, benzylamine (0.247 mmol), MP-cyanoborohydride (0.390 mmol, beads, 2.55 mmol/g), tetrahydrofuran (8 mL) and acetic acid (0.8 mL) is shaken at ambient temperature overnight. The beads are filtered off and the clear filtrate is filtered through an Elut SCX(acid) column washing with methanol (12 mL). The solvent is evaporated and the residue is dissolved in dichloromethane (2 mL) and treated with 1.0 N ethereal hydrochloric acid. The resulting solids are collected by filtration to afford the title compound as a yellow solid (64% yield). LC/MS: RT 2.07 min; m/e=323 (M+H); $^1$H NMR (δ, ppm): 9.82 (1H, br), 7.37-7.60 (6H, m), 6.70 (1H, d), 6.52 (1H, d), 4.08-4.40 (m, buried under water peak), 2.41 (2H, q), 2.37 (3H, s), 1.12 (3H, t).

Method B: Alternatively the title compound is also prepared as follows. To a mixture of 5-(5-ethyl-2-methyl-6-oxo-1,6-dihydropyridin-3-yl)furan-2-carbaldehyde (65 mg, 0.26 mmol), benzylamine (3-5 equivalents), acetic acid (3-5 equivalents) and methanol (5 mL) is added sodium cyanoborohydride (3-5 equivalents) and the reaction is stirred at room temperature for 12 hr. The reaction is concentrated and the residue is diluted with aqueous sodium bicarbonate and extracted with ethyl acetate. The organic layer is separated, dried, filtered and concentrated. The residue is purified by flash chromatography eluting with dichloromethane-10-20% methanol to afford the title compound as a yellow solid.

Example 124

3-Ethyl-5-[5-(3-hydroxypyrrolidin-1-ylmethyl)furan-2-yl]-6-methyl-1H-pyridin-2-one hydrochloride

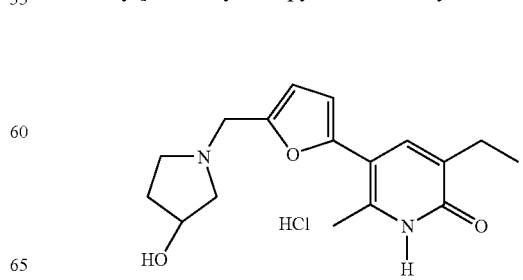

5-(5-Ethyl-2-methyl-6-oxo-1,6-dihydropyridin-3-yl]furan-2-carbaldehyde is reacted with pyrrolidin-3-ol as described in Method A of Example 123 to give the title compound (100% yield) as a yellow solid. LC/MS: RT 1.68 min; m/e 303 (M+H); $^1$H NMR ($\delta$, ppm): 11.72 (1H, br), 11.16 (1H, br d), 7.56 (1H, d), 6.77 (1H, d), 6.52 (1H, s), 2.95-3.67 (7H, m), 2.30-2.50 (5H, m), 1.76-2.30 (2H, m), 1.12 (3H, t).

Example 125

3-Ethyl-5-{5-[(4-hydroxycyclohexylamino)methyl]thiophen-2-yl]-6-methyl-1H-pyridin-2-one hydrochloride

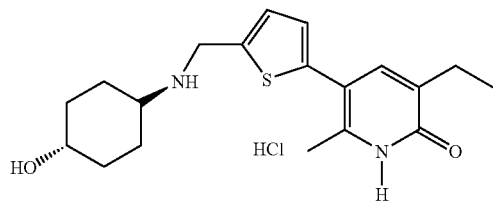

5-(5-Ethyl-2-methyl-6-oxo-1,6-dihydropyridin-3-yl]thiophen-2-carbaldehyde is reacted with 4-aminocyclohexanol as described in Method A of Example 123 to give the title compound (79% yield) as a yellow solid. LC/MS: RT 1.85 min; m/e 346 (M+H); $^1$H NMR ($\delta$, ppm): 7.25 (1H, s), 6.88 (1H, s), 6.86 (1H, s), 4.86 (1H, s), 3.10-3.50 (m), 2.95-3.67 (7H, m), 2.38 (2H, q), 2.25 (3H, s), 1.65-1.88 (4H, m), 1.00-1.17 (7H, m).

Example 126

3-Ethyl-5-[5-(3-hydroxypiperidin-1-ylmethyl)thiophen-2-yl]-6-methyl-1H-pyridin-2-one hydrochloride

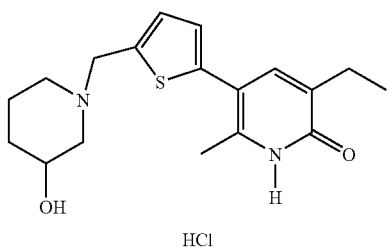

5-(5-Ethyl-2-methyl-6-oxo-1,6-dihydropyridin-3-yl]thiophen-2-carbaldehyde is reacted with 3-hydroxypiperidine as described in Method A of Example 123 to give the title compound (77% yield) as a yellow solid. LC/MS: RT 1.85 min; m/e 332 (M+H); $^1$H NMR ($\delta$, ppm): 7.26 (1H, s), 6.90 (2H, m), 4.50 (1H, br), 3.65 (2H, q), 3.45 (1H, m,), 2.87 (1H, d), 2.70 (1H, m), 2.38 (2H, q), 2.29 (3H, s), 1.12-1.94 (6H, m), 1.10 (3H, t).

Example 127

3-Ethyl-5-[5-(4-hydroxy-piperidin-1-ylmethyl)-thiophen-2-yl]-6-methyl-1H-pyridin-2-one hydrochlorid

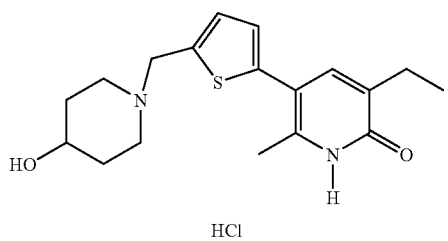

5-(5-Ethyl-2-methyl-6-oxo-1,6-dihydropyridin-3-yl]thiophen-2-carbaldehyde is reacted with 4-hydroxypiperidine as described in Method A of Example 123 to give the title compound (72% yield) as a yellow solid. LC/MS: RT 1.98 min; m/e 333 (M+H); $^1$H NMR ($\delta$, ppm): 7.26 (1H, s), 6.89 (2H, s), 4.50 (1H, br), 3.64 (2H, s), 3.46 (1H, m,), 2.90 (1H, d), 2.72 (1H, m), 2.47 (1H, m), 2.38 (2H, q), 2.29 (3H, s), 2.10 (1H, m), 1.70 (2H, br), 1.37 (1H, m), 1.24 (1H, m), 1.10 (3H, t).

Example 128

3-Ethyl-5-{5-[(2-hydroxy-ethylamino)-methyl]thiophen-2-yl}-6-methyl-1H-pyridin-2-one hydrochloride

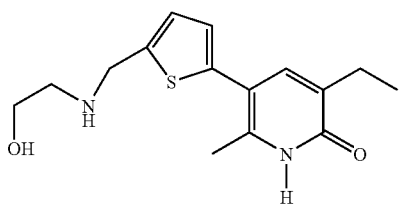

5-(5-Ethyl-2-methyl-6-oxo-1,6-dihydropyridin-3-yl]thiophen-2-carbaldehyde is reacted with 2-hydroxy-ethylamine as described in Method A of Example 123 to give the title compound as a yellow solid (87% yield). LC/MS: RT 1.90 min; m/e 293 (M+H); $^1$H NMR ($\delta$, ppm): 7.26 (1H, d), 6.89 (1H, s), 6.87 (1H, d), 4.50 (1H, br), 3.46 (2H, t), 2.62 (2H, t), 2.38 (2H, q), 2.29 (3H, s), 1.09 (3H, t).

Example 129

5-(5-[1,4']Bipiperidinyl-1'-ylmethyl-thiophen-2-yl)-3-ethyl-6-methyl-1H-pyridin-2-one dihydrochloride

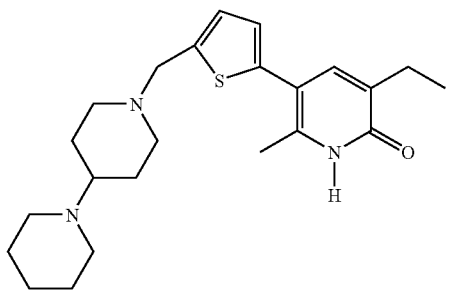

2HCl 5-(5-Ethyl-2-methyl-6-oxo-1,6-dihydropyridin-3-yl]thiophen-2-carbaldehyde is reacted with [1,4']bipiperidinyl as described in Method A of Example 123 to give the title compound (74% yield) as a brown solid. LC/MS: RT 1.87 min; m/e 400 (M+H); $^1$H NMR ($\delta$, ppm): 7.27 (1H, s), 6.88 (2H, s), 3.91 (2H, d), 2.34-2.46 (7H, m), 2.27 (3H, s), 2.16 (1H, m), 1.94 (2H, m), 1.66 (2H, m), 1.33-1.50 (6H, m), 1.09 (3H, t).

Example 130

4-{[5-(5-Ethyl-2-methyl-6-oxo-1,6-dihydro-pyridin-3-yl)-thiophen-2-ylmethyl]-amino}-1-methyl-1H-pyrrole-2-carboxylic acid methyl ester dihydrochloride

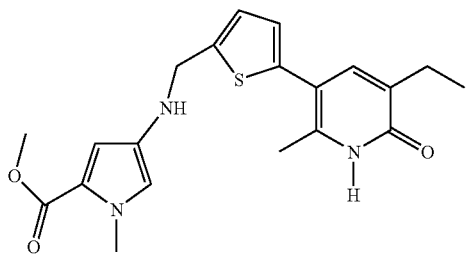

2HCl 5-(5-Ethyl-2-methyl-6-oxo-1,6-dihydropyridin-3-yl]thiophen-2-carbaldehyde is reacted with 4-amino-1-methyl-1H-pyrrole-2-carboxylic acid methyl ester as described in Method A of Example 123 to give the title compound (97% yield) as a brown solid. LC/MS: RT 2.334 min; m/e 386 (M+H); $^1$H NMR ($\delta$, ppm): 7.24 (1H, s), 6.96 (1H, s), 6.87 (1H, s), 6.51 (1H, s), 6.31 (1H, s), 5.10 (1H, br), 4.10 (2H, s), 3.69 (3H, s), 3.74 (3H, s), 2.38 (2H, m), 2.28 (3H, s), 1.09 (3H,t)

Example 131

3-Ethyl-5-[5-(3-hydroxymethyl-piperidin-1-ylmethyl)-thiophen-2-yl]-6-methyl-1H-pyridin-2-one hydrochloride

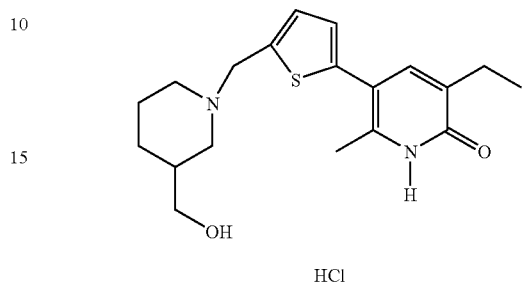

HCl 5-(5-Ethyl-2-methyl-6-oxo-1,6-dihydropyridin-3-yl]thiophen-2-carbaldehyde is reacted with (piperidin-3-yl)methanol as described in Method A of Example 123 to give the title compound (84% yield) as a yellow solid. LC/MS: RT 1.92 min; m/e 347 (M+H); $^1$H NMR ($\delta$, ppm): 7.27 (1H, s), 6.90 (2H, s), 4.37 (1H, br), 3.63 (2H, s), 3.15-3.30 (m), 2.74 (2H, m), 2.10-2.56 (m), 2.38 (2H, q), 2.28 (3H, s), 1.94 (1H, m), 1.18-1.74 (5H, m), 1.09 (3H, t).

Example 132

5-{5-[(1-Cyclohexylmethyl-piperidin-4-ylamino)-methyl]thiophen-2-yl}-3-ethyl-6-methyl-1H-pyridin-2-one dihydrochloride

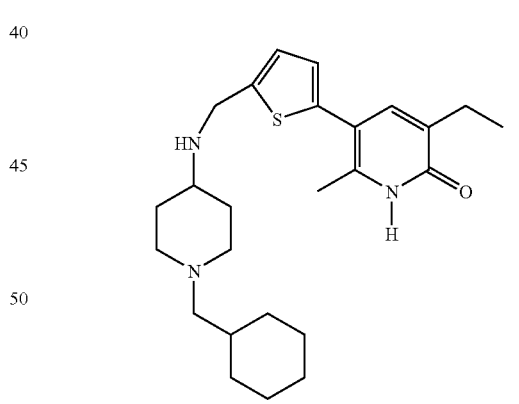

2 HCl 5-(5-Ethyl-2-methyl-6-oxo-1,6-dihydropyridin-3-yl]thiophen-2-carbaldehyde is reacted with 1-(cyclohexylmethyl)(piperidin-4-yl)amine as described in Method A of Example 123 to give the title compound (82% yield) as a brown solid. LC/MS: RT 1.88 min; m/e 428 (M+H); $^1$H NMR ($\delta$, ppm): 7.25 (1H, s), 6.90 (1H, s), 6.87 (2H, d), 3.88 (1H, s), 2.73 (2H, d), 2.38 (2H, q), 2.27 (3H, s), 2.02 (1H, m), 1.57-1.94 (2H, m), 1.44 (2H, m), 1.12-1.30 (6H, m), 1.09 (3H, t), 0.90 (2H, m).

Example 133

5-{5-[Methyl(1-methylpyrrolidin-3-yl)amino-methyl]thiophen-2-yl}-3-ethyl-6-methyl-1H-pyridin-2-one dihdrochloride

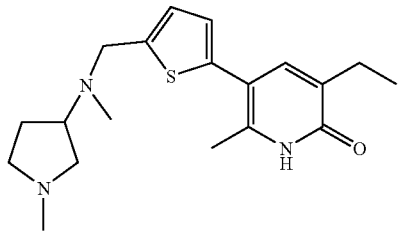

2 HCl 5-(5-Ethyl-2-methyl-6-oxo-1,6-dihydropyridin-3-yl]thiophen-2-carbaldehyde is reacted with methyl(1-methylpyrrolidin-3-yl)amine as described in Method A of Example 123 to give the title compound (78% yield) as a yellow solid. LC/MS: RT 1.73 min; m/e 346 (M+H); $^1$H NMR (δ, ppm): 7.26 (1H, s), 6.89 (2H, m), 3.66 (2H, q), 3.14 (1H, m), 2.40-2.60 (m), 2.38 (2H, q), 2.27 (3H, s), 2.24 (3H, s), 2.14 (3H, s), 2.12-2.30 (m), 1.47-2.12 (2H, m), 1.09 (3H, t).

Example 134

3-Ethyl-6-methyl-5-{5-[(1,2,3,4-tetrahydro-naphthalen-2-ylamino)-methyl]thiophen-2-yl}-1H-pyridin-2-one hydrochloride

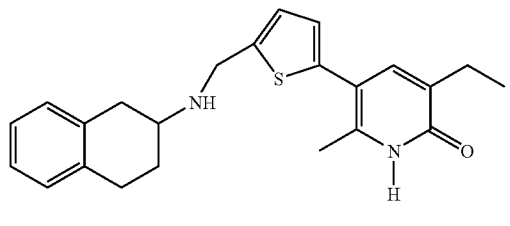

HCl 5-(5-Ethyl-2-methyl-6-oxo-1,6-dihydropyridin-3-yl]thiophen-2-carbaldehyde is reacted with 1,2,3,4-tetrahydro-naphthalen-2-ylamine as described in Method A of Example 123 to give the title compound (68% yield) as a yellow solid. LC/MS: RT 2.49 min; m/e 379 (M+H); $^1$H NMR (δ, ppm): 7.44 (1H, d), 7.26 (1H, s), 7.13 (2H, m), 7.05 (1H, d), 6.95 (1H, m), 6.88 (1H, m), 3.96 (2H, s), 3.74 (1H, t), 2.60-2.80 (2H, m), 2.38 (2H, q), 2.28 (3H, s), 1.55-2.00 (4H, m), 1.09 (3H, t).

Example 135

3-Ethyl-6-methyl-5-{5-[(1-phenyl-ethylamino)-methyl]thiophen-2-yl}-1H-pyridin-2-one hydrochloride

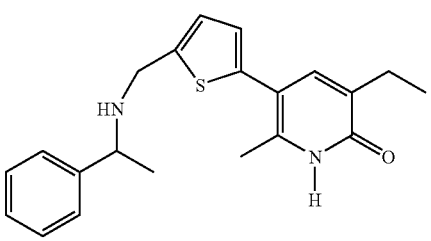

HCl 5-(5-Ethyl-2-methyl-6-oxo-1,6-dihydropyridin-3-yl]thiophen-2-carbaldehyde is reacted with 1-phenyl-ethylamine as described in Method A of Example 123 to give the title compound (82% yield) as a yellow solid. LC/MS: RT 2.41 min; m/e 353 (M+H); $^1$H NMR (δ, ppm): 7.30-7.40 (4H, m), 7.18-7.27 (2H, m), 6.85 (1H, s), 6.82 (1H, d), 3.76 (1H, q), 3.64 (2H, s), 2.38 (2H, q), 2.26 (3H, s), 1.27 (3H, d), 1.09 (3H, t).

Example 136

3-Ethyl-6-methyl-5-{5-[(1-methyl-3-phenyl-propylamino)-methyl]thiophen-2-yl}-1H-pyridin-2-one hydrochloride

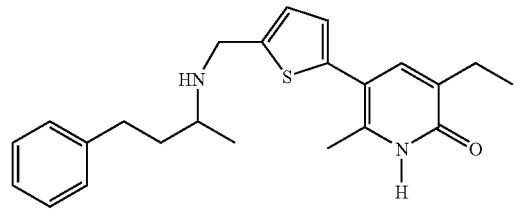

HCl 5-(5-Ethyl-2-methyl-6-oxo-1,6-dihydropyridin-3-yl]thiophen-2-carbaldehyde is reacted with 5-methyl-3-phenyl-propylamine as described in Method A of Example 123 to give the title compound (96% yield) as a yellow solid. LC/MS: RT 2.53 min; m/e 381 (M+H); $^1$H NMR (δ, ppm): 7.10-7.28 (6H, m), 6.88 (1H, s), 6.85 (1H, d), 3.86 (2H, q), 2.50-2.84 (3H, m), 2.38 (2H, q), 2.26 (3H, s), 1.51-1.75 (2H, m), 1.09 (3H, t), 1.04 (3H, d).

Example 137

5-(5-Cyclobutylaminomethyl-thiophen-2-yl)-3-ethyl-6-methyl-1H-pyridin-2-one hydrochloride

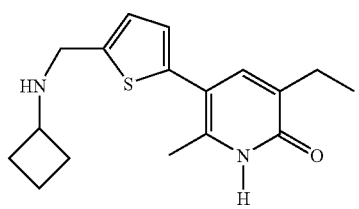

HCl 5-(5-Ethyl-2-methyl-6-oxo-1,6-dihydropyridin-3-yl]thiophen-2-carbaldehyde is reacted with cyclobutylamine as described in Method A of Example 123 to give the title compound (67% yield) as a yellow solid. LC/MS: RT ?? min; m/e 303 (M+H); ¹H NMR (δ, ppm): 11.64 (1H, br), 7.25 (1H, s), 6.89 (2H, m), 3.76 (2H, s), 3.20 (1H, m), 2.38 (2H, q), 2.24 (3H, s), 1.45-2.15 (6H, m), 1.09 (3H, t).

Example 138

3-Ethyl-5-{5-[(2-methoxyethylamino)-methyl]thiophen-2-yl}-6-methyl-1H-pyridin-2-one hydrochloride

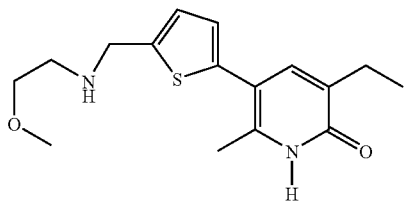

HCl 5-(5-Ethyl-2-methyl-6-oxo-1,6-dihydropyridin-3-yl]thiophen-2-carbaldehyde is reacted with 2-methoxyethylamine as described in Method A of Example 123 to give the title compound (68% yield) as a yellow solid. LC/MS: RT 2.55 min; m/e 307 (M+H); ¹H NMR (δ, ppm): 11.65 (1H, br), 7.26 (1H, d), 6.85-6.87 (2H, m), 3.36-3.54 (2H, m), 3.24 (3H, s), 2.70 (2H, t), 2.38 (2H, q), 2.24 (3H, s), 1.10 (3H, t).

Example 139

3-Ethyl-6-methyl-5-{5-[1-(4-trifluoromethylpyrimidin-2-yl)piperidin-4-ylamino]-thiophen-2-yl}-1H-pyridin-2-one dihydrochloride

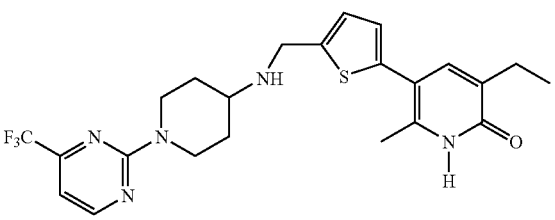

2HCl 5-(5-Ethyl-2-methyl-6-oxo-1,6-dihydropyridin-3-yl]thiophen-2-carbaldehyde is reacted with 1-(4-trifluoromethylpyrimidin-2-yl)(piperidin-4-yl)amine as described in Method A of Example 123 to give the title compound (88% yield) as a yellow solid. LC/MS: RT 2.47min; m/e 478 (M+H); ¹H NMR (δ, ppm): 8.65 (1H, d), 7.25 (1H, s), 6.83-7.00 (3H, m), 4.45 (2H, d), 3.95 (2H, s), 2.93-3.40 (4H, m), 2.70-2.85 (1H, m), 2.38 (2H, q), 2.26 (3H, s), 1.78-1.98 (2H, m), 1.26 (2H, m), 1.09 (3H, t).

Example 140

5-(5-{[1-(3,5-Difluoro-benzyl)-)-piperidin-4-ylmethyl]-amino}methyl-thiophen-2-yl)-3-ethyl-6-methyl-1H-pyridin-2-one hydrochloride

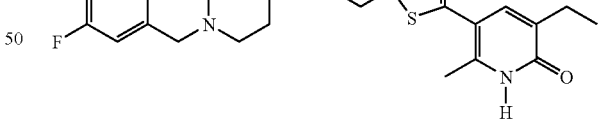

2HCl 5-(5-Ethyl-2-methyl-6-oxo-1,6-dihydropyridin-3-yl]thiophen-2-carbaldehyde is reacted with [1-(3,5-difluorobenzyl)-piperidin-4-]-methylamine as described in Method A of Example 123 to give the title compound as a white solid (54% yield). LC/MS: RT 1.78 min; m/e 472 (M+H); ¹H NMR (δ, ppm): 7.24 (1H, s), 6.82-7.15 (6H, m), 3.89 (2H, s), 3.48 (2H, s), 2.40-2.60 (m, buried), 2.38 (2H, q), 2.26 (3H, s), 1.67-2.10 (5H, m), 1.18-1.50 (2H, m), 1.10 (3H, t).

Example 140A 5-(5-{[1-(3,5-Difluoro-benzyl)-piperidin-4-ylamino]-methyl}-thiophen-2-yl)-3-ethyl-6-methyl-1H-pyridin-2-one

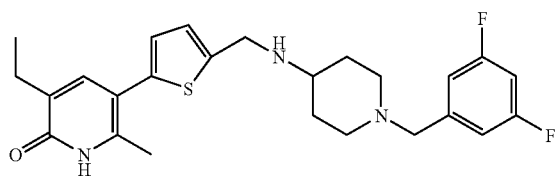

5-(5-Ethyl-2-methyl-6-oxo-1,6-dihydropyridin-3-yl]thiophen-2-carbaldehyde is reacted with 1-(3,5-difluoro-benzyl)-piperidin-4-ylamine as described in Method A of Example 123 to give the title compound. MS: m/e 458 (M+H).

Example 141

3-Ethyl-6-methyl-5-{5-[(2-pyridin-2-ylethylamino)methyl]thiophen-2-yl}-1H-pyridin-2-one dihydrochloride

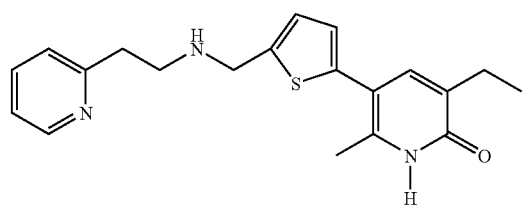

5-(5-Ethyl-2-methyl-6-oxo-1,6-dihydropyridin-3-yl]thiophen-2-carbaldehyde is reacted 2-(pyridin-2-yl)ethylamine as described in Method A of Example 123 to give the title compound (65% yield) as a white solid. LC/MS: RT 1.82 min; m/e 354 (M+H); $^1$H NMR (δ, ppm): 8.46 (1H, d), 7.70 (1H, t), 7.13-7.35 (3H, m), 6.89 (2H, m), 3.90 (2H, s), 2.80-3.10 (4H, m), 2.38 (2H, q), 2.26 (3H, s), 1.10 (3H, t).

Example 142

5-(5-Cyclopropylaminomethyl-thiophen-2-yl)-3-ethyl-6-methyl-1H-pyridin-2-one hydrochloride

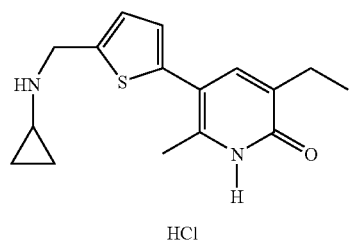

5-(5-Ethyl-2-methyl-6-oxo-1,6-dihydropyridin-3-yl]thiophen-2-carbaldehyde is reacted with cyclopropylamine as described in Method A of Example 123 to give the title compound (62% yield) as a white solid. LC/MS: RT 1.88 min; m/e 289 (M+H); $^1$H NMR (δ, ppm): 11.66 (1H, br), 7.27 (1H, s), 6.94 (2H, s), 3.90 (2H, s), 3.50 (m, buried), 2.38 (2H, q), 2.24 (3H, s), 1.88-2.70 (m, buried), 1.09 (3H, t), 0.33-0.80 (2H, m).

Example 143

5-(5-Cyclohexylmethylaminomethylthiophen-2-yl)-3-ethyl-6-methyl-1H-pyridin-2-one hydrochloride

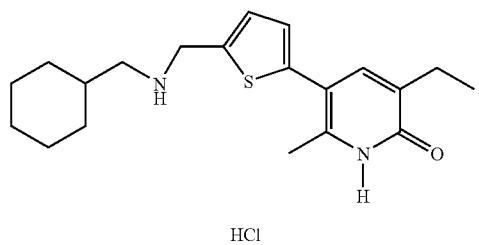

5-(5-Ethyl-2-methyl-6-oxo-1,6-dihydropyridin-3-yl]thiophen-2-carbaldehyde is reacted with cyclohexylmethylamine as described in Method A of Example 123 to give the title compound (66% yield) as a white solid. LC/MS: RT 2.27 min; m/e 345 (M+H); $^1$H NMR (δ, ppm): 11.63 (1H, br), 7.25 (1H, s), 6.89 (2H, s), 3.83 (2H, s), 2.30-2.70 (4H, m), 2.27 (3H, s), 1.00-1.90 (12H, m), 0.75-0.98 (2H, m).

Example 144

5-{5-[(2-Cyclohex-1-enyl-ethylamino)-methyl]thiophen-2-yl}-3-ethyl-6-methyl-1H-pyridin-2-one hydrochloride

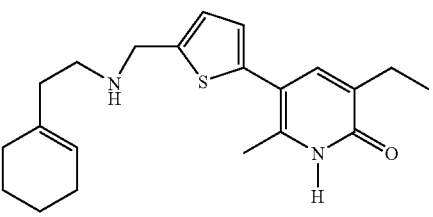

5-(5-Ethyl-2-methyl-6-oxo-1,6-dihydropyridin-3-yl]thiophen-2-carbaldehyde is reacted with 2-(cyclohex-1-enyl)ethylamine as described in Method A of Example 123 to give the title compound (74% yield) as a white solid. LC/MS: RT 2.32 min; m/e 357 (M+H); $^1$H NMR (δ, ppm): 7.26 (1H, s), 6.90 (2H, m), 5.38 (1H, s), 3.85 (2H, s), 2.60 (2H, m), 2.38 (2H, q), 2.27 (3H, s), 1.80-2.20 (6H, m), 1.53 (4H, m), 1.10 (3H, t).

Example 145

5-{5-[(3,5-Difluoro-phenylamino)-ethyl]thiophen-2-yl}-3-ethyl-6-methyl-1H-pyridin-2-one hydrochloride

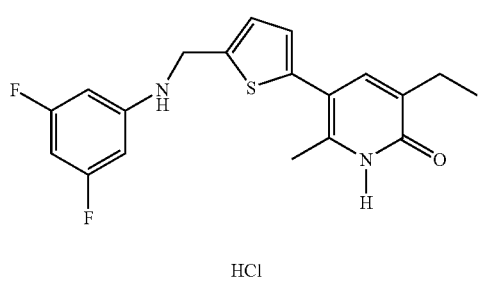

5-(5-Ethyl-2-methyl-6-oxo-1,6-dihydropyridin-3-yl]thiophen-2-carbaldehyde is reacted with 3,5-difluoroaniline as described in Method A of Example 123 to give the title compound (54% yield) as a brown solid. LC/MS: RT 3.44 min; m/e 361 (M+H); $^1$H NMR (δ, ppm): 11.76 (1H, br), 7.24 (1H, s), 7.02 (1H, d), 6.90 (2H, m), 6.50-6.37 (3H, m), 4.45 (1H, d), 2.38 (2H, q), 2.26 (3H, s), 1.09 (3H, t).

Example 146

3-Ethyl-6-methyl-5-{5-[(2-phenoxyethylamino)-methyl]thiophen-2-yl}-1H-pyridin-2-one hydrochloride

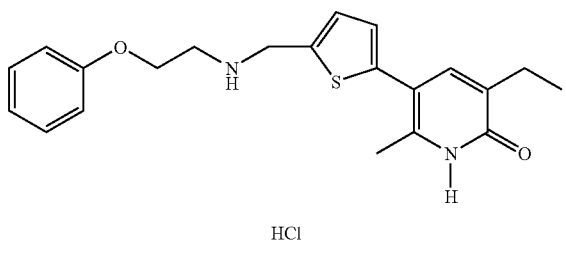

5-(5-Ethyl-2-methyl-6-oxo-1,6-dihydropyridin-3-yl]thiophen-2-carbaldehyde is reacted with 2-phenoxyethylamine as described in Method A of Example 123 to give the title compound (85% yield) as a white solid. LC/MS: RT 2.23 min; m/e 369 (M+H); $^1$H NMR (δ, ppm): 7.18-7.35 (3H, m), 6.80-7.00 (5H, m), 4.03 (2H, t), 2.95 (2H, s), 2.93 (2H, t), 2.38 (2H, q), 2.26 (3H, s), 1.09 (3H, t).

Example 147

5-{5-[(3-methylbut-2-ylamino)methyl]thiophen-2-yl}-3-ethyl-6-methyl-1H-pyridin-2-one hydrochloride

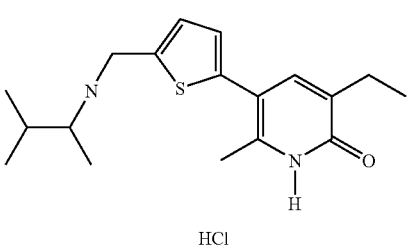

5-(5-Ethyl-2-methyl-6-oxo-1,6-dihydropyridin-3-yl]thiophen-2-carbaldehyde is reacted with 3-methylbut-2-ylamine as described in Method A of Example 123 to give the title compound (74% yield) as a white solid. LC/MS: RT 2.07 min; m/e 319 (M+H); $^1$H NMR (δ, ppm): 7.23 (1H, s), 6.85 (2H, m), 3.85 (2H, q), 2.39-2.50 (m, buried), 2.37 (2H, q), 2.24 (3H, s), 1.65 (1H, m), 1.08 (3H, t), 0.75-0.95 (9H, m).

Example 148

3-ethyl-6-methyl-5-(5-piperidin-1-ylmethy-thiophen-2-yl)-1H-pyridin-2-one hydrochloride

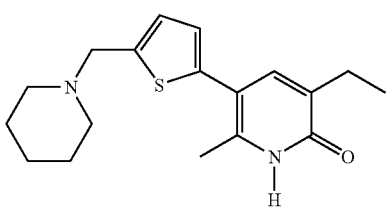

5-(5-Ethyl-2-methyl-6-oxo-1,6-dihydropyridin-3-yl]thiophen-2-carbaldehyde is reacted with piperidine as described in Method A of Example 123 to give the title compound (68% yield) as a white solid. LC/MS: RT 1.93 min; m/e 317 (M+H); $^1$H NMR (δ, ppm): 7.27 (1H, s), 6.88 (2H, s), 3.60 (2H, s), 2.30-2.50 (6H, m), 2.27 (3H, s), 1.30-1.60 (6H, m), 1.10 (3H, t).

Example 149

5-[5-(1,4-Dioxa-8-aza-spiro[4,5]dec-8-ylmethy)-thiophen-2-yl)-3-ethyl-6-methyl-1H-pyridin-2-one hydrochloride

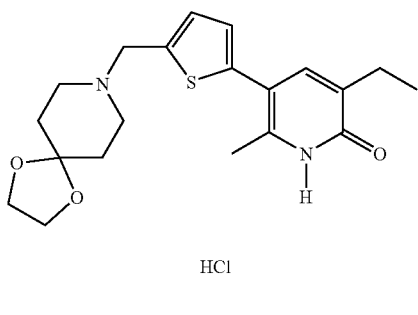

HCl 5-(5-Ethyl-2-methyl-6-oxo-1,6-dihydropyridin-3-yl]thiophen-2-carbaldehyde is reacted with 1,4-dioxa-8-aza-spiro[4,5]decane as described in Method A of Example 123 to give the title compound (59% yield) as a brown solid. LC/MS: RT 2.03 min; m/e 375 (M+H); $^1$H NMR (δ, ppm): 11.86 (1H, br), 10.37 (1H, br), 8.61 (1H, br), 7.34 (1H, m), 7.30 (1H, s), 7.12 (1H, m), 4.58 (2H, d), 3.93 (4H, s), 2.40 (2H, q), 2.36 (3H, s), 1.76-2.10 (4H, m), 1.10 (3H, t).

Example 150

3-Ethyl-6-methyl-5-[5-(4-oxo-piperidin-1-ylmethy)-thiophen-2-yl]-1H-pyridin-2-one hydrochloride

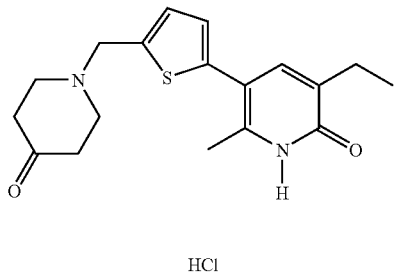

HCl 5-(5-Ethyl-2-methyl-6-oxo-1,6-dihydropyridin-3-yl]thiophen-2-carbaldehyde is reacted with piperidin-4-one as described in Method A of Example 123 to give the title compound (53% yield) as a brown solid. LC/MS: RT 0.75 min; m/e 331 (M+H); $^1$H NMR (δ, ppm): 11.68 (1H, br), 7.29 (1H, s), 6.96 (1H, d), 6.92 (1H, d), 3.92 (2H, s), 2.74 (4H, m), 2.32-2.46 (6H, m), 2.30 (3H, s), 1.10 (3H, t).

Example 151

5-{5-[(1-Benzyl-piperidin-4-ylamino)-methyl]thiophen-2-yl}-3-ethyl-6-methyl-1H-pyridin-2-one dihydrochloride

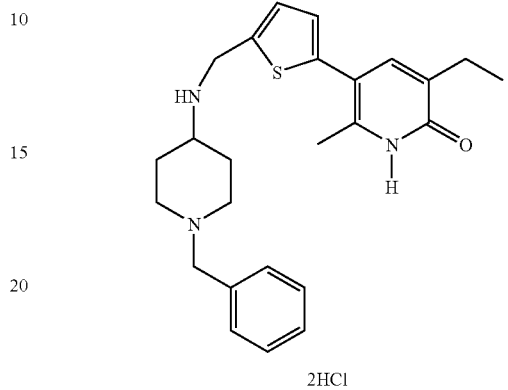

2HCl 5-(5-Ethyl-2-methyl-6-oxo-1,6-dihydropyridin-3-yl]thiophen-2-carbaldehyde is reacted with 1-benzyl-piperidin-4-ylamine as described in Method A of Example 123 to give the title compound (63% yield) as a white solid. LC/MS: RT 1.80 min; m/e 422 (M+H); $^1$H NMR (δ, ppm): 7.17-7.36 (7H, m), 6.87 (2H, m), 3.89 (2H, s), 3.42 (2H, s), 2.25-2.80 (m, buried), 2.38 (2H, q), 2.26 (3H, s), 1.65-2.00 (m), 1.18-1.37 (2H, m), 1.09 (3H, t).

Example 152

3-Ethyl-6-methyl-5-{5-{[(pyridin-4-ylmethyl)-amino]-methyl-thiophen-2-yl)-1H-pyridin-2-one dihydrochloride

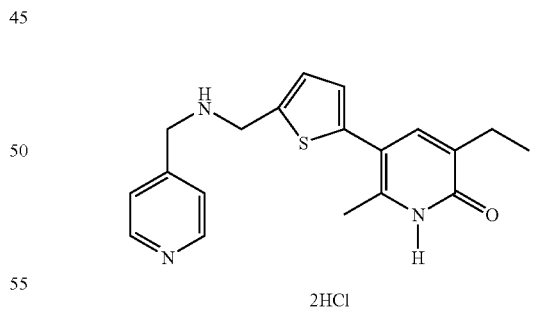

2HCl 5-(5-Ethyl-2-methyl-6-oxo-1,6-dihydropyridin-3-yl]thiophen-2-carbaldehyde is reacted with pyridin-4-yl-methylamine as described in Method A of Example 123 to give the title compound (100% yield) as a brown solid. LC/MS: RT 1.77 min; m/e 340 (M+H); $^1$H NMR (δ, ppm): 11.67 (1H, br), 8.60 (1H, d), 8.50 (1H, d), 7.85 (1H, d), 7.35 (1H, d), 7.25 (1H, d), 6.90 (2H, m), 3.68-4.02 (4H, m), 2.38 (2H, q), 2.27 (3H, s), 1.09 (3H, t).

Example 153

3-Ethyl-6-methyl-5-{5-[(3-imidazol-1-yl-propy-lamino)-methyl]thiophen-2-yl)-1H-pyridin-2-one dihydrochloride

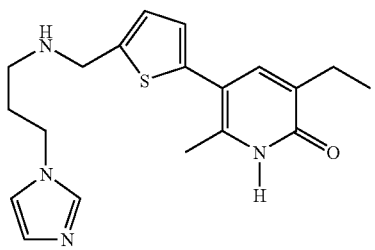

2HCl 5-(5-Ethyl-2-methyl-6-oxo-1,6-dihydropyridin-3-yl]thiophen-2-carbaldehyde is reacted with 3-(imidazol-1-yl)propylamine as described in Method A of Example 123 to give the title compound (90% yield) as a brown solid. LC/MS: RT 1.55 min; m/e 357 (M+H); $^1$H NMR (δ, ppm): 7.53 (1H, s), 7.25 (1H, s), 7.13 (1H, s), 6.87 (3H, m), 3.95-4.07 (2H, m), 3.84 (2H, s), 2.42-2.56 (m, buried), 2.39 (2H, q), 2.27 (3H, s), 1.75-1.90 (2H, m), 1.09 (3H, t).

Example 154

3-Ethyl-6-methyl-5-{5-{[(2-pyrrolidin-1-ylethy-lamino)-methyl]thiophen-2-yl)-1H-pyridin-2-one dihydrochloride

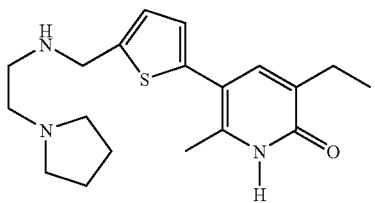

2HCl 5-(5-Ethyl-2-methyl-6-oxo-1,6-dihydropyridin-3-yl]thiophen-2-carbaldehyde is reacted with 2-(pyrrolidin-1-yl)ethylamine as described in Method A of Example 123 to give the title compound (73% yield) as a white solid. LC/MS: RT 0.47 min; m/e 346 (M+H); $^1$H NMR (δ, ppm): 7.25 (1H, s), 6.90 (2H, d), 3.88 (2H, s), 2.30-2.70 (m, buried), 2.27 (3H, s), 1.65 (4H, s), 1.09 (3H, t).

Example 155

3-Ethyl-5-(5-{[(2-(3H-imidazol-4-yl)ethylamino]methyl}thiophen-2-yl)-6-methyl-1H-pyridin-2-one dihydrochloride

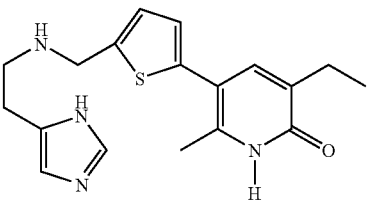

2HCl 5-(5-Ethyl-2-methyl-6-oxo-1,6-dihydropyridin-3-yl]thiophen-2-carbaldehyde is reacted with 2-(3H-imidazol-4-yl)ethylamine as described in Method A, Example 123 to give the title compound (90% yield) as a yellow solid. LC/MS: RT 1.57 min; m/e 343 (M+H); $^1$H NMR (δ, ppm): 7.45-7.55 (1H, m), 7.25 (1H, d), 7.70-7.97 (3H, m), 3.87 (2H, s), 3.17 (2H, s), 2.58-2.85 (4H, m), 2.38 (2H, q), 2.27 (3H, s), 1.09 (3H, t).

Example 156

3-Ethyl-5-[5-(indan-2-ylaminomethyl)-thiophen-2-yl]-6-methyl-1H-pyridin-2-one hydrochloride

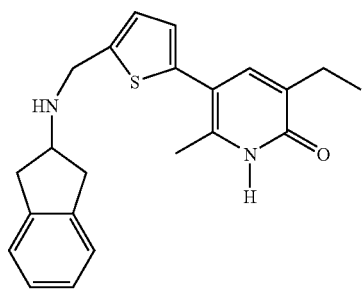

HCl 5-(5-Ethyl-2-methyl-6-oxo-1,6-dihydropyridin-3-yl]thiophen-2-carbaldehyde is reacted with (indan-2-yl)amine as described in Method A, Example 123 to give the title compound (82% yield) as beige solid. LC/MS: RT 1.75 min; m/e 365 (M+H); $^1$H NMR (δ, ppm): 7.25 (1H, s), 7.08-7.21 (5H, m), 6.87-6.96 (2H, m), 3.94 (2H, s), 3.57 (1H, m), 3.00-3.14 (2H, m), 2.66-2.77 (2H, m), 2.38 (2H, q), 2.27 (3H, s), 1.09 (3H, t).

Example 157

5-[5-(Benzylamino-methyl)-thiophen-2-yl]-3-ethyl-6-methyl-1H-pyridin-2-one hydrochloride

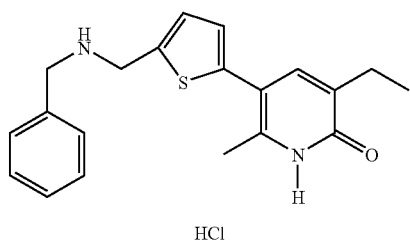

HCl 5-(5-Ethyl-2-methyl-6-oxo-1,6-dihydropyridin-3-yl]thiophen-2-carbaldehyde is reacted with benzylamine as described in Method A, Example 123 to give the title compound (100% yield) as a white solid. LC/MS: RT 2.20 min; m/e 339 (M+H); $^1$H NMR (δ, ppm): 7.17-7.40 (6H, m), 6.90 (2H, s), 3.50-3.91 (4H, m), 2.39 (2H, q), 2.28 (3H, s), 1.09 (3H, t).

Example 158

5-[5-(3,5-Difluorobenzylaminomethyl)thiophen-2-yl]-3-ethyl-6-methyl-1H-pyridin-2-one hydrochloride

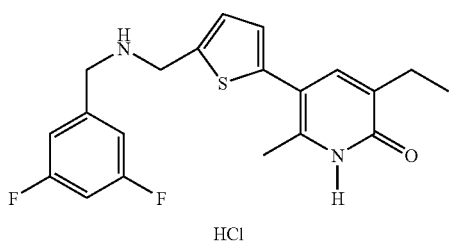

HCl 5-(5-Ethyl-2-methyl-6-oxo-1,6-dihydropyridin-3-yl]thiophen-2-carbaldehyde is reacted with 3,5-difluorobenzylamine as described in Method A, Example 123 to give the title compound (72% yield) as a beige solid. LC/MS: RT 2.27 min; m/e 375 (M+H); $^1$H NMR (δ, ppm): 11.65 (1H, br), 7.25 (1H, s), 7.00-7.17 (3H, m), 6.90 (2H, m), 3.84 (2H, s), 3.75 (42H, s), 2.38 (2H, q), 2.25 (3H, s), 1.09 (3H, t).

Example 159

5-{5-[(1-Benzyl-pyrrolidin-3-ylamino)-methyl]-thiophen-2-yl}-3-ethyl-6-methyl-1H-pyridin-2-one dihydrochloride

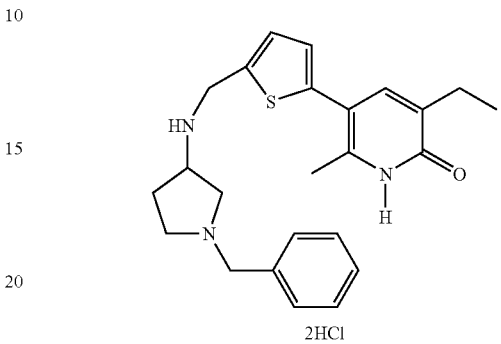

2HCl 5-(5-Ethyl-2-methyl-6-oxo-1,6-dihydropyridin-3-yl]thiophen-2-carbaldehyde is reacted with (1-benzylpyrrolidin-3-yl)amine as described in Method A, Example 123 to give the title compound (78% yield) as a white solid. LC/MS: RT 1.87 min; m/e 408 (M+H); $^1$H NMR (δ, ppm): 7.18-7.34 (7H, m), 6.88 (2H, m), 3.80 (2H, s), 3.54 (2H, s), 2.43-2.73 (m, buried), 2.38 (2H, q), 2.26 (3H, s), 1.90-2.18 (1H, m), 1.44-1.57 (1H, m), 1.09 (3H, t).

Example 160

3-Ethyl-6-methyl-5-[5-(4-pyrrolidin-1-ylpiperidin-1-ylmethyl)-thiophen-2-yl]1-1H-pyridin-2-one dihydrochloride

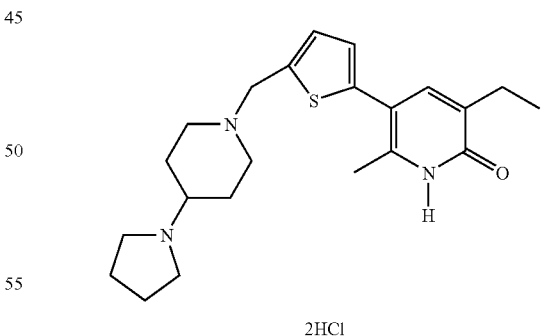

2HCl 5-(5-Ethyl-2-methyl-6-oxo-1,6-dihydropyridin-3-yl]thiophen-2-carbaldehyde is reacted with (4-pyrrolidin-1-yl)piperidine as described in Method A, Example 123 to give the title compound (70% yield) as a white solid. LC/MS: RT 1.52 min; m/e 386 (M+H); $^1$H NMR (δ, ppm): 7.27 (1H, s), 6.89 (2H, s), 3.62 (2H, s), 2.34-3.00 (m, buried), 2.27 (3H, s), 1.56-2.10 (m), 1.10 (3H, t).

Example 161

3-Ethyl-6-methyl-5-(5-{[(1-methyl-1H-imidazol-2-yl)methyl)amino]methyl}-thiophen-2-yl)-1H-pyridin-2-one dihydrochloride

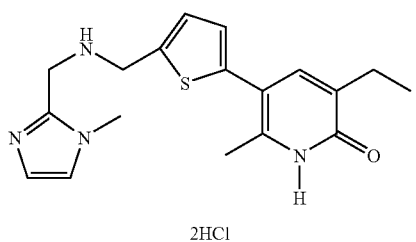

2HCl 5-(5-Ethyl-2-methyl-6-oxo-1,6-dihydropyridin-3-yl]thiophen-2-carbaldehyde is reacted with (1-methyl-1H-imidazol-2-yl)methylamine as described in Method A, Example 123 to give the title compound (76% yield) as an beige solid. LC/MS: RT 2.14 min; m/e 343 (M+H); $^1$H NMR ($\delta$, ppm): 11.64 (1H, br), 7.23 (1H, s), 6.70-7.13 (4H, m), 3.66 (2H, m), 3.60 (2H, s), 2.37 (2H, q), 2.25 (3H, s), 1.08 (3H, t).

Example 162

3-Ethyl-6-methyl-5-{5-{[(pyridin-3-ylmethyl)amino]methyl}thiophen-2-yl)-1H-pyridin-2-one dihydrochloride

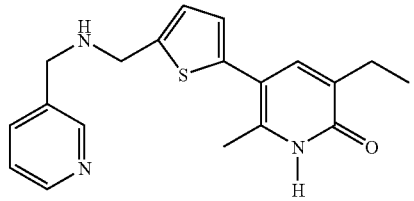

2HCl 5-(5-Ethyl-2-methyl-6-oxo-1,6-dihydropyridin-3-yl]thiophen-2-carbaldehyde is reacted with (pyridin-3-yl)methylamine as described in Method A, Example 123 to give the title compound (78% yield) as a white solid. LC/MS: RT 2.10 min; m/e 340 (M+H); $^1$H NMR ($\delta$, ppm): 8.23-8.68 (2H, d), 7.70-7.90 (1H, m), 7.35 (1H, m), 7.25 (1H, s), 6.90 (2H, m), 3.70-3.95 (4H, m), 2.38 (2H, q), 2.28 (3H, s), 1.09 (3H, t).

Example 163

3-Ethyl-6-methyl-5-{5-{[(pyridin-3-ylethyl)amino]methyl}thiophen-2-yl)-1H-pyridin-2-one dihydrochloride

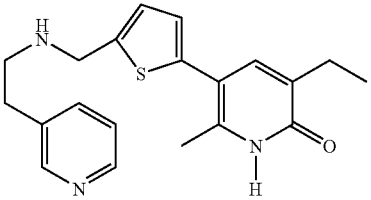

2HCl 5-(5-Ethyl-2-methyl-6-oxo-1,6-dihydropyridin-3-yl]thiophen-2-carbaldehyde is reacted with (pyridin-3-yl)ethylamine as described in Method A, Example 123 to give the title compound (96% yield) as a beige solid. LC/MS: RT 1.98 min; m/e 354 (M+H); $^1$H NMR ($\delta$, ppm): 8.16-8.64 (2H, m), 7.56-7.86 (1H, m), 7.30 (1H, m), 7.23 (1H, s), 6.87 (2H, m), 3.88 (2H, s), 2.62-2.94 (m), 2.38 (2H, q), 2.28 (3H, s), 1.09 (3H, t).

Example 164

5-{5-[(3-Chlorobenzylamino)methyl]thiophen-2-y}]-3-ethyl-6-methyl-1H-pyridin-2-one hydrochloride

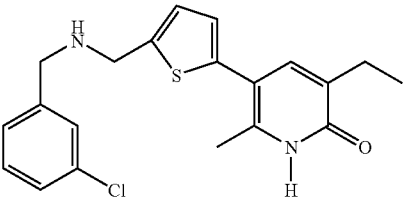

HCl 5-(5-Ethyl-2-methyl-6-oxo-1,6-dihydropyridin-3-yl]thiophen-2-carbaldehyde is reacted with 3-chlorobenzylamine as described in Method A, Example 123 to give the title compound (86% yield) as a white solid. LC/MS: RT 2.30 min; m/e 373 (M+H); $^1$H NMR ($\delta$, ppm): 7.43 (1H, s), 7.24-7.36 (4H, m), 6.85-6.90 (2H, m), 3.84 (2H, s), 3.75 (2H, s), 2.38 (2H, q), 2.27 (3H, s), 1.09 (3H, t).

Example 165

5-{5-[(3-Methylbenzylamino)methyl]thiophen-2-y}]-3-ethyl-6-methyl-1H-pyridin-2-one hydrochloride

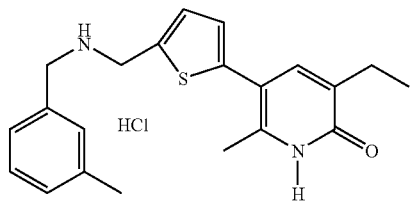

5-(5-Ethyl-2-methyl-6-oxo-1,6-dihydropyridin-3-yl]thiophen-2-carbaldehyde is reacted with 3-methylbenzylamine as described in Method A, Example 123 to give the title compound (95% yield) as a white solid. LC/MS: RT 2.28 min; m/e 353 (M+H); $^1$H NMR ($\delta$, ppm): 7.03-7.27 (5H, m), 6.90 (1H, s), 6.87 (1H, s), 3.83 (2H, s), 3.69 (2H, s), 2.38 (2H, q), 2.29 (2H, s), 2.27 (3H, s), 1.10 (3H, t).

Example 166

5-{5-[(4-Methylbenzylamino)methyl]thiophen-2-y}]-3-ethyl-6-methyl-1H-pyridin-2-one hydrochloride

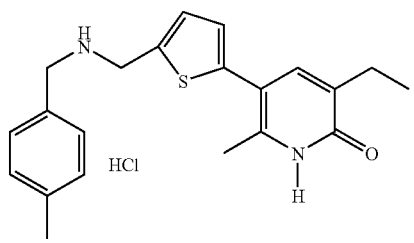

5-(5-Ethyl-2-methyl-6-oxo-1,6-dihydropyridin-3-yl]thiophen-2-carbaldehyde is reacted with 4-methylbenzylamine as described in Method A, Example 123 to give the title compound (72% yield) as a white solid. LC/MS: RT 2.30 min; m/e 353 (M+H); $^1$H NMR ($\delta$, ppm): 7.21-7.27 (3H, m), 7.10-7.15 (2H, m), 6.85-6.90 (2H, m), 3.81 (2H, s), 3.68 (2H, s), 2.38 (2H, q), 2.27 (6H, d), 1.09 (3H, t).

Example 167

5-{5-[(3-Methoxybenzylamino)methyl]thiophen-2-y}]-3-ethyl-6-methyl-1H-pyridin-2-one hydrochloride

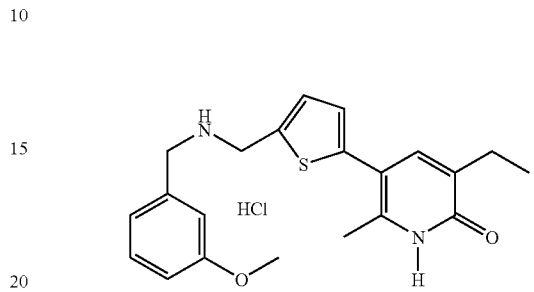

5-(5-Ethyl-2-methyl-6-oxo-1,6-dihydropyridin-3-yl]thiophen-2-carbaldehyde is reacted with 3-methoxybenzylamine as described in Method A, Example 123 to give the title compound (82% yield) as a white solid. LC/MS: RT 2.20 min; m/e 369 (M+H); $^1$H NMR ($\delta$, ppm): 7.19-7.27 (3H, m), 6.86-6.97 (3H, m), 6.77-6.80 (1H, d), 3.83 (2H, s), 3.75 (3H, s), 3.70 (2H, s), 2.38 (2H, q), 2.28 (3H, s), 1.10 (3H, t).

Example 168

5-{5-[(4-chlorobenzylamino)methyl]thiophen-2-y}]-3-ethyl-6-methyl-1H-pyridin-2-one hydrochloride

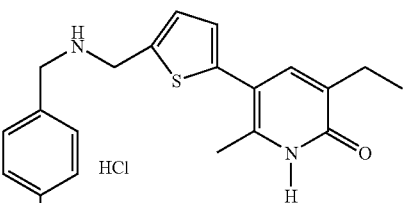

5-(5-Ethyl-2-methyl-6-oxo-1,6-dihydropyridin-3-yl]thiophen-2-carbaldehyde is reacted with 4-chlorobenzylamine as described in Method A, Example 123 to give the title compound (73% yield) as a white solid. LC/MS: RT 2.32 min; m/e 373 (M+H); $^1$H NMR ($\delta$, ppm): 7.37 (4H, s), 7.25 (1H, m), 6.89 (2H, t), 3.83 (2H, s), 3.73 (2H, s), 2.38 (2H, q), 2.27 (3H, s), 1.09 (3H, t).

Example 169

5-{5-[(4-Methoxybenzylamino)methyl]thiophen-2-yl}]-3-ethyl-6-methyl-1H-pyridin-2-one hydrochloride

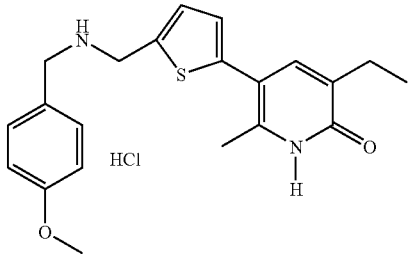

5-(5-Ethyl-2-methyl-6-oxo-1,6-dihydropyridin-3-yl]thiophen-2-carbaldehyde is reacted with 4-methyoxybenzylamine as described in Method A, Example 123 to give the title compound (93% yield) as a white solid. LC/MS: RT 2.23 min; m/e 369 (M+H); $^1$H NMR (δ, ppm): 7.25 (3H, m), 6.89 (4H, m), 3.81 (2H, s), 3.75 (3H, s), 3.66 (2H, s), 2.38 (2H, q), 2.26 (3H, s), 1.1 (3H, t).

Example 170

3-Ethyl-6-methyl-5-(5-{[(thiophen-2-ylmethyl)amino]methyl}-thiophen-2-yl)-1H-pyridin-2-one hydrochloride

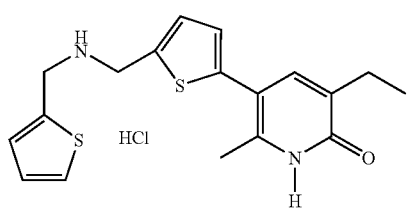

5-(5-Ethyl-2-methyl-6-oxo-1,6-dihydropyridin-3-yl]thiophen-2-carbaldehyde is reacted with (thiophen-2-yl)methylamine as described in Method A, Example 123 to give the title compound (76% yield) as a white solid. LC/MS: RT 2.15 min; m/e 345 (M+H); $^1$H NMR (δ, ppm): 7.37 (1H, d), 7.26 (1H, s), 6.96 (2H, s), 6.92 (1H, s), 6.88 (1H, s), 3.90 (2H, s), 3.86 (2H, s), 2.38 (2H, q), 2.26 (3H, s), 1.09 (3H, t).

Example 171

3-Ethyl-6-methyl-5-(5-pyrrolidin-1-ylmethylthiophen-2-yl)-1H-pyridin-2-one hydrochloride

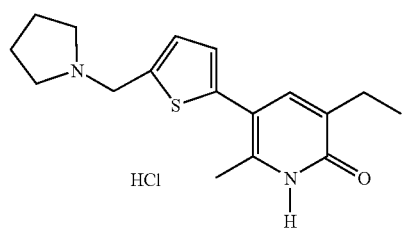

5-(5-Ethyl-2-methyl-6-oxo-1,6-dihydropyridin-3-yl]thiophen-2-carbaldehyde is reacted with pyrrolidine as described in Method A, Example 123 to give the title compound (100% yield) as a yellow solid. LC/MS: RT 1.93 min; m/e 303 (M+H); $^1$H NMR (δ, ppm): 11.67 (1H, br), 7.29 (1H, s), 6.90 (21H, d), 3.78 (2H, br), 2.45-2.62 (m, buried), 2.38 (2H, q), 2.27 (3H, s), 1.72 (4H, s), 1.1 (3H, t).

Example 172

5-{5-[(3,3-Difluoropyrrolidin-1-ylmethyl)(thiophen-2-yl)-3-ethyl-6-methyl-1H-pyridin-2-one hydrochloride

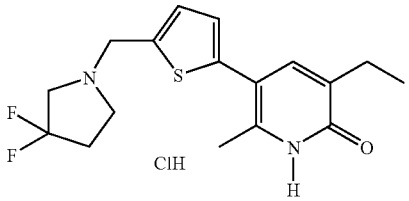

5-(5-Ethyl-2-methyl-6-oxo-1,6-dihydropyridin-3-yl]thiophen-2-carbaldehyde is reacted with 3,3-difluoropyrrolidine as described in Method A, Example 123 to give the title compound as a solid (64% yield). LC/MS: RT 2.28 min; m/e 339 (M+H); $^1$H NMR (δ, ppm): 12.8 (1H, br s), 7.4 (1H, s); 7.3 (1H, s); 7.05 (1H, s), 4.62 (2H, s); 3.9 (4H, m); 2.5 (2H, m), 2.4 (2H, q), 2.35 (3H, m), 1.1 (3H, t).

Example 173

5-{5-[(3-Fluoropyrrolidin-1-ylmethyl)(thiophen-2-yl)-3-ethyl-6-methyl-1H-pyridin-2-one hydrochloride

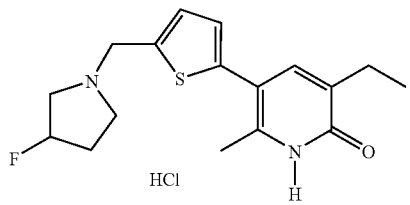

5-(5-Ethyl-2-methyl-6-oxo-1,6-dihydropyridin-3-yl]thiophen-2-carbaldehyde is reacted with 3-fluoropyrrolidine as described in Method A, Example 123 to give the title compound as a solid (65% yield). LC/MS: RT 1.89 min; m/e 321 (M+H); $^1$H NMR ($\delta$, ppm): 11.8 (1H, br s), 7.3 (1H, br s); 7.0 (1H, s); 5.4 (1H, d), 4.4 (2H, br s); 3.4 (4H, br s); 2.4 (2H, q), 2.2 (2H, br s), 2.35 (3H, m), 1.1 (3H, t).

Example 174

3-Ethyl-5-{5-[(3-methoxypyrrolidin-1-ylmethyl)(thiophen-2-yl)-6-methyl-1H-pyridin-2-one hydrochloride

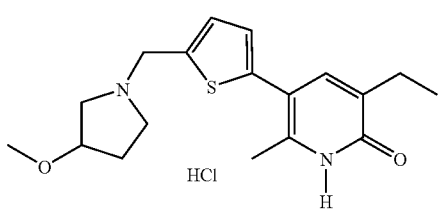

5-(5-Ethyl-2-methyl-6-oxo-1,6-dihydropyridin-3-yl]thiophen-2-carbaldehyde is reacted with 3-methoxypyrrolidine as described in Method A, Example 123 to give the title compound as a solid (68% yield). LC/MS: RT 1.93 min; m/e 333 (M+H); $^1$H NMR ($\delta$, ppm): 11.8 (1H, br s), 10.8 (1H, br s), 7.3 (1H, s); 7.2 (1H, s); 7.0 (1H, s), 4.2 (2H, br s); 4.0 (1H, s), 3.2 (3H, s); 3.05 (4H, m), 2.4 (2H, q), 2.35 (3H, s), 1.9 (2H, br s), 1.1 (2H, m), 1.05 (3H, t).

Example 175

5-(5-Aminomethylthiophen-2-yl)-3-ethyl-6-methyl-1H-pyridin-2-one hydrochloride

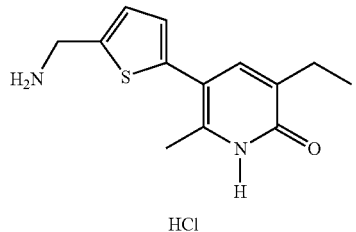

To a nitrogen flushed mixture of 3-ethyl-2-methoxy-6-methyl-5-(4,4,5,5-tetramethyl-[1,3,2-dioxaborolan-2-yl)pyridine (1.0 g, 3.6 mmol), cesium carbonate (3.52 g, 11 mmol), and (5-bromo-thiophen-2-ylmethyl)-carbamic acid tert-butyl ester (1.2 g, 4.0 mmol) in 1,2-dimethoxyethane (20 mL) and water (4 mL) is added palladium tetrakis(triphenylphosphine) (290 mg, 0.25 mmol) and the reaction mixture is heated to about 110° C. After maintaining the reaction mixture at 110° C. for 12 hr, the mixture is cooled, poured into ethyl acetate (50 mL) and washed with water and brine, dried over sodium sulfate, filtered and concentrated. The residue is chromatographed on SiO$_2$, eluting with heptane-30% ethyl acetate to afford 0.98 g of [5-(5-ethyl-6-methoxy-2-methyl-pyridin-3-yl)-thiophen-2-ylmethyl]-carbamic acid tert-butyl ester. A solution of this ester in MeOH is then treated with saturated HCl in EtOAc (50 mL) and heated to about 75° C. After 6 hr at 75° C., the mixture is concentrated, and triturated with acetonitrile/water to afford 2.8 g of 5-(5-aminomethylthiophen-2-yl)-3-ethyl-6-methyl-1H-pyridin-2-one hydrochloride as a white solid (78% yield). LC/MS: RT 1.77 min; m/e 249 (M+H).

Example 175A 5-(5-Aminomethyl-furan-2-yl)-3-ethyl-6-methyl-1H-pyridin-2-one

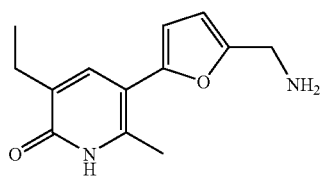

Example 175 is substantially repeated in this Example 175A except for utilizing 5-(5-Ethyl-2-methyl-6-oxo-1,6-dihydropyridin-3-yl]furan-2-carbaldehyde as the starting material to afford the title compound. MS: m/e=233 (M+H). $^1$H NMR (CDCl$_3$, $\delta$, ppm): 7.86 (s, 1H); 6.43 (d, 1H, J=3.2 Hz); 6.27 (d, 1H, J=3.2 Hz); 4.15 (s, 2H); 2.64 (q, 2H, J=7.3 Hz); 2.60 (s, 3H); 1.24 (t, 3H J=7.3 Hz).

Example 176

N-[5-(5-Ethyl-2-methyl-6-oxo-1,6-dihydropyridin-3-yl)thiophen-2-ylmethyl]-2-(pyrrolidin-1-yl)acetamide hydrochloride

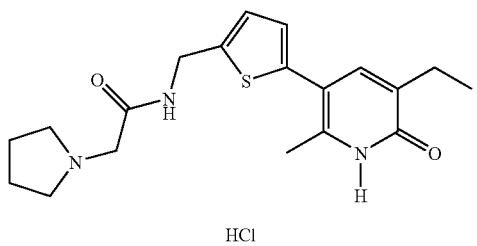

HCl

To a solution of 5-(5-aminomethylthiophen-2-yl)-3-ethyl-6-methyl-1H-pyridin-2-one (0.5 g, 2 mmol) and triethylamine (0.6 mL) in THF (5 mL) and dichloromethane (20 mL) is added chloroacetyl chloride (0.24 mL, 3 mmol) at 0° C. After 2 hr at rt, the mixture is quenched with aqueous NaHCO$_3$ solution, and extracted with EtOAc. The extracts are washed with water and brine, dried over sodium sulfate, filtered and concentrated. The residue is chromatographed on SiO$_2$, eluting with CH$_2$Cl$_2$-5% MeOH to afford 0.3 g of 2-chloro-N-[5-(5-ethyl-2-methyl-6-oxo-1,6-dihydro-pyridin-3-yl)-thiophen-2-ylmethyl]-acetamide. A mixture of so formed 2-chloro-N-[5-(5-ethyl-2-methyl-6-oxo-1,6-dihydro-pyridin-3-yl)-thiophen-2-ylmethyl]-acetamide (0.15 g, 0.46 mmol), and excess of pyrrolidine and potassium carbonate in acetonitrile (10 mL) is heated for 6 hr at 75° C., and extracted with EtOAc. The extracts are washed with water and brine, dried over sodium sulfate, filtered and concentrated. The residue is chromatographed on SiO$_2$, eluting with CH$_2$Cl$_2$-10% MeOH to afford the free base, which is dissolved in HCl-EtOAc and concentrated. Lyophilization in acetonitrile and water affords 60 mg (33%) of N-[5-(5-ethyl-2-methyl-6-oxo-1,6-dihydropyridin-3-yl)thiophen-2-ylmethyl]-2-(pyrrolidin-1-yl)acetamide hydrochloride as a solid. LC/MS: RT 1.93 min; m/e 360 (M+H); $^1$H NMR (DMSO-d$_6$, δ, ppm): 10.5 (1H, brs), 9.4 (1H, t), 7.2 (1H, s), 6.98 (1H, d), 6.95 (1H, d), 4.5 (2H, d), 4.1 (2H, d), 3.55 (2H, brs), 3.02 (2H, brs), 2.4 (2H, q), 2.25 (3H, s), 1.8-2.05 (4H, m), 1.22 (3H, t).

Example 177

2-Dimethylamino-N-[5-(5-ethyl-2-methyl-6-oxo-1,6-dihydropyridin-3-yl)thiophen-2-ylmethyl]acetamide hydrochloride

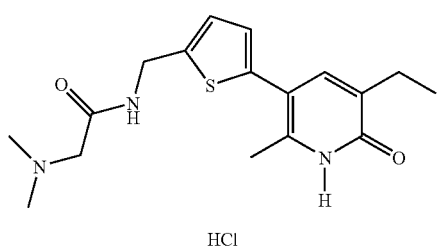

HCl

Example 176 is substantially repeated in this Example 177 except for utilizing 2M solution of dimethylamine in MeOH as one of the starting materials to afford the title compound (53% yield). LC/MS: RT 1.87 min; m/e 334 (M+H); $^1$H NMR (DMSO-d$_6$, δ, ppm): 10.2 (1H, brs), 9.4 (1H, t), 7.2 (1H, s), 6.98 (1H, d), 6.95 (1H, d), 4.5 (2H, d), 4.0 (2H, d), 2.8 (6H, s), 2.4 (2H, q), 2.25 (3H, s), 1.05 (3H, t).

Example 178

3-Ethyl-5-{5-[(2-fluoro-3-trifluoromethylbenzylamino)methyl](thiophen-2-yl)-6-methyl-1H-pyridin-2-one hydrochloride

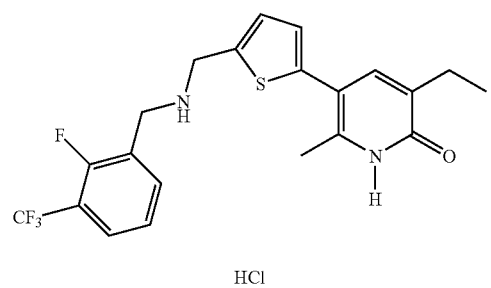

HCl 5-(5-Ethyl-2-methyl-6-oxo-1,6-dihydropyridin-3-yl]furan-2-carbaldehyde is reacted with 2-fluoro-3-trifluoromethylbenzylamine as described in Method A, Example 123 to give the title compound as a solid (50% yield). LC/MS: RT 1.43 min; m/e 425 (M+H); $^1$H NMR (δ, ppm): 11.7 (1H, br s), 9.8 (1H, br s), 8.0-6.8 (6H, m); 4.5 (1H, br s), 4.3 (1H, br s), 2.4 (2H, q), 2.25 (3H, s), 1.05 (3H, t).

Example 179

5-{5-[(Benzyl methylamino)methyl]furan-2-yl)-3-ethyl-6-methyl-1H-pyridin-2-one

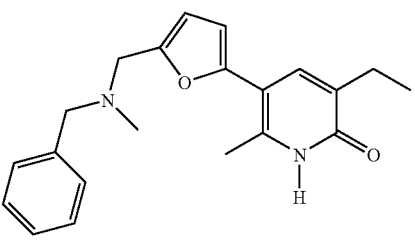

5-(5-Ethyl-2-methyl-6-oxo-1,6-dihydropyridin-3-yl]furan-2-carbaldehyde is reacted with benzyl methylamine as described in Method A, Example 123 to give the title compound as a solid (53% yield). LC/MS: RT 2.08 min; m/e 337 (M+H); $^1$H NMR (δ, ppm): 11.6 (1H, s), 7.46 (1H, s); 7.3 (5H, m); 6.4 (2H, dd), 3.6 (2H, s), 3.55 (2H, s), 2.4 (2H, m), 2.36 (2H, s), 2.2 (3H, s), 1.05 (3H, t).

Example 180

3-Ethyl-6-methyl-5-{5-[(morpholin-4-ylmethylfuran-2-yl)-1H-pyridin-2-one

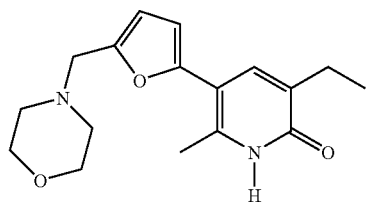

5-(5-Ethyl-2-methyl-6-oxo-1,6-dihydropyridin-3-yl]furan-2-carbaldehyde is reacted with morpholine as described in Method A, Example 123 to give the title compound as a solid (47% yield). LC/MS: RT 1.72 min; m/e 303 (M+H); $^1$H NMR (CHCl$_3$, δ, ppm): 12.9 (1H, br s), 7.6 (1H, s); 6.3 (2H, dd); 3.76 (4H, s), 3.62 (2H, s), 2.6 (9H, m), 1.24 (3H, t).

Example 181

3-Ethyl-6-methyl-5-{5-[(pyrolidin-1-ylmethylfuran-2-yl)-1H-pyridin-2-one

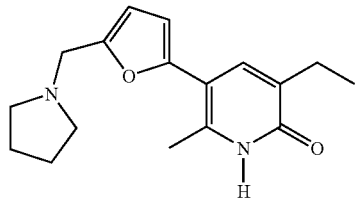

5-(5-Ethyl-2-methyl-6-oxo-1,6-dihydropyridin-3-yl]furan-2-carbaldehyde is reacted with pyrrolidine as described in Method A, Example 123 to give the title compound as a solid (62% yield). LC/MS: RT 1.82 min; m/e 287 (M+H); $^1$H NMR (δ, ppm): 11.4 (1H, br s), 7.6 (1H, s); 6.8 (1H, s); 6.52 (1H, s), 3.4 (2H, br s); 3.02 (2H, br s), 2.5 (2H, br s), 2.4 (5H, m), 1.93 (4H, m), 1.1 (3H, t).

Example 181A

3-Ethyl-6-methyl-5-{5-[(pyrolidin-1-ylmethylfuran-3-yl)-1H-pyridin-2-one

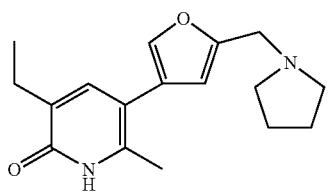

4-(5-Ethyl-2-methyl-6-oxo-1,6-dihydro-pyridin-3-yl)-furan-2-carbaldehyde is reacted with pyrrolidine as described in Method A, Example 123 to give the title compound. MS: m/e 287 (M+H); $^1$H NMR (δ, ppm): 7.50 (s, 1H); 7.45 (s, 1H); 6.73 (s, 1H); 4.32 (s, 2H); 3.76 (m, 2H); 3.00 (m, 2H); 2.60 (q, 2H, J=7.4 Hz); 2.44 (s, 3H); 2.14 (m, 4H); 1.11 (t, 3H, J=7.4 Hz).

Example 182

3-Ethyl-6-methyl-5-{5-[(3-fluoropyrolidin-1-ylmethylfuran-2-yl)-1H-pyridin-2-one hydrochloride

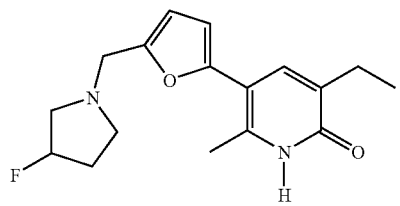

5-(5-Ethyl-2-methyl-6-oxo-1,6-dihydropyridin-3-yl]furan-2-carbaldehyde is reacted with 3-fluoropyrrolidine as described in Method A, Example 123 to give the title compound as a solid (75% yield). LC/MS: RT 1.85 min; m/e 305 (M+H); $^1$H NMR (δ, ppm): 7.4 (1H, s); 7.3 (2H, s), 6.9 (2H, m), 4.95 (1H, br s); 4.5 (2H, d), 4.0 (3H, s), 2.6 (2H, q), 2.56 (3H, s), 1.5 (2H, s), 1.22 (3H, t).

Example 182A

5-{5-[(Benzyl-pyridin-3-ylmethyl-amino)-methyl]-furan-2-yl}-3-ethyl-6-methyl-1H-pyridin-2-one

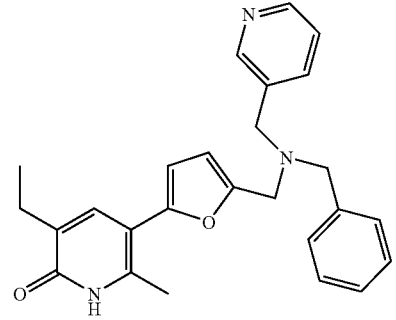

Example 182 is substantially repeated except for reacting the 5-(5-Ethyl-2-methyl-6-oxo-1,6-dihydropyridin-3-yl]furan-2-carbaldehyde with appropriate amine to afford the title compound. MS: m/e=414 (M+H).

Example 182B

N-[4-({[5-(5-Ethyl-2-methyl-6-oxo-1,6-dihydro-pyridin-3-yl)-furan-2-ylmethyl]-amino}-methyl)-phenyl]-acetamide

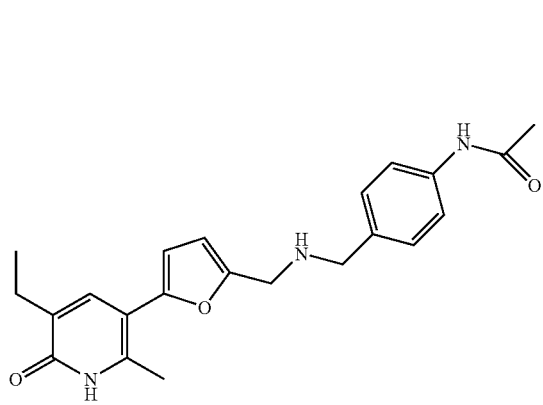

Example 182 is substantially repeated except for reacting the 5-(5-Ethyl-2-methyl-6-oxo-1,6-dihydropyridin-3-yl]furan-2-carbaldehyde with appropriate amine to afford the title compound. MS: m/e=380 (M+H).

Example 182C

2-Chloro-5-(2-{[5-(5-ethyl-2-methyl-6-oxo-1,6-di-hydro-pyridin-3-yl)-furan-2-ylmethyl]-amino}-ethyl)-benzenesulfonamide

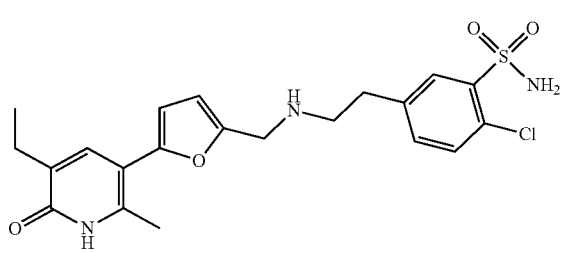

Example 182 is substantially repeated except for reacting the 5-(5-Ethyl-2-methyl-6-oxo-1,6-dihydropyridin-3-yl]furan-2-carbaldehyde with appropriate amine to afford the title compound. MS: m/e=450 (M+H).

Example 182D

3-Ethyl-6-methyl-5-(5-{[(1-methyl-1H-pyrazol-4-ylmethyl)-amino]-methyl}-furan-2-yl)-1H-pyridin-2-one

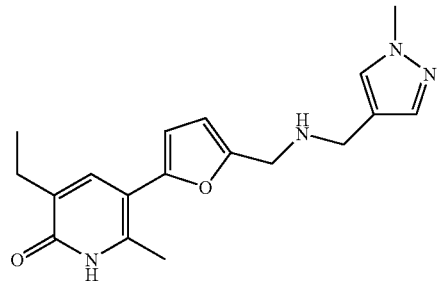

Example 182 is substantially repeated except for reacting the 5-(5-Ethyl-2-methyl-6-oxo-1,6-dihydropyridin-3-yl]furan-2-carbaldehyde with appropriate amine to afford the title compound. MS: m/e=327 (M+H).

Example 182E

3-Ethyl-6-methyl-5-{5-[(2-trifluoromethoxy-benzylamino)-methyl]-furan-2-yl}-1H-pyridin-2-one

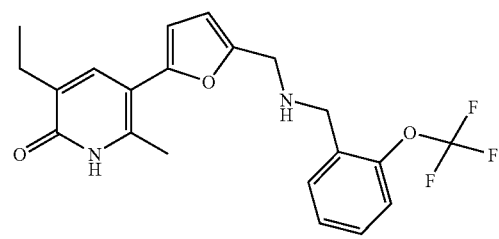

Example 182 is substantially repeated except for reacting the 5-(5-Ethyl-2-methyl-6-oxo-1,6-dihydropyridin-3-yl]furan-2-carbaldehyde with appropriate amine to afford the title compound. MS: m/e=407 (M+H).

Example 182F

3-Ethyl-6-methyl-5-(5-{[(pyridin-2-ylmethyl)-amino]-methyl}-furan-3-yl)-1H-pyridin-2-one

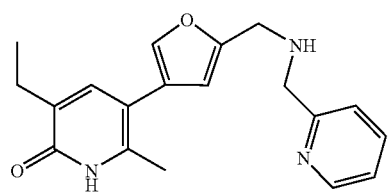

Example 182 is substantially repeated except for reacting the 5-(5-Ethyl-2-methyl-6-oxo-1,6-dihydropyridin-3-yl]furan-2-carbaldehyde with appropriate amine to afford the title compound. MS: m/e=324 (M+H).

Example 182G

5'-Ethyl-2'-methyl-6-pyrrolidin-1-ylmethyl-1'H-[2,3']bipyridinyl-6'-one

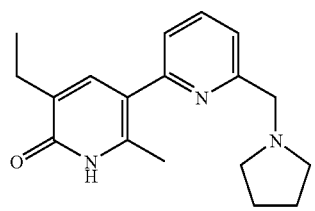

5'-Ethyl-2'-methyl-6'-oxo-1',6'-dihydro-[2,3']bipyridinyl-6-carbaldehyde prepared in accordance with PREPARATION 11 is reacted with pyrrolidine as described in Method A, Example 123 to give the title compound. MS: m/e=298 (M+H). $^1$H NMR (CDCl$_3$, δ ppm): 7.89 (t, 1H, J=7.8 Hz); 7.77 (s, 1H); 7.61 (d, 1H, J=7.8 Hz); 7.41 (d, 1H, J=7.8 Hz); 4.43 (s, 2H); 3.80 (m, 2H); 3.07 (m, 2H); 2.66 (q, 2H, J=7.4 Hz); 2.55 (s, 3H); 2.13 (m, 4H); 1.25 (t, 3H, J=7.4 Hz).

Example 182H

5'-Ethyl-2'-methyl-6-{[(pyridin-2-ylmethyl)-amino]-methyl}-1'H-[2,3']bipyridinyl-6'-one

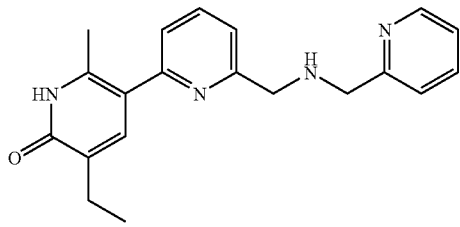

5'-Ethyl-2'-methyl-6'-oxo-1',6'-dihydro-[2,3']bipyridinyl-6-carbaldehyde prepared in accordance with PREPARATION 11 is reacted with pyridin-2-ylmethylamine as described in Method A, Example 123 to give the title compound. MS: m/e=335 (M+H).

Example 182I

5'-Ethyl-6-(4-hydroxy-piperidin-1-ylmethyl)-2'-methyl-1'H-[2,3']bipyridinyl-6'-one

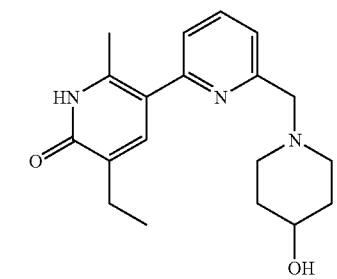

5'-Ethyl-2'-methyl-6'-oxo-1',6'-dihydro-[2,3']bipyridinyl-6-carbaldehyde prepared in accordance with PREPARATION 11 is reacted with 4-hydroxypiperidine as described in Method A, Example 123 to give the title compound. MS: m/e=328 (M+H).

Example 182J 6-(4-Acetyl-piperazin-1-ylmethyl)-5'-ethyl-2'-methyl-1'H-[2,3']bipyridinyl-6'-one

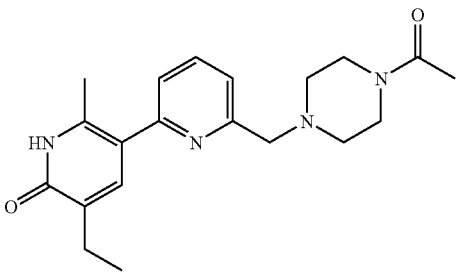

5'-Ethyl-2'-methyl-6'-oxo-1',6'-dihydro-[2,3']bipyridinyl-6-carbaldehyde prepared in accordance with PREPARATION 11 is reacted with 4-acetylpiperazine as described in Method A, Example 123 to give the title compound. MS: m/e=355 (M+H).

Example 182K

5'-Ethyl-2'-methyl-6-(4-pyrrolidin-1-yl-piperidin-1-ylmethyl)-1'H-[2,3']bipyridinyl-6'one

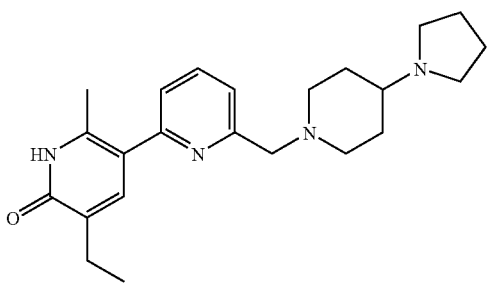

5'-Ethyl-2'-methyl-6'-oxo-1',6'-dihydro-[2,3']bipyridinyl-6-carbaldehyde prepared in accordance with PREPARATION 11 is reacted with 4-pyrrolidinyl-piperidine as described in Method A, Example 123 to give the title compound. MS: m/e=381 (M+H).

Example 183

5-[5-(4-Benzylpiperidin-1-ylmethyl)thiophen-2-yl]-3-ethyl-6-methyl-1H-pyridin-2-one hydrochloride

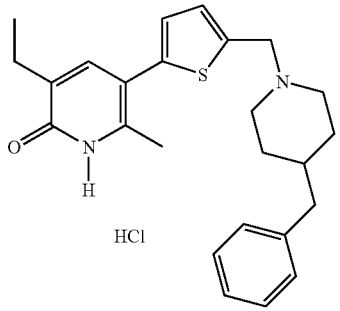

5-(5-Ethyl-2-methyl-6-oxo-1,6-dihydropyridin-3-yl)thiophene-2-carbaldehyde is reacted with 4-benzylpiperidine as described in Method A, Example 123 to give the title compound as a yellow solid (85% yield). LC/MS: RT 2.737 min; m/e 407 (M+H); $^1$H NMR (δ, ppm): 11.8 (1H, br), 10.0 (1H, br), 9.85 (1H, s), 8.0 (1H, s), 7.4-7.1 (8H, m), 4.2 (8H, s), 3.4 (4H, s), 3.2-2.8 (6H, m), 2.5 (8H, s), 2.4 (4H, s), 1.8-1.4 (10H, m), 1.2 (3H, s).

Example 184

3-Ethyl-6-methyl-5-[5-(4-phenylpiperidin-1-ylmethyl)thiophen-2-yl]-1H-pyridin-2-one hydrochloride

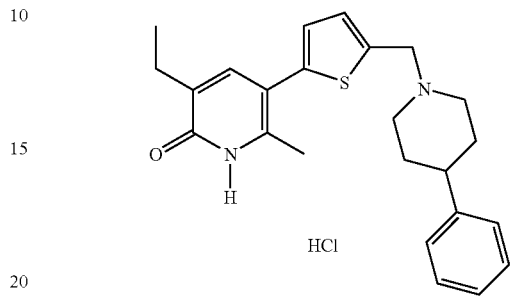

5-(5-Ethyl-2-methyl-6-oxo-1,6-dihydropyridin-3-yl)thiophene-2-carbaldehyde is reacted with 4-phenylpiperidine as described in Method A, Example 123 to give the title compound as a yellow solid (66% yield). LC/MS: RT 2.65 min; m/C 393 (M+H); $^1$H NMR (δ, ppm): 11.8 (1H, br), 10.2 (1H, br), 9.85 (1H, s), 8.0 (1H, s), 7.4-7.1 (8H, m), 4.2 (9H, s), 3.4-2.8 (10H, m), 2.5 (7H, s), 2.4 (5H, s), 1.8-1.4 (9H, m), 1.2 (3H, s).

Example 185

3-Ethyl-5-[5-(4-hydroxy-4-phenylpiperidin-1-ylmethyl)thiophen-2-yl]-6-methyl-1H-pyridin-2-one hydrochloride

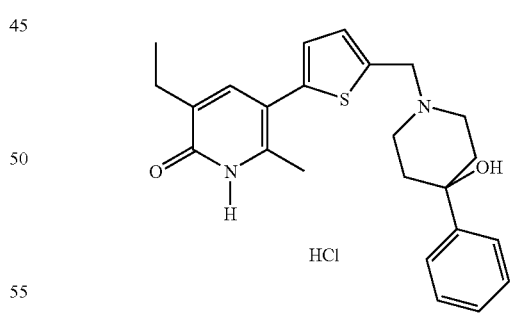

5-(5-Ethyl-2-methyl-6-oxo-1,6-dihydropyridin-3-yl)thiophene-2-carbaldehyde is reacted 4-phenylpiperidin-4-ol as described in Method A, Example 123 to give the title compound as a yellow solid (87% yield). $^1$H NMR (δ, ppm): 11.8 (1H, br), 10.4 (1H, br), 9.85 (1H, s), 8.0 (1H, s), 7.4-7.1 (8H, m), 4.2 (10H, s), 3.4-3.2 (2H, m), 2.5 (6H, s), 2.4 (6H, s), 1.8-1.4 (6H, m), 1.2 (3H, s).

Example 186

3-Ethyl-6-methyl-5-[(5-piperidin-1-yl)methylthiophen-2-yl]-1H-pyridin-2-one hydrochloride

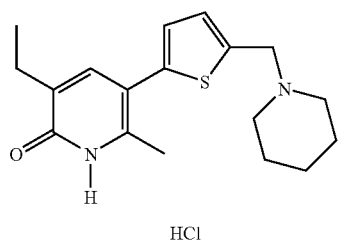

HCl 5-(5-Ethyl-2-methyl-6-oxo-1,6-dihydropyridin-3-yl)thiophene-2-carbaldehyde is reacted with piperidine as described in Method A, Example 123 to give the title compound as a yellow solid (18% yield). LC/MS: RT 2.26 min; m/e 317 (M+H); $^1$H NMR (δ, ppm): 11.8 (1H, br), 9.90 (1H, s), 8.0 (1H, s), 7.4-7.1 (2H, m), 4.2 (7H, s), 3.5-2.8 (2H, m), 2.5 (4H, s), 2.4 (5H, s), 1.8 (2H, S), 1.2 (3H, s).

Example 187

3-Ethyl-5-{5-[(2-methoxybenzylamino)methyl]thiophen-2-yl}-6-methyl-1H-pyridin-2-one hydrochloride

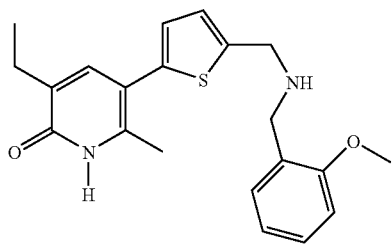

5-(5-Ethyl-2-methyl-6-oxo-1,6-dihydropyridin-3-yl)thiophene-2-carbaldehyde is reacted with 2-methoxybenzylamine as described in Method A, Example 123 to give the title compound as a yellow solid (42% yield). LC/MS: RT 2.27 min; m/e 369 (M+H); $^1$H NMR (CD$_3$OD, δ, ppm): 7.3-7.6 (4H, m), 7.0-7.15 (3H, m), 4.5 (2H, s), 4.32 (2H, s), 3.9 (3H, s), 2.59 (2H, q), 2.42 (3H, s), 1.2 (3H, t).

Example 188

5-{5-[(2-Chlorobenzylamino)methyl]thiophen-2-yl}-3-ethyl-6-methyl-1H-pyridin-2-one hydrochloride

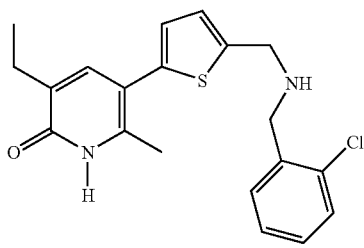

5-(5-Ethyl-2-methyl-6-oxo-1,6-dihydropyridin-3-yl)thiophene-2-carbaldehyde is reacted with 2-chlorobenzylamine as described in Method A, Example 123 to give the title compound as a yellow solid (98% yield). LC/MS: RT 2.22 min; m/e 373 (M+H); $^1$H NMR (CD$_3$OD, δ, ppm): 7.70 (2H, m), 7.0-7.58 (7H, m), 4.53 (2H, s), 4.28-4.47 (4H, d), 3.55 (1H, m), 2.62 (2H, q), 2.46 (3H, s), 4.46 (4H, d), 1.20 (3H, t).

Example 189

5-(5-Cyclopentylaminomethylthiophen-2-yl)-3-ethyl-6-methyl-1H-pyridin-2-one hydrochloride

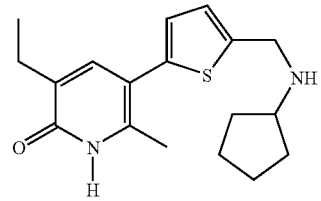

5-(5-Ethyl-2-methyl-6-oxo-1,6-dihydropyridin-3-yl)thiophene-2-carbaldehyde is reacted with cyclopentylamine as described Method A, Example 123 to give the title compound as a yellow solid (11% yield). LC/MS: RT 2.07 min; m/e 317 (M+H); $^1$H NMR (CD$_3$OD, δ, ppm): 7.4 (1H, s), 7.32 (1H, s), 7.13 (1H, s), 4.45 (2H, s), 3.64 (1H, m), 3.3 (2H, s), 2.53 (2H, q), 2.39 (3H, s), 2.20 (2H, s), 1.8-1.95 (6H, m), 1.3 (2H, s), 1.2 (3H, t), 0.9 (1H, m).

Example 190

5-(5-Cyclohexylaminomethylthiophen-2-yl)-3-ethyl-6-methyl-1H-pyridin-2-one hydrochloride

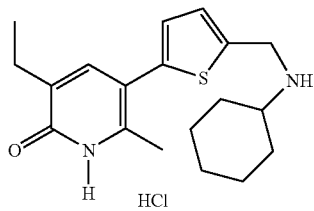

5-(5-Ethyl-2-methyl-6-oxo-1,6-dihydropyridin-3-yl)thiophene-2-carbaldehyde is reacted with cyclohexylamine as described Method A, Example 123 to give the title compound as a yellow solid (15% yield). LC/MS: RT 2.15 min; m/e 331 (M+H); $^1$H NMR (CD$_3$OD, δ, ppm): 7.4 (1H, s), 7.32 (1H, s), 7.12 (1H, s), 4.48 (2H, s), 3.36 (2H, s), 3.18 (1H, m), 2.5 (2H, q), 2.38 (3H, s), 2.2 (2H s), 1.90 (2H, s), 1.87 (1H, d), 1.02-1.5 (9H, m), 0.9 (1H, m).

Example 191

3-Ethyl-5-{5-[(S)-2-methoxymethylpyrrolidin-1-ylmethyl]thiophen-2-yl}-6-methyl-1H-pyridin-2-one hydrochloride

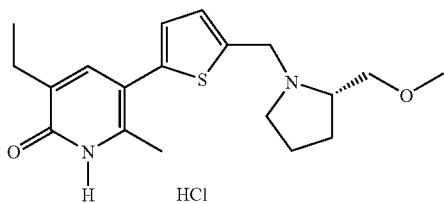

5-(5-Ethyl-2-methyl-6-oxo-1,6-dihydropyridin-3-yl)thiophene-2-carbaldehyde is reacted with (S)-2-methoxymethylpyrrolidine as described in Example 123 to give the title compound as a yellow solid (83% yield). LC/MS: RT 2.02 min; m/e 347 (M+H); $^1$H NMR (δ, ppm): 11.78 (1H, s), 10.62 (1H, s), 7.3 (1H, s), 7.23 (1H, s), 7.07 (1H, s), 4.6 (2H, dd), 3.3 (3H, s), 2.52 (5H, s), 2.4 (2H, d), 2.31 (3H, s), 1.6-2.2 (6H, m), 1.09 (3H, s).

Example 192

3-Ethyl-5-{5-[(2-fluoro-benzylamino)-methyl]-thiophen-2-yl}-6-methyl-1H-pyridin-2-one hydrochloride

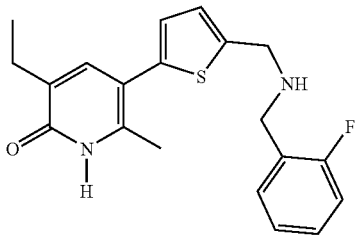

5-(5-Ethyl-2-methyl-6-oxo-1,6-dihydropyridin-3-yl)thiophene-2-carbaldehyde is reacted with 2-fluorobenzylamine as described in Method A, Example 123 to give the title compound as a yellow solid (60% yield). LC/MS: RT 2.17 min; m/e 357 (M+H); $^1$H NMR (CD$_3$OD, δ, ppm): 7.1-7.87 (5H, m), 4.62 (2H, d), 4.4 (1H, s), 2.68 (2H, m), 2.52 (2H, d), 1.13 (3H, t).

Example 193

3-Ethyl-5-[5-(3-fluoropiperidin-1-ylmethyl)thiophen-2-yl]-6-methyl-1H-pyridin-2-one hydrochloride

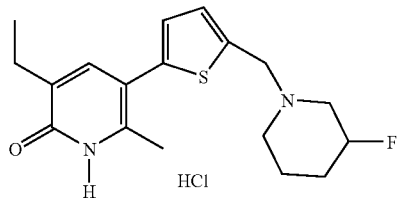

5-(5-Ethyl-2-methyl-6-oxo-1,6-dihydropyridin-3-yl)thiophene-2-carbaldehyde is reacted with 3-fluoropiperidine as described in Method A, Example 123 to give the title compound as a yellow solid (96% yield). LC/MS: RT 1.90 min; m/e 335 (M+H); $^1$H NMR (CD$_3$OD, δ, ppm): 7.4 (1H, s), 7.32 (1H, s), 7.12 (1H, s), 5.02-5.2 (1H, d), 4.6 (1H, s), 3.63 (2H, m), 3.45 (1H, m), 3.38 (4H, s), 3 (1H, m) 2.54 (2H, q), 2.41 (3H, s), 2.2 (2H s), 1.9 (2H, s), 1.1 (3H, t).

Example 194

3-Ethyl-5-[5-(3-methoxypiperidin-1-ylmethyl)thiophen-2-yl]-6-methyl-1H-pyridin-2-one hydrochloride

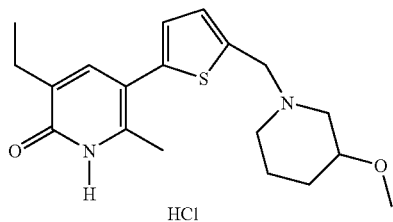

5-(5-Ethyl-2-methyl-6-oxo-1,6-dihydropyridin-3-yl)thiophene-2-carbaldehyde is reacted with 3-methoxypiperidine as described in Example 123 to give the title compound as a yellow solid (49% yield). LC/MS: RT 1.97 min; m/e 347 (M+H); $^1$H NMR (CD$_3$OD, δ, ppm): 7.79 (1H, s), 7.41 (1H, s), 7.20 (1H, s), 4.60 (2H, m), 3.35-3.80 (5H, m), 3.27 (8H, m), 2.10 (3H, m), 1.60-1.85 (2H, d), 1.02 (3H, t).

Example 195

3-Ethyl-6-methyl-5-(5-{[(pyridin-2-ylmethyl)amino]methyl}thiophen-2-yl)-1H-pyridin-2-one hydrochloride

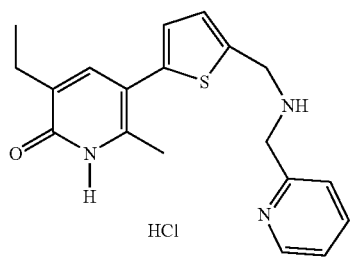

5-(5-Ethyl-2-methyl-6-oxo-1,6-dihydropyridin-3-yl)thiophene-2-carbaldehyde is reacted with (pyridin-2-yl)methylamine as described in Method A, Example 123 to give the title compound as a yellow solid (23% yield). LC/MS: RT 2.00 min; m/e 340 (M+H); $^1$H NMR (CD$_3$OD, δ, ppm): 8.76 (1H, s), 8.12 (1H, t), 7.71 (1H, d), 7.60 (1H, s), 7.39 (1H, d), 7.10 (1H, s), 4.62 (2H, s), 4.58 (2H, s), 3.30 (2H, s), 2.60 (2H, q), 2.43 (3H, s), 1.20 (3H, t).

Example 196

5-[5-(2-Benzylaminoethyl)(thiophen-2-yl)-3-ethyl-6-methyl-1H-pyridin-2-one hydrochloride

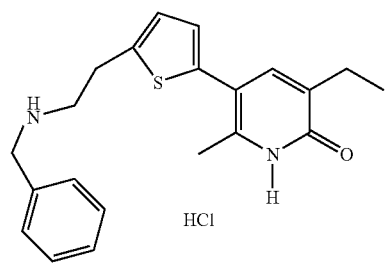

5-[5-(Ethyl-2-methyl-6-oxo-1,6-dihydropyridin-3-yl)thiophen-2-yl]acetaldehyde is reacted with benzylamine as described in Method A, Example 123 to give the title compound as a solid (13% yield). LC/MS: RT 2.22 min; m/e 353 (M+H); $^1$H NMR (δ, ppm): 11.8 (1H, br s), 7.3 (6H, m), 6.8 (2H, m); 4.84 (2H, s), 2.98 (4H, m), 2.4 (2H, q), 2.25 (3H, s), 1.1 (3H, t).

Example 197

3-Ethyl-6-methyl-5-[5-(2-pyrrolidin-1-ylethyl)thiophen-2-yl]-1H-pyridin-2-one hydrochloride

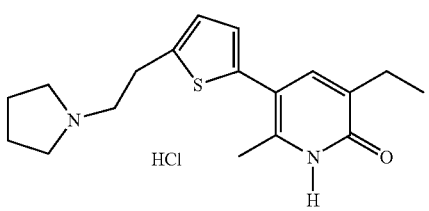

5-[5-(Ethyl-2-methyl-6-oxo-1,6-dihydropyridin-3-yl)thiophen-2-yl]acetaldehyde is reacted with pyrrolidine as described in Method A, Example 123 to give the title compound as a solid (52% yield). LC/MS: RT 2.03 min; m/e 317 (M+H); $^1$H NMR (δ, ppm): 11.6 (1H, br s), 7.2 (1H, s), 6.9 (2H, s); 3.3 (6H, m), 3.0 (2H, m), 2.4 (2H, q), 2.35 (3H, s), 1.9 (4H, m), 1.1 (3H, t).

Example 198

3-Ethyl-2-methyl-6-oxo-1,6-dihydropyridin-3-yl) thiophene-2-carbaldehyde O-(2-pyrrolidin-1-ylethyl) oxime hydrochloride

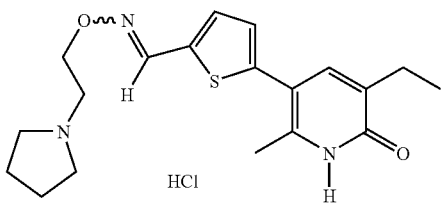

Glacial acetic acid is added to a solution of 5-(5-ethyl-2-methyl-6-oxo-1,6-dihydropyridin-3-yl]thiophene-2-carbaldehyde and 2-pyrrolidinylethoxyamine (2 molar equivalents) in methanol (12 mL/mmol), and the entire mixture is stirred at room temperature for 18 hr. The reaction mixture is concentrated and chromatographed on silica gel. The isolated compound is dissolved in a mixture of hydrogen chloride-glacial acetic acid and diluted with acetonitrile/water. Freeze drying of the product affords the title compound as a solid. LC/MS: RT 2.08 min; m/e 360 (M+H); $^1$H NMR (DMSO-$d_6$, δ, ppm): 11.8 (1H, s), 11.0 (1H, d), 7.6-7.1 (4H, m), 4.5 (1H, s), 4.4 (1H, s), 3.5 (4H, m), 3.0 (3H, m), 2.4 (2H, q), 2.3 (3H, s), 2.0 (4H, s), 1.1 (3H, s).

Example 199

3-Ethyl-2-methyl-6-oxo-1,6-dihydropyridin-3-yl) furan-2-carbaldehyde O-(2-pyrrolidin-1-ylethyl) oxime hydrochloride

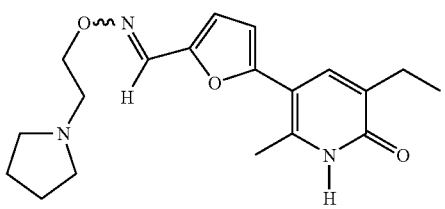

Example 198 is substantially repeated except for utilizing 5-(5-ethyl-2-methyl-6-oxo-1,6-dihydropyridin-3-yl]furan-2-carbaldehyde to afford the title compound. LC/MS: RT 2.07 min; m/e=344 (M+H); $^1$H NMR (δ, ppm): 11.8 (s, 1H); 10.8 (br s, 1H); 8.2-6.65 (m, 4H); 4.6-4.4 (m, 2H); 3.6-3.4 (m, 4H); 3.0 (br s, 2H); 2.45-2.37 (m, 5H); 2.2-1.75 (m, 4H); 1.10 (t, 3H).

Example 199A 5-(5-Ethyl-2-methyl-6-oxo-1,6-dihydro-pyridin-3-yl)-furan-2-carbaldehyde oxime

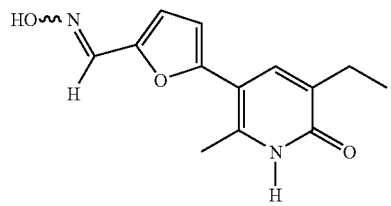

Example 198 is substantially repeated except for utilizing 5-(5-ethyl-2-methyl-6-oxo-1,6-dihydropyridin-3-yl]furan-2-carbaldehyde and hydroxylamine to afford the title compound. MS: m/e=247 (M+H).

Example 199B 5-(5-Ethyl-2-methyl-6-oxo-1,6-dihydro-pyridin-3-yl)-furan-2-carbaldehyde-O-benzyl-oxime

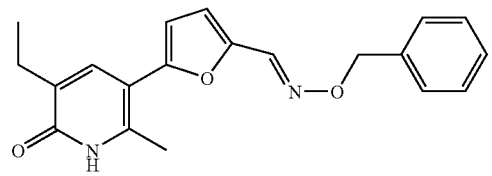

Example 198 is substantially repeated except for utilizing 5-(5-ethyl-2-methyl-6-oxo-1,6-dihydropyridin-3-yl]furan-2-carbaldehyde and benzyloxyamine to afford the title compound. MS: m/e=337 (M+H).

Example 200

5-(5-Ethyl-2-methyl-6-oxo-1,6-dihydropyridin-3-yl] thiophen-2-methanol

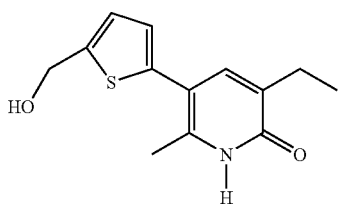

To a solution of 5-(5-ethyl-2-methyl-6-oxo-1,6-dihydropyridin-3-yl]thiophen-2-carbaldehyde in methanol (5 mL/mmol) is added one molar equivalent of sodium borohydride at room temperature and the reaction mixture is stirred for about 6 hrs. at room temperature. The reaction mixture is then concentrated, taken up in dichloromethane and washed with water. The organic phase is concentrated and purified by RP-HPLC to give the title compound (20% yield) as a yellow solid. LC/MS: RT 1.90 min; m/e 250 (M+H); $^1$H NMR (δ, ppm): 11.66 (1H, br d), 7.25 (1H, s), 6.90 (2H, m), 5.45 (1H, t), 4.50 (2H, d), 2.38 (2H, q), 2.27 (3H, s), 1.11 (3H, t).

Example 200A

3-Ethyl-5-(5-hydroxymethyl-furan-2-yl)-6-methyl-1H-pyridin-2-one

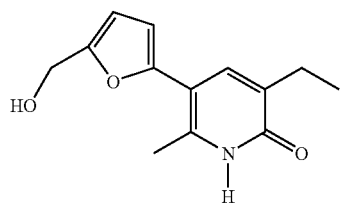

Example 200 is substantially repeated except for utilizing 5-(5-ethyl-2-methyl-6-oxo-1,6-dihydropyridin-3-yl]furan-2-carbaldehyde to afford the title compound. MS: m/e=234 (M+H).

Example 201

3-Ethyl-6-methyl-5-[5-(4-phenyl-piperazine-1-carbonyl)-furan-2-yl]-1H-pyridin-2-one

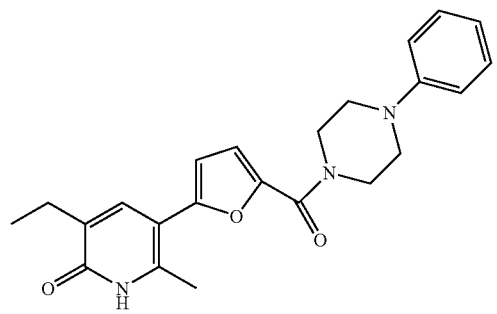

Two equivalents of potassium iodide and two equivalents of trimethylchlorosilane are added to a solution of one equivalent of [5-(5-ethyl-6-methoxy-2-methylpyridin-3-yl)-furan-2-yl]-(4-phenylpiperazin-1-yl)-methanone in anhydrous acetonitrile (3-5 ml/mmol) under argon, the latter being prepared in accordance with the procedure set out in PREPARATION 6, and the cloudy mixture is heated at 60-80° C. for 1-3 h. The mixture is then cooled to rt and diluted with water. The precipitated product is filtered off with suction, washed with water and dried in a vacuum oven at 40° C. The filtrate is extracted with ethyl acetate and, after concentration, occasionally affords further product, which is purified by chromatography on silica gel. MS: m/e=392 (M+H). $^1$H NMR (D$_6$-DMSO, δ ppm): 11.79 (s, 1H); 7.53 (s, 1H); 7.27 (m, 2H); 7.13 (d, 1H); 6.99 (m, 2H); 6.85 (m, 1H); 6.69 (d, 1H); 3.85 (br s, 4H); 3.23 (m, 4H); 2.50 (m, 5H); 1.12 (t, 3H).

Example 202

5-(5-Ethyl-2-methyl-6-oxo-1,6-dihydropyridin-3-yl)-furan-2-carboxylic acid cyclopropylamide

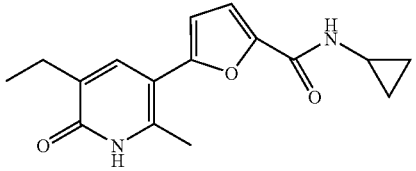

Example 201 is substantially repeated except for utilizing [5-(5-ethyl-6-methoxy-2-methylpyridin-3-yl)-furan-2-yl]-(cyclopropylamino)-methanone, the latter being prepared in accordance with the procedures of PREPARATION 6. MS: m/e=287 (M+H).

Example 203

5-(5-Ethyl-2-methyl-6-oxo-1,6-dihydro-pyridin-3-yl)-thiophene-2-carboxylic acid 3,5-difluoro-benzylamide

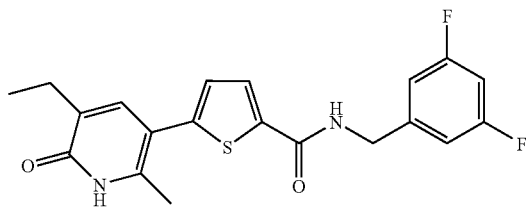

Example 201 is substantially repeated except for utilizing [5-(5-ethyl-6-methoxy-2-methylpyridin-3-yl)-thiophen-2-yl]-(3,5-difluoro-benzylamino)-methanone, the latter being prepared in accordance with the procedures of PREPARATION 6. MS: m/e=389 (M+H). $^1$H NMR (D$_6$-DMSO, δ ppm): 11.76 (s, 1H); 9.10 (t, 1H); 7.78 (d, 1H); 7.34 (s, 1H); 7.13 (m, 4H); 4.48 (d, 2H); 2.50 (m, 5H); 1.10 (t, 3H).

Example 204

5-(5-Ethyl-2-methyl-6-oxo-1,6-dihydro-pyridin-3-yl)-thiophene-2-carboxylic acid (pyridin-2-ylmethyl)-amide

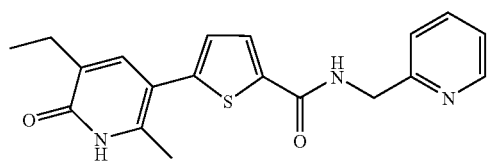

Example 201 is substantially repeated except for utilizing [5-(5-ethyl-6-methoxy-2-methylpyridin-3-yl)-thiophen-2-yl]-(pyridin-2-ylmethylamino)-methanone, the latter being prepared in accordance with the procedures of PREPARATION 6. MS: m/e=354 (M+H).

Example 205

5'-Ethyl-2'-methyl-6'-oxo-1',6'-dihydro-[2,3']bipyridinyl-6-carboxylic acid [2-(4-nitro-phenyl)-ethyl]-amide

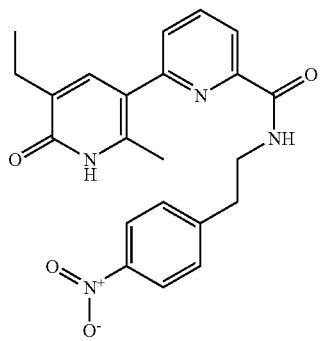

The title compound and the subsequent examples through Example 265K are prepared in accordance with either one of the procedures set forth below starting from the corresponding carboxylic acid, which is prepared in accordance with the procedures of PREPARATION 9.

Method 1: Four equivalents of triethylamine, 1.2 eq. of TFFH and 1.3 eq. of 2-(4-nitrophenyl)ethylamine are added to 5'-ethyl-2'-methyl-6'-oxo-1',6'-dihydro-[2,3']bipyridinyl-6-carboxylic acid in dichloromethane (approx. 15 mL/mmol), the latter being prepared in accordance with the procedures of PREPARATION 9. The mixture is stirred at rt for 16 hrs and water is added. The organic phase is concentrated and acetonitrile is added. Precipitated product is filtered off with suction. If the product remains in solution, it is purified by RP-HPLC or on silica gel. In the RP-HPLC purification, the title compound is isolated as trifluoroacetate salt. MS: m/e=407 (M+H).

Method 2: Four equivalents of N-methylmorpholine, 0.1 eq. of DMAP, 1.2 eq. of the amine and 2 eq. of PPA (50% solution in DMF) are added to the acid prepared in accordance with PREPARATION 9 (typically approx. 0.2 mmol) in dichloromethane (approx. 3 ml). The mixture is stirred at rt for 16 hrs and saturated NaHCO₃ solution is added. The organic phase is concentrated and purified by RP-HPLC.

Example 206

5'-Ethyl-2'-methyl-6'-oxo-1',6'-dihydro-[2,3']bipyridinyl-6-carboxylic acid butylamide

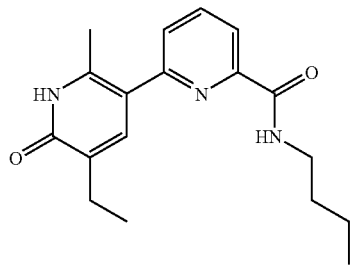

Method 1, Example 205 is substantially repeated except for utilizing 5'-ethyl-2'-methyl-6'-oxo-1',6'-dihydro-[2,3']bipyridinyl-6-carboxylic acid and n-butyl amine to afford the title compound. MS: m/e=314 (M+H).

Example 207

5'-Ethyl-2'-methyl-6-(pyrrolidine-1-carbonyl)-1'H-[2,3']bipyridinyl-6'-one

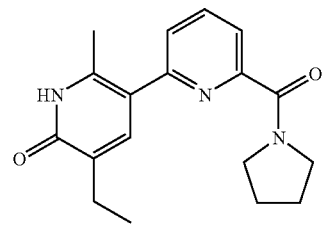

Method 1, Example 205 is substantially repeated except for utilizing 5'-ethyl-2'-methyl-6'-oxo-1',6'-dihydro-[2,3']bipyridinyl-6-carboxylic acid and pyrrolidine to afford the title compound. MS: m/e=312 (M+H).

Example 208

5'-Ethyl-2'-methyl-6'-oxo-1',6'-dihydro-[2,3']bipyridinyl-5-carboxylic acid (pyridin-2-ylmethyl)-amide

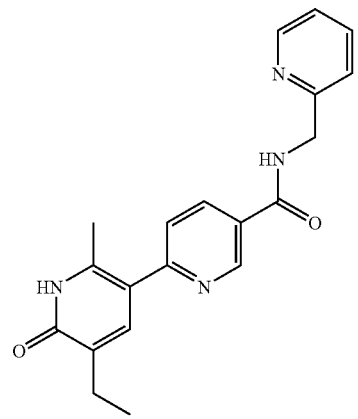

Method 1, Example 205 is substantially repeated except for utilizing 5'-ethyl-2'-methyl-6'-oxo-1',6'-dihydro-[2,3']bipyridinyl-5-carboxylic acid and (pyridin-2-ylmethyl)-amine to afford the title compound. MS: m/e=349 (M+H). ¹H NMR (δ ppm): 11.71 (s, 1H); 9.28 (t, 1H, J=5.8 Hz); 9.07 (s, 1H); 858 (s, 1H); 8.47 (dd, 1H, J=4.6 and 1.5 Hz); 8.24 (dd, 1H, J=8.3 and 2.5 Hz); 7.75 (m, 1H); 7.63 (d, 1H, J=8.3 Hz); 7.54 (s, 1H); 7.37 (dd, 1H, J=7.7 and 4.6 Hz); 4.53 (d, 2H, J=5.8 Hz); 2.42 (q, 2H, J=7.4 Hz); 2.35 (s, 3H); 1.11 (t, 3H, J=7.4 Hz).

Example 209

5'-Ethyl-2'-methyl-6'-oxo-1',6'-dihydro-[2,3']bipyridinyl-5-carboxylic acid butylamide

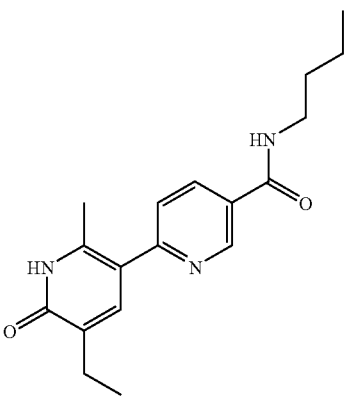

Method 1, Example 205 is substantially repeated except for utilizing 5'-ethyl-2'-methyl-6'-oxo-1',6'-dihydro-[2,3']bipyridinyl-5-carboxylic acid and n-butyl amine to afford the title compound. MS: m/e=314 (M+H).

Example 210

5'-Ethyl-5-(3-hydroxy-pyrrolidine-1-carbonyl)-2'-methyl-1'H-[2,3']bipyridinyl-6'-one

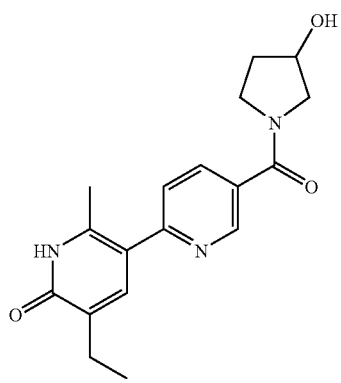

Method 1, Example 205 is substantially repeated except for utilizing 5'-ethyl-2'-methyl-6'-oxo-1',6'-dihydro-[2,3']bipyridinyl-5-carboxylic acid and 3-hydroxy-pyrrolidine to afford the title compound. MS: m/e=328 (M+H).

Example 211

5'-Ethyl-2'-methyl-5-(pyrrolidine-1-carbonyl)-1'H-[2,3']bipyridinyl-6'-one

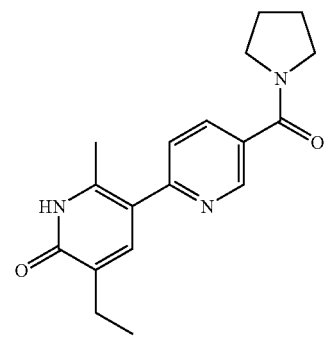

Method 1, Example 205 is substantially repeated except for utilizing 5'-ethyl-2'-methyl-6'-oxo-1',6'-dihydro-[2,3']bipyridinyl-5-carboxylic acid and pyrrolidine to afford the title compound. MS: m/e=312 (M+H).

Example 212

5'-Ethyl-2'-methyl-6'-oxo-1',6'-dihydro-[2,3']bipyridinyl-5-carboxylic acid cyclopentylamide

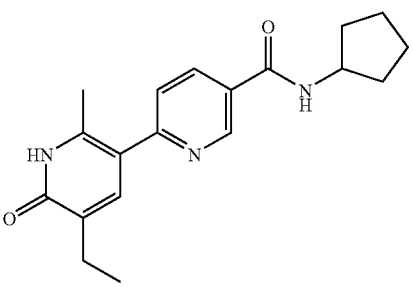

Method 1, Example 205 is substantially repeated except for utilizing 5'-ethyl-2'-methyl-6'-oxo-1',6'-dihydro-[2,3']bipyridinyl-5-carboxylic acid and cyclopentyl amine to afford the title compound. MS: m/e=326 (M+H).

Example 213

5'-Ethyl-2'-methyl-6'-oxo-1',6'-dihydro-[2,3']bipyridinyl-4-carboxylic acid [2-(4-nitro-phenyl)-ethyl]-amide

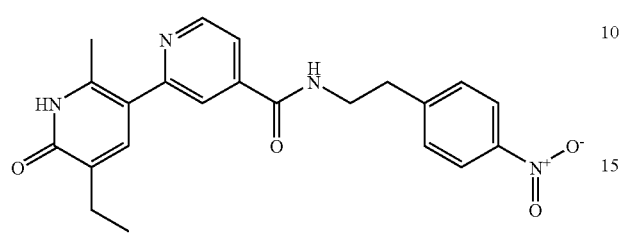

Method 1, Example 205 is substantially repeated except for utilizing 5'-ethyl-2'-methyl-6'-oxo-1',6'-dihydro-[2,3']bipyridinyl-4-carboxylic acid and 2-(4-nitro-phenyl)-ethyl-amine to afford the title compound. MS: m/e=407 (M+H).

Example 214

5'-Ethyl-2'-methyl-4-(pyrrolidine-1-carbonyl)-1'H-[2,3']bipyridinyl-6'-one

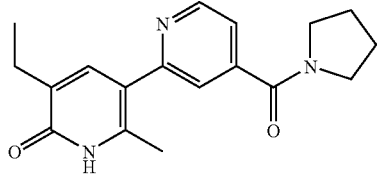

Method 1, Example 205 is substantially repeated except for utilizing 5'-ethyl-2'-methyl-6'-oxo-1',6'-dihydro-[2,3']bipyridinyl-4-carboxylic acid and pyrrolidine to afford the title compound. MS: m/e=312 (M+H).

Example 215

5'-Ethyl-2'-methyl-6'-oxo-1',6'-dihydro-[2,3']bipyridinyl-4-carboxylic acid butylamide

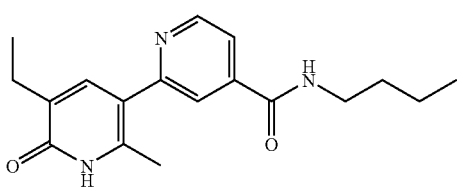

Method 1, Example 205 is substantially repeated except for utilizing 5'-ethyl-2'-methyl-6'-oxo-1',6'-dihydro-[2,3']bipyridinyl-4-carboxylic acid and n-butyl amine to afford the title compound. MS: m/e=314 (M+H).

Example 216

5'-Ethyl-2'-methyl-6'-oxo-1',6'-dihydro-[2,3']bipyridinyl-4-carboxylic acid cyclopentylamide

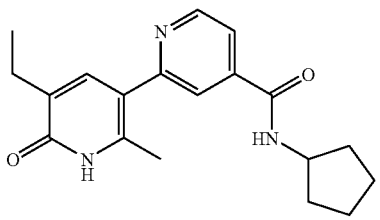

Method 1, Example 205 is substantially repeated except for utilizing 5'-ethyl-2'-methyl-6'-oxo-1',6'-dihydro-[2,3']bipyridinyl-4-carboxylic acid and cyclopentyl amine to afford the title compound. MS: m/e=326 (M+H).

Example 217

5'-Ethyl-2'-methyl-6'-oxo-1',6'-dihydro-[2,3']bipyridinyl-4-carboxylic acid (2-morpholin-4-yl-ethyl)-amide

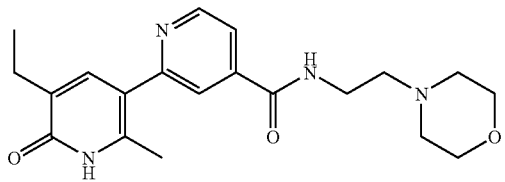

Method 1, Example 205 is substantially repeated except for utilizing 5'-ethyl-2'-methyl-6'-oxo-1',6'-dihydro-[2,3']bipyridinyl-4-carboxylic acid and 2-(morpholin-4-yl-ethyl)-amine to afford the title compound. MS: m/e=371 (M+H).

Example 218

5'-Ethyl-2'-methyl-6'-oxo-1',6'-dihydro-[2,3']bipyridinyl-4-carboxylic acid (2-pyridin-4-yl-ethyl)-amide

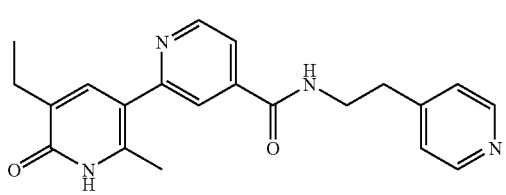

Method 1, Example 205 is substantially repeated except for utilizing 5'-ethyl-2'-methyl-6'-oxo-1',6'-dihydro-[2,3']bipyridinyl-4-carboxylic acid and 2-(pyridin-4-yl-ethyl)-amine to afford the title compound. MS: m/e=363 (M+H).

Example 219

5'-Ethyl-2'-methyl-6'-oxo-1',6'-dihydro-[3,3']bipyridinyl-5-carboxylic acid cyclopentylamide

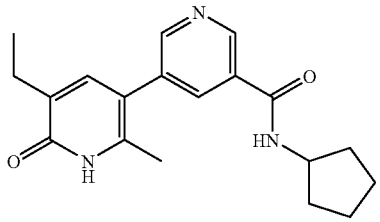

Method 1, Example 205 is substantially repeated except for utilizing 5'-ethyl-2'-methyl-6'-oxo-1',6'-dihydro-[3,3']bipyridinyl-5-carboxylic acid and cyclopentyl amine to afford the title compound. MS: m/e=326 (M+H).

Example 220

5'-Ethyl-2'-methyl-6'-oxo-1',6'-dihydro-[3,3']bipyridinyl-5-carboxylic acid benzylamide

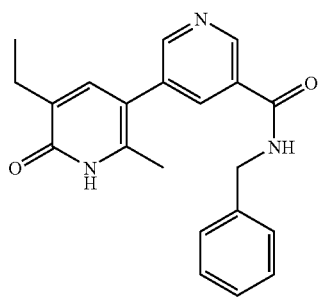

Method 1, Example 205 is substantially repeated except for utilizing 5'-ethyl-2'-methyl-6'-oxo-1',6'-dihydro-[3,3']bipyridinyl-5-carboxylic acid and benzyl amine to afford the title compound. MS: m/e=348 (M+H).

Example 221

5'-Ethyl-2'-methyl-6'-oxo-1',6'-dihydro-[3,3']bipyridinyl-5-carboxylic acid (pyridin-2-ylmethyl)-amide

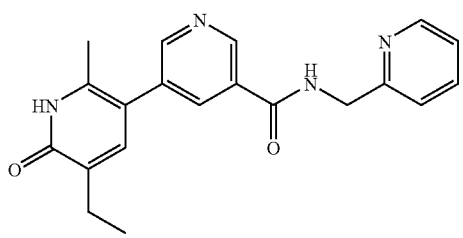

Method 1, Example 205 is substantially repeated except for utilizing 5'-ethyl-2'-methyl-6'-oxo-1',6'-dihydro-[3,3']bipyridinyl-5-carboxylic acid and pyridin-2-ylmethyl amine to afford the title compound. MS: m/e=349 (M+H).

Example 222

5'-Ethyl-2'-methyl-6'-oxo-1',6'-dihydro-[3,3']bipyridinyl-5-carboxylic acid (pyridin-3-ylmethyl)-amide

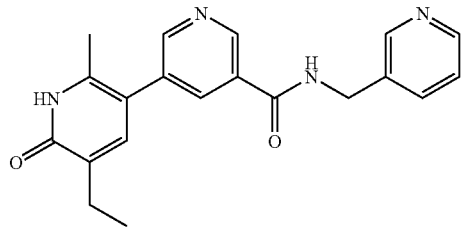

Method 1, Example 205 is substantially repeated except for utilizing 5'-ethyl-2'-methyl-6'-oxo-1',6'-dihydro-[3,3']bipyridinyl-5-carboxylic acid and pyridin-3-ylmethyl amine to afford the title compound. MS: m/e=349 (M+H).

Example 223

5'-Ethyl-2'-methyl-6'-oxo-1',6'-dihydro-[3,3']bipyridinyl-5-carboxylic acid butylamide

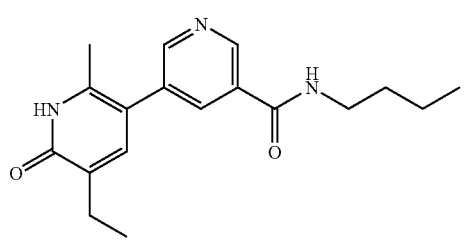

Method 1, Example 205 is substantially repeated except for utilizing 5'-ethyl-2'-methyl-6'-oxo-1',6'-dihydro-[3,3']bipyridinyl-5-carboxylic acid and n-butyl amine to afford the title compound. MS: m/e=314 (M+H).

Example 224

5'-Ethyl-2'-methyl-6'-oxo-1',6'-dihydro-[3,3']bipyridinyl-5-carboxylic acid [1-(6-methyl-pyridin-3-yl)-propyl]-amide

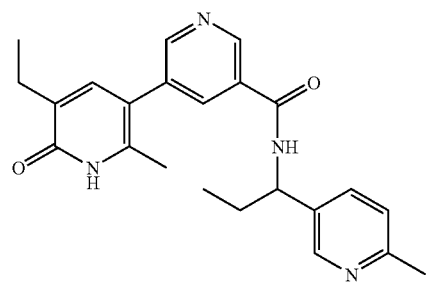

Method 1, Example 205 is substantially repeated except for utilizing 5'-ethyl-2'-methyl-6'-oxo-1',6'-dihydro-[3,3']bipyridinyl-5-carboxylic acid and 1-(6-methyl-pyridin-3-yl)-propyl amine to afford the title compound. MS: m/e=391 (M+H).

Example 225

5'-Ethyl-2'-methyl-6'-oxo-1',6'-dihydro-[3,3']bipyridinyl-5-carboxylic acid carbamoylmethyl-amide

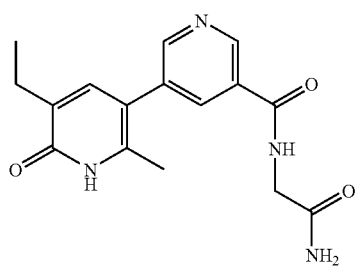

Method 1, Example 205 is substantially repeated except for utilizing 5'-ethyl-2'-methyl-6'-oxo-1',6'-dihydro-[3,3']bipyridinyl-5-carboxylic acid and α-aminoacetamide to afford the title compound. MS: m/e=315 (M+H).

Example 226

5-Ethyl-2-methyl-5'-(pyrrolidine-1-carbonyl)-1H-[3,3']bipyridinyl-6-one

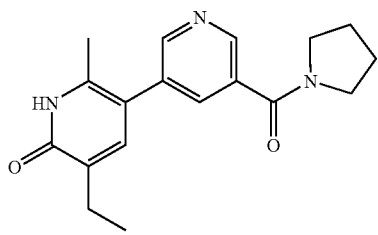

Method 1, Example 205 is substantially repeated except for utilizing 5'-ethyl-2'-methyl-6'-oxo-1',6'-dihydro-[3,3']bipyridinyl-5-carboxylic acid and pyrrolidine to afford the title compound. MS: m/e=312 (M+H).

Example 227

5'-Ethyl-2'-methyl-6'-oxo-1',6'-dihydro-[3,3']bipyridinyl-5-carboxylic acid diethylamide

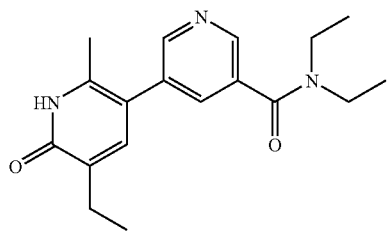

Method 1, Example 205 is substantially repeated except for utilizing 5'-ethyl-2'-methyl-6'-oxo-1',6'-dihydro-[3,3']bipyridinyl-5-carboxylic acid and diethyl amine to afford the title compound. MS: m/e=314 (M+H).

Example 228

5'-Ethyl-2'-methyl-6'-oxo-1',6'-dihydro-[3,3']bipyridinyl-5-carboxylic acid (cyclopropyl-pyridin-3-yl-methyl)-amide

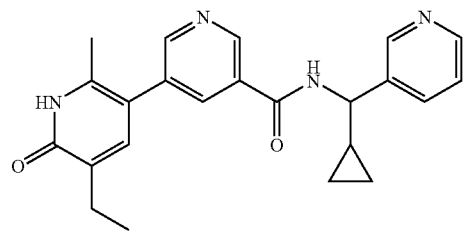

Method 1, Example 205 is substantially repeated except for utilizing 5'-ethyl-2'-methyl-6'-oxo-1',6'-dihydro-[3,3']bipyridinyl-5-carboxylic acid and (cyclopropyl-pyridin-3-yl-methyl)-amine to afford the title compound. MS: m/e=389 (M+H).

Example 229

5'-Ethyl-2'-methyl-6'-oxo-1',6'-dihydro-[3,3']bipyridinyl-5-carboxylic acid (2-hydroxy-propyl)-amide

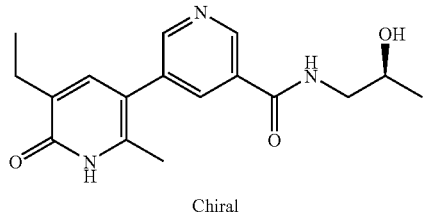

Chiral

Method 1, Example 205 is substantially repeated except for utilizing 5'-ethyl-2'-methyl-6'-oxo-1',6'-dihydro-[3,3']bipyridinyl-5-carboxylic acid and 2-hydroxy-propylamine to afford the title compound. MS: m/e=316 (M+H).

Example 230

5'-Ethyl-2'-methyl-6'-oxo-1',6'-dihydro-[3,3']bipyridinyl-5-carboxylic acid [2-(4-nitro-phenyl)ethyl]-amide

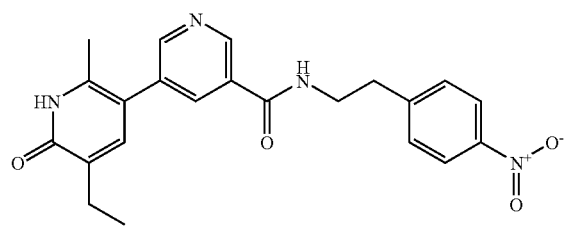

Method 1, Example 205 is substantially repeated except for utilizing 5'-ethyl-2'-methyl-6'-oxo-1',6'-dihydro-[3,3']bipyridinyl-5-carboxylic acid and 2-(4-nitro-phenyl)-ethyl-amine to afford the title compound. MS: m/e=407 (M+H). $^1$H NMR (δ ppm): 11.72 (s, 1H); 8.87 (d, 1H, J=2.1 Hz); 8.78 (t, 1H, J=5.4 Hz); 8.68 (d, 1H, 2.1 Hz); 8.17 (d, 2H, J=8.6 Hz); 8.05 (t, 1H, J=2.1 Hz); 7.55 (d, 2H, J=8.6 Hz); 7.27 (s, 1H); 3.58 (m, 2H); 3.02 (t, 2H, J=7.1 Hz); 2.43 (q, 2H, J=7.4 Hz); 2.17 (s, 3H); 1.11 (t, 3H, J=7.4 Hz).

Example 231

1-(5'-Ethyl-2'-methyl-6'-oxo-1',6'-dihydro-[3,3']bipyridinyl-5-carbonyl)-4-hydroxy-pyrrolidine-2-carboxylic acid methyl ester

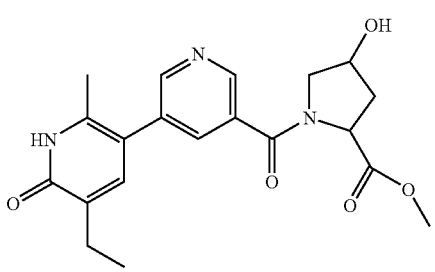

Method 1, Example 205 is substantially repeated except for utilizing 5'-ethyl-2'-methyl-6'-oxo-1',6'-dihydro-[3,3']bipyridinyl-5-carboxylic acid and 4-hydroxy-pyrrolidine-2-carboxylic acid methyl ester to afford the title compound. MS: m/e=386 (M+H).

Example 232

5'-Ethyl-2'-methyl-6'-oxo-1',6'-dihydro-[3,3']bipyridinyl-5-carboxylic acid [2-(2-hydroxy-phenyl)-ethyl]-amide

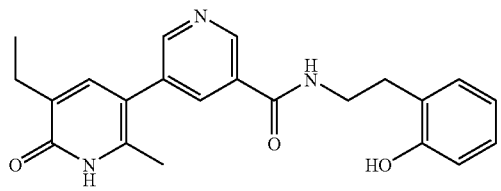

Method 1, Example 205 is substantially repeated except for utilizing 5'-ethyl-2'-methyl-6'-oxo-1',6'-dihydro-[3,3']bipyridinyl-5-carboxylic acid and 2-(2-hydroxy-phenyl)-ethyl-amine to afford the title compound. MS: m/e=378 (M+H).

Example 233

5'-Ethyl-2'-methyl-6'-oxo-1',6'-dihydro-[3,3']bipyridinyl-5-carboxylic acid carbamoylmethyl-methyl-amide

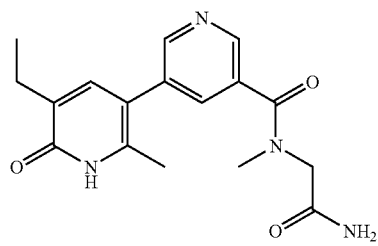

Method 1, Example 205 is substantially repeated except for utilizing 5'-ethyl-2'-methyl-6'-oxo-1',6'-dihydro-[3,3']bipyridinyl-5-carboxylic acid and 2-methylamino-acetamide to afford the title compound. MS: m/e=329 (M+H).

Example 234

5-Ethyl-2-methyl-5'-(4-oxo-piperidine-1-carbonyl)-1H-[3,3']bipyridinyl-6-one

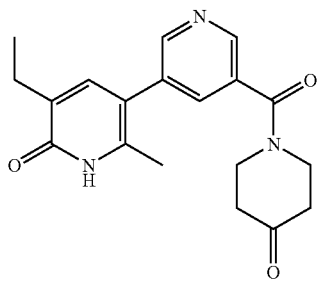

Method 1, Example 205 is substantially repeated except for utilizing 5'-ethyl-2'-methyl-6'-oxo-1',6'-dihydro-[3,3']bipyridinyl-5-carboxylic acid and 4-oxo-piperidine to afford the title compound. MS: m/e=340 (M+H).

Example 235

5'-Ethyl-2'-methyl-6'-oxo-1',6'-dihydro-[3,3']bipyridinyl-5-carboxylic acid ethyl-pyridin-4-ylmethyl-amide

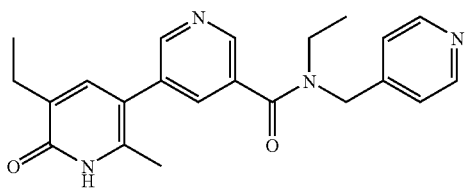

Method 1, Example 205 is substantially repeated except for utilizing 5'-ethyl-2'-methyl-6'-oxo-1',6'-dihydro-[3,3']bipyridinyl-5-carboxylic acid and ethyl-pyridin-4-ylmethyl-amine to afford the title compound. MS: m/e=377 (M+H).

Example 236

5'-Ethyl-2'-methyl-6'-oxo-1',6'-dihydro-[3,3']bipyridinyl-5-carboxylic acid phenethyl-amide

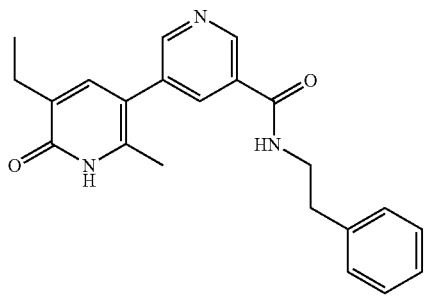

Method 1, Example 205 is substantially repeated except for utilizing 5'-ethyl-2'-methyl-6'-oxo-1',6'-dihydro-[3,3']bipyridinyl-5-carboxylic acid and phenethyl-amine to afford the title compound. MS: m/e=362 (M+H).

Example 237

5'-Ethyl-2'-methyl-6'-oxo-1',6'-dihydro-[3,3']bipyridinyl-5-carboxylic acid [2-(4-sulfamoyl-phenyl)-ethyl]-amide

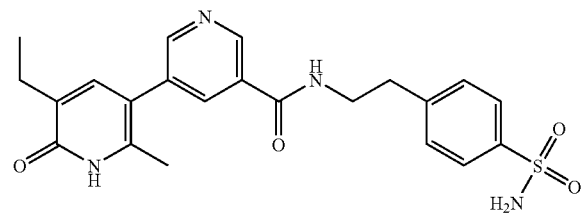

Method 1, Example 205 is substantially repeated except for utilizing 5'-ethyl-2'-methyl-6'-oxo-1',6'-dihydro-[3,3']bipyridinyl-5-carboxylic acid and 2-(4-sulfamoyl-phenyl)-ethylamine to afford the title compound. MS: m/e=441 (M+H).

Example 238

5'-Ethyl-2'-methyl-6'-oxo-1',6'-dihydro-[3,3']bipyridinyl-5-carboxylic acid (2-pyridin-4-yl-ethyl)-amide

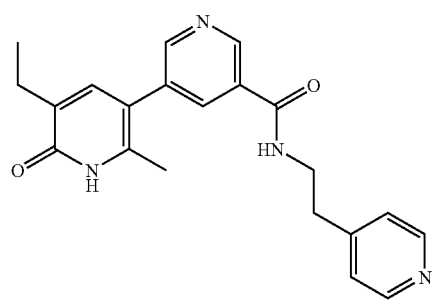

Method 1, Example 205 is substantially repeated except for utilizing 5'-ethyl-2'-methyl-6'-oxo-1',6'-dihydro-[3,3']bipyridinyl-5-carboxylic acid and 2-(pyridin-4-yl)-ethyl-amine to afford the title compound. MS: m/e=363 (M+H). $^1$H NMR ($\delta$ ppm): 11.72 (s, 1H); 8.87 (d, 1H, J=2.1 Hz); 8.77 (t, 1H, J=5.4 Hz); 8.67 (d, 1H, 2.1 Hz); 8.47 (m, 2H); 8.04 (t, 1H, J=2.1 Hz); 7.29 (m, 3H); 3.57 (q, 2H, J=7.1 Hz); 2.89 (t, 2H, J=7.1 Hz); 2.42 (q, 2H, J=7.4 Hz); 2.17 (s, 3H); 1.11 (t, 3H, J=7.4 Hz).

Example 239

5'-Ethyl-2'-methyl-6'-oxo-1',6'-dihydro-[3,3']bipyridinyl-5-carboxylic acid [2-(4-methoxy-phenyl)-ethyl]-amide

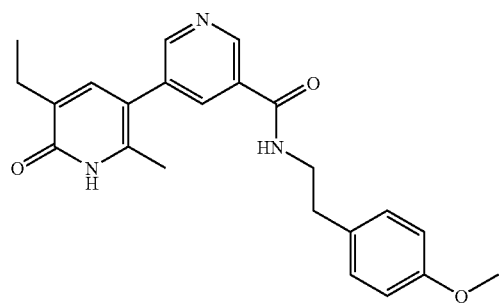

Method 1, Example 205 is substantially repeated except for utilizing 5'-ethyl-2'-methyl-6'-oxo-1',6'-dihydro-[3,3']bipyridinyl-5-carboxylic acid and 2-(4-methoxy-phenyl)-ethylamine to afford the title compound. MS: m/e=392 (M+H).

Example 240

5'-Ethyl-2'-methyl-6'-oxo-1',6'-dihydro-[3,3']bipyridinyl-5-carboxylic acid [2-(3-methoxy-phenyl)-ethyl]-amide

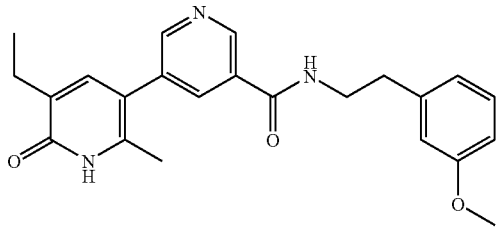

Method 1, Example 205 is substantially repeated except for utilizing 5'-ethyl-2'-methyl-6'-oxo-1',6'-dihydro-[3,3']bipyridinyl-5-carboxylic acid and 2-(3-methoxy-phenyl)-ethyl-amine to afford the title compound. MS: m/e=392 (M+H).

Example 241

5'-Ethyl-2'-methyl-6'-oxo-1',6'-dihydro-[3,3']bipyridinyl-5-carboxylic acid (2-morpholin-4-yl-ethyl)-amide

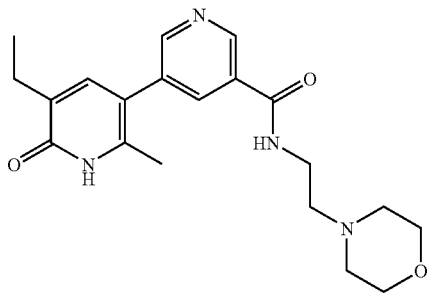

Method 1, Example 205 is substantially repeated except for utilizing 5'-ethyl-2'-methyl-6'-oxo-1',6'-dihydro-[3,3']bipyridinyl-5-carboxylic acid and 2-(morpholin-4-yl)-ethyl-amine to afford the title compound. MS: m/e=371 (M+H).

Example 242

5'-Ethyl-2'-methyl-6'-oxo-1',6'-dihydro-[3,3']bipyridinyl-5-carboxylic acid [2-(tetrahydro-pyran-4-yl)-ethyl]-amide

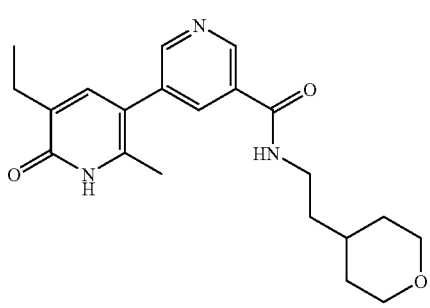

Method 1, Example 205 is substantially repeated except for utilizing 5'-ethyl-2'-methyl-6'-oxo-1',6'-dihydro-[3,3']bipyridinyl-5-carboxylic acid and 2-(tetrahydropyran-4-yl)-ethyl-amine to afford the title compound. MS: m/e=370 (M+H).

Example 243

4-{2-[(5'-Ethyl-2'-methyl-6'-oxo-1',6'-dihydro-[3,3']bipyridinyl-5-carbonyl)-amino]-ethyl}-benzoic acid

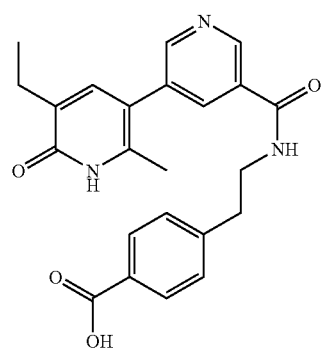

Method 1, Example 205 is substantially repeated except for utilizing 5'-ethyl-2'-methyl-6'-oxo-1',6'-dihydro-[3,3']bipyridinyl-5-carboxylic acid and 4-(2-amino-ethyl)-benzoic acid to afford the title compound. MS: m/e=406 (M+H).

Example 244

5'-Ethyl-2'-methyl-6'-oxo-1',6'-dihydro-[3,3']bipyridinyl-5-carboxylic acid (2-oxo-2-phenyl-ethyl)-amide

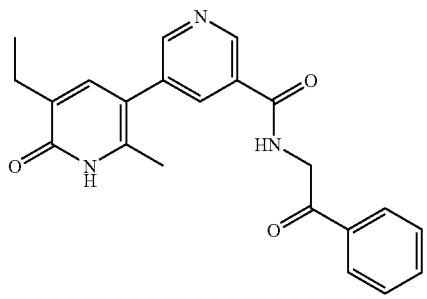

Method 1, Example 205 is substantially repeated except for utilizing 5'-ethyl-2'-methyl-6'-oxo-1',6'-dihydro-[3,3']bipyridinyl-5-carboxylic acid and 2-oxo-2-phenyl-ethyl-amine to afford the title compound. MS: m/e=376 (M+H). $^1$H NMR (δ ppm): 11.74 (s, 1H); 9.13 (t, 1H, J=5.5 Hz); 8.99 (d, 1H, J=2.2 Hz); 8.72 (d, 1H, J=2.2 Hz); 8.19 (t, 1H, J=2.2 Hz); 8.05 (m, 2H); 7.70 (m, 1H); 7.58 (m, 2H); 7.32 (s, 1H); 4.85 (d, 2H, J=5.5 Hz); 2.42 (q, 2H, J=7.4 Hz); 2.20 (s, 3H); 1.12 (t, 3H, J=7.4 Hz).

Example 245

5'-Ethyl-2'-methyl-6'-oxo-1',6'-dihydro-[3,3']bipyridinyl-5-carboxylic acid [2-(1H-benzoimidazol-2-yl)-ethyl]-amide

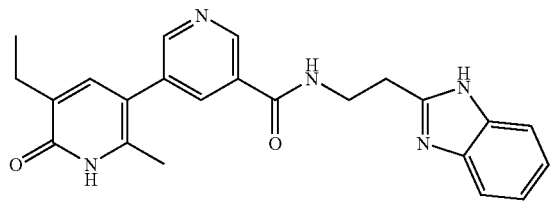

Method 1, Example 205 is substantially repeated except for utilizing 5'-ethyl-2'-methyl-6'-oxo-1',6'-dihydro-[3,3']bipyridinyl-5-carboxylic acid and 2-(1H-benzoimidazol-2-yl)-ethyl-amine to afford the title compound. MS: m/e=402 (M+H).

Example 246

5'-Ethyl-2'-methyl-6'-oxo-1',6'-dihydro-[3,3']bipyridinyl-5-carboxylic acid (4-acetyl-phenyl)-amide

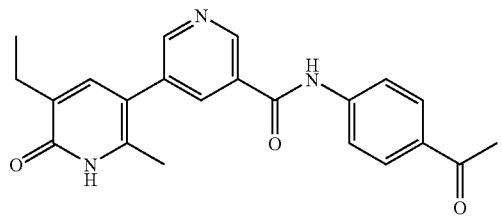

Method 1, Example 205 is substantially repeated except for utilizing 5'-ethyl-2'-methyl-6'-oxo-1',6'-dihydro-[3,3']bipyridinyl-5-carboxylic acid and 4-amino-acetophenone to afford the title compound. MS: m/e=376 (M+H).

Example 247

5'-Ethyl-2'-methyl-6'-oxo-1',6'-dihydro-[3,3']bipyridinyl-5-carboxylic acid (3-[1,2,4]triazol-1-yl-propyl)-amide

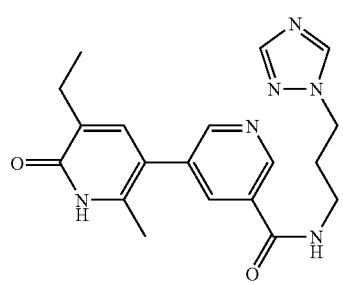

Method 1, Example 205 is substantially repeated except for utilizing 5'-ethyl-2'-methyl-6'-oxo-1',6'-dihydro-[3,3']bipyridinyl-5-carboxylic acid and 3-[1,2,4]triazol-1-yl-propyl)-amine to afford the title compound. MS: m/e=367 (M+H).

Example 248

5'-Ethyl-2'-methyl-6'-oxo-1',6'-dihydro-[3,3']bipyridinyl-5-carboxylic acid (3-methoxy-phenyl)-amide

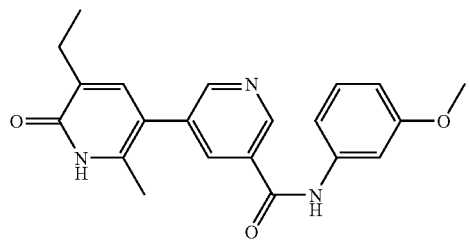

Method 1, Example 205 is substantially repeated except for utilizing 5'-ethyl-2'-methyl-6'-oxo-1',6'-dihydro-[3,3']bipyridinyl-5-carboxylic acid and 3-methoxy-aniline to afford the title compound. MS: m/e=364 (M+H).

Example 249

5'-Ethyl-2'-methyl-6'-oxo-1',6'-dihydro-[3,3']bipyridinyl-5-carboxylic acid [2-(2-methyl-5-nitro-imidazol-1-yl)-ethyl]-amide

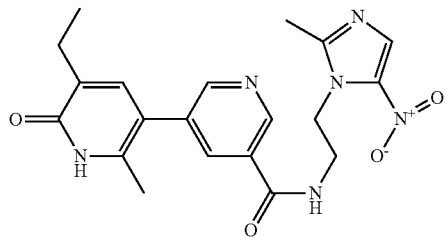

Method 1, Example 205 is substantially repeated except for utilizing 5'-ethyl-2'-methyl-6'-oxo-1',6'-dihydro-[3,3']bipyridinyl-5-carboxylic acid and 2-(2-methyl-5-nitro-imidazol-1-yl)-ethyl-amine to afford the title compound. MS: m/e=411 (M+H).

Example 250

5'-Ethyl-2'-methyl-6'-oxo-1',6'-dihydro-[3,3']bipyridinyl-5-carboxylic acid (thiazol-2-ylmethyl)-amide

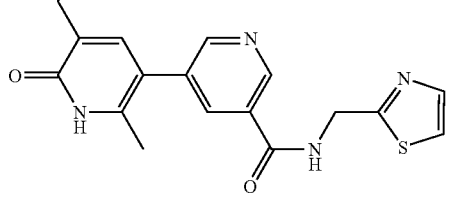

Method 1, Example 205 is substantially repeated except for utilizing 5'-ethyl-2'-methyl-6'-oxo-1',6'-dihydro-[3,3']bipyridinyl-5-carboxylic acid and (thiazol-2-ylmethyl)-amine to afford the title compound. MS: m/e=355 (M+H).

Example 251

5'-Ethyl-2'-methyl-6'-oxo-1',6'-dihydro-[3,3']bipyridinyl-5-carboxylic acid (2-carbamoylmethyl-phenyl)-amide

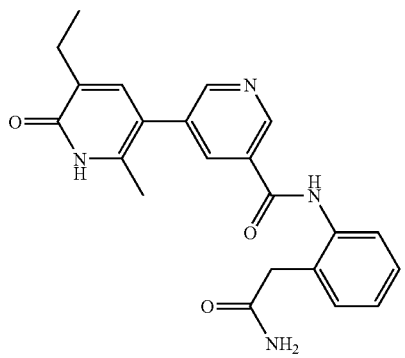

Method 1, Example 205 is substantially repeated except for utilizing 5'-ethyl-2'-methyl-6'-oxo-1',6'-dihydro-[3,3']bipyridinyl-5-carboxylic acid and (2-carbamoylmethyl-phenyl)-amine to afford the title compound. MS: m/e=391 (M+H).

Example 252

5'-(4-Cyclopropanecarbonyl-piperazine-1-carbonyl)-5-ethyl-2-methyl-1H-[3,3']bipyridinyl-6-one

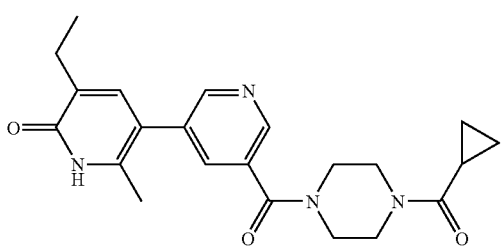

Method 1, Example 205 is substantially repeated except for utilizing 5'-ethyl-2'-methyl-6'-oxo-1',6'-dihydro-[3,3']bipyridinyl-5-carboxylic acid and 4-cyclopropanecarbonyl-piperazine to afford the title compound. MS: m/e=395 (M+H).

Example 253

5'-Ethyl-2'-methyl-6'-oxo-1',6'-dihydro-[3,3']bipyridinyl-5-carboxylic acid (2-hydroxy-2-phenyl-ethyl)-amide

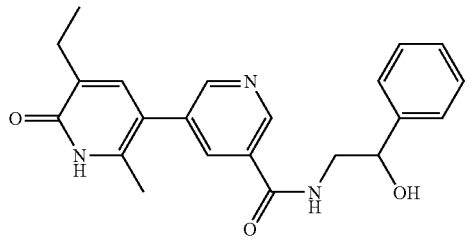

Method 1, Example 205 is substantially repeated except for utilizing 5'-ethyl-2'-methyl-6'-oxo-1',6'-dihydro-[3,3']bipyridinyl-5-carboxylic acid and (2-hydroxy-2-phenyl-ethyl)-amine to afford the title compound. MS: m/e=378 (M+H).

Example 254

5'-Ethyl-2'-methyl-6'-oxo-1',6'-dihydro-[3,3']bipyridinyl-5-carboxylic acid [2-(2,4-dioxo-thiazolidin-3-yl)-ethyl]-amide

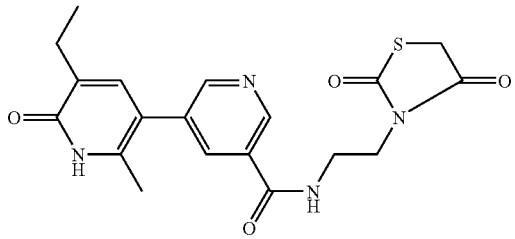

Method 1, Example 205 is substantially repeated except for utilizing 5'-ethyl-2'-methyl-6'-oxo-1',6'-dihydro-[3,3']bipyridinyl-5-carboxylic acid and [2-(2,4-dioxo-thiazolidin-3-yl)-ethyl]-amine to afford the title compound. MS: m/e=401 (M+H).

Example 255

5'-Ethyl-2'-methyl-6'-oxo-1',6'-dihydro-[3,3']bipyridinyl-5-carboxylic acid 4-sulfamoyl-benzylamide

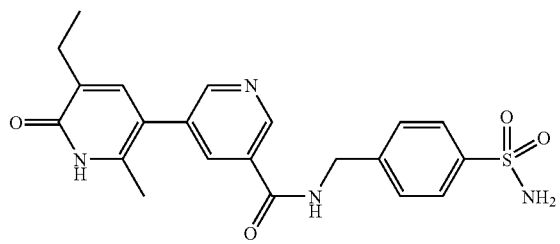

Method 1, Example 205 is substantially repeated except for utilizing 5'-ethyl-2'-methyl-6'-oxo-1',6'-dihydro-[3,3']bipyridinyl-5-carboxylic acid and 4-sulfamoyl-benzyl-amine to afford the title compound. MS: m/e=427 (M+H).

Example 256

5'-Ethyl-2'-methyl-6'-oxo-1',6'-dihydro-[3,3']bipyridinyl-5-carboxylic acid [2-(4-methoxy-phenyl)-2-oxo-ethyl]-amide

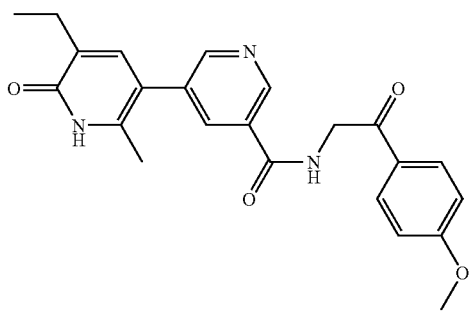

Method 1, Example 205 is substantially repeated except for utilizing 5'-ethyl-2'-methyl-6'-oxo-1',6'-dihydro-[3,3']bipyridinyl-5-carboxylic acid and [2-(4-methoxy-phenyl)-2-oxo-ethyl]-amine to afford the title compound. MS: m/e=406 (M+H).

Example 257

5'-Ethyl-2'-methyl-6'-oxo-1',6'-dihydro-[3,3']bipyridinyl-5-carboxylic acid (3-pyridin-4-yl-4,5-dihydro-isoxazol-5-ylmethyl)-amide

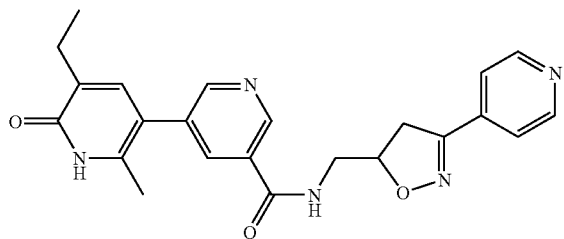

Method 1, Example 205 is substantially repeated except for utilizing 5'-ethyl-2'-methyl-6'-oxo-1',6'-dihydro-[3,3']bipyridinyl-5-carboxylic acid and (3-pyridin-4-yl-4,5-dihydro-isoxazol-5-ylmethyl)-amine to afford the title compound. MS: m/e=418 (M+H).

Example 258

5'-Ethyl-2'-methyl-6'-oxo-1',6'-dihydro-[3,3']bipyridinyl-5-carboxylic acid (5-tert-butyl-1H-pyrazol-3-yl)-amide

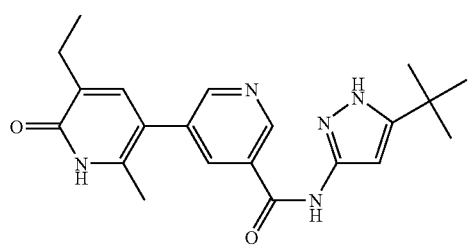

Method 1, Example 205 is substantially repeated except for utilizing 5'-ethyl-2'-methyl-6'-oxo-1',6'-dihydro-[3,3']bipyridinyl-5-carboxylic acid and (5-tert-butyl-1H-pyrazol-3-yl)-amine to afford the title compound. MS: m/e=380 (M+H).

Example 259

5'-Ethyl-2'-methyl-6'-oxo-1',6'-dihydro-[3,3']bipyridinyl-5-carboxylic acid (5-tert-butyl-isoxazol-3-yl)-amide

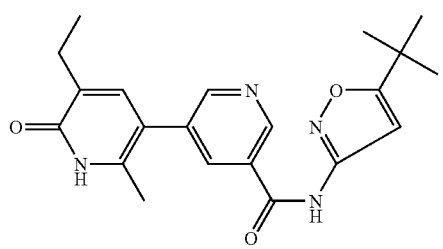

Method 1, Example 205 is substantially repeated except for utilizing 5'-ethyl-2'-methyl-6'-oxo-1',6'-dihydro-[3,3']bipyridinyl-5-carboxylic acid and (5-tert-butyl-isoxazol-3-yl)-amine to afford the title compound. MS: m/e=381 (M+H).

Example 260

5'-Ethyl-2'-methyl-6'-oxo-1',6'-dihydro-[3,3']bipyridinyl-5-carboxylic acid ((1S,6R)-6-carbamoyl-cyclohex-3-enyl)-amide

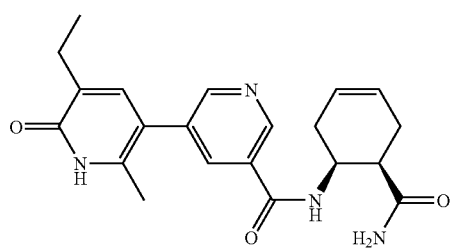

Method 1, Example 205 is substantially repeated except for utilizing 5'-ethyl-2'-methyl-6'-oxo-1',6'-dihydro-[3,3']bipyridinyl-5-carboxylic acid and ((1S,6R)-6-carbamoyl-cyclohex-3-enyl)-amine to afford the title compound. MS: m/e=381 (M+H).

Example 261

5'-Ethyl-2'-methyl-6'-oxo-1',6'-dihydro-[3,3']bipyridinyl-5-carboxylic acid (2-methoxy-ethyl)-amide

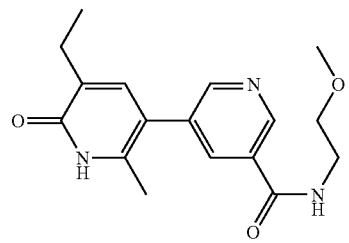

Method 1, Example 205 is substantially repeated except for utilizing 5'-ethyl-2'-methyl-6'-oxo-1',6'-dihydro-[3,3']bipyridinyl-5-carboxylic acid and (2-methoxy-ethyl)-amine to afford the title compound. MS: m/e=316 (M+H).

Example 262

5'-Ethyl-2'-methyl-6'-oxo-1',6'-dihydro-[3,3']bipyridinyl-5-carboxylic acid (4-cyano-cyclohexylmethyl)-amide

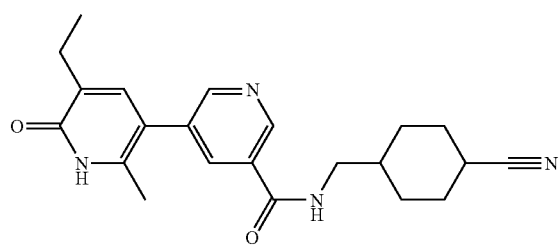

Method 1, Example 205 is substantially repeated except for utilizing 5'-ethyl-2'-methyl-6'-oxo-1',6'-dihydro-[3,3']bipyridinyl-5-carboxylic acid and (4-cyano-cyclohexylmethyl)-amine to afford the title compound. MS: m/e=379 (M+H).

Example 263

5'-Ethyl-2'-methyl-6'-oxo-1',6'-dihydro-[3,3']bipyridinyl-5-carboxylic acid 3-methoxy-benzylamide

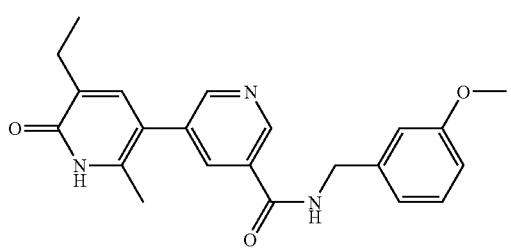

Method 1, Example 205 is substantially repeated except for utilizing 5'-ethyl-2'-methyl-6'-oxo-1',6'-dihydro-[3,3']bipyridinyl-5-carboxylic acid and 3-methoxy-benzylamine to afford the title compound. MS: m/e=378 (M+H).

Example 264

5'-Ethyl-2'-methyl-6'-oxo-1',6'-dihydro-[3,3']bipyridinyl-5-carboxylic acid (2-pyridin-2-yl-ethyl)-amide

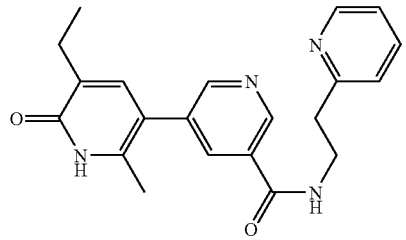

Method 1, Example 205 is substantially repeated except for utilizing 5'-ethyl-2'-methyl-6'-oxo-1',6'-dihydro-[3,3']bipyridinyl-5-carboxylic acid and (2-pyridin-2-yl-ethyl)-amine to afford the title compound. MS: m/e=363 (M+H).

Example 265

5'-Ethyl-2'-methyl-6'-oxo-1',6'-dihydro-[3,3']bipyridinyl-5-carboxylic acid 4-hydroxy-3-methoxy-benzylamide

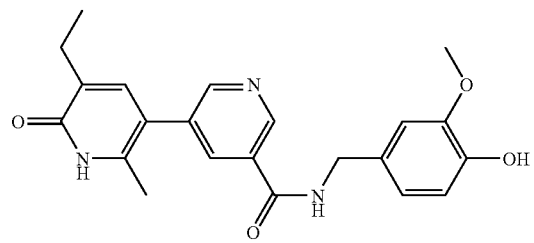

Method 1, Example 205 is substantially repeated except for utilizing 5'-ethyl-2'-methyl-6'-oxo-1',6'-dihydro-[3,3']bipyridinyl-5-carboxylic acid and 4-hydroxy-3-methoxy-benzylamine to afford the title compound. MS: m/e=394 (M+H).

Example 265A 5-(5-Ethyl-2-methyl-6-oxo-1,6-dihydro-pyridin-3-yl)-furan-2-carboxylic acid 3,5-difluoro-benzylamide

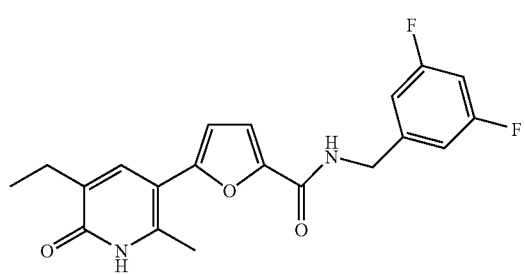

Method 1, Example 205 is substantially repeated except for utilizing 5-(5-ethyl-2-methyl-6-oxo-1,6-dihydropyridin-3- yl)furan-2-carboxylic acid and 3,5-difluoro-benzylamine to give the title compound (91% yield). LC/MS: RT 3.52 min; m/e 373 (M+H).

Example 265B

3-Ethyl-6-methyl-5-[5-(2-methyl-aziridine-1-carbonyl)-furan-2-yl]-1H-pyridin-2-one

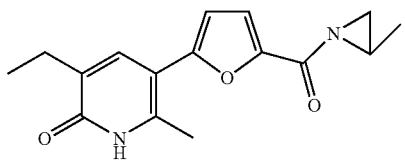

Method 1, Example 205 is substantially repeated except for utilizing 5-(5-ethyl-2-methyl-6-oxo-1,6-dihydropyridin-3-yl)furan-2-carboxylic acid and 2-methylaziridine to give the title compound (81% yield). LC/MS: RT 2.02 min; m/e 287 (M+H).

Example 265C

3-Ethyl-5-{5-[4-(4-fluoro-phenyl)-piperazine-1-carbonyl]-furan-2-yl}-6-methyl-1H-pyridin-2-one

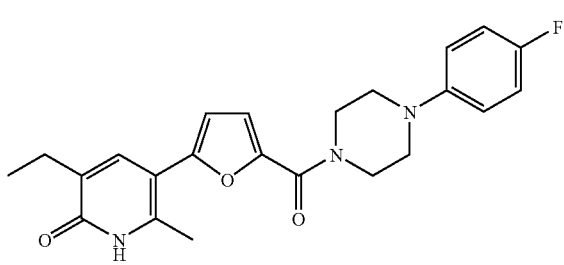

Method 1, Example 205 is substantially repeated except for utilizing 5-(5-ethyl-2-methyl-6-oxo-1,6-dihydropyridin-3-yl)furan-2-carboxylic acid and (4-fluoro-phenyl)-piperazine to afford the title compound (98% yield). LC/MS: RT 2.9 min; m/e 410 (M+H).

Example 265D 5-(5-Ethyl-2-methyl-6-oxo-1,6-dihydro-pyridin-3-yl)-furan-2-carboxylic acid 4-trifluoromethyl-benzylamide

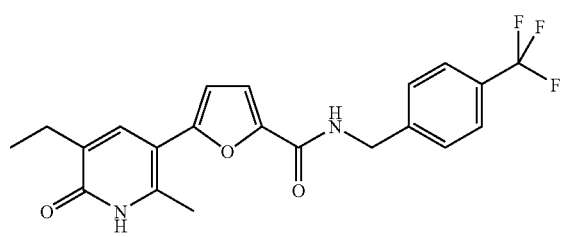

Method 1, Example 205 is substantially repeated except for utilizing 5-(5-ethyl-2-methyl-6-oxo-1,6-dihydro-pyridin-3-yl)-furan-2-carboxylic acid and 4-trifluoromethyl-benzylamine to afford the title compound (60% yield). LC/MS: RT 2.95 min; m/e 405 (M+H).

Example 265E 5-(5-Ethyl-2-methyl-6-oxo-1,6-dihydro-pyridin-3-yl)-furan-2-carboxylic acid dimethylamide

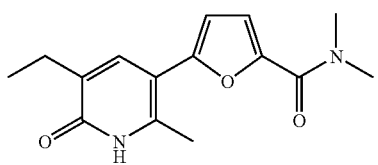

Method 1, Example 205 is substantially repeated except for utilizing 5-(5-ethyl-2-methyl-6-oxo-1,6-dihydro-pyridin-3-yl)-furan-2-carboxylic acid and dimethylamine to afford the title compound (50% yield). LC/MS: RT 2.3 min; m/e 275 (M+H).

Example 265F

5-[5-(4-Benzyl-piperazine-1-carbonyl)-thiophen-2-yl]-3-ethyl-6-methyl-1H-pyridin-2-one

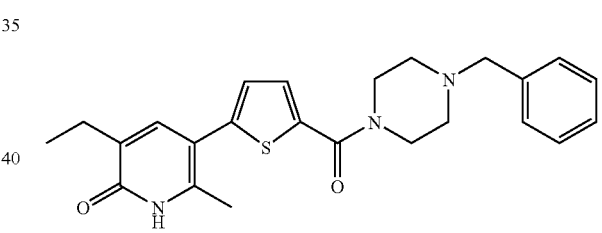

Method 1, Example 205 is substantially repeated except for utilizing 5-(5-ethyl-2-methyl-6-oxo-1,6-dihydro-pyridin-3-yl)-thiophene-2-carboxylic acid and 4-benzyl-piperazine to afford the title compound (60% yield). LC/MS: RT 2.07 min; m/e 422 (M+H).

Example 265G 5-(5-Ethyl-2-methyl-6-oxo-1,6-dihydro-pyridin-3-yl)-thiophene-2-carboxylic acid dimethylamide

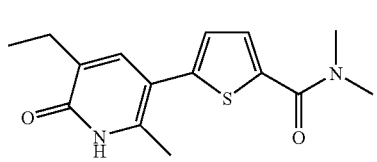

Method 1, Example 205 is substantially repeated except for utilizing 5-(5-ethyl-2-methyl-6-oxo-1,6-dihydro-pyridin-3- yl)-thiophene-2-carboxylic acid and dimethylamine to afford the title compound (77% yield). LC/MS: RT 2.44 min; m/e 291 (M+H).

Example 265H 5-(5-Ethyl-2-methyl-6-oxo-1,6-dihydro-pyridin-3-yl)-thiophene-2-carboxylic acid 4-trifluoromethyl-benzylamide

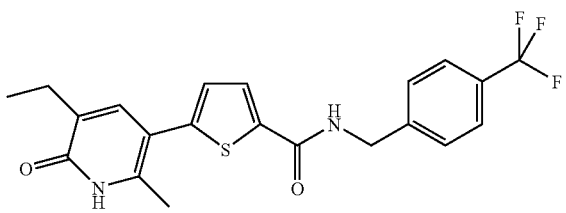

Method 1, Example 205 is substantially repeated except for utilizing 5-(5-ethyl-2-methyl-6-oxo-1,6-dihydro-pyridin-3-yl)-thiophene-2-carboxylic acid and 4-trifluoromethyl-benzylamine to afford the title compound (75% yield). LC/MS: RT 3.15 min; m/e 421 (M+H).

Example 265I 5-(5-Ethyl-2-methyl-6-oxo-1,6-dihydro-pyridin-3-yl)-thiophene-2-carboxylic acid (pyridin-2-ylmethyl)-amide

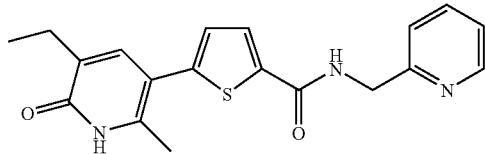

Method 1, Example 205 is substantially repeated except for utilizing 5-(5-ethyl-2-methyl-6-oxo-1,6-dihydro-pyridin-3-yl)-thiophene-2-carboxylic acid and pyridin-2-ylmethylamine to afford the title compound (97% yield). LC/MS: RT 2.07 min; m/e 354 (M+H).

Example 265J 5-(5-Ethyl-2-methyl-6-oxo-1,6-dihydro-pyridin-3-yl)-thiophene-2-carboxylic acid methoxy-methyl-amide

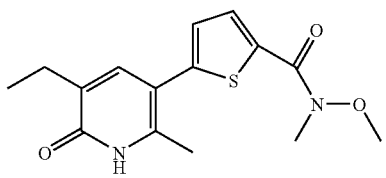

Method 1, Example 205 is substantially repeated except for utilizing 5-(5-ethyl-2-methyl-6-oxo-1,6-dihydro-pyridin-3-yl)-thiophene-2-carboxylic acid and methoxy-methylamine to afford the title compound (85% yield). LC/MS: RT 2.64 min; m/e 307 (M+H).

Example 265K 5-(5-Ethyl-2-methyl-6-oxo-1,6-dihydro-pyridin-3-yl)-furan-2-carboxylic acid amide

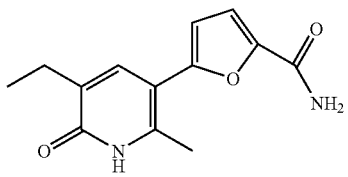

Method 1, Example 205 is substantially repeated except for utilizing 5-(5-ethyl-2-methyl-6-oxo-1,6-dihydro-pyridin-3-yl)-furan-2-carboxylic acid and ammonia to afford the title compound.

Example 266

3-Ethyl-6-methyl-5-[5-(pyridine-2-carbonyl)-thiophen-2-yl]-1H-pyridin-2-one

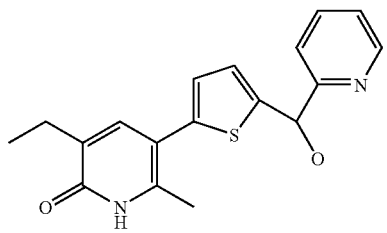

N-Methylmorpholine (3.7 ml) is added to a solution of picolinic acid (2.05 g, 16.65 mmol) in anhydrous dichloromethane (50 mL) and cooled to −15° C. Isobutyl chloroformate (2.2 ml, 16.75 mmol) is added thereto, and the mixture is stirred for 15 hr, after which N,O-dimethylhydroxylamine hydrochloride (1.63 g, 16.71 mmol) is added. After 15 min, the cooling bath is removed and stirring is continued at room temperature for 4 hr. The reaction mixture is added to water (50 ml) and extracted with dichloromethane. The organic phases are washed with water and brine and dried over $Na_2SO_4$. The residue is chromatographed on silica gel to afford N-methoxy-N-methylpyridine-2-carboxamide as a colorless oil (2.2 g; 80% yield).

A solution of 3-ethyl-6-methyl-5-thiophen-2-yl-1H-pyridin-2-one prepared in accordance with the procedures of Example 24, Step 3 (100 mg, 0.456 mmol) in anhydrous THF (3 ml) is cooled to −78° C., and n-BuLi (2.5 M in hexane, 0.4 ml, 1 mmol) is added. The resulting dark green mixture is stirred for 20 min, and then N-methoxy-N-methylpyridine-2-carboxamide (83 mg, 0.5 mmol) in THF (1 ml) is added. The reaction mixture is then added to water (5 ml) and extracted with ethyl acetate. The organic phases are washed and dried, and the residue is purified on silica gel. The product is dissolved in a minimal amount of methanol and treated with HCl in diethyl ether. The resulting brown precipitate is filtered off with suction and dried (12 mg, as hydrochloride). MS:

m/e=325 (M+H). $^1$H-NMR (D$_6$-DMSO, δ ppm) 11.85 (s, 1H); 8.81 (d, 1H); 8.30 (d, 1H); 8.12 (m, 2H); 7.71 (m, 1H); 7.44 (s, 1H); 7.29 (d, 1H) 3.37 (m, 2H); 2.50 (s, 3H); 1.14 (t, 3H, J=7.4 Hz).

Example 267

3-Ethyl-5-[5-(hydroxy-pyridin-2-yl-methyl)-thiophen-2-yl]-6-methyl-1H-pyridin-2-one

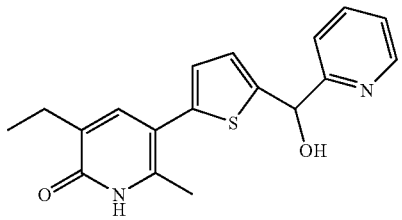

A solution of 3-ethyl-6-methyl-5-thiophen-2-yl-1H-pyridin-2-one prepared in accordance with the procedures of Example 24, Step 3 (97 mg, 0.442 mmol) in anhydrous THF (1 ml) is cooled to −78° C., and n-BuLi (2.5 M in hexane, 0.4 ml, 1 mmol) is added. The resulting dark green mixture is stirred for 30 min, and then pyridine-2-carbaldehyde (80 mg, 0.746 mmol) is added. The cooling bath is removed after 20 min, and the reaction mixture is slowly warmed to room temperature. After 3 hr, water (5 ml) is added to the mixture, and it is extracted with ethyl acetate. The organic phases are washed and dried, and the residue is purified on silica gel to afford a yellow solid (60 mg). MS: m/e=327 (M+H). $^1$H-NMR (D$_6$-DMSO, δ ppm) 11.65 (s, 1H); 8.51 (d, 1H); 7.85 (d, 1H); 7.61 (d, 1H); 7.29 (m, 1H); 7.21 (s, 1H); 6.88 (m, 2H); 6.43 (d, 1H); 5.88 (d, 1H); 2.38 (q, 2H); 2.24 (s, 3H); 1.06 (t, 3H, J=7.4 Hz).

Example 268

3-Ethyl-5-[5-(1-hydroxy-ethyl)-furan-2-yl]-6-methyl-1H-pyridin-2-one

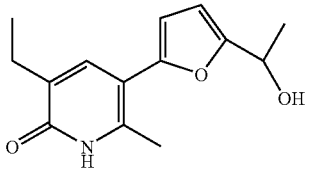

Example 267 is substantially repeated except for utilizing 3-ethyl-6-methyl-5-furan-2-yl-1H-pyridin-2-one prepared in accordance with the procedures of Example 44, Step 2 and acetaldehyde to afford the title compound. MS: m/e=248 (M+H).

Example 269

Cyclopentanecarboxylic acid [5-(5-ethyl-2-methyl-6-oxo-1,6-dihydro-pyridin-3-yl)-furan-2-ylmethyl]-amide

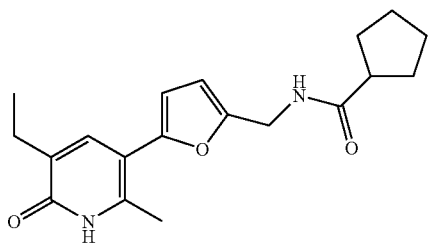

5-(5-aminomethylfuran-2-yl)-3-ethyl-6-methyl-1H-pyridin-2-one prepared in accordance with the procedures of Example 175A (100 mg, 0.43 mmol) is dissolved in 2 ml of dichloromethane. To this solution are added triethylamine (179 μl, 1.29 mmol) and 1.5 eq. of cyclopentane carboxylic acid chloride. The mixture is stirred at room temperature for 6 hr and then water is added. The organic phase is concentrated, and the residue is purified by RP-HPLC. The resulting compound is isolated as trifluoroacetate salt by reacting with trifluoroacetic acid. MS: m/e=329 (M+H).

Example 270

N-[5-(5-Ethyl-2-methyl-6-oxo-1,6-dihydro-pyridin-3-yl)-furan-2-ylmethyl]-2-phenyl-acetamide

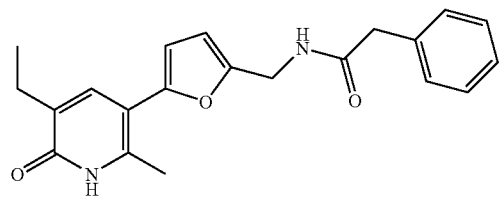

Example 269 is substantially repeated except for utilizing 5-(5-aminomethylfuran-2-yl)-3-ethyl-6-methyl-1H-pyridin-2-one and phenylacetyl chloride to afford the title compound. MS: m/e=351 (M+H).

Example 271

N-[5-(5-Ethyl-2-methyl-6-oxo-1,6-dihydro-pyridin-3-yl)-furan-2-ylmethyl]-benzamide

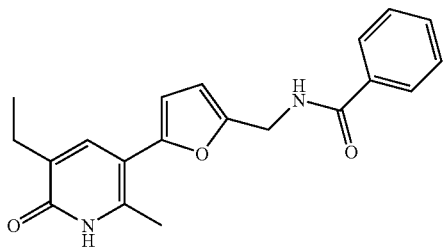

Example 269 is substantially repeated except for utilizing 5-(5-aminomethylfuran-2-yl)-3-ethyl-6-methyl-1H-pyridin-2-one and benzoyl chloride to afford the title compound. MS: m/e=337 (M+H).

Example 272

N-[5-(5-Ethyl-2-methyl-6-oxo-1,6-dihydro-pyridin-3-yl)-furan-2-ylmethyl]-4-methoxy-benzamide

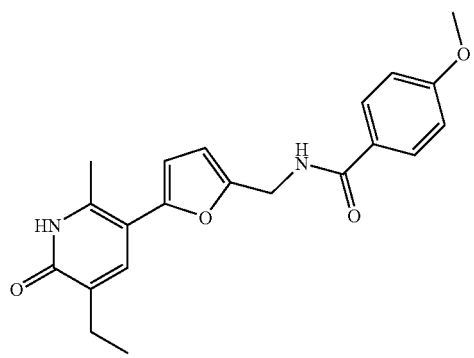

Example 269 is substantially repeated except for utilizing 5-(5-aminomethylfuran-2-yl)-3-ethyl-6-methyl-1H-pyridin-2-one and 4-methoxybenzoyl chloride to afford the title compound. MS: m/e=367 (M+H).

Example 273

Pyridine-2-carboxylic acid [5-(5-ethyl-2-methyl-6-oxo-1,6-dihydro-pyridin-3-yl)-furan-2-ylmethyl]-amide

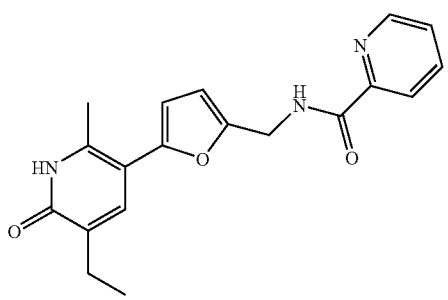

Example 269 is substantially repeated except for utilizing 5-(5-aminomethylfuran-2-yl)-3-ethyl-6-methyl-1H-pyridin-2-one and pyridine-2-carboxylic acid chloride to afford the title compound. MS: m/e=338 (M+H).

Example 274

N-[5-(5-Ethyl-2-methyl-6-oxo-1,6-dihydro-pyridin-3-yl)-furan-2-ylmethyl]-acetamide

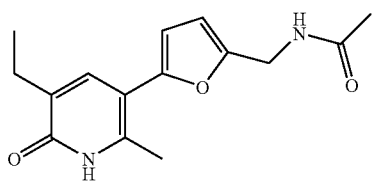

Example 269 is substantially repeated except for utilizing 5-(5-aminomethylfuran-2-yl)-3-ethyl-6-methyl-1H-pyridin-2-one and acetyl chloride to afford the title compound. MS: m/e=275 (M+H). $^1$H NMR (D$_6$-DMSO, δ ppm): 11.64 (s, 1H); 8.30 (t, 1H, J=5.3 Hz); 7.45 (s, 1H); 6.39 (d, 1H, J=3.2 Hz); 6.30 (d, 1H, J=3.2 Hz); 4.26 (d, 2H, J=5.3 Hz); 2.40 (q, 2H, J=7.4 Hz); 2.32 (s, 3H); 1.84 (s, 3H); 1.10 (t, 3H, J=7.4 Hz).

Example 275

3-Dimethylamino-N-[5-(5-ethyl-2-methyl-6-oxo-1,6-dihydro-pyridin-3-yl)-furan-2-ylmethyl]-benzamide

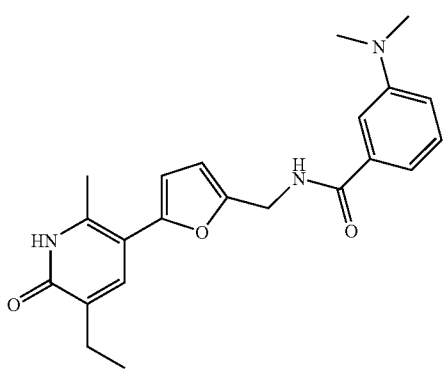

Example 269 is substantially repeated except for utilizing 5-(5-aminomethylfuran-2-yl)-3-ethyl-6-methyl-1H-pyridin-2-one and 3-dimethylamino-benzoyl chloride to afford the title compound. MS: m/e=380 (M+H).

Example 276

N-[5-(5-Ethyl-2-methyl-6-oxo-1,6-dihydropyridin-3-yl)-thiophen-2-ylmethyl]-2-pyrrolidin-1-yl-acetamide

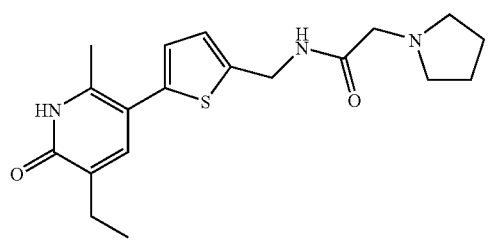

Chloroacetyl chloride (0.24 mL, 3 mmol) is added to a solution of 5-(5-aminomethylthiophen-2-yl)-3-ethyl-6-methyl-1H-pyridin-2-one prepared in accordance with the procedures of Example 175 (0.5 g, 2 mmol) in THF/dichloromethane (1:1, 5 ml) at 0° C. After 2 hr at room temperature, aqueous NaHCO$_3$ solution is added to the reaction mixture, and it is extracted with ethyl acetate. The organic phases are combined and chromatographed on silica gel to afford 0.3 g of the corresponding chloroacetyl derivative. A solution of the chloroacetyl derivative (0.15 g) and an excess of pyrrolidine in acetonitrile is heated at 60° C. for 6 hr and then cooled to room temperature. Aqueous NaHCO$_3$ solution is added to the reaction mixture, and it is extracted with ethyl acetate. The organic phases are combined and chromatographed on silica gel; the resulting product is converted into the HCl salt and freeze-dried. $^1$H-NMR (D6-DMSO, δ ppm): 10.5 (br s, 1H); 9.40 (t, 1H); 7.20 (s, 1H); 6.95 (d, 1H); 6.90 (d, 1H); 4.45 (m, 2H); 4.05 (m, 2H); 3.58 (m, 2H); 3.05 (m, 2H); 2.40 (q, 2H); 2.28 (s, 3H); 2.01-1.8 (m, 4H); 1.10 (t, 3H).

Example 277

N-(5'-Ethyl-2'-methyl-6'-oxo-1',6'-dihydro-[2,3'] bipyridinyl-6-yl)-benzenesulfonamide

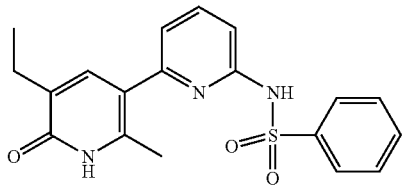

6-Amino-5'-ethyl-2'-methyl-1'H-[2,3']bipyridinyl-6'-one (1 molar equivalent), prepared in accordance with the procedures of PREPARATION 12, is dissolved in pyridine (approx. 10 ml/mmol) and, at room temperature, 1.3 molar equivalent of benzene sulfonyl chloride is added, and the reaction mixture is stirred at room temperature for 36 hrs. The solution is completely concentrated and then purified directly by RP-HPLC. MS: m/e=370 (M+H).

Example 278

N-[4-(5'-Ethyl-2'-methyl-6'-oxo-1',6'-dihydro-[2,3'] bipyridinyl-6-ylsulfamoyl)-phenyl]-acetamide

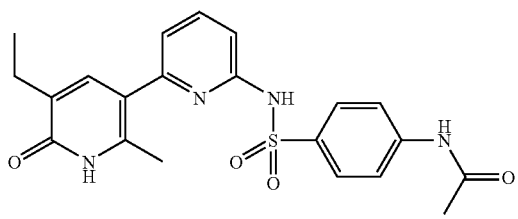

Example 277 is substantially repeated except for utilizing 6-amino-5'-ethyl-2'-methyl-1'H-[2,3']bipyridinyl-6'-one and 4-acetylamino-benzenesulfonyl chloride to afford the title compound. MS: m/e=427 (M+H).

Biological Examples

Example 279

This Example illustrates the biological efficacy of the compounds of this invention in inhibiting the effects of PARP. Two different methods are employed in determining the activity of the compounds of this invention in inhibiting the activity of PARP enzyme, designated as Method A and Method B respectively as set forth below.

Method A: Cloning and Expression, and Partial Purification of Recombinant Human PARP:

Full length human PARP (PARP1) is assembled from PCR fragments of a clone from a human brain cDNA library and two Incyte clones. The PARP gene (3046 bp) is sub-cloned into pFastBac-HTb vector to give PARP-pFastBac-HTb and the sequence of this clone is verified. PARP-pFastBac-HTb is expressed to obtain protein using the Bac-to-Bac expression protocol from Gibco-BRL. The recombinant virus generated is used to scale up the material for purification.

Cell pellets from cell broth of cells expressing PARP are treated with a cocktail of protease inhibitors and lysed by 4 freeze-thaw cycles. The material is suspended in 10 mM HEPES/0.1M NaCl/pH 7.2, stirred, and then centrifuged. A 40%-70% ammonium sulfate cut of protein pellet is obtained from the supernatant. The pellet is solubilized in 10 mM HEPES/pH 7.2 and centrifuged. The supernatant buffer is exchanged to 10 mM HEPES/pH 7.2/0.1M NaCl/25% glycerol by dialysis or with a desalting column. The enzyme preparation is stored at −20° C. until use.

The compounds of this invention are then tested with this enzyme preparation using either the radioactive enzyme assay or by the "ELISA" enzyme assay as set forth below.

Radioactivity Enzyme Assay:

Incorporation of radioactivity from labeled NAD into acid-precipitated protein is measured. The reaction mixture (volume 100 µL or 50 µL, in a test-tube or 96-well plate) contained 100 µg/mL calf thymus DNA (sonicated), 100 µg/mL histones, 100 mM Tris (pH 8.0), 1.0 mM DTT, 10 mM MgCl$_2$, NAD (200 µM, 0.65 microcurie/mL), and varying amounts of enzyme. The reaction was incubated for 10 min at 37° C. or at room temperature for 60 min. The reaction was stopped and protein precipitated by addition of ice-cold trichloroacetic acid (TCA; 10% or 20% aqueous w/v). After brief storage in ice or at 4° C. for 2 hrs, the reaction mixture is filtered under vacuum through a glass fiber filter (2.5 cm disc, or 96-well filter plate). After washing with TCA and ethanol, the filter is dried and counted for tritium CPM after addition of scintillation fluid. 10 µL of a typical enzyme preparation of ~20 mg/mL protein gave 10,000 to 20,000 CPM in the 100 µL assay using filter disc, counted with 6 mL of EcoLume (ICN). Insect cells infected with wild-type virus gave no activity. The Km for NAD is established to be 111 µM (literature 50 to 100 µM). The compounds of this invention which are tested for inhibition are dissolved in water or DMSO and added to the assay to give a range of concentrations. A few of the reference compounds tested gave the following results: 3-Aminobenzamide inhibited the reaction with an IC$_{50}$ of 140 µM, nicotinamide gave IC$_{50}$ 400 µM, and 1,5-isoquinolinediol gave IC$_{50}$ of 1 µM. Another literature standard DPQ gave IC$_{50}$ of 11 µM. The results obtained for the compounds of this invention are summarized in Table 1.

'ELISA' Enzyme Assay:

Incorporation of biotin-NAD into histone coated on plate is measured. A 96-well protein-binding EIA plate is coated with histone and blocked with bovine serum albumin. The reaction mixture (50 µL) contained DNA, buffer, enzyme, (test compound), and 250 µM of NAD and 5 µL of biotin-NAD (Trevigen). After reaction at room temperature the wells are washed and treated with Extravidin (Sigma). After incubation and washing color is developed with the peroxidase substrate TMB (Sigma). The TMB reaction is quenched with 2M sulfuric acid and the absorbance at 450 nm is read.

Method B: PARP Enzyme Assay:

The IC$_{50}$ is determined in this method by incubating the substances to be tested with the DNA-activated, recombinantly expressed and purified PARP-1 enzyme. Specifically, various concentrations of the test substance are incubated in 50 µL of reaction solution, which contains 50 mM Tris, 5 mM MgCl$_2$, 1 mM DTT, 200 μM NAD, 0.1 m Ci/mL tritium-labeled NAD, 0.1 mg/mL DNA, 0.1 mg/mL histones, 2 μg/mL recombinantly expressed human PARP-1 enzyme, pH=8.0, at room temperature for 1 hour. The reaction is stopped by adding 150 μL of 20% trichloroacetic acid, and the radiolabeled protein constituents are precipitated. After incubation on ice for 10 minutes, the labeled, insoluble constituents are separated off through a glass fiber filter and, after washing with 20% trichloroacetic acid three times, the radioactivity incorporated by the PARP-1 enzyme is measured by radioluminescence. Consideration of the incorporation rates determined in this way as a function of the concentration of the test substance results in IC$_{50}$ as the concentration of the test substance which reduces the incorporation rate to half the maximum value attainable (incubation without inhibitor).

The IC$_{50}$ (fifty percent inhibitory concentration of the test substance in a solution—expressed at micromolar (μM) concentration) measured in accordance with these procedures for the compounds of this invention are summarized in Table 1.

TABLE 1

| Example No. | IC$_{50}$ (μM)/Method A | IC$_{50}$ (μM)/Method B |
| --- | --- | --- |
| Example 1 | 0.4 | |
| Example 2 | 4.5 | |
| Example 5 | 0.2 | |
| Example 12 | 1.6 | |
| Example 13 | 2.1 | |
| Example 14 | 0.56 | |
| Example 15 | 0.72 | |
| Example 16 | 0.35 | |
| Example 17 | 1.7 | |
| Example 18 | 0.65 | |
| Example 19 | 0.23 | |
| Example 20 | 1.1 | |
| Example 21 | 0.17 | |
| Example 22 | 0.31 | |
| Example 23 | 0.67 | |
| Example 24 | 0.63 | |
| Example 25 | 0.76 | |
| Example 26 | 0.19 | |
| Example 27 | 0.1 | |
| Example 28 | 0.72 | |
| Example 29 | 0.57 | |
| Example 30 | 10.0 | |
| Example 31 | | 0.44 |
| Example 32 | 2.9 | |
| Example 33 | 10.5 | |
| Example 34 | 4.5 | |
| Example 35 | 10.9 | |
| Example 36 | 3.7 | |
| Example 37 | 2.0 | |
| Example 38 | 0.77 | |
| Example 39 | 0.07 | |
| Example 40 | 0.13 | |
| Example 41-1 | 1.5 | |
| Example 41-2 | 0.52 | |
| Example 43 | | 0.21 |
| Example 43A | | 0.67 |
| Example 45 | 0.22 | |
| Example 46 | 0.46 | |
| Example 47 | 0.89 | |
| Example 48 | 0.36 | |
| Example 49 | 0.18 | |
| Example 50 | 0.27 | |
| Example 51 | 0.22 | |
| Example 52 | 0.38 | |
| Example 53 | 0.16 | |
| Example 54 | 0.31 | |
| Example 55 | 0.22 | |
| Example 57 | 5.7 | |
| Example 58 | 2.3 | |
| Example 60 | 1.7 | |
| Example 61 | 0.43 | |
| Example 62 | 0.6 | |
| Example 63 | 0.42 | |
| Example 64 | 1.5 | |
| Example 65 | 0.67 | |
| Example 66 | 0.67 | |
| Example 67 | 0.3 | |
| Example 68 | 1.9 | |
| Example 69 | 0.26 | |
| Example 70 | 0.26 | |
| Example 72 | 1.2 | |
| Example 73 | 0.42 | |
| Example 74 | 0.36 | |
| Example 75 | 0.3 | |
| Example 76 | 0.23 | |
| Example 77 | 0.28 | |
| Example 78 | 0.2 | |
| Example 79 | 0.45 | |
| Example 80 | 0.43 | |
| Example 81 | 0.54 | |
| Example 82 | 0.48 | |
| Example 83 | 2.8 | |
| Example 84 | 1.6 | |
| Example 85 | 0.31 | |
| Example 86 | 4.5 | |
| Example 87 | 5.3 | |
| Example 89 | 10.8 | |
| Example 90 | 0.68 | |
| Example 91 | 2.9 | |
| Example 92 | 1.3 | |
| Example 93 | 0.85 | |
| Example 94 | 1.4 | |
| Example 95 | 0.2 | |
| Example 96 | 0.72 | |
| Example 97 | 0.18 | |
| Example 98 | 0.41 | |
| Example 99 | 1.3 | |
| Example 100 | 2.2 | |
| Example 101 | 0.17 | |
| Example 102 | 0.49 | |
| Example 103 | 0.14 | |
| Example 104 | 2.5 | |
| Example 105 | 3.1 | |
| Example 106 | 0.43 | |
| Example 107 | 0.08 | |
| Example 108 | 1.0 | |
| Example 109 | 0.1 | |
| Example 110 | 0.08 | |
| Example 111 | 0.21 | |
| Example 112 | 1.2 | |
| Example 113 | 0.9 | |
| Example 114 | 0.37 | |
| Example 116 | 0.45 | |
| Example 117 | | 25.5 |
| Example 118 | 0.15 | |
| Example 119 | 0.38 | |
| Example 122A | | 1.22 |
| Example 122B | | 0.13 |
| Example 122C | | 0.86 |
| Example 122D | | 0.06 |
| Example 123 | | 0.58 |
| Example 125 | 0.45 | |
| Example 126 | 0.43 | |
| Example 127 | 0.67 | |
| Example 128 | 0.46 | |
| Example 129 | 1.8 | |
| Example 130 | 1.2 | |
| Example 131 | 0.47 | |
| Example 132 | 1.3 | |
| Example 133 | 2.8 | |
| Example 134 | 0.8 | |
| Example 135 | 0.35 | |
| Example 136 | 0.46 | |
| Example 137 | 0.52 | |
| Example 138 | 0.63 | |
| Example 139 | 2.6 | |
| Example 140 | 0.64 | |
| Example 141 | 0.54 | |
| Example 142 | 2.1 | |
| Example 143 | 0.39 | |
| Example 144 | 0.62 | |

TABLE 1-continued

| Example No. | IC$_{50}$ (μM)/Method A | IC$_{50}$ (μM)/Method B |
|---|---|---|
| Example 145 | 4.0 | |
| Example 146 | 0.24 | |
| Example 147 | 0.49 | |
| Example 148 | 0.41 | |
| Example 149 | 0.79 | |
| Example 150 | 1.3 | |
| Example 151 | 0.92 | |
| Example 152 | 0.83 | |
| Example 153 | 0.67 | |
| Example 154 | 0.53 | |
| Example 155 | 0.71 | |
| Example 156 | 0.44 | |
| Example 157 | 0.6 | |
| Example 158 | 0.51 | |
| Example 159 | 0.72 | |
| Example 160 | 1.7 | |
| Example 161 | 1.3 | |
| Example 162 | 0.52 | |
| Example 163 | 1.7 | |
| Example 164 | 0.69 | |
| Example 165 | 0.98 | |
| Example 166 | 0.68 | |
| Example 167 | 0.55 | |
| Example 168 | 0.4 | |
| Example 169 | 0.6 | |
| Example 170 | 0.28 | |
| Example 171 | 0.48 | |
| Example 172 | 1.0 | |
| Example 173 | 0.22 | |
| Example 174 | 1.3 | |
| Example 175 | 0.15 | |
| Example 176 | 0.28 | |
| Example 177 | 0.49 | |
| Example 178 | 0.4 | |
| Example 179 | | 2.11 |
| Example 181 | | 0.49 |
| Example 181A | | 2.17 |
| Example 182A | | 17.4 |
| Example 182B | | 0.29 |
| Example 182C | | 0.28 |
| Example 182D | | 0.3 |
| Example 182E | | 1.49 |
| Example 182F | | 1.62 |
| Example 182G | | 3.33 |
| Example 182H | | 1.11 |
| Example 182I | | 8.61 |
| Example 182J | | 14.6 |
| Example 182K | | 4.23 |
| Example 183 | 2.4 | |
| Example 184 | 2.7 | |
| Example 185 | 1.8 | |
| Example 186 | | |
| Example 187 | 0.4 | |
| Example 188 | 0.84 | |
| Example 189 | 0.41 | |
| Example 190 | 0.54 | |
| Example 191 | 0.8 | |
| Example 192 | 0.26 | |
| Example 195 | 0.67 | |
| Example 199 | | 0.18 |
| Example 199A | | 0.51 |
| Example 200A | | 1.03 |
| Example 201 | | 1.35 |
| Example 205 | | 0.57 |
| Example 206 | | 1.14 |
| Example 207 | | 4.72 |
| Example 208 | | 14.8 |
| Example 209 | | 13.0 |
| Example 210 | | 12.1 |
| Example 211 | | 8.6 |
| Example 212 | | 12.9 |
| Example 213 | | 0.21 |
| Example 214 | | 1.4 |
| Example 215 | | 1.25 |
| Example 216 | | 1.5 |
| Example 217 | | 2.87 |
| Example 218 | | 0.58 |
| Example 219 | | 1.53 |
| Example 220 | | 1.27 |
| Example 221 | | 2.04 |
| Example 222 | | 0.75 |
| Example 223 | | 0.92 |
| Example 224 | | 5.9 |
| Example 225 | | 5.5 |
| Example 226 | | 0.95 |
| Example 227 | | 1.98 |
| Example 228 | | 10.7 |
| Example 229 | | 4.7 |
| Example 230 | | 0.13 |
| Example 231 | | 14.8 |
| Example 232 | | 0.82 |
| Example 233 | | 1.65 |
| Example 234 | | 2.46 |
| Example 235 | | 1.86 |
| Example 236 | | 0.44 |
| Example 237 | | 1.34 |
| Example 238 | | 0.35 |
| Example 239 | | 0.94 |
| Example 240 | | 3.88 |
| Example 241 | | 1.25 |
| Example 242 | | 1.79 |
| Example 243 | | 2.29 |
| Example 244 | | 0.32 |
| Example 245 | | 1.9 |
| Example 246 | | 0.64 |
| Example 248 | | 0.85 |
| Example 249 | | 5.0 |
| Example 250 | | 0.64 |
| Example 251 | | 0.1 |
| Example 252 | | 6.1 |
| Example 253 | | 0.49 |
| Example 254 | | 11.7 |
| Example 255 | | 0.28 |
| Example 256 | | 0.45 |
| Example 257 | | 0.57 |
| Example 258 | | 0.62 |
| Example 259 | | 0.73 |
| Example 260 | | 0.8 |
| Example 261 | | 2.07 |
| Example 262 | | 2.22 |
| Example 263 | | 2.67 |
| Example 264 | | 3.14 |
| Example 265 | | 4.1 |
| Example 268 | | 1.8 |
| Example 269 | | 1.97 |
| Example 270 | | 1.18 |
| Example 271 | | 0.5 |
| Example 272 | | 0.44 |
| Example 273 | | 1.4 |
| Example 274 | | 0.83 |
| Example 275 | | 1.26 |
| Example 276 | | 0.8 |
| Example 278 | | 7.9 |

Example 280

The following example illustrates the efficacy of the compounds of this invention in inhibiting the effects of PARP in a cell based assay.

Cell-Based Assay:

Reagents: Media RMPI 1640+Glutamax: Gibco 61870-044); TBST/milk, TBST (Sigma T93039) containing 5% skimmed milk (Nestle Carnation nonfat dry milk)

HL60 cells at $1.0 \times 10^{-6}$ cells/mm in serum free media are seeded into the wells of a 96-well plate at 100 μL/well. The plate is pre-incubated for 3 hr under normal tissue culture conditions. One hundred μL of serum-free media containing compound at 2× the required concentration in 0.6% DMSO are added (or 0.6% DMSO only to controls and blanks). The plate is incubated overnight under normal tissue culture conditions, then centrifuged at 190×g for 5 min at 4° C. to pellet cells. The media is carefully removed by aspiration, and the cells are incubated in 100 µL/well ice-cold 0.56% KCl for 2 min on ice. The plate is centrifuged as above to pellet cells, the KCl removed by aspiration, and 100 µL/well ice-cold methanol added. After 4 min on ice, methanol is removed by aspiration and the cells air-dried for 10-15 min at rt. The cells are washed with PBS×3, then washed with TBST/milk (1 wash, 5 min incubation at rt). The cells are incubated with 100 µL/well 0.25% Triton X 100 in PBS for 10 min at RT, then washed x# with PBS and ×1 with TBST. The cells are blocked for 1 hr with TBST/milk (200 µL/well) and then washed ×1 with TBST. The fixed cells are incubated with primary antibody (Calbiochem cat no. 528815) at 1:2000 dilution in TBST/milk (100 µL/well, overnight at 4 deg C.). The cells are washed with TBST (2 rinses, 1×15 min, 2×5 min at RT). The cells are incubated with secondary antibody (anti-rabbit Ig-biotin conjugate, Amersham RPN1004) in TBST/milk at 1:3500 dilution, 100 µL/well for 1 hr at RT. The cells are washed with TBST (2 rinses, 1×15 min, 2×5 min at RT). The cells are then incubated with 100 µL/well of 4-MUP (Sigma, M3168) in the dark for 4 hrs. The fluorescence is read using a plate reader (excitation at 360 nm, emission at 440 nm). To calculate compound effects, the fluorescence of the blank (no cells) is subtracted from all data. Fluorescence obtained with a standard cell-permeable potent inhibitor at 30 µM is subtracted from all other groups as this appears to represent a true blank. Compound effects can then be determined: a PARP inhibitor blocks the intracellular synthesis of poly(ADP-ribose), and results in a decreased reactivity (reduced final fluorescence) with primary antibody in the fixed and permeabilized cells.

The results obtained from this study are expressed as $EC_{50}$ (median effective concentration of the test compound that was effective in preventing the cell death—expressed in micromolar (µM) concentration) for each of the tested compounds and are summarized in Table 2.

TABLE 2

| Example No. | $EC_{50}$ (µM) |
| --- | --- |
| Example 5 | 0.5 |
| Example 22 | 0.12 |
| Example 25 | 4.88 |
| Example 26 | 2.94 |
| Example 27 | 14.2 |
| Example 39 | 0.5 |
| Example 63 | 0.43 |
| Example 67 | 3.11 |
| Example 70 | 0.26 |
| Example 85 | 0.33 |
| Example 93 | 0.56 |
| Example 95 | 0.22 |
| Example 101 | 0.05 |
| Example 107 | 0.03 |
| Example 109 | 0.24 |
| Example 110 | 0.02 |
| Example 118 | 30 |
| Example 119 | 0.8 |
| Example 126 | 30.8 |
| Example 135 | 12.2 |
| Example 136 | 14.7 |
| Example 143 | 1.43 |
| Example 146 | 0.97 |
| Example 148 | 0.52 |

Example 281

The following animal model can be used to show the efficacy of the compounds of this invention in treating patients suffering from stroke.

Male Fisher rats are anesthetized. The right carotid artery is isolated and ligated, and the right jugular vein is canulated for compound administration. The middle cerebral artery (MCA) was exposed through a craniotomy, and the MCA and its right branch, the lenticulostriate artery are electrocoagulated. The arteries are cut to avoid recanalization. The compounds of this invention (or standard DPQ) are administered i.v. 15 min after the MCA occlusion. The compounds are given as a 10 mg/kg bolus followed by an infusion of 5 mg/kg/hr for 6 hrs (total dose 40 mg/kg).

48 Hours post-MCA occlusion the rats are sacrificed, and the brains removed and cut into 2-mm coronal sections. The sections are incubated with triphenyltetrazolium chloride to demonstrate infarcted area, the extent and location of which is verified and quantified by image analysis.

Example 282

This Example illustrates how to test the efficacy of the compounds of the present invention in treating patients suffering from myocardial ischemia.

Male Sprague-Dawley rats are anesthetized and the chest is opened. A thin silk thread is placed around the left anterior descending coronary artery. The silk is passed through a plastic tube and the chest is closed. After stable hemodynamics, the coronary artery is occluded by applying tension to the thread via the tube. Successful occlusion is confirmed by a decrease in systolic blood pressure and alterations in ECG. Reperfusion is initiated by releasing the tension on the ligature.

For testing efficacy of the compounds of this invention in this animal model, animals are divided into three groups. One group receives a compound of this invention at 10 mg/kg i.v. 10 min prior to occlusion. A second group receives a compound of this invention at the same dose 5 min prior to reperfusion. The third group serves as vehicle control. The period of occlusion is 20 min, followed by reperfusion for 60 min. After sacrifice infarct size is measured by staining of heart tissue slices with triphenyltetrazolium chloride and expressed as a percent (%) of area at risk.

A similar study is carried out with cariporide, a reference standard in order to show the efficacy of the compounds of this invention in comparison with that obtained for cariporide.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound, or an enantiomer, stereoisomer, or a tautomer of said compound or a pharmaceutically acceptable salt thereof, with said compound having the structure shown in formula I:

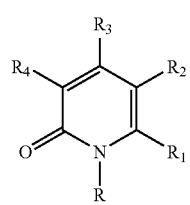

wherein

R is hydrogen or $C_{1-6}$alkyl;

$R_1$ is $C_{1-4}$alkyl, $C_{1-4}$alkenyl, fluoroalkyl or fluoroalkoxy of the formula $C_nH_xF_y$, or $OC_nH_xF_y$, wherein n is an integer from 1 to 4, x is an integer from 0 to 8, y is an integer from 1 to 9 and sum of x and y is 2n+1, wherein said alkyl or alkenyl is optionally substituted with one or more hydroxy or chlorine;

$R_2$ is Ar—Y, wherein

Ar is optionally substituted thienyl wherein said substituents are selected from the group consisting of $C_{1-4}$alkyl, $C_{1-4}$alkoxy, $C_{1-4}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, —NO$_2$, —CH$_2$NH$_2$, —NH$_2$, —NH($C_{1-4}$alkyl), —N($C_{1-4}$alkyl)$_2$, —CN, —C(O)R$_{11}$, —NHC(O)($C_{1-4}$alkyl), —SO$_2$Cl, —SO$_2$($C_{1-4}$alkyl), halogen and hydroxy; and Y is —SO$_2$NR$_5$R$_6$, —(CH$_2$)$_n$NR$_7$R$_8$, and —C(O)NR$_7$R$_8$;

$R_3$ is hydrogen, $C_{1-4}$alkyl, $C_{1-4}$alkenyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1, wherein said alkyl or alkenyl is optionally substituted with one or more hydroxy or chlorine;

$R_4$ is $C_{1-6}$alkyl, $C_{1-6}$alkenyl, $C_{3-8}$cycloalkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and the sum of x and y is 2n+1;

$R_5$ and $R_6$ taken together with the nitrogen atom to which they are attached form an unsubstituted or at least mono-substituted pyrrolidine; or $R_7$ and $R_8$ taken together with the nitrogen atom to which they are attached form an unsubstituted or at least monosubstituted pyrrolidine;

wherein said substituents are selected from: aryl, oxo, fluorine, chlorine, bromine, —CF$_3$, —OCF$_3$, —NO$_2$, —CN, —C(O)R$_{ii}$, —NHC(O)($C_{1-3}$alkyl), —NH$_2$, hydroxy, $C_{1-3}$alkyl, $C_{1-3}$alkoxy, —NH($C_{1-3}$alkyl), —N($C_{1-3}$alkyl)$_2$, —SO$_2$NH$_2$, —SO$_2$($C_{1-3}$alkyl) and —NH—SO$_2$($C_{1-3}$alkyl), and aryl may optionally be at least monosubstituted with fluorine, chlorine, bromine, hydroxy, $C_{1-3}$alkyl or $C_{1-3}$alkoxy;

$R_{11}$ is hydroxy, $C_{1-3}$alkoxy, —O-phenyl, —NH$_2$, —NH($C_{1-3}$alkyl), —N($C_{1-3}$alkyl)$_2$ or phenyl;

n is an integer from 1 to 4; and wherein aryl is a 6 to 10-membered, aromatic mono- or bicyclic ring.

2. The compound as set forth in claim 1, wherein Ar is optionally substituted thienyl and Y is SO$_2$NR$_5$R$_6$ wherein $R_5$ and $R_6$ taken together with the nitrogen atom to which they are attached form a pyrrolidine;

and wherein the aforementioned groups are optionally substituted with one or more substituents selected from the group consisting of fluorine, chlorine, bromine, hydroxy, $C_{1-6}$alkyl, $C_{1-6}$alkoxy, hydroxy-$C_{1-6}$alkyl, hydroxy-$C_{1-6}$alkoxy-$C_{1-6}$alkyl, $C_{3-8}$cycloalkyl-$C_{1-4}$alkyl, trifluoromethyl, $C_{1-6}$alkoxycarbonyl, $C_{1-6}$alkylsulfonyl, amino-$C_{1-6}$alkyl, $C_{1-6}$alkyl-aminio-$C_{1-6}$alkyl, $C_{1-6}$dialkyl-amino-$C_{1-6}$alkyl, substituted or unsubstituted phenyl-$C_{0-4}$alkyl, substituted or unsubstituted phenyl-amino-$C_{0-4}$alkyl and substituted or unsubstituted benzoyl.

3. The compound as set forth in claim 2, wherein R is hydrogen, $R_1$ is methyl, $R_3$ is hydrogen and $R_4$ is ethyl.

4. A compound which is selected from the group consisting of:

5-(5-ethyl-2-methyl-6-oxo-1,6-dihydro-pyridin-3-yl)-thiophene-2-sulfonic acid [3-(3-hydroxy-pyrrolidin-1-yl)-propyl]-amide hydrochloride;

5-(5-ethyl-2-methyl-6-oxo-1,6-dihydropyridin-3-yl) thiophene-2-sulfonic Acid [2-(1-methylpyrrolidin-2-yl)ethyl]amide hydrochloride;

5-(5-ethyl-2-methyl-6-oxo-1,6-dihydro-pyridin-3-yl)-thiophene-2-sulfonic acid [3-(3,3-difluoro-pyrrolidin-1-yl)-propyl]-amide hydrochloride;

5-[5-ethyl-2-methyl-6-oxo-1,6-dihydropyridin-3-yl] thiophene-2-sulfonic acid [3-(2-oxopyrrolidin-1-yl) propyl]amide;

5-[5-ethyl-2-methyl-6-oxo-1,6-dihydropyridin-3-yl] thiophene-2-sulfonic acid methyl (1-methylpyrrolidin-3-yl)amide hydrochloride;

3-ethyl-5-[5-(3-hydroxypyrrolidine-1-sulfonyl)thiophen-2-yl]-6-methyl-1H-pyridin-2-one;

5-(5-ethyl-2-methyl-6-oxo-1,6-dihydropyridin-3-yl) thiophene-2-sulfonic acid (2-pyrrolidin-1-yl)ethylamide hydrochloride;

5-(5-ethyl-2-methyl-6-oxo-1,6-dihydropyridin-3-yl)-thiophene-2-sulfonic acid (1-ethyl-pyrrolidin-2-ylmethyl)amide hydrochloride;

3-ethyl-6-methyl-5-[5-((S)-2-phenylaminomethylpyrrolidine-1-sulfonyl)-thiophen-2-yl]-1H-pyridin-2-one hydrochloride;

5-(5-ethyl-2-methyl-6-oxo-1,6-dihydro-pyridin-3-yl)-thiophene-2-sulfonic acid [3-(2R-hydroxymethyl-pyrrolidin-1-yl)-propyl]-amide hydrochloride;

5-(5-ethyl-2-methyl-6-oxo-1,6-dihydro-pyridin-3-yl)-thiophene-2-sulfonic acid [2-(2R-hydroxymethyl-pyrrolidin-1-yl)-ethyl]-amide hydrochloride;

5-(5-ethyl-2-methyl-6-oxo-1,6-dihydro-pyridin-3-yl)-thiophene-2-sulfonic acid [2-(3,3-difluoro-pyrrolidin-1-yl)-ethyl]-amide; and 1-{2-[5-(5-ethyl-2-methyl-6-oxo-1,6-dihydro-pyridin-3-yl)-thiophene-2-sulfonylamino]-ethyl}-pyrrolidine-2-carboxylic acid.

5. A pharmaceutical composition comprising one or more compounds of claim 1 in combination with one or more pharmaceutically acceptable carriers, diluents or excipients.

6. A pharmaceutical composition comprising one or more compounds of claim 3 in combination with one or more pharmaceutically acceptable carriers, diluents or excipients.

* * * * *

UNITED STATES PATENT AND TRADEMARK OFFICE
CERTIFICATE OF CORRECTION

PATENT NO. : 8,173,682 B2
APPLICATION NO. : 11/535127
DATED : May 8, 2012
INVENTOR(S) : Rhilip M. Weintraub et al.

It is certified that error appears in the above-identified patent and that said Letters Patent is hereby corrected as shown below:

Title Page, Item (73) should read:

(73) Assignee: Aventis Pharmaceuticals Inc.
Bridgewater, NJ (US)

Sanofi-Aventis Deutschland GmbH
Frankfurt Am Main, Germany

Signed and Sealed this
Fourteenth Day of August, 2012

David J. Kappos
*Director of the United States Patent and Trademark Office*